United States Patent
Graupe et al.

(10) Patent No.: US 9,416,115 B2
(45) Date of Patent: Aug. 16, 2016

(54) FUSED HETEROCYCLIC COMPOUNDS AS ION CHANNEL MODULATORS

(71) Applicant: Gilead Sciences, Inc., Foster City, CA (US)

(72) Inventors: Michael Graupe, Foster City, CA (US); Yafan Lu, Foster City, CA (US); Jeff A. Zablocki, Foster City, CA (US)

(73) Assignee: Gilead Scineces, Inc., Foster City, CA (US)

( * ) Notice: Subject to any disclaimer, the term of this patent is extended or adjusted under 35 U.S.C. 154(b) by 0 days.

(21) Appl. No.: 14/559,011

(22) Filed: Dec. 3, 2014

(65) Prior Publication Data

US 2015/0175560 A1    Jun. 25, 2015

Related U.S. Application Data

(60) Provisional application No. 61/919,605, filed on Dec. 20, 2013.

(51) Int. Cl.
| | |
|---|---|
| *C07D 261/20* | (2006.01) |
| *C07D 498/04* | (2006.01) |
| *C07D 471/04* | (2006.01) |
| *C07D 417/12* | (2006.01) |
| *C07D 413/12* | (2006.01) |
| *C07D 413/14* | (2006.01) |

(52) U.S. Cl.
CPC ............ *C07D 261/20* (2013.01); *C07D 413/12* (2013.01); *C07D 413/14* (2013.01); *C07D 417/12* (2013.01); *C07D 471/04* (2013.01); *C07D 498/04* (2013.01)

(58) Field of Classification Search
CPC .. C07D 261/20; C07D 413/12; C07D 498/04; C07D 417/12; C07D 471/04; C07D 413/14
USPC ........ 544/112; 548/143; 546/272.1; 514/210, 514/269
See application file for complete search history.

(56) References Cited

U.S. PATENT DOCUMENTS

| | | | | |
|---|---|---|---|---|
| 4,859,691 | A * | 8/1989 | Bowman ..................... | 514/379 |
| 7,977,360 | B2 * | 7/2011 | Frank .................. | C07D 413/12 |
| | | | | 514/338 |

FOREIGN PATENT DOCUMENTS

| | | |
|---|---|---|
| EP | 0665226 A1 | 8/1995 |
| WO | WO-2005089753 A2 | 9/2005 |
| WO | WO-2006122799 A1 | 11/2006 |
| WO | WO-2012076877 A1 | 6/2012 |
| WO | WO-2013064984 A1 | 5/2013 |

OTHER PUBLICATIONS

International Search Report—Written Opinion dated May 28, 2015 for PCT/US2014/068359.
Zaza et al. (2008) Pathophysiology and Pharmacology of the Cardiac "Late Sodium Current" *Pharmacology and Therapeutics* 119:326-339.

* cited by examiner

*Primary Examiner* — Rita Desai
(74) *Attorney, Agent, or Firm* — Francis O. Ginah

(57) ABSTRACT

The present disclosure relates to compounds that are sodium channel inhibitors and to their use in the treatment of various disease states, including cardiovascular diseases and diabetes. In particular embodiments, the structure of the compounds is given by Formula I:

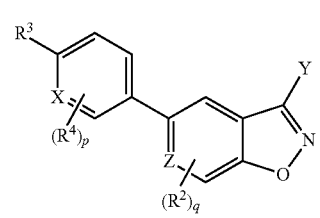

wherein X, Y, Z, $R^2$, $R^3$, $R^4$, p and q are as described herein, to methods for the preparation and use of the compounds and to pharmaceutical compositions containing the same.

4 Claims, No Drawings

FUSED HETEROCYCLIC COMPOUNDS AS ION CHANNEL MODULATORS

CROSS-REFERENCE TO RELATED APPLICATIONS

This application claims benefit under 35 U.S.C. §119(e) to U.S. Provisional Application Ser. No. 61/919,605, filed on Dec. 20, 2013, the entirety of which is incorporated herein by reference.

FIELD

The present disclosure relates to novel compounds and to their use in the treatment of various diseases, including cardiovascular diseases and diabetes. The disclosure also relates to methods for preparation of the compounds and to pharmaceutical compositions comprising such compounds.

BACKGROUND

The late sodium current (INaL) is a sustained component of the fast Na+ current of cardiac myocytes and neurons. Many common neurological and cardiac conditions are associated with abnormal (INaL) enhancement, which contributes to the pathogenesis of both electrical and contactile dysfunction in mammals (particularly humans). See, for example, Pathophysiology and Pharmacology of the Cardiac "Late Sodium Current", Pharmacology and Therapeutics 119 (2008) 326-339. Accordingly, compounds that selectively inhibit (INaL) in mammals, particularly humans, are useful in treating such disease states.

It would be desirable to provide novel compounds that selectively inhibit (INaL) in mammals, particularly humans.

SUMMARY

Accordingly, embodiments the present disclosure provide novel compounds that function as late sodium channel blockers. In one embodiment, the disclosure provides compounds of Formula I:

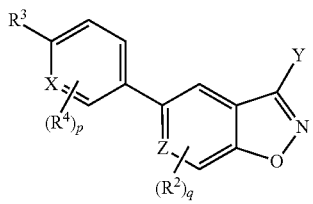

wherein
Y is -L-$R^1$ or a heterocyclyl or heteroaryl ring bonded through a ring nitrogen atom, wherein each heterocyclyl or heteroaryl is optionally substituted with 1 to 3 groups independently selected from the group consisting of $C_1$-$C_6$ alkyl, $C_3$-$C_6$ cycloalkyl, halo, aryl, heterocyclyl, heteroaryl, oxo, $C_1$-$C_6$ alkoxy, —OH, —$NH_2$, —$COR^7$, —$CO_2R^7$, —$NHSO_2R^7$, —$NHCO_2R^7$, and —CN; and wherein each $C_1$-$C_6$ alkyl, $C_3$-$C_6$ cycloalkyl, aryl, heterocyclyl, heteroaryl, and $C_1$-$C_6$ alkoxy is optionally substituted with 1 to 3 $C_1$-$C_6$ alkoxy, halo, —$CF_3$, —CN, —OH, —$NH_2$ or —$OCF_3$;
X is $CR^8$ or N;
Z is $CR^9$ or N;
L is —O—, —$NR^5$—, —$NR^5(CHR^6)_n$—, —$O(CHR^6)_n$, $O(CHR^6)_nC(O)$—, —$O(CHR^6)_nC(O)O$—, —$O(CHR^6)_nNH$—, —$O(CHR^6)_nC(O)NH$—, —$O(CHR^6)_nNHC(O)O$— or —$O(CHR^6)_m$$NHS(O)_2$—;
$R^1$ is hydrogen, $C_1$-$C_6$ alkyl, $C_3$-$C_8$ cycloalkyl, aryl, heterocyclyl or heteroaryl; wherein each cycloalkyl, aryl, heterocyclyl or heteroaryl is optionally substituted with 1 to 3 groups independently selected from the group consisting of $C_1$-$C_6$ alkyl, $C_3$-$C_6$ cycloalkyl, halo, aryl, heterocyclyl, heteroaryl, oxo, —OH, —$NH_2$, —$COR^7$, —$CO_2R^7$, —$NHSO_2R^7$, —$NHCO_2R^7$, and —CN; and wherein each $C_1$-$C_6$ alkyl, $C_3$-$C_6$ cycloalkyl, aryl, heterocyclyl, heteroaryl, and $C_1$-$C_6$ alkoxy is optionally substituted with 1 to 3 $C_1$-$C_6$ alkoxy, halo, —$CF_3$, —CN, —OH, —$NH_2$ or —$OCF_3$;
each $R^2$ is independently halo, $C_1$-$C_6$ alkyl, $C_1$-$C_6$ alkoxy or —$OCF_3$;
$R^3$ is hydrogen, halo, $C_1$-$C_3$ haloalkyl, $C_1$-$C_3$ haloalkoxy, $C_3$-$C_6$ cycloalkyl or phenyl, wherein the cycloalkyl or phenyl is optionally substituted with one or two halo atoms, provided that when $R^3$ is hydrogen, then p is 1 or 2;
each $R^4$ is independently $C_1$-$C_6$ alkyl, halo, $C_1$-$C_6$ alkoxy or —$OCF_3$; or $R^3$ and $R^4$ taken together with the carbon atoms to which they are attached form a $C_4$-$C_8$ ring optionally containing from one to three double bonds and optionally containing from one to three heteroatoms independently selected from the group consisting of O, N, and S, which ring can be optionally substituted with one to three halo, $C_1$-$C_6$ alkyl, $C_1$-$C_3$ haloalkyl or $C_1$-$C_3$ haloalkoxy;
$R^5$ is hydrogen, $C_1$-$C_6$ alkyl, $C_1$-$C_3$ haloalkyl or —$COCH_3$;
each $R^6$ is independently hydrogen, $C_1$-$C_6$ alkyl, $C_1$-$C_3$ haloalkyl, —CN, —OH or —$NH_2$;
$R^7$ is hydrogen, $C_1$-$C_6$ alkyl, aryl or aralkyl;
$R^8$ is independently hydrogen, $C_1$-$C_6$ alkyl, halo, $C_1$-$C_6$ alkoxy or —$OCF_3$; or $R^3$ and $R^8$ taken together with the carbon atoms to which they are attached form a $C_4$-$C_8$ ring optionally containing from one to three double bonds and optionally containing from one to three heteroatoms independently selected from the group consisting of O, N, and S, which ring can be optionally substituted with one to three halo, $C_1$-$C_6$ alkyl, $C_1$-$C_3$ haloalkyl or $C_1$-$C_3$ haloalkoxy;
$R^9$ is hydrogen, halo, $C_1$-$C_6$ alkyl, $C_1$-$C_6$ alkoxy or —$OCF_3$;
each m is independently 2, 3, 4 or 5;
each n is independently 1, 2, 3, 4 or 5; and
p and q are each independently 0, 1 or 2;
or a pharmaceutically acceptable salt, stereoisomer or mixture of stereoisomer thereof.

In another embodiment, the disclosure provides compounds of Formula IA:

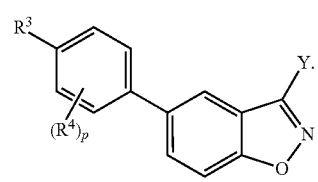

In yet another embodiment, the disclosure provides compounds of Formula IB:

IB

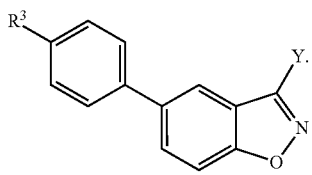

In still another embodiment, the disclosure provides compounds of Formula IC:

IC

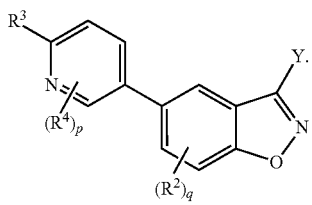

In still another embodiment, the disclosure provides compounds of Formula ID:

ID

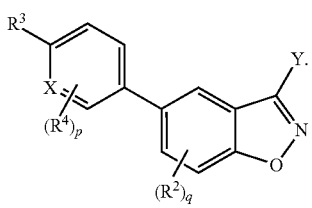

Some embodiments provide a method of using the compounds of Formula I, IA, IB, IC or ID, or additional Formula(s) described throughout, in the treatment of a disease or condition in a mammal, particularly a human, that is amenable to treatment by a late sodium channel blocker. Such diseases include cardiovascular diseases such as atrial and ventricular arrhythmias, heart failure (including congestive heart failure, diastolic heart failure, systolic heart failure, acute heart failure), Prinzmetal's (variant) angina, stable and unstable angina, exercise induced angina, congestive heart disease, ischemia, recurrent ischemia, reperfusion injury, myocardial infarction, acute coronary syndrome, peripheral arterial disease and intermittent claudication. Such diseases may also include diabetes and conditions related to diabetes, e.g. diabetic peripheral neuropathy. Such diseases may also include conditions affecting the neuromuscular system resulting in pain, seizures or paralysis. Such diseases may also include long QT syndrome (i.e., LQT1, LQT2, LQT3, LQT4 or LQT5), including, but not limited to, reducing a prolongation of the QT interval caused by a genetic mutation of SCN5A. Such diseases may also include hypertrophic cardiomyopathy. Therefore, it is contemplated that the compounds of the disclosure and their pharmaceutically acceptable salt, ester, stereoisomer, mixture of stereoisomers and/or tautomer forms are potentially of use as medicaments for the treatment of the aforementioned diseases.

In certain embodiments, the disclosure provides pharmaceutical compositions comprising a therapeutically effective amount of a compound of the disclosure (e.g. a compound of Formula I or additional Formulas described throughout), and at least one pharmaceutically acceptable excipient.

The inventions of this disclosure are described throughout. In addition, specific embodiments of the invention are as disclosed herein.

DETAILED DESCRIPTION

1. Definitions and General Parameters

As used in the present specification, the following words and phrases are generally intended to have the meanings as set forth below, except to the extent that the context in which they are used indicates otherwise.

The term "alkyl" refers to a monoradical branched or unbranched saturated hydrocarbon chain having from 1 to 20 carbon atoms, or from 1 to 15 carbon atoms, or from 1 to 10 carbon atoms, or from 1 to 8 carbon atoms, or from 1 to 6 carbon atoms, or from 1 to 4 carbon atoms. This term is exemplified by groups such as methyl, ethyl, n-propyl, iso-propyl, n-butyl, iso-butyl, t-butyl, n-hexyl, n-decyl, tetradecyl, and the like.

The term "alkylene" refers to a diradical of a branched or unbranched saturated hydrocarbon chain, in some embodiments, having from 1 to 20 carbon atoms (e.g. 1-10 carbon atoms or 1, 2, 3, 4, 5 or 6 carbon atoms). This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—), and the like.

The term "aralkyl" refers to an aryl group covalently linked to an alkylene group, where aryl and alkylene are defined herein. "Optionally substituted aralkyl" refers to an optionally substituted aryl group covalently linked to an optionally substituted alkylene group. Such aralkyl groups are exemplified by benzyl, phenylethyl, 3-(4-methoxyphenyl)propyl, and the like.

The term "aralkyloxy" refers to the group —O-aralkyl. "Optionally substituted aralkyloxy" refers to an optionally substituted aralkyl group covalently linked to an optionally substituted alkylene group. Such aralkyl groups are exemplified by benzyloxy, phenylethyloxy, and the like.

The term "alkenyl" refers to a monoradical of a branched or unbranched unsaturated hydrocarbon group having from 2 to 20 carbon atoms (in some embodiments, from 2 to 10 carbon atoms, e.g. 2 to 6 carbon atoms) and having from 1 to 6 carbon-carbon double bonds, e.g. 1, 2 or 3 carbon-carbon double bonds. In some embodiments, alkenyl groups include ethenyl (or vinyl, i.e. —CH═CH$_2$), 1-propylene (or allyl, i.e. —CH$_2$CH═CH$_2$), isopropylene (—C(CH$_3$)═CH$_2$), and the like.

The term "alkenylene" refers to a diradical of a branched or unbranched unsaturated hydrocarbon group having from 2 to 20 carbon atoms (in some embodiments, from 2 to 10 carbon atoms, e.g. 2 to 6 carbon atoms) and having from 1 to 6 carbon-carbon double bonds, e.g. 1, 2 or 3 carbon-carbon double bonds.

The term "alkynyl" refers to a monoradical of an unsaturated hydrocarbon, in some embodiments, having from 2 to 20 carbon atoms (in some embodiments, from 2 to 10 carbon atoms, e.g. 2 to 6 carbon atoms) and having from 1 to 6 carbon-carbon triple bonds e.g. 1, 2 or 3 carbon-carbon triple bonds. In some embodiments, alkynyl groups include ethynyl (—C≡CH), propargyl (or propynyl, i.e. —C≡CCH$_3$)), and the like.

The term "alkynylene" refers to a diradical of an unsaturated hydrocarbon, in some embodiments, having from 2 to 20 carbon atoms (in some embodiments, from 2 to 10 carbon atoms, e.g. 2 to 6 carbon atoms) and having from 1 to 6 carbon-carbon triple bonds e.g. 1, 2 or 3 carbon-carbon triple bonds.

The term "hydroxy" or "hydroxyl" refers to a group —OH.

The term "alkoxy" refers to the group R—O—, where R is alkyl or —$Y^1$—$Z^1$, in which $Y^1$ is alkylene and $Z^1$ is alkenyl or alkynyl, where alkyl, alkenyl and alkynyl are as defined herein. In some embodiments, alkoxy groups are alkyl-O— and includes, by way of example, methoxy, ethoxy, n-propoxy, iso-propoxy, n-butoxy, tert-butoxy, sec-butoxy, n-pentoxy, n-hexyloxy, 1,2-dimethylbutoxy, and the like.

The term "$C_{1-3}$haloalkyl" refers to an alkyl group having from 1 to 3 carbon atoms covalently bonded to from 1 to 7, or from 1 to 6, or from 1 to 3, halogen(s), where alkyl and halogen are defined herein. In some embodiments, $C_{1-3}$haloalkyl includes, by way of example, trifluoromethyl, difluoromethyl, fluoromethyl, 2,2,2-trifluoroethyl, 2,2-difluoroethyl, 2-fluoroethyl, 3,3,3-trifluoropropyl, 3,3-difluoropropyl, 3-fluoropropyl.

The term "$C_{1-3}$ hydroxyalkyl" refers to an alkyl group having a carbon atom covalently bonded to a hydroxy, where alkyl and hydroxy are defined herein. In some embodiments, $C_{1-3}$ hydroxyalkyl includes, by way of example, 2-hydroxyethyl.

The term "$C_{1-3}$ cyanoalkyl" refers to an alkyl group having a carbon atom covalently bonded to a cyano, where alkyl and cyano are defined herein. In some embodiments, $C_{1-3}$ cyanoalkyl includes, by way of example, 2-cyanoethyl.

The term "$C_{1-3}$ haloalkoxy" refers to an alkoxy group having from 1 to 3 carbon atoms covalently bonded to from 1 to 7, or from 1 to 6, or from 1 to 3, halogen(s), where alkyl and halogen are defined herein. In some embodiments, $C_{1-3}$ haloalkoxy includes, by way of example, trifluoromethoxy, difluoromethoxy, fluoromethoxy, 2,2,2-trifluoroethoxy, 2,2-difluoroethoxy, 2-fluoroethoxy, 3,3,3-trifluoropropoxy, 3,3-difluoropropoxy, 3-fluoropropoxy.

The term "cycloalkyl" refers to cyclic alkyl groups of from 3 to 20 carbon atoms, or from 3 to 10 carbon atoms, having a single cyclic ring or multiple condensed rings. Such cycloalkyl groups include, by way of example, single ring structures such as cyclopropyl, cyclobutyl, cyclopentyl, cyclooctyl and the like or multiple ring structures such as adamantanyl and bicyclo[2.2.1]heptanyl or cyclic alkyl groups to which is fused an aryl group, for example indanyl, and the like, provided that the point of attachment is through the cyclic alkyl group.

The term "cycloalkenyl" refers to cyclic alkyl groups of from 3 to 20 carbon atoms having a single cyclic ring or multiple condensed rings and having at least one double bond and in some embodiments, from 1 to 2 double bonds.

The term "cycloalkoxy" refers to the group cycloalkyl-O—.

The term "cycloalkenyloxy" refers to the group cycloalkenyl-O—.

The term "aryl" refers to an aromatic carbocyclic group of 6 to 20 carbon atoms having a single ring (e.g., phenyl) or multiple rings (e.g., biphenyl) or multiple condensed (fused) rings (e.g., naphthyl, fluorenyl and anthryl). In some embodiments, aryls include phenyl, fluorenyl, naphthyl, anthryl, and the like.

The term "aryloxy" refers to the group aryl-O— wherein the aryl group is as defined above.

The term "heterocyclyl," "heterocycle," or "heterocyclic" refers to a monoradical saturated group having a single ring or multiple condensed rings, having from 1 to 40 carbon atoms and from 1 to 10 hetero atoms, and from 1 to 4 heteroatoms, selected from nitrogen, sulfur, phosphorus, and/or oxygen within the ring. In some embodiments, the heterocyclyl," "heterocycle," or "heterocyclic" group is linked to the remainder of the molecule through one of the heteroatoms within the ring.

The term "heterocycloxy" refers to the group —O-heterocyclyl.

The term "heteroaryl" refers to a group comprising single or multiple rings comprising 1 to 15 carbon atoms and 1 to 4 heteroatoms selected from oxygen, nitrogen and sulfur within at least one ring. Examples of aromatic heteroaryls include pyrrole, thiophene, pyridine, quinoline, pteridine.

Such heteroaryl groups can have a single ring (e.g., pyridyl or furyl) or multiple condensed rings (e.g., indolizinyl, benzothiazole or benzothienyl). Examples of nitrogen heterocyclyls and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, and the like as well as N-alkoxy-nitrogen containing heteroaryl compounds.

The term "heteroaryloxy" refers to the group heteroaryl-O—.

The term "amino" refers to the group —$NH_2$.

The term "substituted amino" refers to the group —NRR where each R is independently selected from the group consisting of hydrogen, alkyl, cycloalkyl, aryl, heteroaryl and heterocyclyl provided that both R groups are not hydrogen or a group —$Y^2$—$Z^2$, in which $Y^2$ is optionally substituted alkylene and $Z^2$ is alkenyl, cycloalkenyl or alkynyl. Unless otherwise constrained by the definition, all substituents may optionally be further substituted by 1, 2 or 3 substituents chosen from alkyl, alkenyl, alkynyl, carboxy, carboxyalkyl, aminocarbonyl, hydroxy, alkoxy, halogen, $CF_3$, amino, substituted amino, cyano, cycloalkyl, heterocyclyl, aryl, heteroaryl, and —$S(O)_nR^a$, in which $R^a$ is alkyl, aryl or heteroaryl and n is 0, 1 or 2.

The term "alkyl amine" refers to R—$NH_2$ in which R is alkyl.

The term "dialkyl amine" refers to R—NHR in which each R is independently an alkyl.

The term "trialkyl amine" refers to $NR_3$ in which each R is independently an alkyl.

The term "cyano" refers to the group —CN.

The term "azido" refers to a group

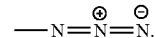

The term "keto" or "oxo" refers to a group =O.

The term "carboxy" refers to a group —C(O)—OH.

The term "ester" or "carboxyester" refers to the group —C(O)OR, where R is alkyl, cycloalkyl, aryl, heteroaryl or heterocyclyl, which may be optionally further substituted by alkyl, alkoxy, halogen, $CF_3$, amino, substituted amino, cyano or —$S(O)_nR^a$, in which $R^a$ is alkyl, aryl or heteroaryl and n is 0, 1 or 2.

The term "acyl" denotes the group —C(O)R, in which R is hydrogen, alkyl, cycloalkyl, heterocyclyl, aryl or heteroaryl. Unless otherwise constrained by the definition, all substituents may optionally be further substituted by 1, 2 or 3 substituents selected from the group consisting of alkyl, alkenyl, alkynyl, carboxy, carboxyalkyl, aminocarbonyl, hydroxy, alkoxy, halogen, $CF_3$, amino, substituted amino, cyano, cycloalkyl, heterocyclyl, aryl, heteroaryl, and —S(O)—$R^a$, in which $R^a$ is alkyl, aryl or heteroaryl and n is 0, 1 or 2.

The term "carboxyalkyl" refers to the groups —C(O)O-alkyl or —C(O)O-cycloalkyl, where alkyl and cycloalkyl are as defined herein, and may be optionally further substituted by alkyl, alkenyl, alkynyl, carboxy, carboxyalkyl, aminocarbonyl, hydroxy, alkoxy, halogen, $CF_3$, amino, substituted amino, cyano, cycloalkyl, heterocyclyl, aryl, heteroaryl, and —S(O)$_n R^a$, in which $R^a$ is alkyl, aryl or heteroaryl and n is 0, 1 or 2.

The term "aminocarbonyl" refers to the group —C(O)NRR where each R is independently hydrogen, alkyl, cycloalkyl, aryl, heteroaryl, or heterocyclyl, or where both R groups are joined to form a heterocyclic group (e.g., morpholino). Unless otherwise constrained by the definition, all substituents may optionally be further substituted by 1, 2 or 3 substituents selected from the group consisting of alkyl, alkenyl, alkynyl, carboxy, carboxyalkyl, aminocarbonyl, hydroxy, alkoxy, halogen, $CF_3$, amino, substituted amino, cyano, cycloalkyl, heterocyclyl, aryl, heteroaryl, and —S(O)$_n R^a$, in which $R^a$ is alkyl, aryl or heteroaryl and n is 0, 1 or 2.

The term "acyloxy" refers to the group —OC(O)—R, in which R is alkyl, cycloalkyl, heterocyclyl, aryl or heteroaryl. Unless otherwise constrained by the definition, all substituents may optionally be further substituted by 1, 2 or 3 substituents selected from the group consisting of alkyl, alkenyl, alkynyl, carboxy, carboxyalkyl, aminocarbonyl, hydroxy, alkoxy, halogen, $CF_3$, amino, substituted amino, cyano, cycloalkyl, heterocyclyl, aryl, heteroaryl, and —S(O)$_n R^a$, in which $R^a$ is alkyl, aryl or heteroaryl and n is 0, 1 or 2.

The term "acylamino" refers to the group —NRC(O)R where each R is independently hydrogen, alkyl, cycloalkyl, aryl, heteroaryl or heterocyclyl. Unless otherwise constrained by the definition, all substituents may optionally be further substituted by 1, 2 or 3 substituents selected from the group consisting of alkyl, alkenyl, alkynyl, carboxy, carboxyalkyl, aminocarbonyl, hydroxy, alkoxy, halogen, $CF_3$, amino, substituted amino, cyano, cycloalkyl, heterocyclyl, aryl, heteroaryl, and —S(O)$_n R^a$, in which $R^a$ is alkyl, aryl or heteroaryl and n is 0, 1 or 2.

The term "alkoxycarbonylamino" refers to the group —N($R^d$)C(O)OR in which R is alkyl and $R^d$ is hydrogen or alkyl. Unless otherwise constrained by the definition, each alkyl may optionally be further substituted by 1, 2 or 3 substituents selected from the group consisting of alkyl, alkenyl, alkynyl, carboxy, carboxyalkyl, aminocarbonyl, hydroxy, alkoxy, halogen, $CF_3$, amino, substituted amino, cyano, cycloalkyl, heterocyclyl, aryl, heteroaryl, and —S(O)$_n R^a$, in which $R^a$ is alkyl, aryl or heteroaryl and n is 0, 1 or 2.

The term "aminocarbonylamino" refers to the group —N$R^c$C(O)NRR, wherein $R^c$ is hydrogen or alkyl and each R is hydrogen, alkyl, cycloalkyl, aryl, heteroaryl or heterocyclyl. Unless otherwise constrained by the definition, all substituents may optionally be further substituted by 1, 2 or 3 substituents selected from the group consisting of alkyl, alkenyl, alkynyl, carboxy, carboxyalkyl, aminocarbonyl, hydroxy, alkoxy, halogen, $CF_3$, amino, substituted amino, cyano, cycloalkyl, heterocyclyl, aryl, heteroaryl, and —S(O)$_n R^a$, in which $R^a$ is alkyl, aryl or heteroaryl and n is 0, 1 or 2.

The term "sulfoxide" refers to a group —S(O)R, in which R is alkyl, cycloalkyl, heterocyclyl, aryl or heteroaryl.

The term "hydroxyamino" refers to the group —NHOH.

The term "halogen" or "halo" refers to fluoro, bromo, chloro and iodo.

"Optional" or "optionally" means that the subsequently described event or circumstance may or may not occur, and that the description includes instances where said event or circumstance occurs and instances in which it does not.

A "substituted" group includes embodiments in which a monoradical substituent is bound to a single atom of the substituted group (e.g. forming a branch), and also includes embodiments in which the substituent may be a diradical bridging group bound to two adjacent atoms of the substituted group, thereby forming a fused ring on the substituted group.

Where a given group (moiety) is described herein as being attached to a second group and the site of attachment is not explicit, the given group may be attached at any available site of the given group to any available site of the second group. For example, a "alkyl-substituted phenyl", where the attachment sites are not explicit, may have any available site of the alkyl group attached to any available site of the phenyl group. In this regard, an "available site" is a site of the group at which a hydrogen of the group may be replaced with a substituent.

A compound of a given formula (e.g. the compound of Formula I, which also includes Formula I, IA, IB, IC or ID) is intended to encompass the compounds of the disclosure, and the pharmaceutically acceptable salts, pharmaceutically acceptable esters, isomers, tautomers, solvates, isotopes, hydrates, polymorphs, and prodrugs of such compounds. Additionally, the compounds of the disclosure may possess one or more asymmetric centers, and can be produced as a racemic mixture or as individual enantiomers or diastereoisomers. The number of stereoisomers present in any given compound of a given formula depends upon the number of asymmetric centers present (there are $2^n$ stereoisomers possible where n is the number of asymmetric centers). The individual stereoisomers may be obtained by resolving a racemic or non-racemic mixture of an intermediate at some appropriate stage of the synthesis or by resolution of the compound by conventional means. The individual stereoisomers (including individual enantiomers and diastereoisomers) as well as racemic and non-racemic mixtures of stereoisomers are encompassed within the scope of the present disclosure, all of which are intended to be depicted by the structures of this specification unless otherwise specifically indicated.

"Isomers" are different compounds that have the same molecular formula. Isomers include stereoisomers, enantiomers and diastereomers.

"Stereoisomers" are isomers that differ only in the way the atoms are arranged in space.

"Enantiomers" are a pair of stereoisomers that are non-superimposable mirror images of each other. A 1:1 mixture of a pair of enantiomers is a "racemic" mixture. The term "(±)" is used to designate a racemic mixture where appropriate.

"Diastereoisomers" are stereoisomers that have at least two asymmetric atoms, but which are not mirror-images of each other.

The absolute stereochemistry is specified according to the Cahn Ingold Prelog R S system. When the compound is a pure enantiomer the stereochemistry at each chiral carbon may be specified by either R or S. Resolved compounds whose absolute configuration is unknown are designated (+) or (−) depending on the direction (dextro- or laevorotary) that they rotate the plane of polarized light at the wavelength of the sodium D line.

Some of the compounds exist as tautomeric isomers. Tautomeric isomers are in equilibrium with one another. For example, amide containing compounds may exist in equilibrium with imidic acid tautomers. Regardless of which tautomer is shown, and regardless of the nature of the equilibrium among tautomers, the compounds are understood by one of ordinary skill in the art to comprise both amide and imidic acid tautomers. Thus, the amide containing compounds are understood to include their imidic acid tautomers. Likewise, the imidic acid containing compounds are understood to include their amide tautomers.

The term "therapeutically effective amount" refers to an amount that is sufficient to effect treatment, as defined below, when administered to a mammal, particularly a human, in need of such treatment. The therapeutically effective amount will vary depending upon the subject and disease condition being treated, the weight and age of the subject, the severity of the disease condition, the manner of administration and the like, which can readily be determined by one of ordinary skill in the art.

The term "polymorph" refers to different crystal structures of a crystalline compound. The different polymorphs may result from differences in crystal packing (packing polymorphism) or differences in packing between different conformers of the same molecule (conformational polymorphism).

The term "prodrug" refers to compounds of Formula I, IA, IB, IC or ID that include chemical groups which, in vivo, can be converted and/or can be split off from the remainder of the molecule to provide for the active drug, a pharmaceutically acceptable salt thereof or a biologically active metabolite thereof.

Any formula or structure given herein, including Formula I, IA, IB, IC or ID compounds, is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, phosphorous, fluorine and chlorine, such as, but not limited to $^2$H (deuterium, D), $^3$H (tritium), $^{11}$C, $^{13}$C, $^{14}$C, $^{15}$N, $^{18}$F, $^{31}$P, $^{32}$P, $^{35}$S, $^{36}$Cl and $^{125}$I. Various isotopically labeled compounds of the present disclosure, for example those into which radioactive isotopes such as $^3$H, $^{13}$C and $^{14}$C are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients.

The disclosure also included compounds of Formula I, IA, IB, IC or ID in which from 1 to n hydrogens attached to a carbon atom is/are replaced by deuterium, in which n is the number of hydrogens in the molecule. Such compounds exhibit increased resistance to metabolism and are thus useful for increasing the half life of any compound of Formula I when administered to a mammal, particularly a human. See, for example, Foster, "Deuterium Isotope Effects in Studies of Drug Metabolism", Trends Pharmacol. Sci. 5(12):524-527 (1984). Such compounds are synthesized by means well known in the art, for example by employing starting materials in which one or more hydrogens have been replaced by deuterium.

Deuterium labelled or substituted therapeutic compounds of the disclosure may have improved DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life, reduced dosage requirements and/or an improvement in therapeutic index. An $^{18}$F labeled compound may be useful for PET or SPECT studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. It is understood that deuterium in this context is regarded as a substituent in the compound of Formula I.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this disclosure any atom specifically designated as a deuterium (D) is meant to represent deuterium.

The term "treatment" or "treating" means any administration of a compound(s) of the disclosure to a mammal (e.g. a human) having a disease alleviable by Late $I_{Na}$ inhibition for the purpose of:
  (i) preventing the disease, that is, causing the clinical symptoms of the disease not to develop;
  (ii) inhibiting the disease, that is, arresting the development of clinical symptoms; and/or
  (iii) relieving the disease, that is, causing the regression of clinical symptoms.

In many cases, the compounds of this disclosure are capable of forming acid and/or base salts by virtue of the presence of amino and/or carboxyl groups or groups similar thereto.

The term "pharmaceutically acceptable salt" of a given compound refers to salts that retain the biological effectiveness and properties of the given compound, and which are not biologically or otherwise undesirable. Pharmaceutically acceptable base addition salts can be prepared from inorganic and organic bases. Salts derived from inorganic bases include, by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl)amines, tri(substituted alkyl)amines, alkenyl amines, dialkenyl amines, trialkenyl amines, substituted alkenyl amines, di(substituted alkenyl)amines, tri(substituted alkenyl)amines, mono, di or tri cycloalkyl amines, mono, di or tri arylamines or mixed amines, etc. Specific examples of suitable amines include, by way of example only, isopropylamine, trimethyl amine, diethyl amine, tri(iso-propyl)amine, tri(n-propyl)amine, ethanolamine, 2-dimethylaminoethanol, piperazine, piperidine, morpholine, N-ethylpiperidine, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

As used herein, "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

"Coronary diseases" or "cardiovascular diseases" refer to diseases of the cardiovasculature arising from any one or more than one of, for example, heart failure (including congestive heart failure, diastolic heart failure and systolic heart failure), acute heart failure, ischemia, recurrent ischemia, myocardial infarction, arrhythmias, angina (including exercise-induced angina, variant angina, stable angina, unstable angina), acute coronary syndrome, diabetes and intermittent claudication.

"Intermittent claudication" means the pain associated with peripheral artery disease. "Peripheral artery disease" or PAD is a type of occlusive peripheral vascular disease (PVD). PAD affects the arteries outside the heart and brain. The most common symptom of PAD is a painful cramping in the hips, thighs or calves when walking, climbing stairs or exercising. The pain is called intermittent claudication. When listing the symptom intermittent claudication, it is intended to include both PAD and PVD.

Arrhythmia refers to any abnormal heart rate. Bradycardia refers to abnormally slow heart rate whereas tachycardia refers to an abnormally rapid heart rate. As used herein, the treatment of arrhythmia is intended to include the treatment of supra ventricular tachycardias such as atrial fibrillation, atrial flutter, AV nodal reentrant tachycardia, atrial tachycardia and the ventricular tachycardias (VTs), including idiopathic ventricular tachycardia, ventricular fibrillation, pre-excitation syndrome and Torsade de Pointes (TdP).

"Long QT Syndrome" or "LQTS" is caused by dysfunction of protein structures in the heart cells called ion channels or protein structures modulating the activity of ion channels. These channels control the flow of ions like potassium, sodium and calcium molecules. The flow of these ions in and out of the cells produces the electrical activity of the heart. Abnormalities of these channels can be acquired or inherited. The acquired form is usually caused by prescription medications, however, the inherited form occurs when a mutation develops in one of several genes that produce or "encode" one of the ion channels that control electrical repolarization. The mutant gene produces abnormal channels to be formed, and as these abnormal channels are dysfunctional and the electrical repolarization of the heart takes longer. This is manifested on the electrocardiogram (ECG, EKG) by a prolonged QT interval.

"QT prolongation", or a prolonged QT interval, makes the heart vulnerable to polymorphic ventricular tachycardias, one kind of which is a fast, abnormal heart rhythm known as Torsade de Pointes. The corrected QT interval (or "QTc") represents the QT interval normalized for a heart rate of 60 beats/min. There are several methods for calculating the QTc, such as Bazett's formula ($QT_B=QT/\sqrt{RR}$), Fridericia's formula ($QT_B=QT/\sqrt[3]{RR}$), or a regression-based approach ($QT_{LC}=QT+0.154(1-RR)$, where RR is the interval from the onset of one QRS complex to the onset of the next QRS complex.

Congenital LQTS is caused by mutations in at least one of fifteen genes with mutations in three genes accounting for approximately 70% of genotype positive cases (LQT1-LQT3):

| Disease | Gene | Chromosome | Ion Channel or Protein |
|---------|------|------------|------------------------|
| LQT1 | KCNQ1 (KVLQT1) | 11p15.5 | $I_{Ks}$ subunit* |
| LQT2 | HERG | 7q35-46 | $I_{Kr}$ |
| LQT3 | SCN5A | 3q21-24 | $I_{Na}$ |
| LQT4 | ANKB | 4q25-27 | Ankyrin B |
| LQT5 | KCNE1 (MinK) | 21q22.1 | $I_{Ks}$ subunit |

*Homozygous carriers of novel mutations of KVLQT1 have Jervell, Lange-Nielsen syndrome. KVLQT1 and MinK coassemble to form the IKs channel.

The LQT diseases and ion channels listed in the table above are the same for acquired LQTS as they are for inherited LQTS. The inherited form of LQTS occurs when a mutation develops in one of several genes that produce or "encode" one of the ion channels or ion channel modulators that control electrical repolarization. There are at least fifteen different forms of inherited LQTS, characterized as LQT1-LQT15. They were originally characterized by the differing shape of the ECG trace, and have subsequently been associated with specific gene mutations. The LQT1 form is the most frequent, accounting for approximately 30-35% of the genotyped patients. LQT2 is next at about 25-30%, and LQT3, from SCN5A mutations accounts for about 5-10%. Patients with two mutations seem to account for less than 1% of all patients, but this may change as more patients are studied with the newer genetic techniques.

"Hypertrophic cardiomyopathy" is a disease in which the heart muscle (myocardium) becomes abnormally thick or hypertrophied. This thickened heart muscle can make it harder for the heart to pump blood. Hypertrophic cardiomyopathy may also affect the heart's electrical system. HCM is the most common genetic cardiac disease, affecting approximately 1 in 500 people. It is caused by autosomal-dominant mutations in genes encoding critical components of the cardiac sarcomere. HCM is recognized clinically as unexplained left ventricular (LV) hypertrophy (typically ≥15 mm thickness of the ventricular wall) in the absence of other cardiac or systemic conditions capable of producing the magnitude of hypertrophy observed. Typical symptoms include shortness of breath, angina, palpitations, fatigue and syncope. In a small percentage of patients, sudden cardiac death may be the first presentation. HCM is a leading cause of sudden cardiac death in young adults.

2. Nomenclature

Names of compounds of the present disclosure are provided using ACD/Name software for naming chemical compounds (Advanced Chemistry Development, Inc., Toronto, Canada). Other compounds or radicals may be named with common names or systematic or non-systematic names. The naming and numbering of the compounds of the disclosure is illustrated with a representative compound of Formula I:

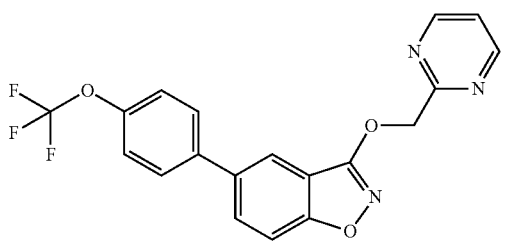 [SMILES: FC(F)(F)Oc1ccc(-c2ccc3onc(OCc4ncccn4)c3c2)cc1]

which is named 3-(pyrimidin-2-ylmethoxy)-5-(4-(trifluoromethoxy)phenyl)benzo[d]isoxazole.

3. Compounds

Accordingly, typical embodiments the present disclosure provide novel compounds that function as late sodium channel blockers. In one embodiment, the disclosure provides compounds of Formula I:

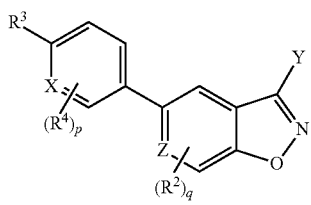

wherein

- Y is -L-$R^1$ or a heterocyclyl or heteroaryl ring bonded through a ring nitrogen atom, wherein each heterocyclyl or heteroaryl is optionally substituted with 1 to 3 groups independently selected from the group consisting of $C_1$-$C_6$ alkyl, $C_3$-$C_6$ cycloalkyl, halo, aryl, heterocyclyl, heteroaryl, oxo, $C_1$-$C_6$ alkoxy, —OH, —$NH_2$, —$COR^7$, —$CO_2R^7$, —$NHSO_2R^7$, —$NHCO_2R^7$, and —CN; and wherein each $C_1$-$C_6$ alkyl, $C_3$-$C_6$ cycloalkyl, aryl, heterocyclyl, heteroaryl, and $C_1$-$C_6$ alkoxy is optionally substituted with 1 to 3 $C_1$-$C_6$ alkoxy, halo, —$CF_3$, —CN, —OH, —$NH_2$ or —$OCF_3$;
- X is $CR^8$ or N;
- Z is $CR^9$ or N;
- L is —O—, —$NR^5$—, —$NR^5(CHR^6)_n$—, —$O(CHR^6)_n$, —$O(CHR^6)_nC(O)$—, —$O(CHR^6)_nC(O)O$—, —$O(CHR^6)_nNH$—, —$O(CHR^6)_nC(O)NH$—, —$O(CHR^6)_nNHC(O)O$— or —$O(CHR^6)_mNHS(O)_2$—;
- $R^1$ is hydrogen, $C_1$-$C_6$ alkyl, $C_3$-$C_8$ cycloalkyl, aryl, heterocyclyl or heteroaryl; wherein each cycloalkyl, aryl, heterocyclyl or heteroaryl is optionally substituted with 1 to 3 groups independently selected from the group consisting of $C_1$-$C_6$ alkyl, $C_3$-$C_6$ cycloalkyl, halo, aryl, heterocyclyl, heteroaryl, oxo, —OH, —$NH_2$, —$COR^7$, —$CO_2R^7$, —$NHSO_2R^7$, —$NHCO_2R^7$, and —CN; and wherein each $C_1$-$C_6$ alkyl, $C_3$-$C_6$ cycloalkyl, aryl, heterocyclyl, heteroaryl, and $C_1$-$C_6$ alkoxy is optionally substituted with 1 to 3 $C_1$-$C_6$ alkoxy, halo, —$CF_3$, —CN, —OH, —$NH_2$ or —$OCF_3$;
- each $R^2$ is independently halo, $C_1$-$C_6$ alkyl, $C_1$-$C_6$ alkoxy or —$OCF_3$;
- $R^3$ is hydrogen, halo, $C_1$-$C_3$ haloalkyl, $C_1$-$C_3$ haloalkoxy, $C_3$-$C_6$ cycloalkyl or phenyl, wherein the cycloalkyl or phenyl is optionally substituted with one or two halo atoms, provided that when $R^3$ is hydrogen, then p is 1 or 2;
- each $R^4$ is independently $C_1$-$C_6$ alkyl, halo, $C_1$-$C_6$ alkoxy or —$OCF_3$; or $R^3$ and $R^4$ taken together with the carbon atoms to which they are attached form a $C_4$-$C_8$ ring optionally containing from one to three double bonds and optionally containing from one to three heteroatoms independently selected from the group consisting of O, N, and S, which ring can be optionally substituted with one to three halo, $C_1$-$C_6$ alkyl, $C_1$-$C_3$ haloalkyl or $C_1$-$C_3$ haloalkoxy;
- $R^5$ is hydrogen, $C_1$-$C_6$ alkyl, $C_1$-$C_3$ haloalkyl or —$COCH_3$;
- each $R^6$ is independently hydrogen, $C_1$-$C_6$ alkyl, $C_1$-$C_3$ haloalkyl, —CN, —OH or —$NH_2$;
- $R^7$ is hydrogen, $C_1$-$C_6$ alkyl, aryl or aralkyl;
- $R^8$ is independently hydrogen, $C_1$-$C_6$ alkyl, halo, $C_1$-$C_6$ alkoxy or —$OCF_3$; or $R^3$ and $R^8$ taken together with the carbon atoms to which they are attached form a $C_4$-$C_8$ ring optionally containing from one to three double bonds and optionally containing from one to three heteroatoms independently selected from the group consisting of O, N, and S, which ring can be optionally substituted with one to three halo, $C_1$-$C_6$ alkyl, $C_1$-$C_3$ haloalkyl or $C_1$-$C_3$ haloalkoxy;
- $R^9$ is hydrogen, halo, $C_1$-$C_6$ alkyl, $C_1$-$C_6$ alkoxy or —$OCF_3$;
- each m is independently 2, 3, 4 or 5;
- each n is independently 1, 2, 3, 4 or 5; and
- p and q are each independently 0, 1 or 2;
- or a pharmaceutically acceptable salt, stereoisomer or mixture of stereoisomer thereof.

In another embodiment, the disclosure provides compounds of Formula IA:

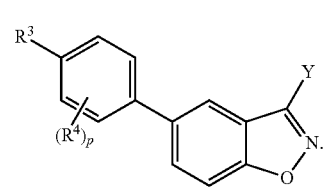

In yet another embodiment, the disclosure provides compounds of Formula IB:

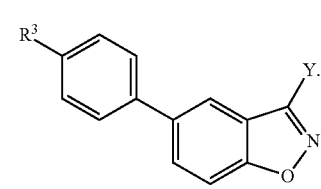

In still another embodiment, the disclosure provides compounds of Formula IC:

IC

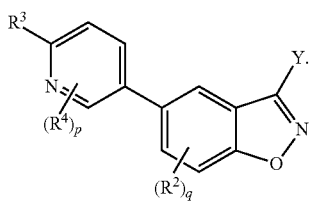

In still another embodiment, the disclosure provides compounds of Formula ID:

ID

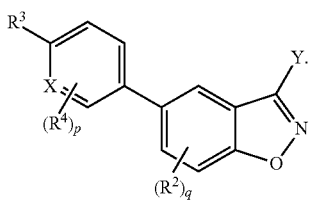

In some embodiments, Y is a heterocyclyl or heteroaryl ring bonded through a ring nitrogen atom, wherein each heterocyclyl or heteroaryl is optionally substituted with 1 to 3 groups independently selected from the group consisting of $C_1$-$C_6$ alkyl, $C_3$-$C_6$ cycloalkyl, halo, aryl, heterocyclyl, heteroaryl, oxo, $C_1$-$C_6$ alkoxy, —OH, —NH$_2$, —COR$^7$, —CO$_2$R$^7$, —NHSO$_2$R$^7$, —NHCO$_2$R$^7$, and —CN; and wherein each $C_1$-$C_6$ alkyl, $C_3$-$C_6$ cycloalkyl, aryl, heterocyclyl, heteroaryl, and $C_1$-$C_6$ alkoxy is optionally substituted with 1 to 3 $C_1$-$C_6$ alkoxy, halo, —CF$_3$, —CN, —OH, —NH$_2$ or —OCF$_3$.

In some embodiments, Y is a heterocyclyl or heteroaryl ring bonded through a ring nitrogen atom, wherein each heterocyclyl or heteroaryl is optionally substituted with 1 to 3 groups independently selected from the group consisting of $C_1$-$C_6$ alkyl, aryl, and oxo, wherein the $C_1$-$C_6$ alkyl is optionally substituted with 1 to 3 halo or —OH.

In some embodiments, Y is -L-R$^1$.
In some embodiments, L is —O(CHR$^6$)$_n$—.
In some embodiments, each R$^6$ is independently hydrogen or $C_1$-$C_6$ alkyl.
In some embodiments, R$^1$ is hydrogen.
In some embodiments, R$^1$ is $C_1$-$C_6$ alkyl.
In some embodiments, R$^1$ is $C_3$-$C_8$ cycloalkyl, aryl, heterocyclyl or heteroaryl; wherein each cycloalkyl, aryl, heterocyclyl or heteroaryl is optionally substituted with 1 to 3 groups independently selected from the group consisting of $C_1$-$C_6$ alkyl, $C_3$-$C_6$ cycloalkyl, halo, aryl, heterocyclyl, heteroaryl, oxo, —OH, —NH$_2$, —COR$^7$, —CO$_2$R$^7$, —NHSO$_2$R$^7$, —NHCO$_2$R$^7$, and —CN; and wherein each $C_1$-$C_6$ alkyl, $C_3$-$C_6$ cycloalkyl, aryl, heterocyclyl, heteroaryl, and $C_1$-$C_6$ alkoxy is optionally substituted with 1 to 3 $C_1$-$C_6$ alkoxy, halo, —CF$_3$, —CN, —OH, —NH$_2$ or —OCF$_3$.

In some embodiments, R$^1$ is

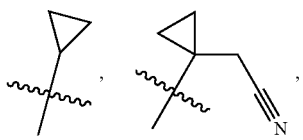

-continued

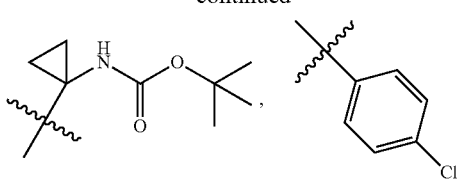

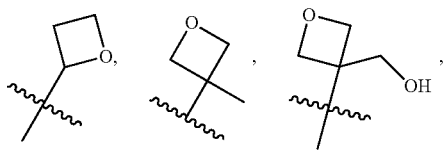

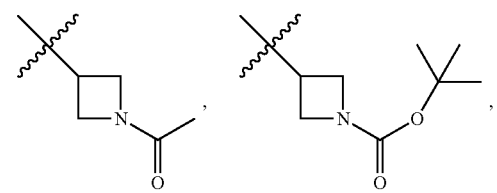

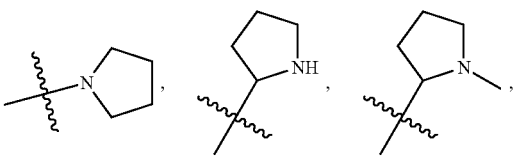

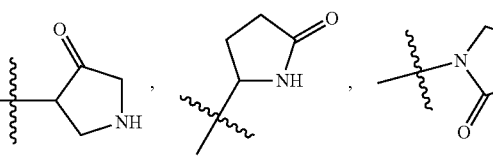

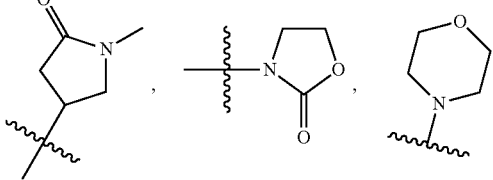

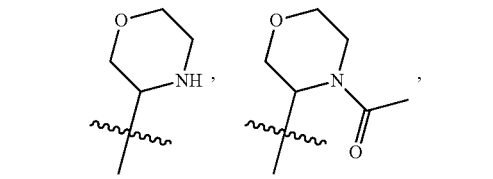

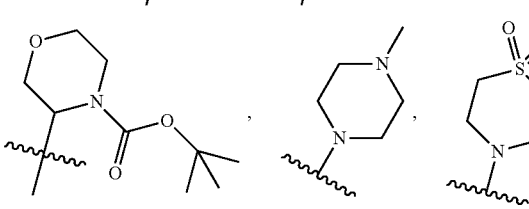

-continued
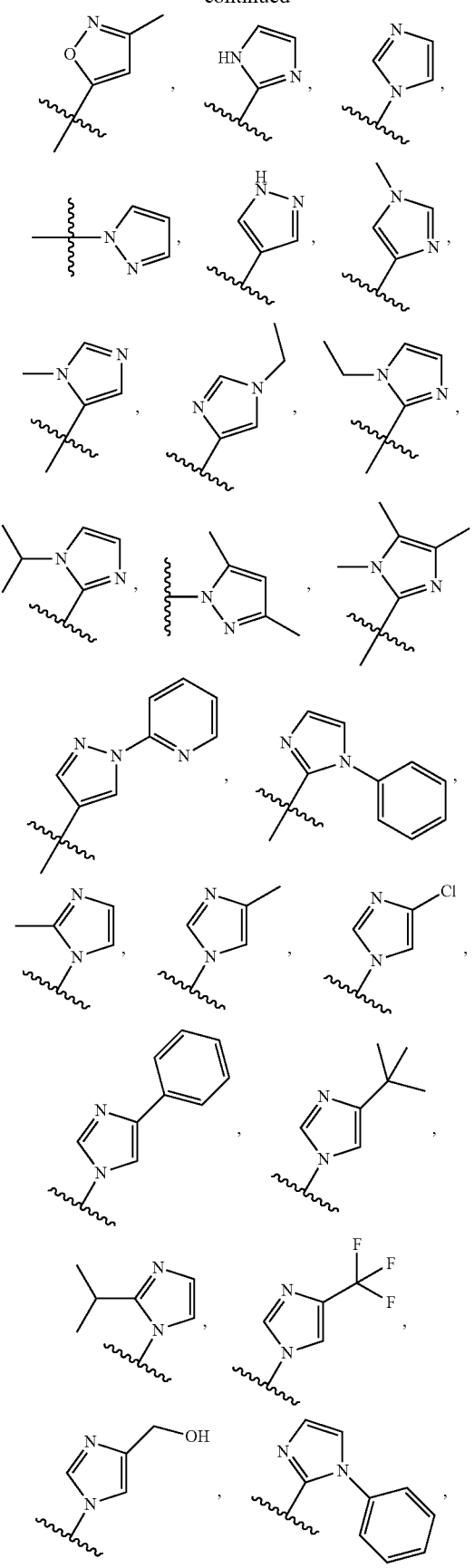
-continued
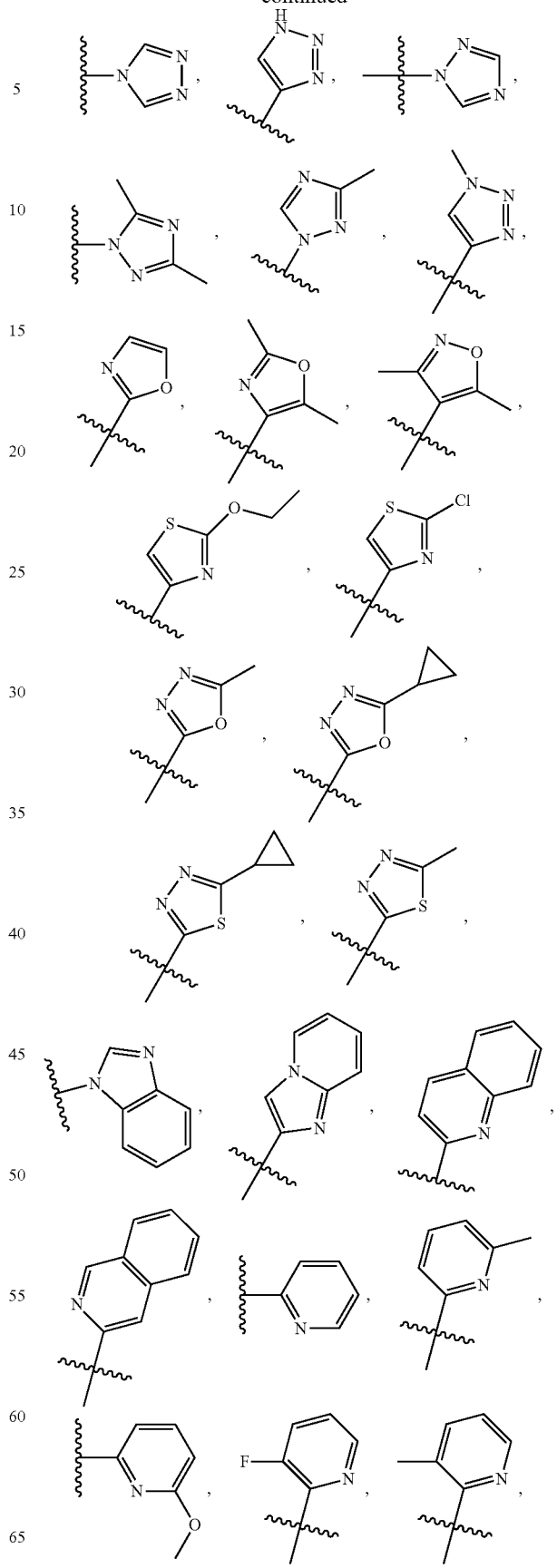

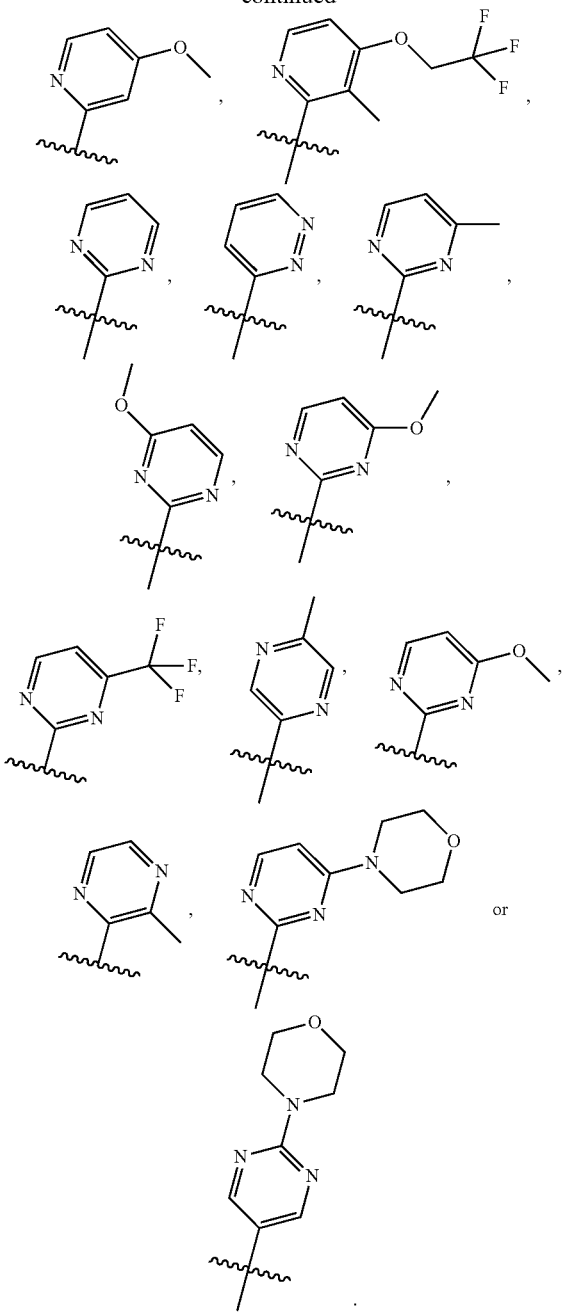

In some embodiments, $R^1$ is hydrogen or $C_1$-$C_6$ alkyl. In some embodiments, $R^1$ is $C_1$-$C_6$ alkyl. In certain embodiments, when $R^1$ is hydrogen or $C_1$-$C_6$ alkyl, then L is not —O— or —$NR^5$—.

In some embodiments, $R^2$ is fluoro, methyl or methoxy.

In some embodiments, $R^3$ is halogen, $C_1$-$C_3$ haloalkyl, $C_1$-$C_3$ haloalkoxy, $C_3$-$C_6$ cycloalkyl or phenyl, wherein the cycloalkyl or phenyl is optionally substituted with one or two halogen atoms.

In some embodiments, $R^3$ is hydrogen, fluoro, —$CF_3$, —$OCF_3$, —O—$CH_2$—$CF_3$ or cyclopropyl.

In some embodiments, $R^4$ is fluoro, chloro, methyl, methoxy or —$OCF_3$.

In some embodiments, X is N.

In some embodiments, X is $CR^8$.

In some embodiments, $R^8$ is hydrogen.

In some embodiments, Z is N.

In some embodiments, Z is $CR^9$.

In some embodiments, $R^9$ is hydrogen.

In some embodiments, q is 0 or 1. In some embodiments, q is 0. In some embodiments, q is 1.

In some embodiments, p is 0 or 1. In some embodiments, p is 0. In some embodiments, p is 1.

In some embodiments, the compound is selected from the group consisting of 3-(pyrimidin-2-ylmethoxy)-5-(4-(trifluoromethoxy)phenyl)benzo[d]isoxazole;

5-(2-fluoro-4-(trifluoromethoxy)phenyl)-3-(pyrimidin-2-ylmethoxy)benzo[d]isoxazole;

5-(2-methyl-4-(trifluoromethoxy)phenyl)-3-(pyrimidin-2-ylmethoxy)benzo[d]isoxazole;

5-(2-methoxy-4-(trifluoromethoxy)phenyl)-3-(pyrimidin-2-ylmethoxy)benzo[d]isoxazole;

3-((4-methylpyrimidin-2-yl)methoxy)-5-(4-(trifluoromethoxy)phenyl)benzo[d]isoxazole;

5-(2-fluoro-4-(trifluoromethyl)phenyl)-3-(pyrimidin-2-ylmethoxy)benzo[d]isoxazole;

5-(3-methyl-4-(trifluoromethoxy)phenyl)-3-(pyrimidin-2-ylmethoxy)benzo[d]isoxazole;

5-(4-chloro-3-fluorophenyl)-3-(pyrimidin-2-ylmethoxy)benzo[d]isoxazole;

3-(pyrimidin-2-ylmethoxy)-5-(4-(trifluoromethyl)phenyl)benzo[d]isoxazole;

3-(pyrimidin-2-ylmethoxy)-5-(3-(trifluoromethoxy)phenyl)benzo[d]isoxazole;

6-methoxy-3-(pyrimidin-2-ylmethoxy)-5-(4-(trifluoromethoxy)phenyl)benzo[d]isoxazole;

5-(2-fluoro-4-(trifluoromethyl)phenyl)-6-methoxy-3-(pyrimidin-2-ylmethoxy)benzo[d]isoxazole;

5-(4-chloro-3-fluorophenyl)-6-methoxy-3-(pyrimidin-2-ylmethoxy)benzo[d]isoxazole;

6-methoxy-5-(3-methyl-4-(trifluoromethoxy)phenyl)-3-(pyrimidin-2-ylmethoxy)benzo[d]isoxazole;

5-(3-chloro-4-fluorophenyl)-6-methoxy-3-(pyrimidin-2-ylmethoxy)benzo[d]isoxazole;

7-methyl-3-(pyrimidin-2-ylmethoxy)-5-(4-(trifluoromethoxy)phenyl)benzo[d]isoxazole;

7-fluoro-3-(pyrimidin-2-ylmethoxy)-5-(4-(trifluoromethoxy)phenyl)benzo[d]isoxazole;

7-methyl-5-(3-methyl-4-(trifluoromethoxy)phenyl)-3-(pyrimidin-2-ylmethoxy)benzo[d]isoxazole;

7-methyl-3-(pyrimidin-2-ylmethoxy)-5-(3-(trifluoromethoxy)phenyl)benzo[d]isoxazole;

5-(6-cyclopropylpyridin-3-yl)-3-(pyrimidin-2-ylmethoxy)benzo[d]isoxazole;

3-(pyrimidin-2-ylmethoxy)-5-(6-(2,2,2-trifluoroethoxy)pyridin-3-yl)benzo[d]isoxazole;

7-methoxy-3-(pyrimidin-2-ylmethoxy)-5-(4-(trifluoromethoxy)phenyl)benzo[d]isoxazole;

7-methoxy-5-(3-methyl-4-(trifluoromethoxy)phenyl)-3-(pyrimidin-2-ylmethoxy)benzo[d]isoxazole;

5-(2-fluoro-4-(trifluoromethyl)phenyl)-7-methoxy-3-(pyrimidin-2-ylmethoxy)benzo[d]isoxazole;

7-methoxy-5-(2-methyl-4-(trifluoromethoxy)phenyl)-3-(pyrimidin-2-ylmethoxy)benzo[d]isoxazole;

6-ethyl-3-(pyrimidin-2-ylmethoxy)-5-(4-(trifluoromethoxy)phenyl)benzo[d]isoxazole;

6-methyl-5-(3-methyl-4-(trifluoromethoxy)phenyl)-3-(pyrimidin-2-ylmethoxy)benzo[d]isoxazole;

5-(2-fluoro-4-(trifluoromethyl)phenyl)-6-methyl-3-(pyrimidin-2-ylmethoxy)benzo[d]isoxazole;

6-methyl-5-(2-methyl-4-(trifluoromethoxy)phenyl)-3-(pyrimidin-2-ylmethoxy)benzo[d]isoxazole;
5-(2,2-difluorobenzo[d][1,3]dioxol-5-yl)-3-(pyrimidin-2-ylmethoxy)benzo[d]isoxazole;
6-fluoro-3-(pyrimidin-2-ylmethoxy)-5-(4-(trifluoromethoxy)phenyl)benzo[d]isoxazole;
6-fluoro-5-(3-methyl-4-(trifluoromethoxy)phenyl)-3-(pyrimidin-2-ylmethoxy)benzo[d]isoxazole;
6-fluoro-5-(2-fluoro-4-(trifluoromethyl)phenyl)-3-(pyrimidin-2-ylmethoxy)benzo[d]isoxazole;
6-fluoro-5-(2-methyl-4-(trifluoromethoxy)phenyl)-3-(pyrimidin-2-ylmethoxy)benzo[d]isoxazole;
5-(2,2-difluorobenzo[d][1,3]dioxol-5-yl)-6-fluoro-3-(pyrimidin-2-ylmethoxy)benzo[d]isoxazole;
3-((5-cyclopropyl-1,3,4-oxadiazol-2-yl)methoxy)-5-(2-methyl-4-(trifluoromethoxy)phenyl)benzo[d]isoxazole;
3-((5-cyclopropyl-1,3,4-oxadiazol-2-yl)methoxy)-5-(4-(trifluoromethyl)phenyl)benzo[d]isoxazole;
3-((5-cyclopropyl-1,3,4-oxadiazol-2-yl)methoxy)-5-(2-fluoro-4-(trifluoromethyl)phenyl)benzo[d]isoxazole;
3-((5-cyclopropyl-1,3,4-oxadiazol-2-yl)methoxy)-5-(2-methoxy-4-(trifluoromethoxy)phenyl)benzo[d]isoxazole;
3-((5-cyclopropyl-1,3,4-oxadiazol-2-yl)methoxy)-5-(3-methyl-4-(trifluoromethoxy)phenyl)benzo[d]isoxazole;
3-((5-cyclopropyl-1,3,4-oxadiazol-2-yl)methoxy)-5-(2-fluoro-4-(trifluoromethoxy)phenyl)benzo[d]isoxazole;
3-(oxetan-2-ylmethoxy)-5-(4-(trifluoromethoxy)phenyl)benzo[d]isoxazole;
3-((1-methyl-1H-imidazol-4-yl)methoxy)-5-(4-(trifluoromethoxy)phenyl)benzo[d]isoxazole;
3-((1-methyl-1H-imidazol-4-yl)methoxy)-5-(4-(trifluoromethoxy)phenyl)benzo[d]isoxazole;
3-((1H-pyrazol-4-yl)methoxy)-5-(4-(trifluoromethoxy)phenyl)benzo[d]isoxazole;
4-(((5-(4-(trifluoromethoxy)phenyl)benzo[d]isoxazol-3-yl)oxy)methyl)pyrrolidin-2-one;
3-((1-ethyl-1H-imidazol-2-yl)methoxy)-5-(4-(trifluoromethoxy)phenyl)benzo[d]isoxazole;
3-((1-isopropyl-1H-imidazol-2-yl)methoxy)-5-(4-(trifluoromethoxy)phenyl)benzo[d]isoxazole;
3-((1-ethyl-1H-imidazol-5-yl)methoxy)-5-(4-(trifluoromethoxy)phenyl)benzo[d]isoxazole;
3-((1-methyl-1H-imidazol-5-yl)methoxy)-5-(4-(trifluoromethoxy)phenyl)benzo[d]isoxazole;
3-(imidazo[1,2-a]pyridin-2-ylmethoxy)-5-(4-(trifluoromethoxy)phenyl)benzo[d]isoxazole;
3-((2,5-dimethyloxazol-4-yl)methoxy)-5-(4-(trifluoromethoxy)phenyl)benzo[d]isoxazole;
3-(oxazol-2-ylmethoxy)-5-(4-(trifluoromethoxy)phenyl)benzo[d]isoxazole;
2-(1-(((5-(4-(trifluoromethoxy)phenyl)benzo[d]isoxazol-3-yl)oxy)methyl)cyclopropyl)acetonitrile;
3-(2-(1H-imidazol-1-yl)ethoxy)-5-(4-(trifluoromethoxy)phenyl)benzo[d]isoxazole;
1-methyl-4-(((5-(4-(trifluoromethoxy)phenyl)benzo[d]isoxazol-3-yl)oxy)methyl)pyrrolidin-2-one;
3-(2-(2-methyl-1H-imidazol-1-yl)ethoxy)-5-(4-(trifluoromethoxy)phenyl)benzo[d]isoxazole;
3-(2-(1H-1,2,4-triazol-1-yl)ethoxy)-5-(4-(trifluoromethoxy)phenyl)benzo[d]isoxazole;
1-(2-((5-(4-(trifluoromethoxy)phenyl)benzo[d]isoxazol-3-yl)oxy)ethyl)pyrrolidin-2-one;
3-(2-methoxyethoxy)-5-(4-(trifluoromethoxy)phenyl)benzo[d]isoxazole;
(R)-5-(((5-(4-(trifluoromethoxy)phenyl)benzo[d]isoxazol-3-yl)oxy)methyl)pyrrolidin-2-one;
(S)-5-(((5-(4-(trifluoromethoxy)phenyl)benzo[d]isoxazol-3-yl)oxy)methyl)pyrrolidin-2-one;
3-(2-(4H-1,2,4-triazol-4-yl)ethoxy)-5-(4-(trifluoromethoxy)phenyl)benzo[d]isoxazole;
3-((1-phenyl-1H-imidazol-2-yl)methoxy)-5-(4-(trifluoromethoxy)phenyl)benzo[d]isoxazole;
3-((1-(pyridin-2-yl)-1H-pyrazol-4-yl)methoxy)-5-(4-(trifluoromethoxy)phenyl)benzo[d]isoxazole;
3-(2-(1H-imidazol-2-yl)ethoxy)-5-(4-(trifluoromethoxy)phenyl)benzo[d]isoxazole;
3-((4-methoxypyrimidin-2-yl)methoxy)-5-(4-(trifluoromethoxy)phenyl)benzo[d]isoxazole;
3-(2-(1H-pyrazol-1-yl)propoxy)-5-(4-(trifluoromethoxy)phenyl)benzo[d]isoxazole;
3-(2-(3,5-dimethyl-1H-pyrazol-1-yl)ethoxy)-5-(4-(trifluoromethoxy)phenyl)benzo[d]isoxazole;
3-(4-morpholinopyrimidin-2-yl)methoxy)-5-(4-(trifluoromethoxy)phenyl)benzo[d]isoxazole;
(S)-3-((1-methylpyrrolidin-2-yl)methoxy)-5-(4-(trifluoromethoxy)phenyl)benzo[d]isoxazole;
(R)-3-((5-(4-(trifluoromethoxy)phenyl)benzo[d]isoxazol-3-yl)oxy)pyrrolidin-2-one;
3-((5-methylpyrazin-2-yl)methoxy)-5-(4-(trifluoromethoxy)phenyl)benzo[d]isoxazole;
3-(pyridazin-3-ylmethoxy)-5-(4-(trifluoromethoxy)phenyl)benzo[d]isoxazole;
3-(2-(5-(4-(trifluoromethoxy)phenyl)benzo[d]isoxazol-3-yl)oxy)ethyl)oxazolidin-2-one;
3-(2-(3,5-dimethyl-1H-1,2,4-triazol-1-yl)ethoxy)-5-(4-(trifluoromethoxy)phenyl)benzo[d]isoxazole;
3-(2-(1H-1,2,4-triazol-1-yl)propoxy)-5-(4-(trifluoromethoxy)phenyl)benzo[d]isoxazole;
3-(2-morpholinoethoxy)-5-(4-(trifluoromethoxy)phenyl)benzo[d]isoxazole;
3-(2-(3,5-dimethyl-1H-1,2,4-triazol-1-yl)propoxy)-5-(4-(trifluoromethoxy)phenyl)benzo[d]isoxazole;
1-(2-((7-fluoro-5-(4-(trifluoromethoxy)phenyl)benzo[d]isoxazol-3-yl)oxy)ethyl)pyrrolidin-2-one;
3-((4-methoxypyridin-2-yl)methoxy)-5-(4-(trifluoromethoxy)phenyl)benzo[d]isoxazole;
3-isoquinolin-3-ylmethoxy)-5-(4-(trifluoromethoxy)phenyl)benzo[d]isoxazole;
3-((1H-1,2,3-triazol-4-yl)methoxy)-5-(4-(trifluoromethoxy)phenyl)benzo[d]isoxazole;
3-(2-(1H-1,2,4-triazol-1-yl)ethoxy)-7-fluoro-5-(4-(trifluoromethoxy)phenyl)benzo[d]isoxazole;
4-(2-((5-(4-(trifluoromethoxy)phenyl)benzo[d]isoxazol-3-yl)oxy)ethyl)thiomorpholine 1,1-dioxide;
5-(4-(trifluoromethoxy)phenyl)-3-((4-(trifluoromethyl)pyrimidin-2-yl)methoxy)benzo[d]isoxazole;
7-methyl-3-((1-methyl-1H-1,2,3-triazol-4-yl)methoxy)-5-(4-(trifluoromethoxy)phenyl)benzo[d]isoxazole;
1-(2-((7-methyl-5-(4-(trifluoromethoxy)phenyl)benzo[d]isoxazol-3-yl)oxy)ethyl)pyrrolidin-2-one;
3-(2-(1H-1,2,4-triazol-1-yl)ethoxy)-7-methyl-5-(4-(trifluoromethoxy)phenyl)benzo[d]isoxazole;
3-((4-methoxypyrimidin-2-yl)methoxy)-7-methyl-5-(4-(trifluoromethoxy)phenyl)benzo[d]isoxazole;
7-methyl-3-(oxazol-2-ylmethoxy)-5-(4-(trifluoromethoxy)phenyl)benzo[d]isoxazole;
3-((3-methyloxetan-3-yl)methoxy)-5-(4-(trifluoromethoxy)phenyl)benzo[d]isoxazole;
3-((3-methylpyridin-2-yl)methoxy)-5-(4-(trifluoromethoxy)phenyl)benzo[d]isoxazole;
3-((3-fluoropyridin-2-yl)methoxy)-5-(4-(trifluoromethoxy)phenyl)benzo[d]isoxazole;

3-((6-methylpyridin-2-yl)methoxy)-5-(4-(trifluoromethoxy) phenyl)benzo[d]isoxazole;
3-((5-cyclopropyl-1,3,4-oxadiazol-2-yl)methoxy)-5-(4-(trifluoromethoxy)phenyl)benzo[d]isoxazole;
(3-(((5-(4-(trifluoromethoxy)phenyl)benzo[d]isoxazol-3-yl) oxy)methyl)oxetan-3-yl)methanol;
3-(1-(pyridin-2-yl)ethoxy)-5-(4-(trifluoromethoxy)phenyl) benzo[d]isoxazole;
3-((5-methyl-1,3,4-oxadiazol-2-yl)methoxy)-5-(4-(trifluoromethoxy)phenyl)benzo[d]isoxazole;
3-((5-isopropyl-1,3,4-oxadiazol-2-yl)methoxy)-5-(4-(trifluoromethoxy)phenyl)benzo[d]isoxazole;
3-((5-methyl-1,3,4-thiadiazol-2-yl)methoxy)-5-(4-(trifluoromethoxy)phenyl)benzo[d]isoxazole;
3-(3-methylisoxazol-5-yl)methoxy)-5-(4-(trifluoromethoxy)phenyl)benzo[d]isoxazole;
2-(5-(4-(trifluoromethoxy)phenyl)benzo[d]isoxazol-3-yl) oxy)acetonitrile;
3-((5-cyclopropyl-1,3,4-oxadiazol-2-yl)methoxy)-7-fluoro-5-(4-(trifluoromethoxy)phenyl)benzo[d]isoxazole;
3-((5-cyclopropyl-1,3,4-oxadiazol-2-yl)methoxy)-7-methyl-5-(4-(trifluoromethoxy)phenyl)benzo[d]isoxazole;
7-methyl-3-((6-methylpyridin-2-yl)methoxy)-5-(4-(trifluoromethoxy)phenyl)benzo[d]isoxazole;
tert-butyl(S)-2-(((5-(4-(trifluoromethoxy)phenyl)benzo[d] isoxazol-3-yl)oxy)methyl)pyrrolidine-1-carboxylate;
(S)-3-(pyrrolidin-2-ylmethoxy)-5-(4-(trifluoromethoxy) phenyl)benzo[d]isoxazole;
(S)-1-(2-(((5-(4-(trifluoromethoxy)phenyl)benzo[d]isoxazol-3-yl)oxy)methyl)pyrrolidin-1-yl)ethan-1-one;
1-(3-((5-(4-(trifluoromethoxy)phenyl)benzo[d]isoxazol-3-yl)oxy)methyl)azetidin-1-yl)ethan-1-one;
tert-butyl(S)-3-(((5-(4-(trifluoromethoxy)phenyl)benzo[d] isoxazol-3-yl)oxy)methyl)morpholine-4-carboxylate;
tert-butyl(R)-3-(((5-(4-(trifluoromethoxy)phenyl)benzo[d] isoxazol-3-yl)oxy)methyl)morpholine-4-carboxylate;
(S)-3-(morpholin-3-ylmethoxy)-5-(4-(trifluoromethoxy) phenyl)benzo[d]isoxazole;
(R)-3-(morpholin-3-ylmethoxy)-5-(4-(trifluoromethoxy) phenyl)benzo[d]isoxazole;
(S)-1-(3-(((5-(4-(trifluoromethoxy)phenyl)benzo[d]isoxazol-3-yl)oxy)methyl)morpholino)ethan-1-one;
(R)-1-(3-(((5-(4-(trifluoromethoxy)phenyl)benzo[d]isoxazol-3-yl)oxy)methyl)morpholino)ethan-1-one;
(R)-1-((5-(4-(trifluoromethoxy)phenyl)benzo[d]isoxazol-3-yl)oxy)propan-2-amine;
(S)-3-methyl-1-((5-(4-(trifluoromethoxy)phenyl)benzo[d] isoxazol-3-yl)oxy)butan-2-amine;
(R)-1-(1-((5-(4-(trifluoromethoxy)phenyl)benzo[d]isoxazol-3-yl)oxy)propan-2-yl)pyrrolidin-2-one;
(S)-1-(3-methyl-1-((5-(4-(trifluoromethoxy)phenyl)benzo [d]isoxazol-3-yl)oxy)butan-2-yl)pyrrolidin-2-one;
1-(pyrrolidin-1-yl)-2-((5-(4-(trifluoromethoxy)phenyl) benzo[d]isoxazol-3-yl)oxy)ethan-1-one;
N-isopropyl-2-((5-(4-(trifluoromethoxy)phenyl)benzo[d] isoxazol-3-yl)oxy)acetamide;
N-(2-((5-(4-(trifluoromethoxy)phenyl)benzo[d]isoxazol-3-yl)oxy)ethyl)pyrimidin-2-amine;
3-(pyrimidin-2-yloxy)-5-(4-(trifluoromethoxy)phenyl) benzo[d]isoxazole;
3-(pyridin-2-yloxy)-5-(4-(trifluoromethoxy)phenyl)benzo [d]isoxazole;
N-(pyrimidin-2-ylmethyl)-5-(4-(trifluoromethoxy)phenyl) benzo[d]isoxazol-3-amine;
3-(4-methylpiperazin-1-yl)-5-(4-(trifluoromethoxy)phenyl) benzo[d]isoxazole;
N-(cyclopropylmethyl)-5-(4-(trifluoromethoxy)phenyl) benzo[d]isoxazol-3-amine;
N-((6-methylpyridin-2-yl)methyl)-5-(4-(trifluoromethoxy) phenyl)benzo[d]isoxazol-3-amine;
3-morpholino-5-(4-(trifluoromethoxy)phenyl)benzo[d]isoxazole;
N-isopropyl-5-(4-(trifluoromethoxy)phenyl)benzo[d]isoxazol-3-amine;
3-(1H-imidazol-1-yl)-5-(4-(trifluoromethoxy)phenyl)benzo [d]isoxazole;
N,N-dimethyl-5-(4-(trifluoromethoxy)phenyl)benzo[d]isoxazol-3-amine;
(R)-5-(((5-(4-(trifluoromethoxy)phenyl)benzo[d]isoxazol-3-yl)amino)methyl)pyrrolidin-2-one;
1-(2-((5-(4-(trifluoromethoxy)phenyl)benzo[d]isoxazol-3-yl)amino)ethyl)pyrrolidin-2-one;
3-(1H-1,2,4-triazol-1-yl)-5-(4-(trifluoromethoxy)phenyl) benzo[d]isoxazole;
N-(2-(1H-1,2,4-triazol-1-yl)ethyl)-5-(4-(trifluoromethoxy) phenyl)benzo[d]isoxazol-3-amine;
3-(2-methyl-1H-imidazol-1-yl)-5-(4-(trifluoromethoxy) phenyl)benzo[d]isoxazole;
3-(4-methyl-1H-imidazol-1-yl)-5-(4-(trifluoromethoxy) phenyl)benzo[d]isoxazole;
3-(4-chloro-1H-imidazol-1-yl)-5-(4-(trifluoromethoxy)phenyl)benzo[d]isoxazole;
3-(3-methyl-1H-1,2,4-triazol-1-yl)-5-(4-(trifluoromethoxy) phenyl)benzo[d]isoxazole;
3-(4-phenyl-1H-imidazol-1-yl)-5-(4-(trifluoromethoxy)phenyl)benzo[d]isoxazole;
3-(4-(tert-butyl)-1H-imidazol-1-yl)-5-(4-(trifluoromethoxy) phenyl)benzo[d]isoxazole;
3-(2-isopropyl-1H-imidazol-1-yl)-5-(4-(trifluoromethoxy) phenyl)benzo[d]isoxazole;
5-(4-(trifluoromethoxy)phenyl)-3-(4-(trifluoromethyl)-1H-imidazol-1-yl)benzo[d]isoxazole;
(1-(5-(4-(trifluoromethoxy)phenyl)benzo[d]isoxazol-3-yl)-1H-imidazol-4-yl)methanol;
5-(4-(trifluoromethoxy)phenyl)benzo[d]isoxazol-3-amine;
3-(pyrimidin-2-ylmethoxy)-5-(4-(trifluoromethoxy)phenyl) isoxazolo[5,4-c]pyridine;
N-((4-methoxypyrimidin-2-yl)methyl)-5-(4-(trifluoromethoxy)phenyl)benzo[d]isoxazol-3-amine;
N,N-diethyl-2-((5-(4-(trifluoromethoxy)phenyl)benzo[d] isoxazol-3-yl)oxy)acetamide;
3-(pyrazin-2-ylmethoxy)-5-(4-(trifluoromethoxy)phenyl) benzo[d]isoxazole;
3-((3-methylpyrazin-2-yl)methoxy)-5-(4-(trifluoromethoxy)phenyl)benzo[d]isoxazole;
3-(1-(5-methyl-1,3,4-oxadiazol-2-yl)ethoxy)-5-(4-(trifluoromethoxy)phenyl)benzo[d]isoxazole;
3-((5-cyclopropyl-1,3,4-thiadiazol-2-yl)methoxy)-5-(4-(trifluoromethoxy)phenyl)benzo[d]isoxazole;
7-fluoro-3-((5-methyl-1,3,4-oxadiazol-2-yl)methoxy)-5-(4-(trifluoromethoxy)phenyl)benzo[d]isoxazole;
N-(oxazol-2-ylmethyl)-5-(4-(trifluoromethoxy)phenyl) benzo[d]isoxazol-3-amine; and
tert-butyl 2-((5-(4-(trifluoromethoxy)phenyl)benzo[d]isoxazol-3-yl)oxy)acetate;
or a pharmaceutically acceptable salt, stereoisomer or mixture of stereoisomer thereof.

4. Further Embodiments

In some embodiments, the compounds provided by the present disclosure are effective in the treatment of conditions or diseases known to respond to administration of late sodium channel blockers, including but not limited to cardiovascular diseases such as atrial and ventricular arrhythmias, including atrial fibrillation, Prinzmetal's (variant) angina, stable angina, unstable angina, ischemia and reperfusion injury in cardiac, kidney, liver and the brain, exercise induced angina, pulmonary hypertension, congestive heart disease including diastolic and systolic heart failure, and myocardial infarction. In some embodiments, compounds provided by the present disclosure which function as late sodium channel blockers may be used in the treatment of diseases affecting the neuromuscular system resulting in pain, itching, seizures, or paralysis, or in the treatment of diabetes or reduced insulin sensitivity, and disease states related to diabetes, such as diabetic peripheral neuropathy.

Certain compounds of the disclosure may also possess a sufficient activity in modulating neuronal sodium channels, i.e., $Na_v$ 1.1., 1.2, 1.3, 1.7, and/or 1.8, and may have appropriate pharmacokinetic properties such that they may be active with regard to the central and/or peripheral nervous system. Consequently, some compounds of the disclosure may also be of use in the treatment of epilepsy or pain or itching or headache of a neuropathic origin.

In one embodiment, this disclosure provides a method of treating a disease state in a mammal, particularly a human, that is alleviable by treatment with an agent capable of reducing late sodium current, comprising administering to a mammal, particularly a human, in need thereof a therapeutically effective dose of a compound of Formula I, IA, IB, IC or ID or other formulas or compounds disclosed herein. In another embodiment, the disease state is a cardiovascular disease selected from one or more of atrial and ventricular arrhythmias, heart failure (including congestive heart failure, diastolic heart failure, systolic heart failure, acute heart failure), Prinzmetal's (variant) angina, stable and unstable angina, exercise induced angina, congestive heart disease, ischemia, recurrent ischemia, reperfusion injury, myocardial infarction, acute coronary syndrome, peripheral arterial disease, pulmonary hypertension, and intermittent claudication.

In another embodiment, the disease state is diabetes or diabetic peripheral neuropathy. In a further embodiment, the disease state results in one or more of neuropathic pain, epilepsy, headache, seizures, or paralysis.

In one embodiment, this disclosure provides a method of treating diabetes in a mammal, particularly a human, comprising administering to a mammal in need thereof a therapeutically effective dose of a compound of Formula I, IA, IB, IC or ID or other formulas or compounds disclosed herein. Diabetes mellitus is a disease characterized by hyperglycemia; altered metabolism of lipids, carbohydrates and proteins; and an increased risk of complications from vascular disease. Diabetes is an increasing public health problem, as it is associated with both increasing age and obesity.

There are two major types of diabetes mellitus: 1) Type I, also known as insulin dependent diabetes (IDDM) and 2) Type II, also known as insulin independent or non-insulin dependent diabetes (NIDDM). Both types of diabetes mellitus are due to insufficient amounts of circulating insulin and/or a decrease in the response of peripheral tissue to insulin.

Type I diabetes results from the body's failure to produce insulin, the hormone that "unlocks" the cells of the body, allowing glucose to enter and fuel them. The complications of Type I diabetes include heart disease and stroke; retinopathy (eye disease); kidney disease (nephropathy); neuropathy (nerve damage); as well as maintenance of good skin, foot and oral health.

Type II diabetes results from the body's inability to either produce enough insulin or the cells inability to use the insulin that is naturally produced by the body. The condition where the body is not able to optimally use insulin is called insulin resistance. Type II diabetes is often accompanied by high blood pressure and this may contribute to heart disease. In patients with type II diabetes mellitus, stress, infection, and medications (such as corticosteroids) can also lead to severely elevated blood sugar levels. Accompanied by dehydration, severe blood sugar elevation in patients with type II diabetes can lead to an increase in blood osmolality (hyperosmolar state). This condition can lead to coma.

It has been suggested that ranolazine (RANEXA®, a selective inhibitor of INaL) may be an antidiabetic agent that causes β-cell preservation and enhances insulin secretion in a glucose-dependent manner in diabetic mice (see, Y. Ning et al. J Pharmacol Exp Ther. 2011, 337(1), 50-8). Therefore it is contemplated that the compounds of Formula I, IA, IB, IC or ID or other formulas or compounds disclosed herein can be used as antidiabetic agents for the treatment of diabetes.

5. Pharmaceutical Compositions and Administration

Compounds provided in accordance with the present disclosure are usually administered in the form of pharmaceutical compositions. This disclosure therefore provides pharmaceutical compositions that contain, as the active ingredient, one or more of the compounds described, or a pharmaceutically acceptable salt or ester thereof, and one or more pharmaceutically acceptable excipients, carriers, including inert solid diluents and fillers, diluents, including sterile aqueous solution and various organic solvents, permeation enhancers, solubilizers and adjuvants. The pharmaceutical compositions may be administered alone or in combination with other therapeutic agents. Such compositions are prepared in a manner well known in the pharmaceutical art (see, e.g., Remington's Pharmaceutical Sciences, Mace Publishing Co., Philadelphia, Pa. 17th Ed. (1985); and Modern Pharmaceutics, Marcel Dekker, Inc. 3rd Ed. (G. S. Banker & C. T. Rhodes, Eds.)

The pharmaceutical compositions may be administered in either single or multiple doses by any of the accepted modes of administration of agents having similar utilities, for example as described in those patents and patent applications incorporated by reference, including rectal, buccal, intranasal and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer.

One mode for administration is parenteral, particularly by injection. The forms in which the novel compositions of the present disclosure may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles. Aqueous solutions in saline are also conventionally used for injection, but less preferred in the context of the present disclosure. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating a compound according to the present disclosure in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. Preferably, for parenteral administration, sterile injectable solutions are prepared containing a therapeutically effective amount, e.g., 0.1 to 700 mg, of a compound described herein. It will be understood, however, that the amount of the compound actually administered usually will be determined by a physician, in the light of the relevant circumstances, including the condition to be treated, the chosen route of administration, the actual compound administered and its relative activity, the age, weight, and response of the individual patient, the severity of the patient's symptoms, and the like.

Oral administration is another route for administration of compounds in accordance with the disclosure. Administration may be via capsule or enteric coated tablets, or the like. In making the pharmaceutical compositions that include at least one compound described herein, the active ingredient is usually diluted by an excipient and/or enclosed within such a carrier that can be in the form of a capsule, sachet, paper or other container. When the excipient serves as a diluent, it can be in the form of a solid, semi-solid, or liquid material (as above), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl and propylhydroxy-benzoates; sweetening agents; and flavoring agents.

The compositions of the disclosure can be formulated so as to provide quick, sustained or delayed release of the active ingredient after administration to the patient by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345. Another formulation for use in the methods of the present disclosure employs transdermal delivery devices ("patches"). Such transdermal patches may be used to provide continuous or discontinuous infusion of the compounds of the present disclosure in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

The compositions are preferably formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient (e.g., a tablet, capsule, ampoule). The compounds are generally administered in a pharmaceutically effective amount. Preferably, for oral administration, each dosage unit contains from 1 mg to 2 g, or alternatively, or 100 mg to 500 mg, of a compound described herein, and for parenteral administration, preferably from 0.1 mg to 700 mg, or alternatively, 0.1 mg to 100 mg, of a compound a compound described herein. It will be understood, however, that the amount of the compound actually administered usually will be determined by a physician, in the light of the relevant circumstances, including the condition to be treated, the chosen route of administration, the actual compound administered and its relative activity, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present disclosure. When referring to these preformulation compositions as homogeneous, it is meant that the active ingredient is dispersed evenly throughout the composition so that the composition may be readily subdivided into equally effective unit dosage forms such as tablets, pills and capsules.

The tablets or pills of the present disclosure may be coated or otherwise compounded to provide a dosage form affording the advantage of prolonged action, or to protect from the acid conditions of the stomach. For example, the tablet or pill can comprise an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably, the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a facemask tent, or intermittent positive pressure breathing machine. Solution, suspension, or powder compositions may be administered, preferably orally or nasally, from devices that deliver the formulation in an appropriate manner.

Combination Therapy

Patients being treated by administration of the late sodium channel blockers of the disclosure often exhibit diseases or conditions that benefit from treatment with other therapeutic agents. These diseases or conditions can be of cardiovascular nature or can be related to pulmonary disorders, metabolic disorders, gastrointestinal disorders and the like. Additionally, some coronary patients being treated by administration of the late sodium channel blockers of the disclosure exhibit conditions that can benefit from treatment with therapeutic agents that are antibiotics, analgesics, and/or antidepressants and anti-anxiety agents.

Cardiovascular Agent Combination Therapy

Cardiovascular related diseases or conditions that can benefit from a combination treatment of the late sodium channel blockers of the disclosure with other therapeutic agents include, without limitation, angina including stable angina, unstable angina (UA), exercised-induced angina, variant angina, arrhythmias, intermittent claudication, myocardial infarction including non-STE myocardial infarction (NSTEMI), pulmonary hypertension including pulmonary arterial hypertension, heart failure including congestive (or chronic) heart failure and diastolic heart failure and heart failure with preserved ejection fraction (diastolic dysfunction), acute heart failure, or recurrent ischemia.

Therapeutic agents suitable for treating cardiovascular related diseases or conditions include anti-anginals, heart failure agents, antithrombotic agents, antiarrhythmic agents, antihypertensive agents, and lipid lowering agents.

The co-administration of the late sodium channel blockers of the disclosure with therapeutic agents suitable for treating cardiovascular related conditions allows enhancement in the standard of care therapy the patient is currently receiving. In some embodiments, the late sodium channel blockers of the disclosure are co-administered with ranolazine (RANEXA®).

Anti-Anginals

Anti-anginals include beta-blockers, calcium channel blockers, and nitrates. Beta blockers reduce the heart's need for oxygen by reducing its workload resulting in a decreased heart rate and less vigorous heart contraction. Examples of beta-blockers include acebutolol (Sectral®), atenolol (Tenormin®), betaxolol (Kerlone®), bisoprolol/hydrochlorothiazide (Ziac® bisoprolol (Zebeta®), carteolol (Cartrol®), esmolol (Brevibloc®), labetalol (Normodyne®, Trandate®), metoprolol (Lopressor®, Toprol® XL), nadolol (Corgard®), propranolol (Inderal®), sotalol (Betapace®), and timolol (Blocadren®).

Nitrates dilate the arteries and veins thereby increasing coronary blood flow and decreasing blood pressure. Examples of nitrates include nitroglycerin, nitrate patches, isosorbide dinitrate, and isosorbide-5-mononitrate.

Calcium channel blockers prevent the normal flow of calcium into the cells of the heart and blood vessels causing the blood vessels to relax thereby increasing the supply of blood and oxygen to the heart. Examples of calcium channel blockers include amlodipine (Norvasc®, Lotrel®), bepridil (Vascor®), diltiazem (Cardizem®, Tiazac®), felodipine (Plendil®), nifedipine (Adalat®, Procardia®), nimodipine (Nimotop®), nisoldipine (Sular®), verapamil (Calan®, Isoptin®, Verelan®), and nicardipine.

Heart Failure Agents

Agents used to treat heart failure include diuretics, ACE inhibitors, vasodilators, and cardiac glycosides. Diuretics eliminate excess fluids in the tissues and circulation thereby relieving many of the symptoms of heart failure. Examples of diuretics include hydrochlorothiazide, metolazone (Zaroxolyn®), furosemide (Lasix®), bumetanide (Bumex®), spironolactone (Aldactone®), and eplerenone (Inspra®).

Angiotensin converting enzyme (ACE) inhibitors reduce the workload on the heart by expanding the blood vessels and decreasing resistance to blood flow. Examples of ACE inhibitors include benazepril (Lotensin®), captopril (Capoten®), enalapril (Vasotec®), fosinopril (Monopril®), lisinopril (Prinivil®, Zestril®), moexipril (Univasc), perindopril (Aceon®), quinapril (Accupril®), ramipril (Altace®), and trandolapril (Mavik®).

Vasodilators reduce pressure on the blood vessels by making them relax and expand. Examples of vasodilators include hydralazine, diazoxide, prazosin, clonidine, and methyldopa. ACE inhibitors, nitrates, potassium channel activators, and calcium channel blockers also act as vasodilators.

Cardiac glycosides are compounds that increase the force of the heart's contractions. These compounds strengthen the pumping capacity of the heart and improve irregular heartbeat activity. Examples of cardiac glycosides include digitalis, digoxin, and digitoxin.

Antithrombotic Agents

Antithrombotics inhibit the clotting ability of the blood. There are three main types of antithrombotics—platelet inhibitors, anticoagulants, and thrombolytic agents.

Platelet inhibitors inhibit the clotting activity of platelets, thereby reducing clotting in the arteries. Examples of platelet inhibitors include acetylsalicylic acid (aspirin), ticlopidine, clopidogrel (Plavix), prasugrel (Effient®), dipyridamole, cilostazol, persantine sulfinpyrazone, dipyridamole, indomethacin, and glycoprotein llb/llla inhibitors, such as abciximab, tirofiban, and eptifibatide (Integrelin®). Beta blockers and calcium channel blockers also have a platelet-inhibiting effect.

Anticoagulants prevent blood clots from growing larger and prevent the formation of new clots. Examples of anticoagulants include bivalirudin (Angiomax®), warfarin (Coumadin®), unfractionated heparin, low molecular weight heparin, danaparoid, lepirudin, and argatroban.

Thrombolytic agents act to break down an existing blood clot. Examples of thrombolytic agents include streptokinase, urokinase, and tenecteplase (TNK), and tissue plasminogen activator (t-PA).

Antiarrhythmic Agents

Antiarrhythmic agents are used to treat disorders of the heart rate and rhythm. Examples of antiarrhythmic agents include amiodarone, dronedarone, quinidine, procainamide, lidocaine, and propafenone. Cardiac glycosides and beta blockers are also used as antiarrhythmic agents.

Combinations with amiodarone and dronedarone are of particular interest (see U.S. Patent Application Publication No. 2010/0056536 and U.S. Patent Application Publication No. 2011/0183990, the entirety of which are incorporated herein).

Antihypertensive Agents

Antihypertensive agents are used to treat hypertension, a condition in which the blood pressure is consistently higher than normal. Hypertension is associated with many aspects of cardiovascular disease, including congestive heart failure, atherosclerosis, and clot formation. Examples of antihypertensive agents include alpha-1-adrenergic antagonists, such as prazosin (Minipress®), doxazosin mesylate (Cardura®), prazosin hydrochloride (Minipress®), prazosin, polythiazide (Minizide®), and terazosin hydrochloride (Hytrin®); beta-adrenergic antagonists, such as propranolol (Inderal®), nadolol (Corgard®), timolol (Blocadren®), metoprolol (Lopressor®), and pindolol (Visken®); central alpha-adrenoceptor agonists, such as clonidine hydrochloride (Catapres®), clonidine hydrochloride and chlorthalidone (Clorpres®, Combipres®), guanabenz Acetate (Wytensin®), guanfacine hydrochloride (Tenex®), methyldopa (Aldomet®), methyldopa and chlorothiazide (Aldoclor®), methyldopa and hydrochlorothiazide (Aldoril®); combined alpha/beta-adrenergic antagonists, such as labetalol (Normodyne®, Trandate®), carvedilol (Coreg®); adrenergic neuron blocking agents, such as guanethidine (Ismelin®), reserpine (Serpasil®); central nervous system-acting antihypertensives, such as clonidine (Catapres®), methyldopa (Aldomet®), guanabenz (Wytensin®); anti-angiotensin II agents; ACE inhibitors, such as perindopril (Aceon®) captopril (Capoten®), enalapril (Vasotec®), lisinopril (Prinivil®, Zestril®); angiotensin-II receptor antagonists, such as candesartan (Atacand®), eprosartan (Tevete®), irbesartan (Avapro®), losartan (Cozaar®), telmisartan (Micardis®), valsartan (Diovan®); calcium channel blockers, such as verapamil (Calan®, Isoptin®), diltiazem (Cardizem®), nifedipine (Adalat®, Procardia®); diuretics; direct vasodilators, such as nitroprusside (Nipride), diazoxide (Hyperstat® IV), hydralazine (Apresoline), minoxidil (Loniten®), verapamil; and potassium channel activators, such as aprikalim, bimakalim, cromakalim, emakalim, nicorandil, and pinacidil.

Lipid Lowering Agents

Lipid lowering agents are used to lower the amounts of cholesterol or fatty sugars present in the blood. Examples of lipid lowering agents include bezafibrate (Bezalip®), ciprofibrate (Modalim®), and statins, such as atorvastatin (Lipitor®), fluvastatin (Lescol®), lovastatin (Mevacor®, Altocor), mevastatin, pitavastatin (Livalo®, Pitava) pravastatin (Lipostat®), rosuvastatin (Crestor®), and simvastatin (Zocor).

In this disclosure, the patient presenting with an acute coronary disease event often suffers from secondary medical conditions such as one or more of a metabolic disorder, a pulmonary disorder, a peripheral vascular disorder, or a gastrointestinal disorder. Such patients can benefit from treatment of a combination therapy comprising administering to the patient a compound as disclosed herein (e.g., Formula I, IA, IB, IC or ID) in combination with at least one therapeutic agent.

Pulmonary Disorders Combination Therapy

Pulmonary disorder refers to any disease or condition related to the lungs. Examples of pulmonary disorders include, without limitation, asthma, chronic obstructive pulmonary disease (COPD), bronchitis, and emphysema.

Examples of therapeutics agents used to treat pulmonary disorders include bronchodilators including beta2 agonists and anticholinergics, corticosteroids, and electrolyte supplements. Specific examples of therapeutic agents used to treat pulmonary disorders include epinephrine, terbutaline (Brethaire®, Bricanyl®), albuterol (Proventil), salmeterol (Serevent®, Serevent Diskus®), theophylline, ipratropium bromide (Atrovent®), tiotropium (Spiriva®), methylprednisolone (Solu-Medrol®, Medrol®), magnesium, and potassium.

Metabolic Disorders Combination Therapy

Examples of metabolic disorders include, without limitation, diabetes, including type I and type II diabetes, metabolic syndrome, dyslipidemia, obesity, glucose intolerance, hypertension, elevated serum cholesterol, and elevated triglycerides.

Examples of therapeutic agents used to treat metabolic disorders include antihypertensive agents and lipid lowering agents, as described in the section "Cardiovascular Agent Combination Therapy" above. Additional therapeutic agents used to treat metabolic disorders include insulin, sulfonylureas, biguanides, alpha-glucosidase inhibitors, and incretin mimetics.

Peripheral Vascular Disorders Combination Therapy

Peripheral vascular disorders are disorders related to the blood vessels (arteries and veins) located outside the heart and brain, including, for example peripheral arterial disease (PAD), a condition that develops when the arteries that supply blood to the internal organs, arms, and legs become completely or partially blocked as a result of atherosclerosis.

Gastrointestinal Disorders Combination Therapy

Gastrointestinal disorders refer to diseases and conditions associated with the gastrointestinal tract. Examples of gastrointestinal disorders include gastroesophageal reflux disease (GERD), inflammatory bowel disease (IBD), gastroenteritis, gastritis and peptic ulcer disease, and pancreatitis.

Examples of therapeutic agents used to treat gastrointestinal disorders include proton pump inhibitors, such as pantoprazole (Protonix®), lansoprazole (Prevacid®), esomeprazole (Nexium®), omeprazole (Prilosec®), rabeprazole; H2 blockers, such as cimetidine (Tagamet®), ranitidine (Zantac®), famotidine (Pepcid®), nizatidine (Axid®); prostaglandins, such as misoprostol (Cytotec®); sucralfate; and antacids.

Antibiotics, Analgesics, Antidepressants and Anti-Anxiety Agents Combination Therapy Patients presenting with an acute coronary disease event may exhibit conditions that benefit from administration of therapeutic agent or agents that are antibiotics, analgesics, antidepressant and anti-anxiety agents in combination with a compound as disclosed herein (e.g., Formula I, IA, IB, IC or ID).

Antibiotics

Antibiotics are therapeutic agents that kill, or stop the growth of, microorganisms, including both bacteria and fungi. Example of antibiotic agents include β-Lactam antibiotics, including penicillins (amoxicillin), cephalosporins, such as cefazolin, cefuroxime, cefadroxil (Duricef®), cephalexin (Keflex®), cephradine (Velosef®), cefaclor (Ceclor®), cefuroxime axtel (Ceftin®), cefprozil (Cefzil), loracarbef (Lorabid®), cefixime (Suprax®), cefpodoxime proxetil (Vantin®), ceftibuten (Cedax®), cefdinir (Omnicef®), ceftriaxone (Rocephin®), carbapenems, and monobactams; tetracyclines, such as tetracycline; macrolide antibiotics, such as erythromycin; aminoglycosides, such as gentamicin, tobramycin, amikacin; quinolones such as ciprofloxacin; cyclic peptides, such as vancomycin, streptogramins, polymyxins; lincosamides, such as clindamycin; oxazolidinoes, such as linezolid; and sulfa antibiotics, such as sulfisoxazole.

Analgesics

Analgesics are therapeutic agents that are used to relieve pain. Examples of analgesics include opiates and morphinomimetics, such as fentanyl and morphine; paracetamol; NSAIDs, and COX-2 inhibitors. Given the ability of the late sodium channel blockers of the disclosure to treat neuropathic pain via inhibition of the Nav 1.7 and 1.8 sodium channels, combination with analgesics are particularly envisioned. See U.S. Patent Application Publication 20090203707.

Antidepressant and Anti-Anxiety Agents

Antidepressant and anti-anxiety agents include those agents used to treat anxiety disorders, depression, and those used as sedatives and tranquillers. Examples of antidepressant and anti-anxiety agents include benzodiazepines, such as diazepam, lorazepam, and midazolam; enzodiazepines; barbiturates; glutethimide; chloral hydrate; meprobamate; sertraline (Zoloft®, Lustral®, Apo-Sertral®, Asentra®, Gladem®, Serlift®, Stimuloton®); escitalopram (Lexapro®, Cipralex®); fluoxetine (Prozac®, Sarafem®, Fluctin®, Fontex®, Prodep®, Fludep®, Lovan®); venlafaxine (Effexor® XR, Efexor®); citalopram (Celexa®, Cipramil®, Talohexane®); paroxetine (Paxil®, Seroxat®, Aropax); trazodone (Desyrel®); amitriptyline (Elavil®); and bupropion (Wellbutrin®, Zyban®).

Accordingly, one aspect of the disclosure provides for a composition comprising the late sodium channel blockers of the disclosure and at least one therapeutic agent. In an alternative embodiment, the composition comprises the late sodium channel blockers of the disclosure and at least two therapeutic agents. In further alternative embodiments, the composition comprises the late sodium channel blockers of the disclosure and at least three therapeutic agents, the late sodium channel blockers of the disclosure and at least four therapeutic agents, or the late sodium channel blockers of the disclosure and at least five therapeutic agents.

The methods of combination therapy include co-administration of a single formulation containing the late sodium channel blockers of the disclosure and therapeutic agent or agents, essentially contemporaneous administration of more than one formulation comprising the late sodium channel blocker of the disclosure and therapeutic agent or agents, and consecutive administration of a late sodium channel blocker of the disclosure and therapeutic agent or agents, in any order, wherein preferably there is a time period where the late sodium channel blocker of the disclosure and therapeutic agent or agents simultaneously exert their therapeutic affect.

6. Synthesis of Example Compounds

The compounds of the disclosure may be prepared using methods disclosed herein and routine modifications thereof which will be apparent given the disclosure herein and methods well known in the art. Conventional and well-known synthetic methods may be used in addition to the teachings herein. The synthesis of typical compounds described herein, e.g. compounds having structures described by one or more of Formula I, IA, IB, IC or ID or other formulas or compounds disclosed herein, may be accomplished as described in the following examples. If available, reagents may be purchased commercially, e.g. from Sigma Aldrich or other chemical suppliers.

General Syntheses

Typical embodiments of compounds in accordance with the present disclosure may be synthesized using the general reaction schemes described below. It will be apparent given the description herein that the general schemes may be altered by substitution of the starting materials with other materials having similar structures to result in products that are correspondingly different. Descriptions of syntheses follow to provide numerous examples of how the starting materials may vary to provide corresponding products. Given a desired product for which the substituent groups are defined, the necessary starting materials generally may be determined by inspection. Starting materials are typically obtained from commercial sources or synthesized using published methods. For synthesizing compounds which are embodiments of the present disclosure, inspection of the structure of the compound to be synthesized will provide the identity of each substituent group. The identity of the final product will generally render apparent the identity of the necessary starting materials by a simple process of inspection, given the examples herein.

Synthetic Reaction Parameters

The compounds of this disclosure can be prepared from readily available starting materials using, for example, the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts (1999) *Protecting Groups in Organic Synthesis,* 3rd Edition, Wiley, New York, and references cited therein.

Furthermore, the compounds of this disclosure may contain one or more chiral centers. Accordingly, if desired, such compounds can be prepared or isolated as pure stereoisomers, i.e., as individual enantiomers or diastereomers or as stereoisomer-enriched mixtures. All such stereoisomers (and enriched mixtures) are included within the scope of this disclosure, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents, and the like.

The starting materials for the following reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Emka-Chemce or Sigma (St. Louis, Mo., USA). Others may be prepared by procedures or obvious modifications thereof, described in standard reference texts such as Fieser and Fieser's Reagents for Organic Synthesis, Volumes 1-15 (John Wiley, and Sons, 1991), Rodd's Chemistry of Carbon Compounds, Volumes 1-5, and Supplementals (Elsevier Science Publishers, 1989) organic Reactions, Volumes 1-40 (John Wiley, and Sons, 1991), March's Advanced Organic Chemistry, (John Wiley, and Sons, $5^{th}$ Edition, 2001), and Larock's Comprehensive Organic Transformations (VCH Publishers Inc., 1989).

The terms "solvent," "inert organic solvent" or "inert solvent" refer to a solvent inert under the conditions of the reaction being described in conjunction therewith (including, for example, benzene, toluene, acetonitrile, tetrahydrofuran ("THF"), dimethylformamide ("DMF"), chloroform, methylene chloride (or dichloromethane), diethyl ether, methanol, pyridine and the like). Unless specified to the contrary, the solvents used in the reactions of the present disclosure are inert organic solvents, and the reactions are carried out under an inert gas, preferably nitrogen.

The term "q.s." means adding a quantity sufficient to achieve a stated function, e.g., to bring a solution to the desired volume (i.e., 100%).

Synthesis of the Compounds of Formula I

The compounds of Formula I (including Formula IA, IB, IC or ID) may prepared by first providing the benzoisoxazole core, and then attaching the desired substituents using suitable coupling conditions (e.g., Suzuki coupling, Mitsunobu reaction, alkylation, etc.). Exemplary processes are show below in Schemes 1 and 2 for the synthesis of a compound of Formula I.

Scheme 1 shows the preparation of compounds of Formula I, where L' comprises a —O— group attached to the benzoisoxazole core, wherein LG is a leaving group (e.g., halo) and alkyl, X, Z, $R^1$, $R^2$, $R^3$, $R^4$, p and q are as defined herein.

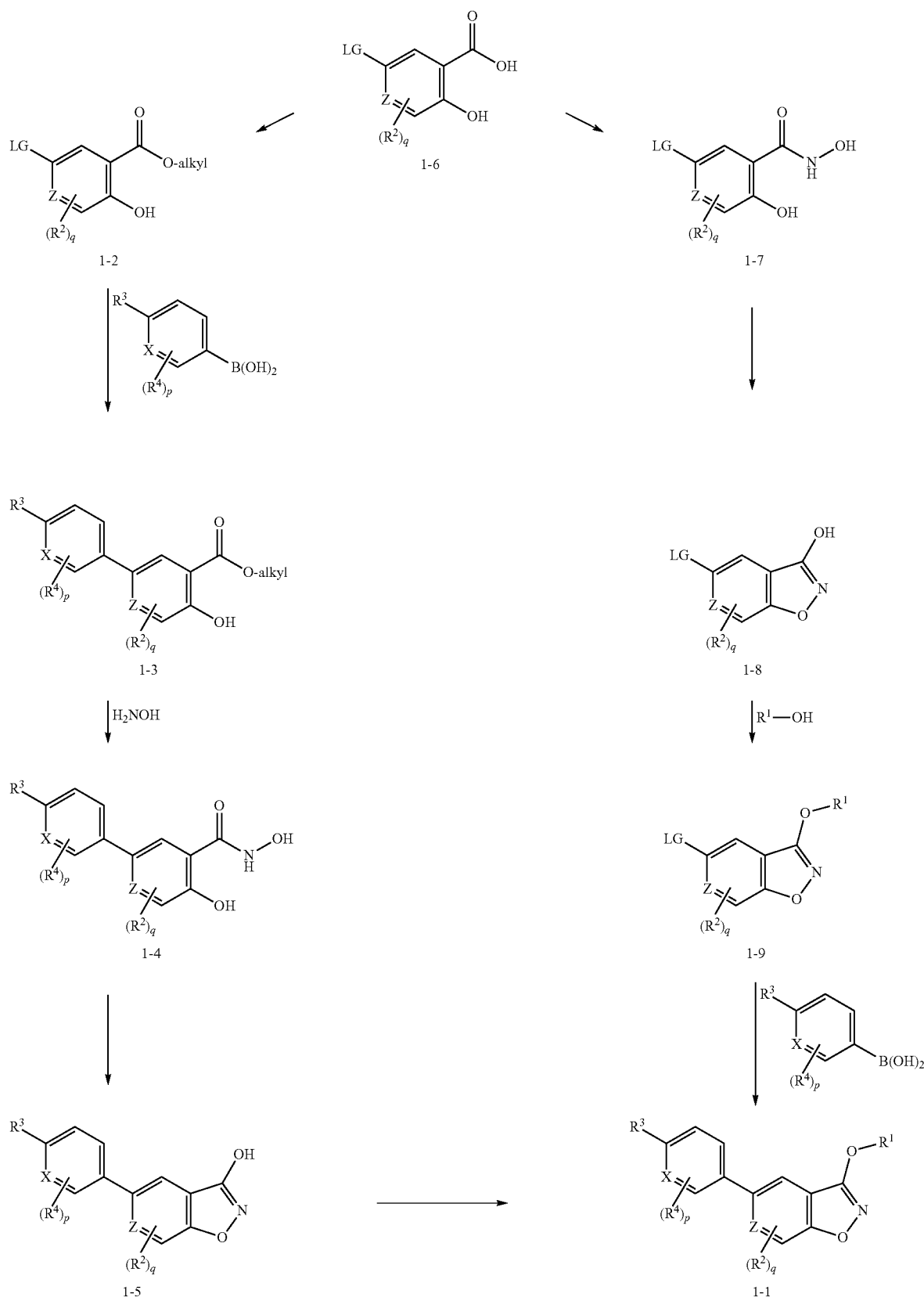

In Scheme 1, suitably substituted 5-bromo-2-hydroxybenzoate 1-2, which can be obtained from the corresponding benzoic acid 1-6 through standard esterification conditions, is coupled with suitably substituted arylboronic acid or ester in the presence of a palladium catalyst to provide biaryl ester 1-3. The ester is converted to hydroxamic acid 1-4 by heating with hydroxylamine. Hydroxybenzisoxazole 1-5 is obtained by cyclization with carbonyldiimidazole. Alkylation of 1-5 to obtain compound 1-1 is achieved by reaction with a suitable halide in the presence of a base such as cesium- or potassium carbonate in DMF or alternately by reaction with an alcohol in the presence of an azodicarboxylate reagent (DIAD, DEAD, etc) and triphenylphosphine under Mitsunobu conditions.

Alternately, benzoic acid 1-6 is transformed to the hydroxamic acid 1-7 using standard conditions, followed by cyclization to the hydroxybenzisoxazole 1-8. Alkylated product 1-9 is obtained by reaction with a suitable alkyl halide in the presence of a base such as cesium- or potassium carbonate in DMF or alternately by reaction with an alcohol in the presence of an azodicarboxylate reagent (DIAD, DEAD, etc) and triphenylphosphine under Mitsunobu conditions. Bromobenzisoxazole 1-9 is then converted to compound 1-1 by coupling with a suitably substituted arylboronic acid or ester in the presence of a palladium catalyst under standard Suzuki coupling conditions. Each of the intermediates in the above scheme may be isolated and/or purified prior to the subsequent step, or used in the next step without isolation.

Schemes 2 and 3 show the preparation of compounds of Formula I, where $L^1$ comprises a —NH— group attached to the benzoisoxazole core or Y is a heterocyclic or heteroaryl ring. In Schemes 2 and 3, LG is a leaving group (e.g., halo) and Z, X, $R^1$, $R^2$, $R^3$, $R^4$, p and q are as defined herein.

In Scheme 2, chlorobenzisoxazole 2-1 is converted to compound 2-2 by coupling with a suitably substituted arylboronic acid or ester in the presence of a palladium catalyst under standard Suzuki coupling conditions. Compound 2-2 may be isolated and/or purified, or used in the next step without isolation. Amination of 2-2 to obtain compounds 2-3 and 2-4 is achieved by reaction with a suitable amine in the presence of a base such as diazabicyclo[5.4.0]undec-7-ene. The reaction may be facilitated by use of a microwave reactor.

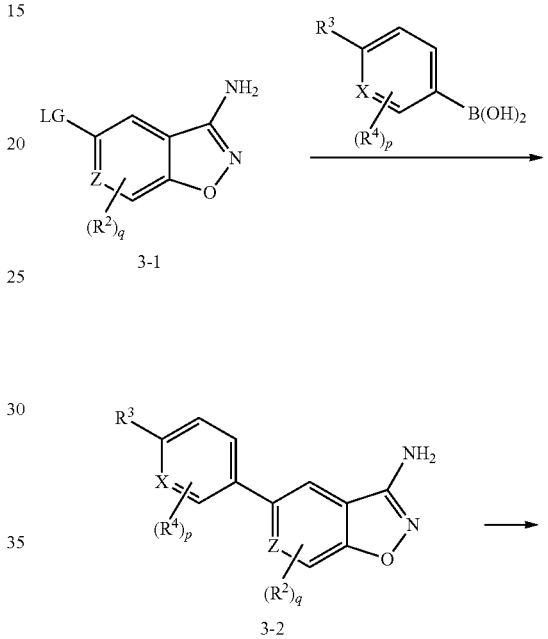

Scheme 3

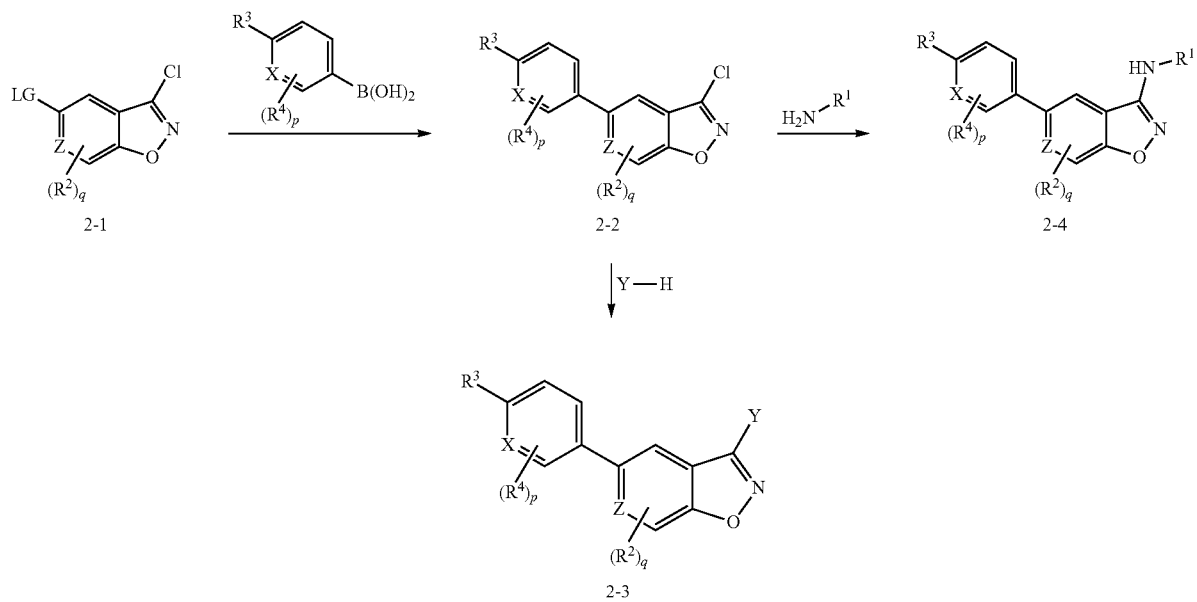

Scheme 2

-continued

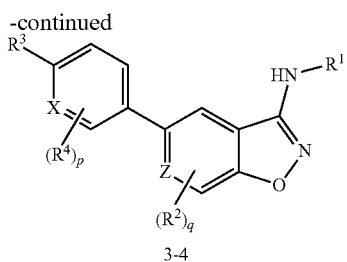

3-4

In Scheme 3, aminobenzisoxazole 3-1 is converted to compound 3-2 by coupling with a suitably substituted arylboronic acid or ester in the presence of a palladium catalyst under standard Suzuki coupling conditions. Compound 3-2 may be isolated and/or purified, or used in the next step without isolation. Alkylation of 3-2 to obtain 3-3 is achieved by reaction with a suitable carbonyl-containing compound under standard reductive amination conditions, typically with the use of a drying agent followed by the addition of a reducing agent, such as sodium borohydride.

It will also be appreciated that the addition of any substituent may result in the production of a number of isomeric products any or all of which may be isolated and purified using conventional techniques.

EXAMPLES

The following examples are included to demonstrate preferred embodiments of the disclosure. It should be appreciated by those of skill in the art that the techniques disclosed in the examples which follow represent techniques discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

LIST OF ABBREVIATIONS AND ACRONYMS

Abbreviation Meaning
° C. Degree Celcius
anal Analytical
ATP Adenosine-5'-triphosphate
ATX II Anemonia sulcata toxin
ACN Acetonitrile
CHO Chinese hamster ovary
conc. Concentrated
d Doublet
DABCO 1,4-Diazabicyclo[2.2.2]octane
dd Doublet of doublets
DCM Dichloromethane
DIPEA N,N-diisopropylethylamine
DMF Dimethylformamide
DMSO Dimethylsulfoxide
dppf 1,1'-Bis(diphenylphosphino)ferrocene
EA Ethyl alcohol
ECF Extracellular fluid
EDTA Ethylenediaminetetraacetic acid
EGTA Ethylene glycol tetraacetic acid
equiv/eq Equivalents
ESI Electrospray ionization
Ac Acetate
Et Ethyl
g Grams
HEPES (4-(2-Hydroxyethyl)-1-piperazineethanesulfonic acid)
HATU 2-(7-Aza-1H-Benzotriazole-1-yl)-1,1,3,3-tetramethyluronium hexafluorophosphate
hERG human Ether-à-go-go Related Gene
HPLC High-performance liquid chromatography
h Hours
Hz Hertz
$IC_{50}$ The half maximal inhibitory concentration
IMR-32 Human neuroblastoma cell line
J Coupling constant
Kg Kilogram
kHz Kilohertz
LCMS/LC-MS Liquid chromatography-mass spectrometry
M Molar
m multiplet
m/z mass-to-charge ratio
M+ Mass peak
M+H Mass peak plus hydrogen
Me Methyl
mg Milligram
MHz Megahertz
minim Minute
ml/mL Milliliter
mM Millimolar
mmol Millimole
nmol Nanomole
mOsmol Milliosmole
MRM Magnetic Resonance Microscopy
MS Mass spectroscopy
ms Millisecond
mV Millivolt
mw Microwave
N Normal
mol Mole
NMR Nuclear magnetic resonance
pA Picoamps
Ph Phenyl
prep Preparative
q.s. Quantity sufficient to achieve a stated function
Rf Retention factor
RT/rt Room temperature
s Second
s Singlet
SEM Standard error of the mean
t Triplet
TB Tonic Block
TEA Triethylamine
TFA Trifluoroacetic acid
THE Tetrahydrofuran
TLC Thin layer chromatography
TTX Tetrodotoxin
UDB Use Dependent Block
WT Wild type
δ Chemical shift
μg Microgram
μt/μl Microliter
μM Micromolar
μm Micrometer
μmol Micromole

Example 1

3-(pyrimidin-2-ylmethoxy)-5-(4-(trifluoromethoxy)phenyl)benzo[d]isoxazole

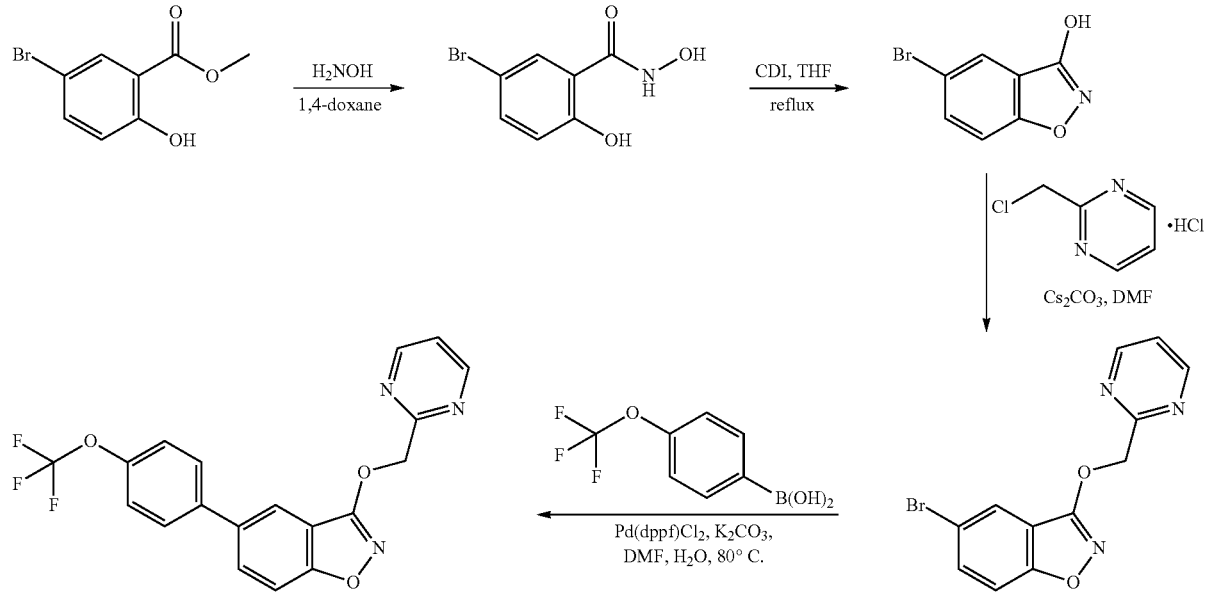

Step 1: Methyl 5-bromosalicylate (5 g, 21.6 mmol) was dissolved in 90 mL 1,4-dioxane and 10 mL water. 10 mL 50% aqueous hydroxylamine solution was added and the mixture was stirred at ambient temperature for 24 hours. After concentrating the mixture under vacuum, water was added. The formed precipitate was filtered, washed with water and dried yielding 5-bromo-N,2-dihydroxybenzamide (4.12 g, 17.76 mmol) as off-white solid.

Step 2: 5-bromo-N,2-dihydroxybenzamide (4.12 g, 17.76 mmol) was suspended in 100 mL THF. Carbonyldiimidazole (5.76 g, 35.5 mmol) was added and the mixture was heated under reflux for three hours. The solvent was evaporated under vacuum, 100 mL water was added and the solution was acidified to pH 1 with 1N HCl under rapid stirring. The formed precipitate was filtered, washed with water and dried, giving 5-bromobenzo[d]isoxazol-3-ol (3.71 g, 17.3 mmol) as off-white solid.

Step 3: 5-bromobenzo[d]isoxazol-3-ol (200 mg, 0.93 mmol), 2-(chloromethyl)pyrimidine hydrochloride (200 mg, 1.21 mmol) and cesium carbonate (1 g) were combined in 10 mL DMF and stirred at ambient temperature for two days. The reaction mixture was diluted with 60 mL ethyl acetate, washed with water and brine and evaporated under vacuum. Flash chromatographic purification on 12 g silica gel with 0-100% ethyl acetate in hexane gave O-alkylated product 5-bromo-3-(pyrimidin-2-ylmethoxy)benzo[d]isoxazole (120 mg, 0.39 mmol).

Step 4: 5-Bromo-3-(pyrimidin-2-ylmethoxy)benzo[d]isoxazole (120 mg, 0.39 mmol), 4-(trifluoromethoxy)phenylboronic acid (120 mg, 0.58 mmol), potassium carbonate (500 mg), and [1,1'-Bis(diphenylphosphino)ferrocene]dichloropalladium(II) (25 mg, 0.034 mmol) were combined in 6 mL DMF. 3 mL water was added and the mixture was stirred at 80° C. for two hours. The reaction mixture was diluted with 60 mL ethyl acetate, washed with water and brine and evaporated under vacuum. Flash chromatographic purification on 12 g silica gel with 0-60% ethyl acetate in hexane gave 3-(pyrimidin-2-ylmethoxy)-5-(4-(trifluoromethoxy)phenyl)benzo[d]isoxazole (94 mg, 0.24 mmol).

$^1$H NMR (400 MHz, DMSO-d$_6$) δ 8.83 (d, J=4.9 Hz, 2H), 8.07-8.01 (m, 1H), 7.97 (dd, J=8.8, 1.8 Hz, 1H), 7.91-7.83 (m, 2H), 7.72 (d, J=8.8 Hz, 1H), 7.51-7.40 (m, 3H), 5.67 (s, 2H). MS: 388 (MH$^+$).

The following compounds were synthesized using the above procedure, substituting with the appropriate boronic acid.

Example 2

5-(2-fluoro-4-(trifluoromethoxy)phenyl)-3-(pyrimidin-2-ylmethoxy)benzo[d]isoxazole

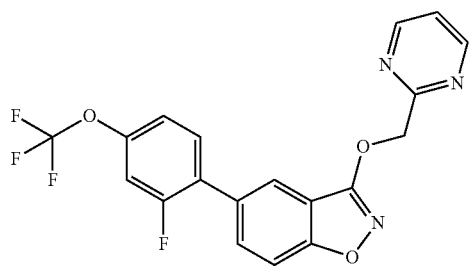 [SMILES: Fc1cc(OC(F)(F)F)ccc1-c1ccc2onc(OCc3ncccn3)c2c1]

$^1$H NMR (400 MHz, DMSO-d$_6$) δ 8.82 (d, J=4.9 Hz, 2H), 7.98-7.93 (m, 1H), 7.84 (dt, J=8.8, 1.7 Hz, 1H), 7.80-7.71 (m, 2H), 7.58-7.50 (m, 1H), 7.47 (t, J=4.9 Hz, 1H), 7.39-7.31 (m, 1H), 5.67 (s, 2H). MS: 406 (MH$^+$).

Example 3

5-(2-methyl-4-(trifluoromethoxy)phenyl)-3-(pyrimidin-2-ylmethoxy)benzo[d]isoxazole

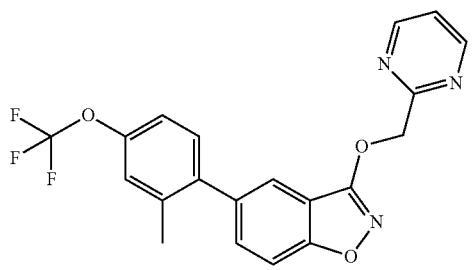

¹H NMR (400 MHz, DMSO-d₆) δ 8.82 (d, J=4.9 Hz, 2H), 7.75-7.71 (m, 1H), 7.69 (d, 1H), 7.64 (dd, J=8.7, 1.7 Hz, 1H), 7.47 (t, J=4.9 Hz, 1H), 7.38 (d, J=8.4 Hz, 1H), 7.36-7.31 (m, 1H), 7.29-7.22 (m, 1H), 5.66 (s, 2H), 2.25 (s, 3H). MS: 402 (MH⁺).

Example 4

5-(2-methoxy-4-(trifluoromethoxy)phenyl)-3-(pyrimidin-2-ylmethoxy)benzo[d]isoxazole

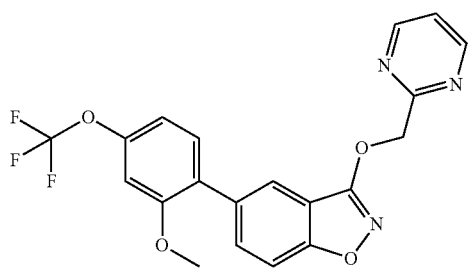 [SMILES: COc1cc(OC(F)(F)F)ccc1-c1ccc2onc(OCc3ncccn3)c2c1]

¹H NMR (400 MHz, DMSO-d₆) δ 8.82 (d, J=4.9 Hz, 2H), 7.84-7.79 (m, 1H), 7.74 (dd, J=8.8, 1.7 Hz, 1H), 7.66 (d, J=8.8 Hz, 1H), 7.52-7.43 (m, 2H), 7.16-7.11 (m, 1H), 7.07-6.98 (m, 1H), 5.66 (s, 2H), 3.81 (s, 3H). MS: 418 (MH⁺).

Example 5

3-((4-methylpyrimidin-2-yl)methoxy)-5-(4-(trifluoromethoxy)phenyl)benzo[d]isoxazole

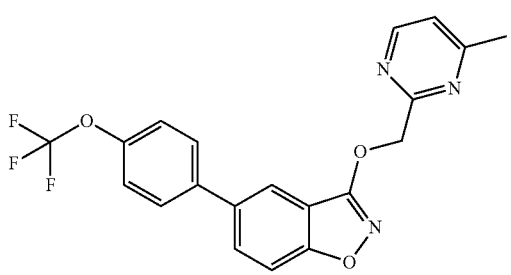 [SMILES: Cc1ccnc(COc2noc3ccc(-c4ccc(OC(F)(F)F)cc4)cc23)n1]

¹H NMR (400 MHz, DMSO-d₆) δ 8.65 (d, J=5.1 Hz, 1H), 8.05 (dd, J=1.9, 0.8 Hz, 1H), 7.97 (dd, J=8.8, 1.9 Hz, 1H), 7.92-7.83 (m, 2H), 7.73 (dd, J=8.8, 0.7 Hz, 1H), 7.44 (d, J=7.6 Hz, 2H), 7.35 (d, J=5.1 Hz, 1H), 5.60 (s, 2H), 2.46 (s, 3H). MS: 402 (MH⁺).

Example 6

5-(2-fluoro-4-(trifluoromethyl)phenyl)-3-(pyrimidin-2-ylmethoxy)benzo[d]isoxazole

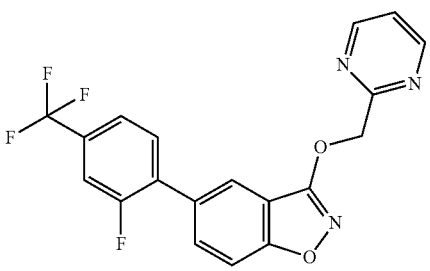 [SMILES: Fc1cc(C(F)(F)F)ccc1-c1ccc2onc(OCc3ncccn3)c2c1]

1H NMR (400 MHz, DMSO-d6) δ 8.82 (d, J=4.9 Hz, 2H), 8.01 (t, J=1.4 Hz, 1H), 7.91-7.84 (m, 2H), 7.82 (dd, J=10.8, 1.7 Hz, 1H), 7.77 (d, J=8.9 Hz, 1H), 7.68 (dd, J=8.2, 1.7 Hz, 1H), 7.47 (t, J=4.9 Hz, 1H), 5.67 (s, 2H). m/z: 390 (MH+)

Example 7

5-(3-methyl-4-(trifluoromethoxy)phenyl)-3-(pyrimidin-2-ylmethoxy)benzo[d]isoxazole

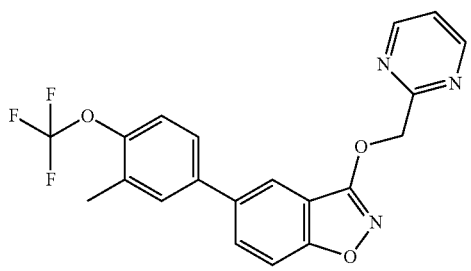 [SMILES: Cc1cc(-c2ccc3onc(OCc4ncccn4)c3c2)ccc1OC(F)(F)F]

1H NMR (400 MHz, DMSO-d6) δ 8.83 (d, J=4.9 Hz, 2H), 8.04 (d, J=1.7 Hz, 1H), 7.97 (dd, J=8.8, 1.9 Hz, 1H), 7.81 (d, J=2.3 Hz, 1H), 7.71 (d, J=8.8 Hz, 1H), 7.68 (dd, J=8.5, 2.5 Hz, 1H), 7.48 (t, J=4.9 Hz, 1H), 7.37 (dt, J=8.5, 1.6 Hz, 1H), 5.66 (s, 2H), 2.34 (s, 3H). m/z: 402 (MH+).

Example 8

5-(4-chloro-3-fluorophenyl)-3-(pyrimidin-2-ylmethoxy)benzo[d]isoxazole

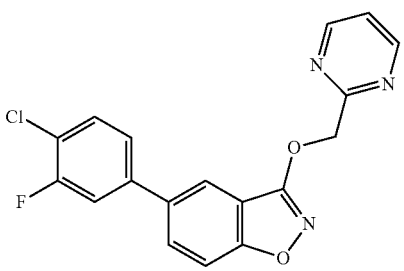 [SMILES: Fc1cc(-c2ccc3onc(OCc4ncccn4)c3c2)ccc1Cl]

1H NMR (400 MHz, DMSO-d6) δ 8.83 (d, J=4.9 Hz, 2H), 8.13 (d, J=1.7 Hz, 1H), 8.02 (dd, J=8.8, 1.9 Hz, 1H), 7.92-7.85 (m, 1H), 7.73 (d, J=8.8 Hz, 1H), 7.67-7.64 (m, 2H), 7.48 (t, J=4.9 Hz, 1H), 5.67 (s, 2H). m/z: 356 (MH+)

Example 9

3-(pyrimidin-2-ylmethoxy)-5-(4-(trifluoromethyl)phenyl)benzo[d]isoxazole

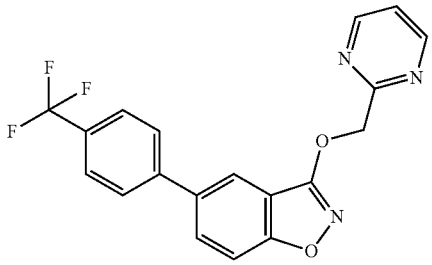 [SMILES: FC(F)(F)c1ccc(-c2ccc3onc(OCc4ncccn4)c3c2)cc1]

1H NMR (400 MHz, DMSO-d6) δ 8.85 (d, J=4.9 Hz, 2H), 8.15 (d, J=1.7 Hz, 1H), 8.05 (dd, J=8.8, 1.8 Hz, 1H), 8.01 (d, J=8.1 Hz, 2H), 7.83 (d, J=8.2 Hz, 2H), 7.78 (d, J=8.8 Hz, 1H), 7.50 (t, J=4.9 Hz, 1H), 5.70 (s, 2H). m/z: 372 (MH+)

Example 10

3-(pyrimidin-2-ylmethoxy)-5-(3-(trifluoromethoxy)phenyl)benzo[d]isoxazole

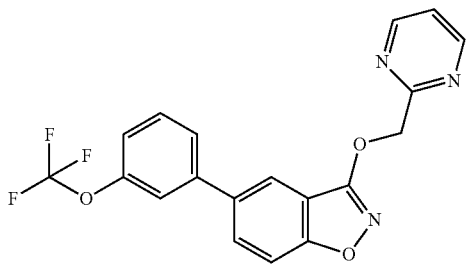 [SMILES: FC(F)(F)Oc1cccc(-c2ccc3onc(OCc4ncccn4)c3c2)c1]

1H NMR (400 MHz, DMSO-d6) δ 8.83 (d, J=4.9 Hz, 2H), 8.10 (d, J=1.7 Hz, 1H), 8.01 (dd, J=8.8, 1.9 Hz, 1H), 7.81 (ddd, J=7.9, 1.9, 1.0 Hz, 1H), 7.78-7.75 (m, 1H), 7.73 (d, J=8.8 Hz, 1H), 7.60 (t, J=8.0 Hz, 1H), 7.48 (t, J=4.9 Hz, 1H), 7.40-7.33 (m, 1H), 5.67 (s, 2H). m/z: 388 (MH+)

Example 11

6-methoxy-3-(pyrimidin-2-ylmethoxy)-5-(4-(trifluoromethoxy)phenyl)benzo[d]isoxazole

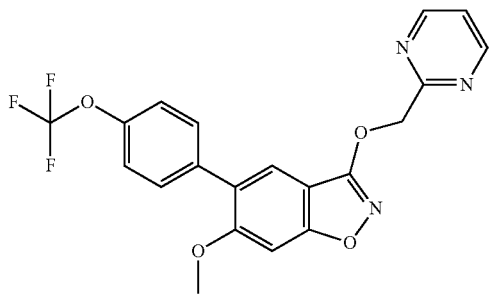 [SMILES: COc1cc2onc(OCc3ncccn3)c2cc1-c1ccc(OC(F)(F)F)cc1]

1H NMR (400 MHz, DMSO-d6) δ 8.75 (d, J=4.9 Hz, 2H), 7.56-7.48 (m, 2H), 7.42 (t, J=4.9 Hz, 1H), 7.39-7.32 (m, 3H), 7.24 (s, 1H), 5.27 (s, 2H), 3.77 (s, 3H). m/z: 418 (MH+).

Example 12

5-(2-fluoro-4-(trifluoromethyl)phenyl)-6-methoxy-3-(pyrimidin-2-ylmethoxy)benzo[d]isoxazole

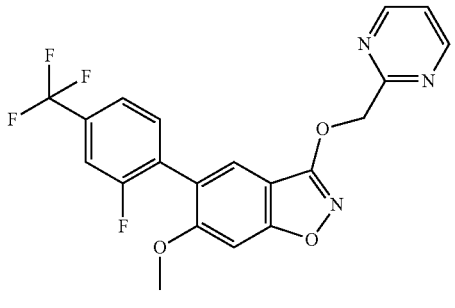 [SMILES: COc1cc2onc(OCc3ncccn3)c2cc1-c1ccc(C(F)(F)F)cc1F]

1H NMR (400 MHz, DMSO-d6) δ 8.75 (d, J=4.9 Hz, 2H), 7.69 (dd, J=9.9, 1.7 Hz, 1H), 7.62-7.57 (m, 1H), 7.52 (t, J=7.6 Hz, 1H), 7.42 (t, J=4.9 Hz, 1H), 7.39 (s, 1H), 7.21 (s, 1H), 5.25 (s, 2H), 3.76 (s, 3H). m/z: 420 (MH+).

Example 13

5-(4-chloro-3-fluorophenyl)-6-methoxy-3-(pyrimidin-2-ylmethoxy)benzo[d]isoxazole

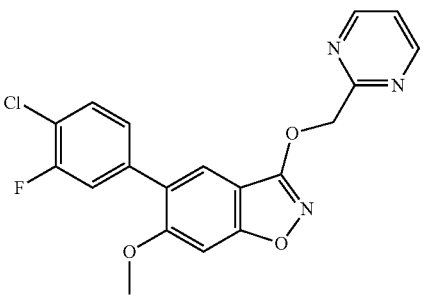 [SMILES: COc1cc2onc(OCc3ncccn3)c2cc1-c1ccc(Cl)c(F)c1]

1H NMR (400 MHz, DMSO-d6) δ 8.75 (d, J=4.9 Hz, 2H), 7.57 (t, J=8.2 Hz, 1H), 7.46 (dd, J=11.0, 2.0 Hz, 1H), 7.42 (t, J=4.9 Hz, 1H), 7.35 (s, 1H), 7.32-7.26 (m, 2H), 5.28 (s, 2H), 3.78 (s, 3H). m/z: 386 (MH+)

Example 14

6-methoxy-5-(3-methyl-4-(trifluoromethoxy)phenyl)-3-(pyrimidin-2-ylmethoxy)benzo[d]isoxazole

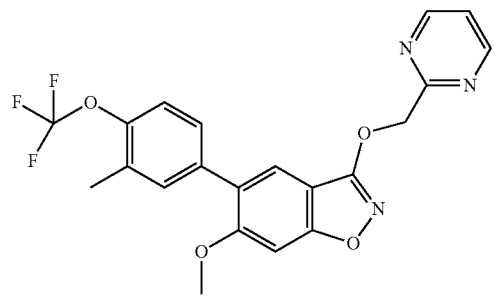 [SMILES: COc1cc2onc(OCc3ncccn3)c2cc1-c1ccc(OC(F)(F)F)c(C)c1]

1H NMR (400 MHz, DMSO-d6) δ 8.84 (d, J=4.9 Hz, 2H), 7.50 (t, J=4.9 Hz, 1H), 7.48 (d, J=2.1 Hz, 1H), 7.44-7.40 (m, 2H), 7.37 (dd, J=8.5, 1.5 Hz, 1H), 7.31 (s, 1H), 5.36 (s, 2H), 3.85 (s, 3H), 2.35 (s, 3H). m/z: 432 (MH+)

Example 15

5-(3-chloro-4-fluorophenyl)-6-methoxy-3-(pyrimidin-2-ylmethoxy)benzo[d]isoxazole

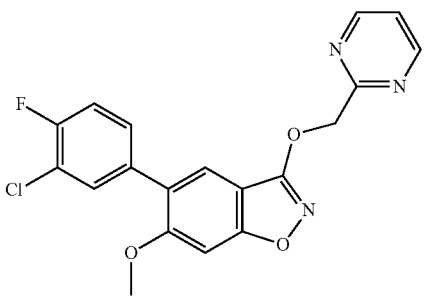 [SMILES: COc1cc2onc(OCc3ncccn3)c2cc1-c1ccc(F)c(Cl)c1]

1H NMR (400 MHz, DMSO-d6) δ 8.75 (d, J=4.9 Hz, 2H), 7.61-7.56 (m, 1H), 7.44-7.39 (m, 3H), 7.34 (s, 1H), 7.27 (s, 1H), 5.28 (s, 2H), 3.77 (s, 3H). m/z: 386 (MH+).

Example 16

7-methyl-3-(pyrimidin-2-ylmethoxy)-5-(4-(trifluoromethoxy)phenyl)benzo[d]isoxazole

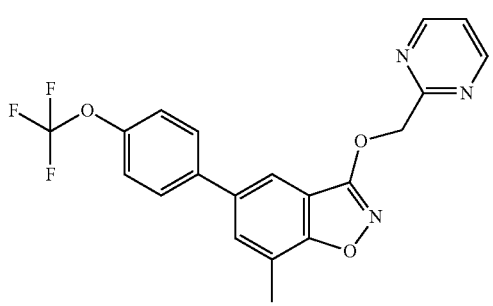 [SMILES: Cc1cc(-c2ccc(OC(F)(F)F)cc2)cc2c(OCc3ncccn3)noc12]

1H NMR (400 MHz, DMSO-d6) δ 8.82 (d, J=4.9 Hz, 2H), 7.88-7.83 (m, 3H), 7.81 (t, J=1.4 Hz, 1H), 7.47 (t, J=4.9 Hz, 1H), 7.44 (d, J=8.5 Hz, 2H), 5.66 (s, 2H), 2.49 (s, 3H). m/z: 402 (MH+).

Example 17

7-fluoro-3-(pyrimidin-2-ylmethoxy)-5-(4-(trifluoromethoxy)phenyl)benzo[d]isoxazole

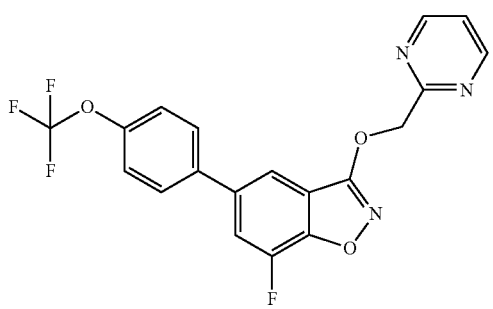 [SMILES: Fc1cc(-c2ccc(OC(F)(F)F)cc2)cc2c(OCc3ncccn3)noc12]

1H NMR (400 MHz, DMSO-d6) δ 8.83 (d, J=4.9 Hz, 2H), 8.01 (dd, J=12.2, 1.5 Hz, 1H), 7.97-7.89 (m, 3H), 7.54-7.40 (m, 3H), 5.69 (s, 2H). m/z: 406 (MH+).

Example 18

7-methyl-5-(3-methyl-4-(trifluoromethoxy)phenyl)-3-(pyrimidin-2-ylmethoxy)benzo[d]isoxazole

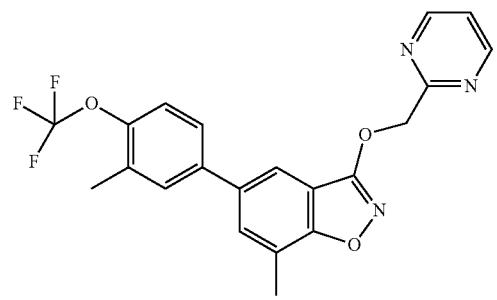 [SMILES: Cc1cc(-c2cc(C)c3onc(OCc4ncccn4)c3c2)ccc1OC(F)(F)F]

1H NMR (400 MHz, DMSO-d6) δ 8.82 (d, J=4.9 Hz, 2H), 7.93 (d, J=1.8 Hz, 1H), 7.90-7.82 (m, 2H), 7.67-7.63 (m, 2H), 7.48 (t, J=4.9 Hz, 1H), 5.66 (s, 2H), 2.49 (s, 3H), 2.48 (s, 3H). m/z: 416 (MH+).

Example 19

7-methyl-3-(pyrimidin-2-ylmethoxy)-5-(3-(trifluoromethoxy)phenyl)benzo[d]isoxazole

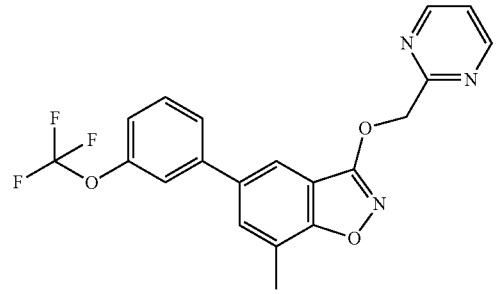 [SMILES: Cc1cc(-c2cccc(OC(F)(F)F)c2)cc2c(OCc3ncccn3)noc12]

1H NMR (400 MHz, DMSO-d6) δ 8.83 (d, J=5.0 Hz, 2H), 7.93-7.89 (m, 1H), 7.86 (dd, J=1.8, 1.0 Hz, 1H), 7.83-7.78 (m, 1H), 7.75 (s, 1H), 7.59 (t, J=8.0 Hz, 1H), 7.48 (t, J=4.9 Hz, 1H), 7.40-7.32 (m, 1H), 5.66 (s, 2H), 2.50 (s, 3H). m/z: 402 (MH+).

Example 20

5-(6-cyclopropylpyridin-3-yl)-3-(pyrimidin-2-ylmethoxy)benzo[d]isoxazole

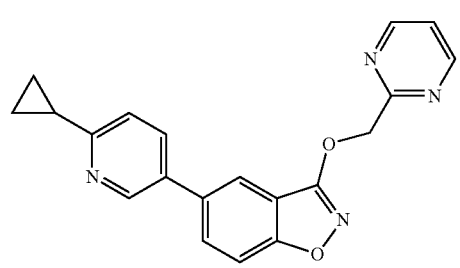 [SMILES: c1cnc(COc2noc3ccc(-c4ccc(C5CC5)nc4)cc23)nc1]

1H NMR (400 MHz, DMSO-d6) δ 8.83 (d, J=4.9 Hz, 2H), 8.76 (dd, J=2.5, 0.8 Hz, 1H), 8.05 (dd, J=1.9, 0.7 Hz, 1H), 8.01 (dd, J=8.2, 2.5 Hz, 1H), 7.97 (dd, J=8.8, 1.9 Hz, 1H), 7.72 (dd, J=8.8, 0.7 Hz, 1H), 7.48 (t, J=4.9 Hz, 1H), 7.37 (dd, J=8.2, 0.8 Hz, 1H), 5.67 (s, 2H), 2.14 (tt, J=7.7, 5.2 Hz, 1H), 1.00-0.93 (m, 4H). m/z: 345 (MH+).

Example 21

3-(pyrimidin-2-ylmethoxy)-5-(6-(2,2,2-trifluoroethoxy)pyridin-3-yl)benzo[d]isoxazole

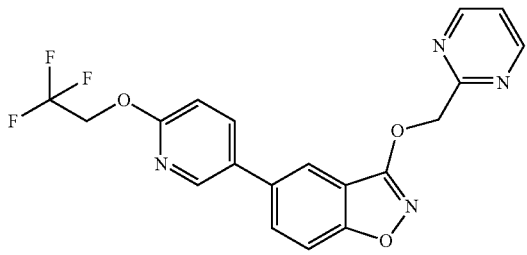 [SMILES: FC(F)(F)COc1ccc(-c2ccc3onc(OCc4ncccn4)c3c2)cn1]

1H NMR (400 MHz, DMSO-d6) δ 8.83 (d, J=4.9 Hz, 2H), 8.58 (dd, J=2.6, 0.8 Hz, 1H), 8.21 (dd, J=8.6, 2.6 Hz, 1H), 8.07 (dd, J=1.8, 0.8 Hz, 1H), 7.98 (dd, J=8.8, 1.9 Hz, 1H), 7.73 (dd, J=8.8, 0.7 Hz, 1H), 7.48 (t, J=4.9 Hz, 1H), 7.08 (dd, J=8.6, 0.7 Hz, 1H), 5.67 (s, 2H), 5.04 (q, J=9.1 Hz, 2H). m/z: 403 (MH+).

Example 22

7-methoxy-3-(pyrimidin-2-ylmethoxy)-5-(4-(trifluoromethoxy)phenyl)benzo[d]isoxazole

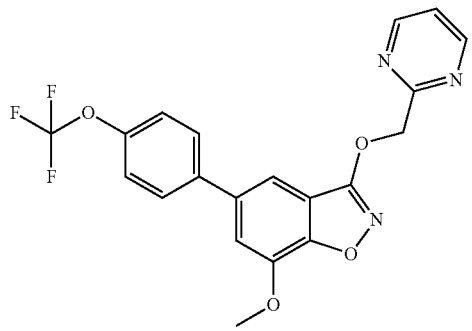 [SMILES: COc1cc(-c2ccc(OC(F)(F)F)cc2)cc2c(OCc3ncccn3)noc12]

1H NMR (400 MHz, DMSO-d6) δ 8.82 (d, J=4.9 Hz, 2H), 7.94-7.85 (m, 2H), 7.55 (d, J=1.4 Hz, 1H), 7.51-7.40 (m, 4H), 5.66 (s, 2H), 4.04 (s, 3H). m/z: 418 (MH+).

Example 23

7-methoxy-5-(3-methyl-4-(trifluoromethoxy)phenyl)-3-(pyrimidin-2-ylmethoxy)benzo[d]isoxazole

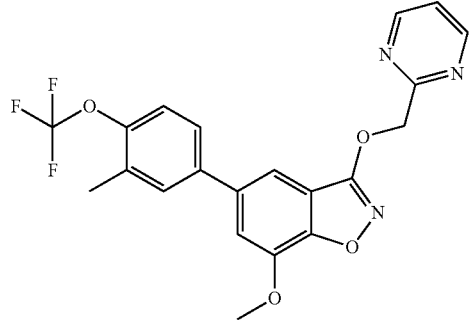 [SMILES: COc1cc(-c2ccc(OC(F)(F)F)c(C)c2)cc2c(OCc3ncccn3)noc12]

1H NMR (400 MHz, DMSO-d6) δ 8.83 (d, J=4.9 Hz, 2H), 7.83 (d, J=2.3 Hz, 1H), 7.71 (dd, J=8.5, 2.4 Hz, 1H), 7.55 (d, J=1.4 Hz, 1H), 7.51-7.45 (m, 2H), 7.37 (dt, J=8.5, 1.5 Hz, 1H), 5.65 (s, 2H), 4.04 (s, 3H), 2.35 (s, 3H). m/z: 432 (MH+).

Example 24

5-(2-fluoro-4-(trifluoromethyl)phenyl)-7-methoxy-3-(pyrimidin-2-ylmethoxy)benzo[d]isoxazole

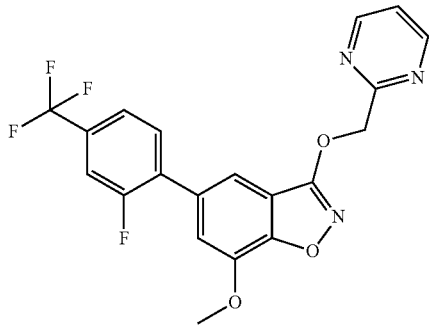 [SMILES: COc1cc(-c2ccc(C(F)(F)F)cc2F)cc2c(OCc3ncccn3)noc12]

1H NMR (400 MHz, DMSO-d6) δ 8.82 (d, J=4.9 Hz, 2H), 7.89 (t, J=7.9 Hz, 1H), 7.86-7.79 (m, 1H), 7.72-7.66 (m, 1H), 7.52 (t, J=1.5 Hz, 1H), 7.47 (t, J=4.9 Hz, 1H), 7.42 (t, J=1.3 Hz, 1H), 5.66 (s, 2H), 4.01 (s, 3H). m/z: 420 (MH+).

Example 25

7-methoxy-5-(2-methyl-4-(trifluoromethoxy)phenyl)-3-(pyrimidin-2-ylmethoxy)benzo[d]isoxazole

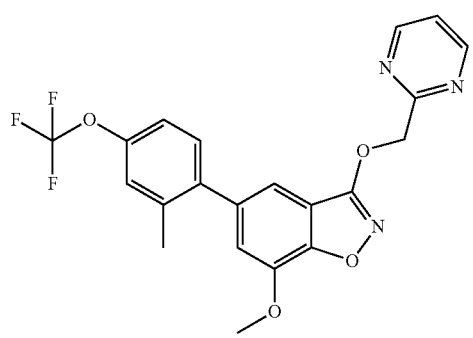

1H NMR (400 MHz, DMSO-d6) δ 8.81 (d, J=4.9 Hz, 2H), 7.47 (t, J=4.9 Hz, 1H), 7.40 (d, J=8.4 Hz, 1H), 7.36-7.31 (m, 1H), 7.28-7.23 (m, 1H), 7.22 (d, J=1.3 Hz, 1H), 7.18 (d, J=1.3 Hz, 1H), 5.64 (s, 2H), 3.96 (s, 3H), 2.28 (s, 3H). m/z: 432 (MH+).

Example 26

6-methyl-3-(pyrimidin-2-ylmethoxy)-5-(4-(trifluoromethoxy)phenyl)benzo[d]isoxazole

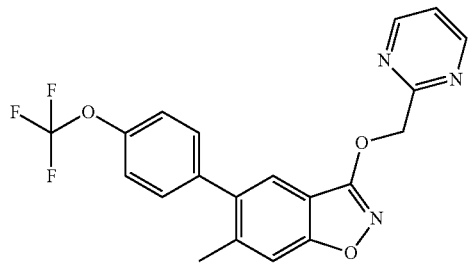 [SMILES: Cc1cc2onc(OCc3ncccn3)c2cc1-c1ccc(OC(F)(F)F)cc1]

1H NMR (400 MHz, DMSO-d6) δ 8.81 (d, J=4.9 Hz, 2H), 7.61-7.58 (m, 1H), 7.56 (s, 1H), 7.54-7.49 (m, 2H), 7.49-7.40 (m, 3H), 5.63 (s, 2H), 2.31 (s, 3H). m/z: 402 (MH+)

Example 27

6-methyl-5-(3-methyl-4-(trifluoromethoxy)phenyl)-3-(pyrimidin-2-ylmethoxy)benzo[d]isoxazole

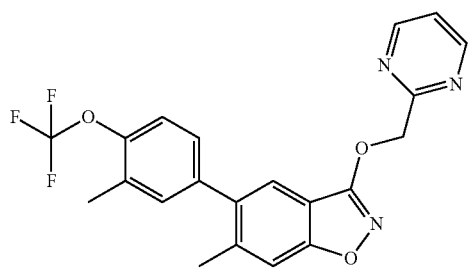 [SMILES: Cc1cc(-c2cc3c(OCc4ncccn4)noc3cc2C)ccc1OC(F)(F)F]

1H NMR (400 MHz, DMSO-d6) δ 8.81 (d, J=4.9 Hz, 21-1), 7.62-7.57 (m, 1H), 7.55 (s, 1H), 7.47 (t, J=4.9 Hz, 1H), 7.43 (d, J=2.0 Hz, 1H), 7.37 (dd, J=8.3, 1.5 Hz, 1H), 7.33 (dd, J=8.4, 2.1 Hz, 1H), 5.63 (s, 2H), 2.32 (s, 6H). m/z: 416 (MH+)

Example 28

5-(2-fluoro-4-(trifluoromethyl)phenyl)-6-methyl-3-(pyrimidin-2-ylmethoxy)benzo[d]isoxazole

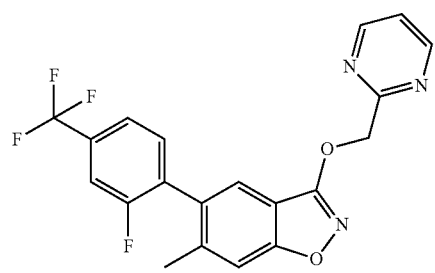 [SMILES: Cc1cc2onc(OCc3ncccn3)c2cc1-c1ccc(C(F)(F)F)cc1F]

1H NMR (400 MHz, DMSO-d6) δ 8.81 (d, J=4.9 Hz, 2H), 7.82 (dd, J=9.8, 1.4 Hz, 1H), 7.73-7.60 (m, 4H), 7.46 (t, J=4.9 Hz, 1H), 5.64 (s, 2H), 2.23 (s, 3H). m/z: 404 (MH+)

Example 29

6-methyl-5-(2-methyl-4-(trifluoromethoxy)phenyl)-3-(pyrimidin-2-ylmethoxy)benzo[d]isoxazole

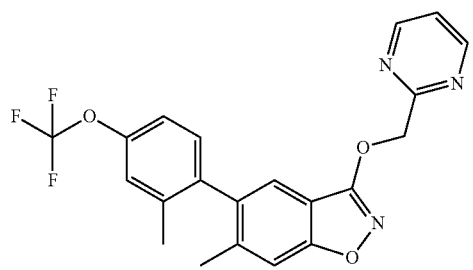

1H NMR (400 MHz, DMSO-d6) δ 8.81 (d, J=4.9 Hz, 2H), 7.63-7.58 (m, 1H), 7.49-7.43 (m, 2H), 7.35 (s, 1H), 7.24 (s, 2H), 5.62 (s, 2H), 2.08 (s, 3H), 2.02 (s, 3H). m/z: 416 (MH+)

Example 30

5-(2,2-difluorobenzo[d][1,3]dioxol-5-yl)-3-(pyrimidin-2-ylmethoxy)benzo[d]isoxazole

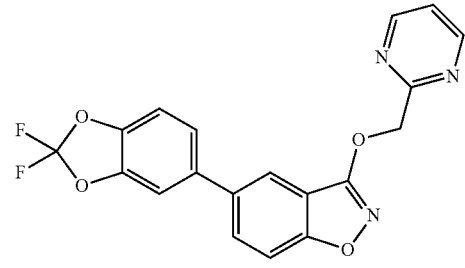 [SMILES: FC1(F)Oc2ccc(-c3ccc4onc(OCc5ncccn5)c4c3)cc2O1]

1H NMR (400 MHz, DMSO-d6) δ 8.83 (d, J=4.9 Hz, 2H), 8.07-8.02 (m, 1H), 7.96 (dd, J=8.8, 1.8 Hz, 1H), 7.87 (d, J=1.7 Hz, 1H), 7.72 (d, J=8.8 Hz, 1H), 7.59 (dd, J=8.4, 1.8 Hz, 1H), 7.52-7.45 (m, 2H), 5.67 (s, 2H). m/z: 384 (MH+)

Example 31

6-fluoro-3-(pyrimidin-2-ylmethoxy)-5-(4-(trifluoromethoxy)phenyl)benzo[d]isoxazole

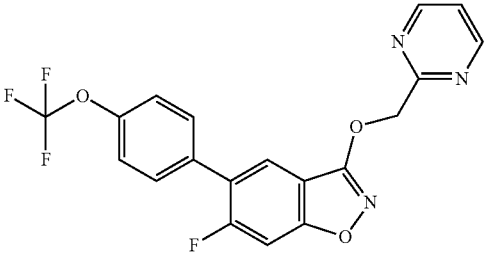 [SMILES: Fc1cc2onc(OCc3ncccn3)c2cc1-c1ccc(OC(F)(F)F)cc1]

1H NMR (400 MHz, DMSO-d6) δ 8.82 (d, J=4.9 Hz, 2H), 7.95 (d, J=7.4 Hz, 1H), 7.80 (d, J=10.5 Hz, 1H), 7.76-7.69 (m, 2H), 7.52-7.44 (m, 3H), 5.65 (s, 2H). m/z: 406 (MH+)

Example 32

6-fluoro-5-(3-methyl-4-(trifluoromethoxy)phenyl)-3-(pyrimidin-2-ylmethoxy)benzo[d]isoxazole

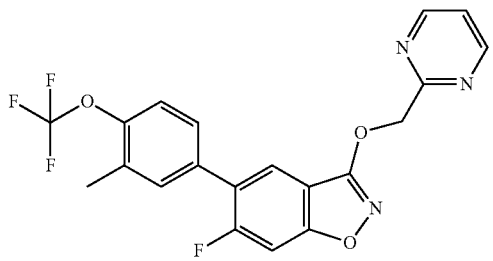 [SMILES: Cc1cc(-c2cc3c(OCc4ncccn4)noc3cc2F)ccc1OC(F)(F)F]

1H NMR (400 MHz, DMSO-d6) δ 8.83 (d, J=4.9 Hz, 2H), 7.94 (d, J=7.3 Hz, 1H), 7.79 (d, J=10.4 Hz, 1H), 7.64 (s, 1H), 7.53 (dt, J=8.6, 2.1 Hz, 1H), 7.48 (t, J=4.9 Hz, 1H), 7.41 (dd, J=8.4, 1.7 Hz, 1H), 5.65 (s, 2H), 2.33 (s, 3H). m/z: 420 (MH+)

Example 33

6-fluoro-5-(2-fluoro-4-(trifluoromethyl)phenyl)-3-(pyrimidin-2-ylmethoxy)benzo[d]isoxazole

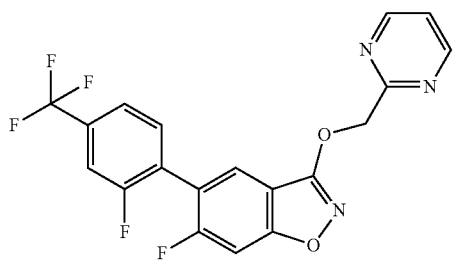 [SMILES: Fc1cc(C(F)(F)F)ccc1-c1cc2c(OCc3ncccn3)noc2cc1F]

1H NMR (400 MHz, DMSO-d6) δ 8.82 (d, J=4.9 Hz, 2H), 8.02 (d, J=6.9 Hz, 1H), 7.89-7.83 (m, 2H), 7.81 (t, J=7.6 Hz, 1H), 7.75-7.70 (m, 1H), 7.48 (t, J=4.9 Hz, 1H), 5.66 (s, 2H). m/z: 408 (MH+)

Example 34

6-fluoro-5-(2-methyl-4-(trifluoromethoxy)phenyl)-3-(pyrimidin-2-ylmethoxy)benzo[d]isoxazole

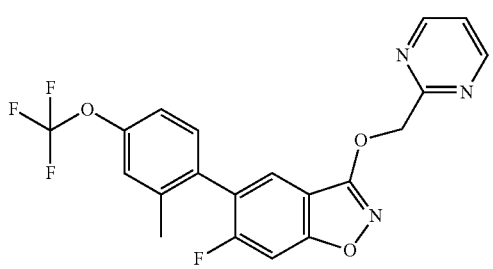 [SMILES: Cc1cc(OC(F)(F)F)ccc1-c1cc2c(OCc3ncccn3)noc2cc1F]

1H NMR (400 MHz, DMSO-d6) δ 8.82 (d, J=4.9 Hz, 2H), 7.79 (s, 1H), 7.77 (d, J 3.6 Hz, 1H), 7.47 (t, J=4.9 Hz, 1H), 7.39 (d, J=8.4 Hz, 1H), 7.38-7.35 (m, 1H), 7.31-7.24 (m, 1H), 5.64 (s, 2H), 2.16 (s, 3H). m/z: 420 (MH+)

Example 35

5-(2,2-difluorobenzo[d][1,3]dioxol-5-yl)-6-fluoro-3-(pyrimidin-2-ylmethoxy)benzo[d]isoxazole

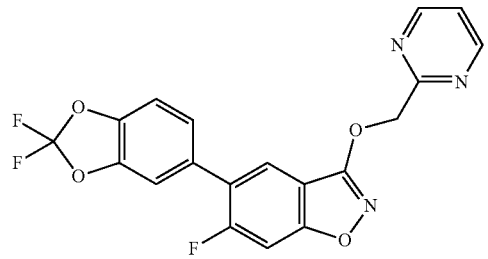 [SMILES: Fc1cc2onc(OCc3ncccn3)c2cc1-c1ccc2c(c1)OC(F)(F)O2]

1H NMR (400 MHz, DMSO-d6) δ 8.82 (d, J=4.9 Hz, 2H), 7.93 (d, J=7.4 Hz, 1H), 7.79 (d, J=10.4 Hz, 1H), 7.69 (t, J=1.5 Hz, 1H), 7.52 (d, J=8.4 Hz, 1H), 7.48 (t, J=4.9 Hz, 1H), 7.42 (dt, J=8.4, 1.7 Hz, 1H), 5.65 (s, 2H). m/z: 402 (MH+)

Example 36

3-((5-cyclopropyl-1,3,4-oxadiazol-2-yl)methoxy)-5-(2-methyl-4-(trifluoromethoxy)phenyl)benzo[d]isoxazole

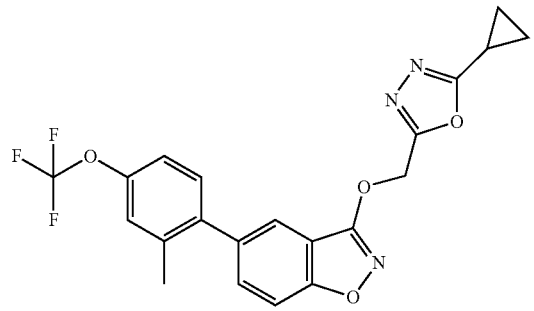 [SMILES: Cc1cc(OC(F)(F)F)ccc1-c1ccc2onc(OCc3nnc(C4CC4)o3)c2c1]

1H NMR (400 MHz, DMSO-d6) δ 7.76-7.70 (m, 2H), 7.66 (dd, J=8.7, 1.8 Hz, 1H), 7.37 (d, J=8.4 Hz, 1H), 7.35-7.32 (m, 1H), 7.28-7.21 (m, 1H), 5.70 (s, 2H), 2.30-2.25 (m, 1H), 2.23 (s, 3H), 1.19-1.11 (m, 2H), 1.04-0.96 (m, 2H). m/z: 432 (MH+)

Example 37

3-((5-cyclopropyl-1,3,4-oxadiazol-2-yl)methoxy)-5-(4-(trifluoromethyl)phenyl)benzo[d]isoxazole

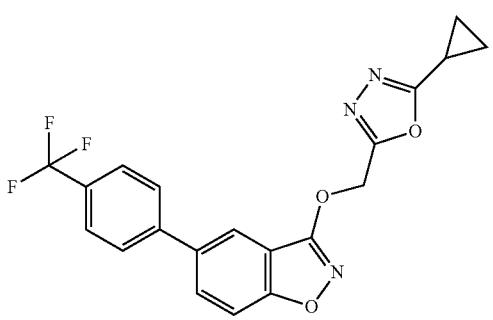 [SMILES: FC(F)(F)c1ccc(-c2ccc3onc(OCc4nnc(C5CC5)o4)c3c2)cc1]

1H NMR (400 MHz, DMSO-d6) δ 8.12 (dd, J=1.8, 0.8 Hz, 1H), 8.06 (dd, J=8.9, 1.9 Hz, 1H), 8.01-7.95 (m, 2H), 7.84-7.77 (m, 3H), 5.72 (s, 2H), 2.28 (tt, J=8.4, 4.9 Hz, 1H), 1.20-1.12 (m, 2H), 1.05-0.97 (m, 2H). m/z: 402 (MH+)

Example 38

3-((5-cyclopropyl-1,3,4-oxadiazol-2-yl)methoxy)-5-(2-fluoro-4-(trifluoromethyl)phenyl)benzo[d]isoxazole

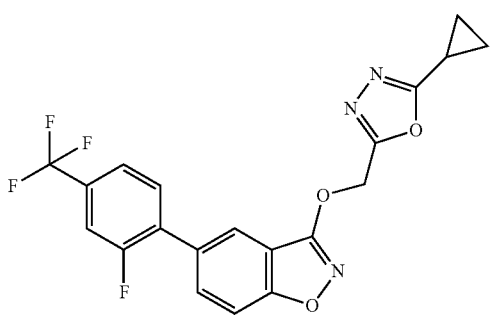 [SMILES: Fc1cc(C(F)(F)F)ccc1-c1ccc2onc(OCc3nnc(C4CC4)o3)c2c1]

1H NMR (400 MHz, DMSO-d6) δ 7.99 (dt, J=1.9, 1.0 Hz, 1H), 7.90 (dt, J=8.8, 1.7 Hz, 1H), 7.87-7.77 (m, 3H), 7.71-7.63 (m, 1H), 5.71 (s, 2H), 2.27 (tt, J=8.4, 4.9 Hz, 1H), 1.18-1.11 (m, 2H), 1.04-0.97 (m, 2H). m/z: 420 (MH+)

Example 39

3-((5-cyclopropyl-1,3,4-oxadiazol-2-yl)methoxy)-5-(2-methoxy-4-(trifluoromethoxy)phenyl)benzo[d]isoxazole

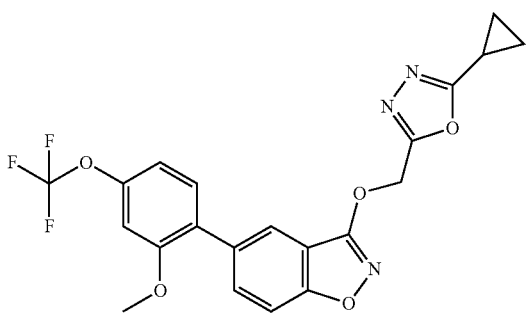 [SMILES: COc1cc(OC(F)(F)F)ccc1-c1ccc2onc(OCc3nnc(C4CC4)o3)c2c1]

1H NMR (400 MHz, DMSO-d6) δ 7.80-7.74 (m, 2H), 7.69 (dd, J=8.7, 0.9 Hz, 1H), 7.46 (d, J=8.4 Hz, 1H), 7.14-7.10 (m, 1H), 7.04-6.98 (m, 1H), 5.69 (s, 2H), 3.80 (s, 3H), 2.26 (tt, J=8.4, 4.9 Hz, 1H), 1.18-1.11 (m, 2H), 1.04-0.97 (m, 2H). m/z: 448 (MH+)

Example 40

3-((5-cyclopropyl-1,3,4-oxadiazol-2-yl)methoxy)-5-(3-methyl-4-(trifluoromethoxy)phenyl)benzo[d]isoxazole

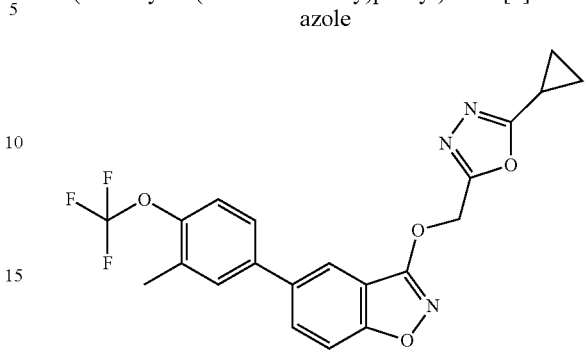

1H NMR (400 MHz, DMSO-d6) δ 8.04 (dd, J=1.9, 0.8 Hz, 1H), 8.00 (dd, J=8.8, 1.9 Hz, 1H), 7.82-7.79 (m, 1H), 7.76 (dd, J=8.8, 0.8 Hz, 1H), 7.71-7.64 (m, 1H), 7.37 (dd, J=8.5, 1.7 Hz, 1H), 5.71 (s, 2H), 2.34 (s, 3H), 2.28 (tt, J=8.4, 4.9 Hz, 1H), 1.19-1.12 (m, 2H), 1.05-0.98 (m, 2H). m/z: 432 (MH+)

Example 41

3-((5-cyclopropyl-1,3,4-oxadiazol-2-yl)methoxy)-5-(2-fluoro-4-(trifluoromethoxy)phenyl)benzo[d]isoxazole

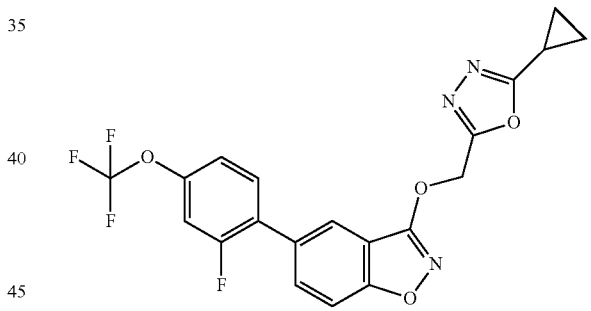

1H NMR (400 MHz, DMSO-d6) δ 7.96-7.91 (m, 1H), 7.86 (dt, J=8.8, 1.7 Hz, 1H), 7.79 (dd, J=8.7, 0.8 Hz, 1H), 7.75 (t, J=8.8 Hz, 1H), 7.56-7.50 (m, 1H), 7.38-7.31 (m, 1H), 5.71 (s, 2H), 2.27 (tt, J=8.4, 4.9 Hz, 1H), 1.18-1.11 (m, 2H), 1.04-0.98 (m, 2H). m/z: 436 (MH+)

Example 42

3-(oxetan-2-ylmethoxy)-5-(4-(trifluoromethoxy)phenyl)benzo[d]isoxazole

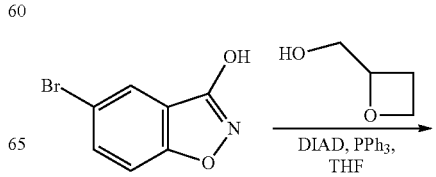

-continued

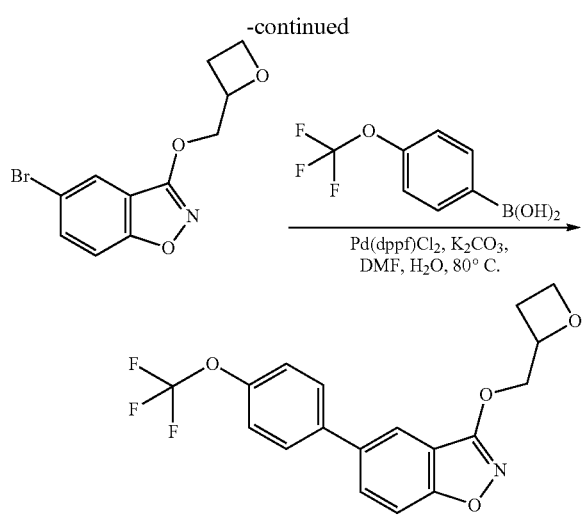

Step 1: Diisopropylazodicarboxylate (0.38 mL, 0.70 mmol) was added under stirring to a solution of 5-bromobenzo[d]isoxazol-3-ol (100 mg, 0.47 mmol), triphenylphosphine (184 mg, 0.70 mmol), and oxetan-2-ylmethanol (62 mg, 0.70 mmol) in THF. The reaction mixture was stirred at ambient temperature overnight. Volatiles were evaporated under vacuum and the residue was purified on 12 g silica gel with 0-100% ethyl acetate in hexane and gave 5-bromo-3-(oxetan-2-ylmethoxy)benzo[d]isoxazole (114 mg, 0.40 mmol).

Step 2: 5-Bromo-3-(pyrimidin-2-ylmethoxy)benzo[d]isoxazole (114 mg, 0.40 mmol), 4-(trifluoromethoxy)phenylboronic acid (100 mg, 0.49 mmol), potassium carbonate (500 mg), and [1,1'-Bis(diphenylphosphino)ferrocene]dichloropalladium(II) (25 mg, 0.034 mmol) were combined in 3 mL DMF. 1.5 mL water was added and the mixture was stirred at 60° C. for 30 minutes. The reaction mixture was diluted with 60 mL ethyl acetate, washed with water and brine and evaporated under vacuum. Flash chromatographic purification on 12 g silica gel with 0-60% ethyl acetate in hexane gave the title compound (115 mg, 0.31 mmol).

$^1$H NMR (400 MHz, DMSO-$d_6$) δ 8.04-7.99 (m, 1H), 7.97 (dd, J=8.8, 1.9 Hz, 1H), 7.91-7.82 (m, 2H), 7.73 (d, J=8.8 Hz, 1H), 7.44 (d, J=8.2 Hz, 2H), 5.16-5.06 (m, 1H), 4.65-4.49 (m, 4H), 2.81-2.68 (m, 1H), 2.68-2.56 (m, 1H). MS: 366 (MH$^+$).

Example 43

3-((1-methyl-1H-imidazol-4-yl)methoxy)-5-(4-(trifluoromethoxy)phenyl)benzo[d]isoxazole

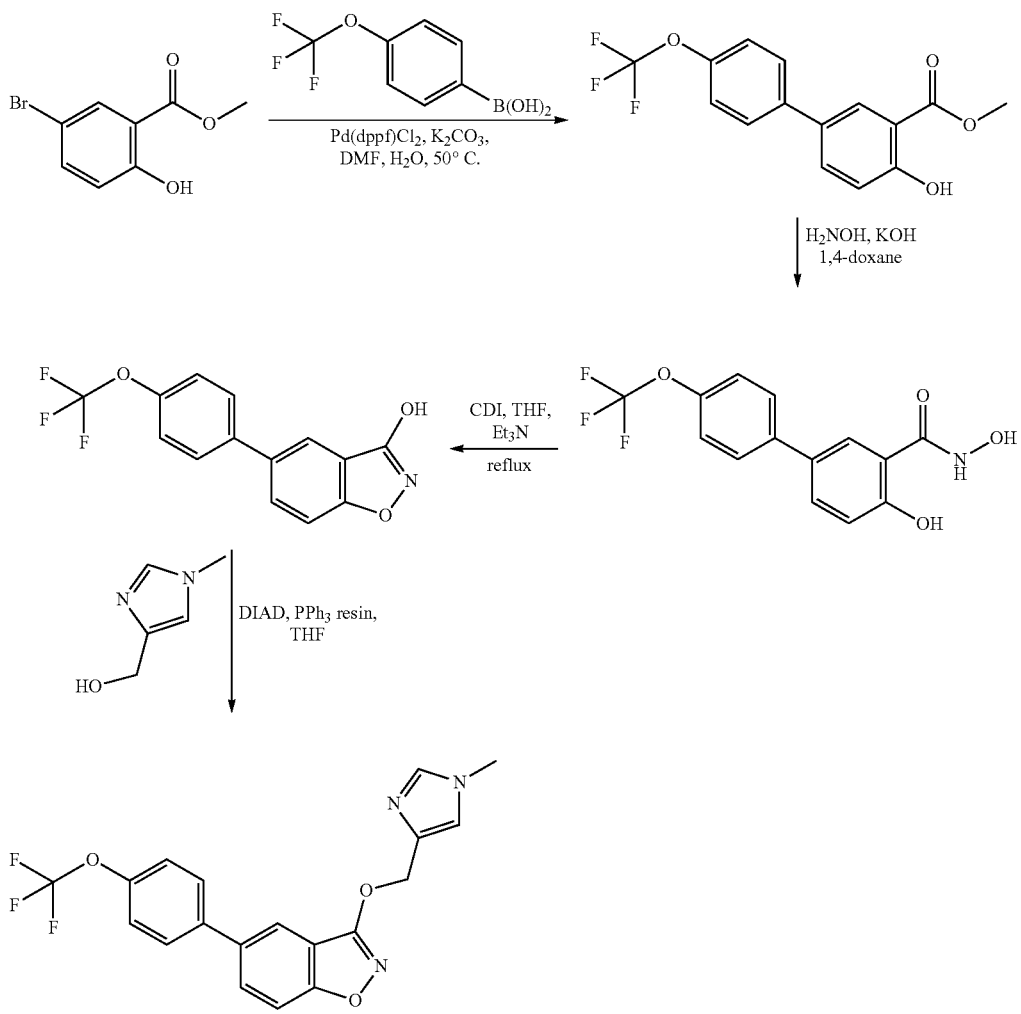

Step 1: Methyl 5-bromosalicylate (5 g, 21.6 mmol), 4-(trifluoromethoxy)phenylboronic acid (4.43 g, 21.6 mmol), potassium carbonate (10 g) and [1,1'-Bis(diphenylphosphino)ferrocene]dichloropalladium(II) (800 mg, 1.09 mmol) were combined in 10 mL DMF. 5 mL water was added and the mixture was stirred at 50° C. for 60 minutes. The reaction mixture was diluted with 300 mL ethyl acetate, washed with water and brine and evaporated under vacuum. Flash chromatographic purification on 120 g silica gel with 0-100% ethyl acetate in hexane gave methyl 4-hydroxy-4'-(trifluoromethoxy)-[1,1'-biphenyl]-3-carboxylate (5.7 g, 18.3 mmol).

Step 2: A solution of 4-hydroxy-4'-(trifluoromethoxy)-[1,1'-biphenyl]-3-carboxylate (5.7 g, 18.3 mmol) in 10 mL 1,4-dioxane was added to a mixture of 10 mL 50% aqueous KOH and 10 mL 50% aqueous hydroxylamine over 10 minutes. The reaction mixture was stirred at ambient temperature for 4 hours. After acidifying with concentrated HCl, the formed precipitate was filtered, washed with water and dried.

Step 3: The precipitate from Step 2 was dissolved in 50 mL THF. Carbonyldiimidazole (6.23 g, 38.4 mmol) was added and stirred for 10 minutes. 12 mL triethylamine was added and the mixture was heated at reflux for two hours. After cooling, the volatiles were removed under vacuum. To the residue was added 50 mL water and the pH was adjusted to pH 1 with 1N HCl. The formed precipitate was filtered, washed with water and dried giving 5-(4-(trifluoromethoxy)phenyl)benzo[d]isoxazol-3-ol (4.5 g, 15.2 mmol) as a tan solid.

Step 4: Diisopropylazodicarboxylate 40% solution in toluene (0.27 mL, 0.51 mmol) was added under stirring to a solution of 5-(4-(trifluoromethoxy)phenyl)benzo[d]isoxazol-3-ol (100 mg, 0.34 mmol), triphenylphosphine on resin (3 mmol/g) (330 mg, 1 mmol), and 1-methylimidazol-4-yl methanol (60 mg, 0.51 mmol) in THF. The reaction mixture was stirred at ambient temperature overnight. Volatiles were evaporated under vacuum and the residue was purified on 12 g silica gel with 0-20% methanol in dichloromethane and gave the title compound (40 mg, 0.103 mmol) as yellowish oil.

$^1$H NMR (400 MHz, DMSO-d$_6$) δ 8.07-7.97 (m, 2H), 7.89-7.81 (m, 2H), 7.54 (d, J=8.7 Hz, 1H), 7.50-7.41 (m, 3H), 7.12 (d, J=1.3 Hz, 1H), 5.03 (s, 2H), 3.59 (s, 3H). MS: 390 (MH$^+$).

The following compounds were synthesized using the same procedure but substituting the appropriate alcohol in Step 4:

Example 44

3-((1-methyl-1H-imidazol-4-yl)methoxy)-5-(4-(trifluoromethoxy)phenyl)benzo[d]isoxazole

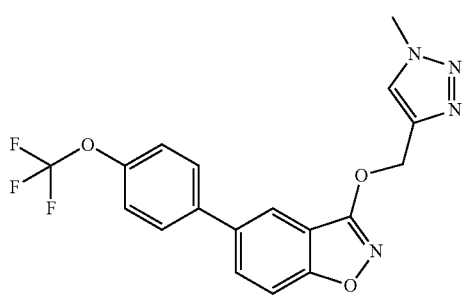 [SMILES: Cn1cc(COc2noc3ccc(-c4ccc(OC(F)(F)F)cc4)cc23)nn1]

$^1$H NMR (400 MHz, DMSO-d$_6$) δ 8.30 (s, 1H), 8.01-7.91 (m, 2H), 7.90-7.79 (m, 2H), 7.79-7.71 (m, 1H), 7.46-7.39 (m, 2H), 5.54 (s, 2H), 4.06 (s, 3H). MS: 391 (MH$^+$).

Example 45

3-((1H-pyrazol-4-yl)methoxy)-5-(4-(trifluoromethoxy)phenyl)benzo[d]isoxazole

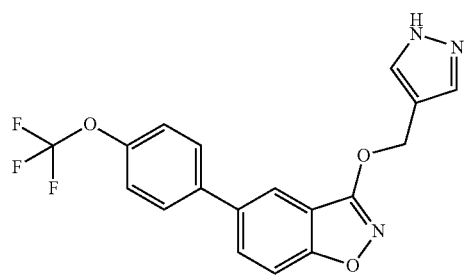 [SMILES: FC(F)(F)Oc1ccc(-c2ccc3onc(OCc4cn[nH]c4)c3c2)cc1]

$^1$H NMR (400 MHz, DMSO-d$_6$) δ 12.93 (s, 1H), 8.00-7.92 (m, 3H), 7.90-7.81 (m, 2H), 7.76-7.66 (m, 2H), 7.46-7.38 (m, 2H), 5.39 (s, 2H). MS: 376 (MH$^+$).

Example 46

4-(((5-(4-(trifluoromethoxy)phenyl)benzo[d]isoxazol-3-yl)oxy)methyl)pyrrolidin-2-one

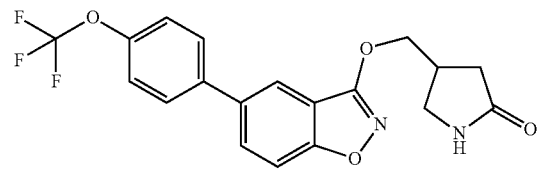 [SMILES: O=C1CC(COc2noc3ccc(-c4ccc(OC(F)(F)F)cc4)cc23)CN1]

$^1$H NMR (400 MHz, DMSO-d$_6$) δ 8.01-7.93 (m, 2H), 7.90-7.81 (m, 2H), 7.73 (dd, J=8.6, 0.9 Hz, 1H), 7.61 (s, 1H), 7.49-7.41 (m, 2H), 4.47-4.39 (m, 2H), 3.44 (t, J=9.5, 8.4 Hz, 1H), 3.17 (dd, J=9.9, 5.7 Hz, 1H), 3.06-2.90 (m, 1H), 2.35 (dd, J=16.7, 9.0 Hz, 1H), 2.14 (dd, J=16.7, 6.9 Hz, 1H). MS: 393 (MH$^+$).

Example 47

3-((1-ethyl-1H-imidazol-2-yl)methoxy)-5-(4-(trifluoromethoxy)phenyl)benzo[d]isoxazole

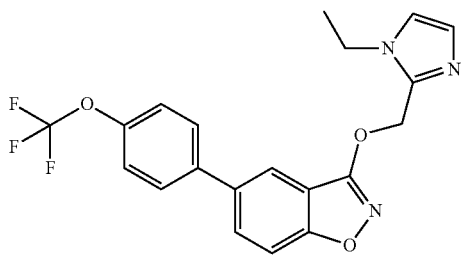 [SMILES: CCn1ccnc1COc1noc2ccc(-c3ccc(OC(F)(F)F)cc3)cc12]

¹H NMR (400 MHz, DMSO-d₆) δ 8.02-7.94 (m, 2H), 7.90-7.81 (m, 2H), 7.76 (d, J=9.3 Hz, 1H), 7.46-7.39 (m, 2H), 7.33 (d, J=1.1 Hz, 1H), 6.95 (d, J=1.1 Hz, 1H), 5.52 (s, 2H), 4.10 (q, J=7.3 Hz, 2H), 1.35 (t, J=7.2 Hz, 3H). MS: 404 (MH⁺).

Example 48

3-((1-isopropyl-1H-imidazol-2-yl)methoxy)-5-(4-(trifluoromethoxy)phenyl)benzo[d]isoxazole

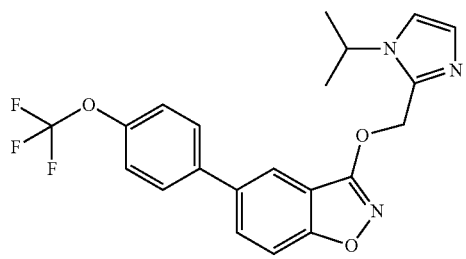 [SMILES: CC(C)n1ccnc1COc1noc2ccc(-c3ccc(OC(F)(F)F)cc3)cc12]

¹H NMR (400 MHz, DMSO-d₆) δ 8.03-7.93 (m, 2H), 7.89-7.80 (m, 2H), 7.80-7.72 (m, 1H), 7.46-7.39 (m, 3H), 7.00-6.94 (m, 1H), 5.54 (s, 2H), 4.60 (p, J=6.5 Hz, 1H), 1.40 (d, J=6.6 Hz, 6H). MS: 418 (MH⁺).

Example 49

3-((1-ethyl-1H-imidazol-5-yl)methoxy)-5-(4-(trifluoromethoxy)phenyl)benzo[d]isoxazole

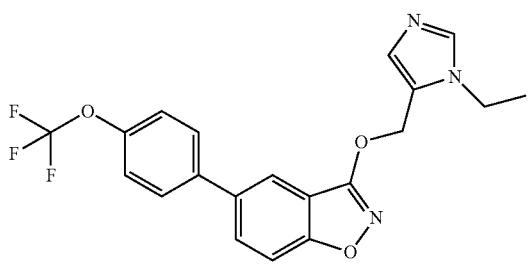 [SMILES: CCn1cncc1COc1noc2ccc(-c3ccc(OC(F)(F)F)cc3)cc12]

¹H NMR (400 MHz, DMSO-d₆) δ 8.01-7.61 (m, 5H), 7.49-7.39 (m, 3H), 7.15 (s, 1H), 5.52 (s, 2H), 4.08 (q, J=7.3 Hz, 2H), 1.37 (t, J=7.3 Hz, 3H). MS: 404 (MH⁺).

Example 50

3-((1-methyl-1H-imidazol-5-yl)methoxy)-5-(4-(trifluoromethoxy)phenyl)benzo[d]isoxazole

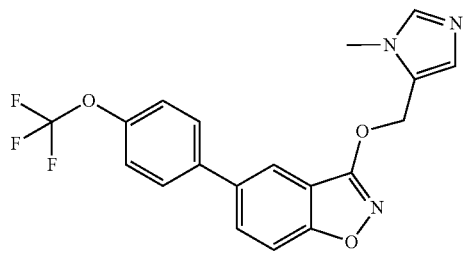 [SMILES: Cn1cncc1COc1noc2ccc(-c3ccc(OC(F)(F)F)cc3)cc12]

¹H NMR (400 MHz, DMSO-d₆) δ 8.01 (dd, J=1.8, 0.8 Hz, 1H), 7.97 (dd, J=8.8, 1.9 Hz, 1H), 7.90-7.81 (m, 2H), 7.74 (dd, J=8.8, 0.8 Hz, 1H), 7.71 (d, J=1.0 Hz, 1H), 7.49-7.39 (m, 2H), 7.14 (d, J=1.0 Hz, 1H), 5.52 (s, 2H), 3.71 (s, 3H). MS: 390 (MH⁺).

Example 51

3-(imidazo[1,2-a]pyridin-2-ylmethoxy)-5-(4-(trifluoromethoxy)phenyl)benzo[d]isoxazole

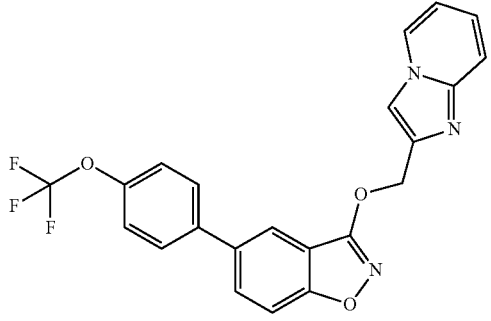 [SMILES: FC(F)(F)Oc1ccc(-c2ccc3onc(OCc4cn5ccccc5n4)c3c2)cc1]

¹H NMR (400 MHz, DMSO-d₆) δ 8.55 (dt, J=6.8, 1.1 Hz, 1H), 8.15 (s, 1H), 8.00-7.93 (m, 2H), 7.89-7.81 (m, 2H), 7.74 (dd, J=8.6, 1.0 Hz, 1H), 7.54 (dt, J=9.2, 1.1 Hz, 1H), 7.42 (dd, J=8.5, 1.4 Hz, 2H), 7.26 (ddd, J=8.9, 6.7, 1.2 Hz, 1H), 6.90 (td, J=6.8, 1.1 Hz, 1H), 5.58 (s, 2H). MS: 426 (MH⁺).

Example 52

3-((2,5-dimethyloxazol-4-yl)methoxy)-5-(4-(trifluoromethoxy)phenyl)benzo[d]isoxazole

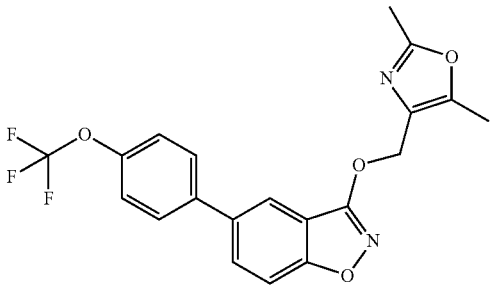 [SMILES: Cc1nc(COc2noc3ccc(-c4ccc(OC(F)(F)F)cc4)cc23)c(C)o1]

¹H NMR (400 MHz, DMSO-d₆) δ 8.00-7.92 (m, 2H), 7.90-7.82 (m, 2H), 7.72 (d, J=9.3 Hz, 1H), 7.42 (dd, J=8.8, 1.3 Hz, 2H), 5.29 (s, 2H), 2.37 (s, 3H), 2.34 (s, 3H). MS: 405 (MH⁺).

Example 53

3-(oxazol-2-ylmethoxy)-5-(4-(trifluoromethoxy)phenyl)benzo[d]isoxazole

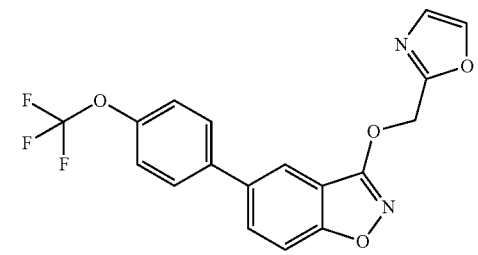 [SMILES: FC(F)(F)Oc1ccc(-c2ccc3onc(OCc4ncco4)c3c2)cc1]

¹H NMR (400 MHz, DMSO-d₆) δ 8.23 (d, J=0.8 Hz, 1H), 8.05-8.01 (m, 1H), 7.99 (dd, J=8.8, 1.9 Hz, 1H), 7.91-7.83 (m,

2H), 7.76 (d, J=8.8 Hz, 1H), 7.43 (dd, J=8.8, 1.2 Hz, 2H), 7.32 (d, J=0.8 Hz, 1H), 5.62 (s, 2H). MS: 377 (MH⁺).

Example 54

2-(1-(((5-(4-(trifluoromethoxy)phenyl)benzo[d]isoxazol-3-yl)oxy)methyl)cyclopropyl)acetonitrile

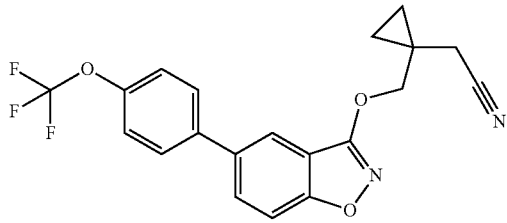 [SMILES: N#CCC1(COc2noc3ccc(-c4ccc(OC(F)(F)F)cc4)cc23)CC1]

¹H NMR (400 MHz, DMSO-d₆) δ 8.05-8.00 (m, 1H), 7.97 (dd, J=8.8, 1.9 Hz, 1H), 7.89-7.81 (m, 2H), 7.73 (d, J=8.7 Hz, 1H), 7.51-7.42 (m, 2H), 4.35 (s, 2H), 2.87 (s, 2H), 0.87-0.79 (m, 2H), 0.75-0.68 (m, 2H). MS: 389 (MH⁺).

Example 55

3-(2-(1H-imidazol-1-yl)ethoxy)-5-(4-(trifluoromethoxy)phenyl)benzo[d]isoxazole

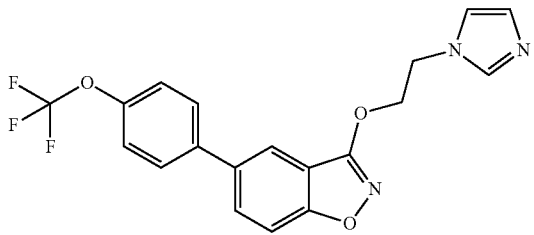 [SMILES: FC(F)(F)Oc1ccc(-c2ccc3onc(OCCn4ccnc4)c3c2)cc1]

¹H NMR (400 MHz, DMSO-d₆) δ 8.00 (dd, J=1.8, 0.8 Hz, 1H), 7.96 (dd, J=8.8, 1.9 Hz, 1H), 7.89-7.80 (m, 2H), 7.78-7.69 (m, 2H), 7.50-7.42 (m, 2H), 7.31 (t, J=1.2 Hz, 1H), 6.88 (t, J=1.0 Hz, 1H), 4.67 (t, J=4.9 Hz, 2H), 4.48 (t, J=4.9 Hz, 2H). MS: 390 (MH⁺).

Example 56

1-methyl-4-(((5-(4-(trifluoromethoxy)phenyl)benzo[d]isoxazol-3-yl)oxy)methyl)pyrrolidin-2-one

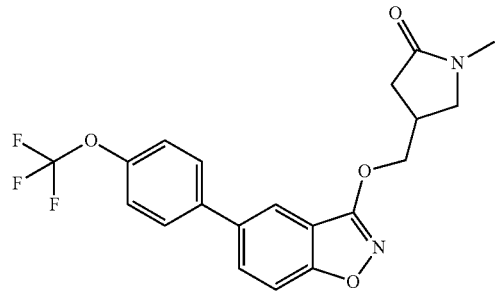 [SMILES: CN1CC(COc2noc3ccc(-c4ccc(OC(F)(F)F)cc4)cc23)CC1=O]

¹H NMR (400 MHz, DMSO-d₆) δ 8.00-7.93 (m, 2H), 7.90-7.79 (m, 2H), 7.77-7.69 (m, 1H), 7.49-7.41 (m, 2H), 4.47-4.37 (m, 2H), 3.54 (dd, J=10.0, 8.1 Hz, 1H), 3.31-3.24 (m, 1H), 2.92 (hept, J=6.7 Hz, 1H), 2.72 (s, 3H), 2.48-2.40 (m, 1H), 2.23 (dd, J=16.8, 6.6 Hz, 1H). MS: 407 (MH⁺).

Example 57

3-(2-(2-methyl-1H-imidazol-1-yl)ethoxy)-5-(4-(trifluoromethoxy)phenyl)benzo[d]isoxazole

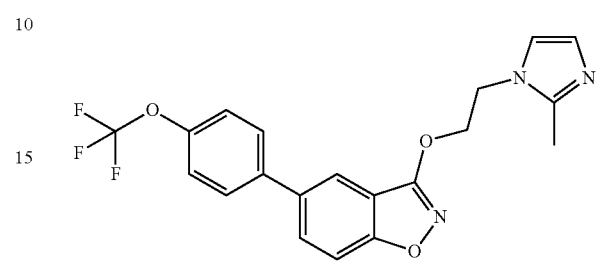

¹H NMR (400 MHz, DMSO-d₆) δ 7.95 (dd, J=8.8, 1.9 Hz, 1H), 7.93-7.87 (m, 1H), 7.87-7.79 (m, 2H), 7.73 (dd, J=8.6, 0.9 Hz, 1H), 7.46 (dd, J=8.4, 1.3 Hz, 2H), 7.19 (d, J=1.3 Hz, 1H), 6.71 (d, J=1.3 Hz, 1H), 4.67 (t, J=4.9 Hz, 2H), 4.39 (t, J=5.0 Hz, 2H), 2.33 (s, 3H). MS: 404 (MH⁺).

Example 58

3-(2-(1H-1,2,4-triazol-1-yl)ethoxy)-5-(4-(trifluoromethoxy)phenyl)benzo[d]isoxazole

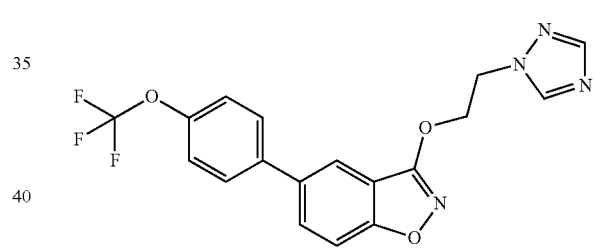

¹H NMR (400 MHz, DMSO-d₆) δ 8.66 (s, 1H), 7.99 (s, 1H), 7.95 (dd, J=8.8, 1.9 Hz, 1H), 7.93-7.88 (m, 1H), 7.89-7.79 (m, 2H), 7.72 (dd, J=8.8, 0.8 Hz, 1H), 7.49-7.40 (m, 2H), 4.82-4.69 (m, 4H). MS: 391 (MH⁺).

Example 59

1-(2-((5-(4-(trifluoromethoxy)phenyl)benzo[d]isoxazol-3-yl)oxy)ethyl)pyrrolidin-2-one

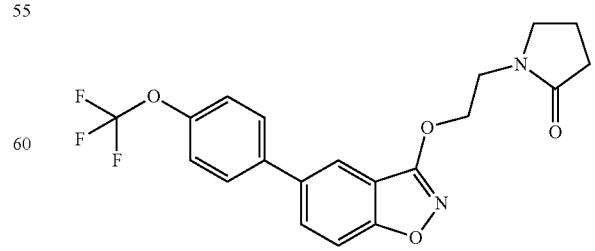

¹H NMR (400 MHz, DMSO-d₆) δ 7.96 (dd, J=8.8, 1.9 Hz, 1H), 7.93-7.89 (m, 1H), 7.89-7.80 (m, 2H), 7.73 (dd, J=8.7, 0.8 Hz, 1H), 7.50-7.42 (m, 2H), 4.54 (t, J=5.3 Hz, 2H), 3.67 (t, J=5.3 Hz, 2H), 3.49 (t, J=7.0 Hz, 2H), 2.19 (dd, J=8.6, 7.5 Hz, 2H), 1.91 (tt, J=7.8, 6.7 Hz, 2H). MS: 407 (MH⁺).

Example 60

3-(2-methoxyethoxy)-5-(4-(trifluoromethoxy)phenyl)benzo[d]isoxazole

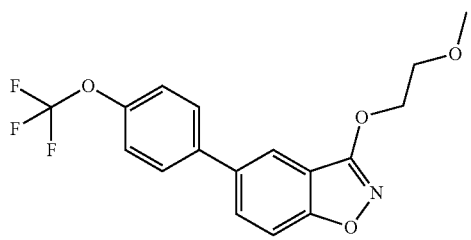 [SMILES: COCCOc1noc2ccc(-c3ccc(OC(F)(F)F)cc3)cc12]

¹H NMR (400 MHz, DMSO-d₆) δ 8.00-7.90 (m, 2H), 7.91-7.82 (m, 2H), 7.76-7.69 (m, 1H), 7.48-7.39 (m, 2H), 4.58-4.51 (m, 2H), 3.80-3.73 (m, 2H), 3.33 (s, 3H). MS: 354 (M⁺)

Example 61

(R)-5-(((5-(4-(trifluoromethoxy)phenyl)benzo[d]isoxazol-3-yl)oxy)methyl)pyrrolidin-2-one

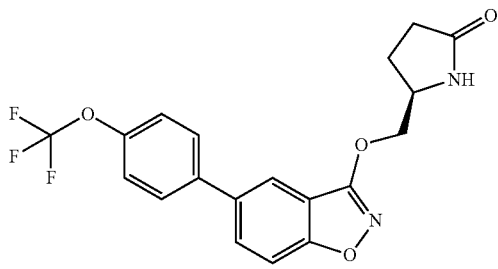 [SMILES: O=C1CC[C@H](COc2noc3ccc(-c4ccc(OC(F)(F)F)cc4)cc23)N1]

¹H NMR (400 MHz, DMSO-d₆) δ 8.03-7.93 (m, 3H), 7.89-7.80 (m, 2H), 7.73 (d, J=8.7 Hz, 1H), 7.50-7.43 (m, 2H), 4.44 (dd, J=10.3, 4.3 Hz, 1H), 4.29 (dd, J=10.3, 6.5 Hz, 1H), 4.08-3.97 (m, 1H), 2.39-2.08 (m, 3H), 1.96-1.84 (m, 1H). MS: 393 (MH⁺).

Example 62

(S)-5-(((5-(4-(trifluoromethoxy)phenyl)benzo[d]isoxazol-3-yl)oxy)methyl)pyrrolidin-2-one

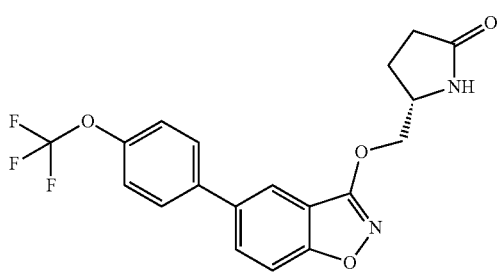 [SMILES: O=C1CC[C@@H](COc2noc3ccc(-c4ccc(OC(F)(F)F)cc4)cc23)N1]

¹H NMR (400 MHz, DMSO-d₆) δ 8.03-7.93 (m, 3H), 7.89-7.80 (m, 2H), 7.73 (dd, J=8.8, 0.8 Hz, 1H), 7.51-7.43 (m, 2H), 4.44 (dd, J=10.3, 4.3 Hz, 1H), 4.29 (dd, J=10.3, 6.6 Hz, 1H), 4.08-3.97 (m, 1H), 2.39-2.08 (m, 3H), 1.96-1.84 (m, 1H). MS: 393 (MH⁺).

Example 63

3-(2-(4H-1,2,4-triazol-4-yl)ethoxy)-5-(4-(trifluoromethoxy)phenyl)benzo[d]isoxazole

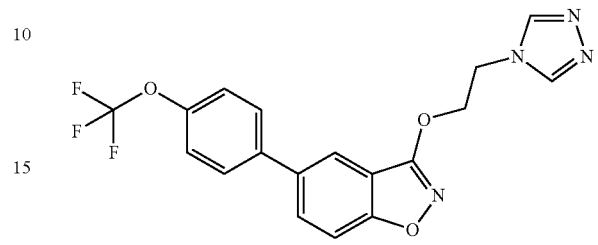

¹H NMR (400 MHz, DMSO-d₆) δ 8.66 (s, 2H), 8.09-8.04 (m, 1H), 7.96 (dd, J=8.8, 1.9 Hz, 1H), 7.89-7.81 (m, 2H), 7.72 (dd, J=8.8, 0.7 Hz, 1H), 7.50-7.43 (m, 2H), 4.70 (t, J=4.8 Hz, 2H), 4.57 (t, J=4.8 Hz, 2H). MS: 391 (MH⁺).

Example 64

3-((1-phenyl-1H-imidazol-2-yl)methoxy)-5-(4-(trifluoromethoxy)phenyl)benzo[d]isoxazole

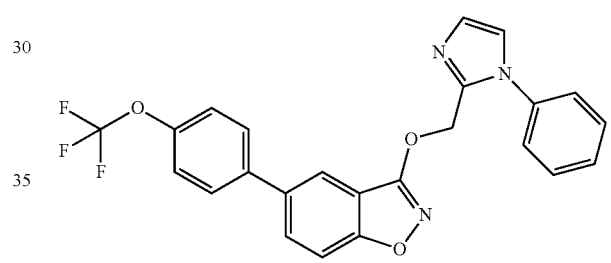

¹H NMR (400 MHz, DMSO-d₆) δ 7.96 (dd, J=8.8, 1.9 Hz, 1H), 7.93-7.88 (m, 1H), 7.88-7.81 (m, 2H), 7.71 (dd, J=8.8, 0.8 Hz, 1H), 7.59-7.35 (m, 8H), 7.16 (d, J=1.3 Hz, 1H), 5.42 (s, 2H). MS: 452 (MH⁺).

Example 65

3-((1-(pyridin-2-yl)-1H-pyrazol-4-yl)methoxy)-5-(4-(trifluoromethoxy)phenyl)benzo[d]isoxazole

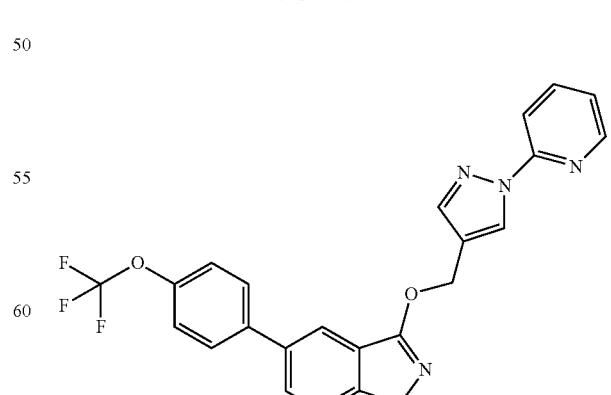

¹H NMR (400 MHz, DMSO-d₆) δ 8.86 (s, 1H), 8.47 (ddd, J=4.9, 1.8, 0.9 Hz, 1H), 8.06-7.89 (m, 5H), 7.90-7.79 (m, 2H), 7.74 (d, J=8.8 Hz, 1H), 7.47-7.39 (m, 2H), 7.37 (ddd, J=7.2, 4.9, 1.1 Hz, 1H), 5.50 (s, 2H). MS: 453 (MH⁺).

Example 66

3-(2-(1H-imidazol-2-yl)ethoxy)-5-(4-(trifluoromethoxy)phenyl)benzo[d]isoxazole

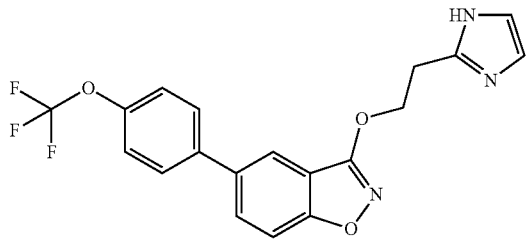 [SMILES: FC(F)(F)Oc1ccc(-c2ccc3onc(OCCc4ncc[nH]4)c3c2)cc1]

¹H NMR (400 MHz, DMSO-d₆) δ 11.85 (s, 1H), 7.99-7.89 (m, 2H), 7.90-7.80 (m, 2H), 7.76-7.69 (m, 1H), 7.48-7.41 (m, 2H), 6.90 (s, 2H), 4.72 (t, J=6.7 Hz, 2H), 3.22 (t, J=6.6 Hz, 2H). MS: 390 (MH⁺).

Example 67

3-((4-methoxypyrimidin-2-yl)methoxy)-5-(4-(trifluoromethoxy)phenyl)benzo[d]isoxazole

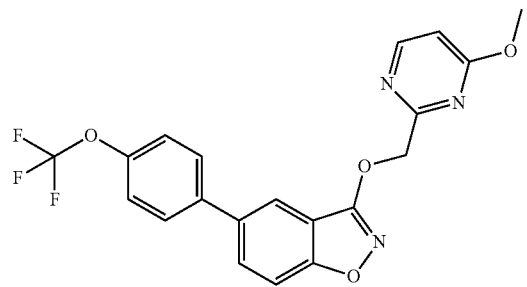 [SMILES: COc1ccnc(COc2noc3ccc(-c4ccc(OC(F)(F)F)cc4)cc23)n1]

¹H NMR (400 MHz, DMSO-d₆) δ 8.50 (d, J=5.8 Hz, 1H), 8.09-8.03 (m, 1H), 7.98 (dd, J=8.8, 1.9 Hz, 1H), 7.92-7.83 (m, 2H), 7.73 (dd, J=8.7, 0.8 Hz, 1H), 7.48-7.41 (m, 2H), 6.88 (d, J=5.8 Hz, 1H), 5.57 (s, 2H), 3.83 (s, 3H). MS: 418 (MH⁺).

Example 68

3-(2-(1H-pyrazol-1-yl)propoxy)-5-(4-(trifluoromethoxy)phenyl)benzo[d]isoxazole

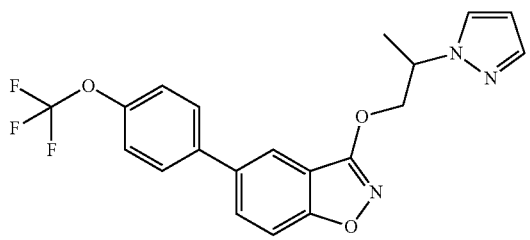 [SMILES: CC(COc1noc2ccc(-c3ccc(OC(F)(F)F)cc3)cc12)n1cccn1]

¹H NMR (400 MHz, DMSO-d₆) δ 7.94 (dd, J=8.8, 1.9 Hz, 1H), 7.91-7.85 (m, 2H), 7.85-7.78 (m, 2H), 7.72 (d, J=8.8 Hz, 1H), 7.48-7.41 (m, 3H), 6.22 (t, J=2.1 Hz, 1H), 5.01-4.88 (m, 1H), 4.74-4.61 (m, 2H), 1.55 (d, J=6.9 Hz, 3H). MS: 404 (MH⁺).

Example 69

3-(2-(3,5-dimethyl-1H-pyrazol-1-yl)ethoxy)-5-(4-(trifluoromethoxy)phenyl)benzo[d]isoxazole

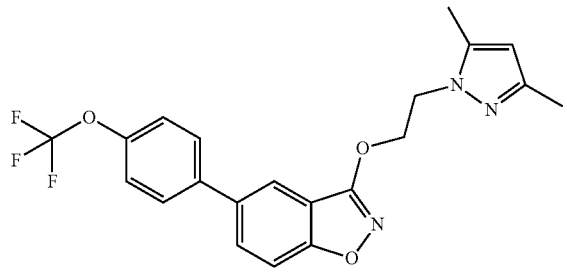

¹H NMR (400 MHz, DMSO-d₆) δ 7.95 (dd, J=8.8, 1.8 Hz, 1H), 7.90-7.78 (m, 3H), 7.73 (d, J=8.8 Hz, 1H), 7.45 (dd, J=8.5, 1.3 Hz, 2H), 5.77 (s, 1H), 4.71 (t, J=5.2 Hz, 2H), 4.43 (t, J=5.2 Hz, 2H), 2.23 (s, 3H), 2.04 (s, 3H). MS: 418 (MH⁺)

Example 70

3-((4-morpholinopyrimidin-2-yl)methoxy)-5-(4-(trifluoromethoxy)phenyl)benzo[d]isoxazole

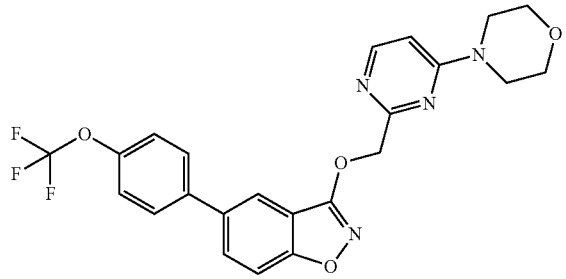 [SMILES: FC(F)(F)Oc1ccc(-c2ccc3onc(OCc4nccc(N5CCOCC5)n4)c3c2)cc1]

¹H NMR (400 MHz, DMSO-d₆) δ 8.19 (d, J=6.2 Hz, 1H), 8.04 (dd, J=1.9, 0.8 Hz, 1H), 7.97 (dd, J=8.8, 1.9 Hz, 1H), 7.91-7.83 (m, 2H), 7.72 (dd, J=8.8, 0.7 Hz, 1H), 7.49-7.38 (m, 2H), 6.74 (d, J=6.2 Hz, 1H), 5.41 (s, 2H), 3.59-3.47 (m, 8H). MS: 473 (MH⁺).

Example 71

(S)-3-((1-methylpyrrolidin-2-yl)methoxy)-5-(4-(trifluoromethoxy)phenyl)benzo[d]isoxazole

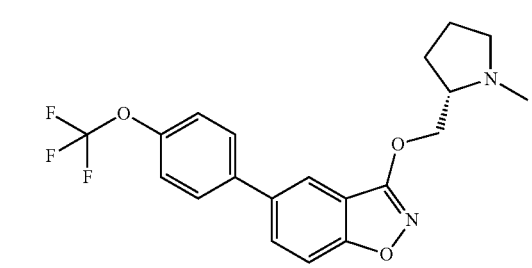 [SMILES: CN1CCC[C@H]1COc1noc2ccc(-c3ccc(OC(F)(F)F)cc3)cc12]

¹H NMR (400 MHz, DMSO-d₆) δ 10.90 (s, 1H), 8.12 (d, J=1.8 Hz, 1H), 7.99 (dd, J=8.8, 1.9 Hz, 1H), 7.90-7.81 (m, 2H), 7.76 (d, J=8.9 Hz, 1H), 7.51-7.43 (m, 2H), 4.86-4.71 (m, 2H), 3.95-3.77 (m, 1H), 3.73-3.55 (m, 1H), 3.17-3.06 (m, 1H), 2.97 (s, 3H), 2.88-2.74 (m, 1H), 2.37-1.69 (m, 3H). MS: 393 (MH⁺).

Example 72

(R)-3-((5-(4-(trifluoromethoxy)phenyl)benzo[d]isoxazol-3-yl)oxy)pyrrolidin-2-one

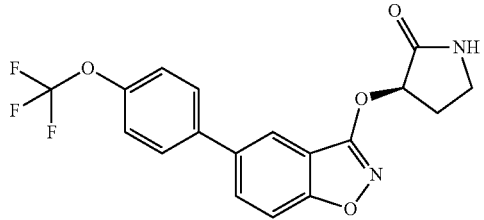 [SMILES: O=C1NCC[C@H]1Oc1noc2ccc(-c3ccc(OC(F)(F)F)cc3)cc12]

¹H NMR (400 MHz, DMSO-d₆) δ 8.25 (s, 1H), 7.99 (dt, J=4.8, 2.3 Hz, 2H), 7.93-7.82 (m, 2H), 7.76 (d, J=9.2 Hz, 1H), 7.45 (dd, J=8.6, 1.2 Hz, 2H), 5.40 (t, J=7.9 Hz, 1H), 3.39-3.20 (m, 2H), 2.78-2.66 (m, 1H), 2.26-2.11 (m, 1H). MS: 379 (MH⁺).

Example 73

3-((5-methylpyrazin-2-yl)methoxy)-5-(4-(trifluoromethoxy)phenyl)benzo[d]isoxazole

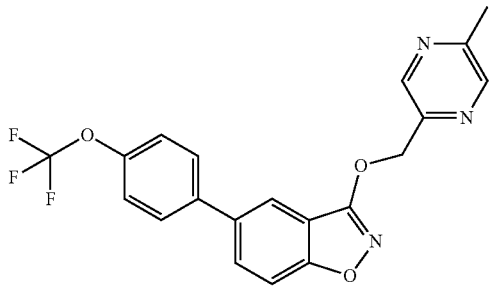 [SMILES: Cc1cnc(COc2noc3ccc(-c4ccc(OC(F)(F)F)cc4)cc23)cn1]

¹H NMR (400 MHz, DMSO-d₆) δ 8.80 (s, 1H), 8.58 (s, 1H), 8.09-8.03 (m, 1H), 7.97 (dd, J=8.8, 1.9 Hz, 1H), 7.90-7.82 (m, 2H), 7.73 (d, J=8.8 Hz, 1H), 7.47-7.39 (m, 2H), 5.58 (s, 2H), 2.51 (s, 3H). MS: 402 (MH⁺).

Example 74

3-(pyridazin-3-ylmethoxy)-5-(4-(trifluoromethoxy)phenyl)benzo[d]isoxazole

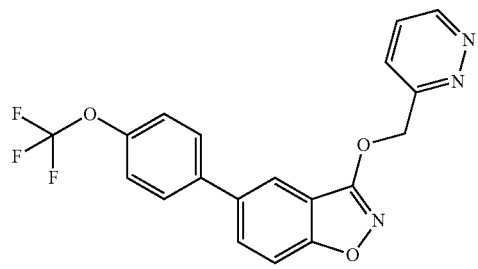 [SMILES: FC(F)(F)Oc1ccc(-c2ccc3onc(OCc4cccnn4)c3c2)cc1]

¹H NMR (400 MHz, DMSO-d₆) δ 9.25 (dd, J=5.0, 1.5 Hz, 1H), 8.09 (d, J=1.8 Hz, 1H), 7.99 (dt, J=8.5, 1.9 Hz, 2H), 7.91-7.82 (m, 2H), 7.83-7.72 (m, 2H), 7.44 (d, J=8.3 Hz, 2H), 5.79 (s, 2H). MS: 388 (MH⁺).

Example 75

3-(2-((5-(4-(trifluoromethoxy)phenyl)benzo[d]isoxazol-3-yl)oxy)ethyl)oxazolidin-2-one

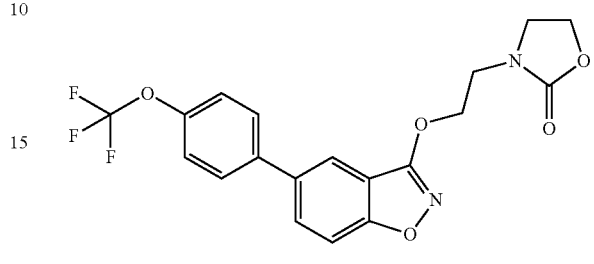

¹H NMR (400 MHz, DMSO-d₆) δ 7.96 (dd, J=8.8, 1.9 Hz, 1H), 7.94-7.90 (m, 1H), 7.89-7.80 (m, 2H), 7.74 (d, J=8.8 Hz, 1H), 7.46 (d, J=8.3 Hz, 2H), 4.58 (t, J=5.1 Hz, 2H), 4.25 (dd, J=8.9, 7.0 Hz, 2H), 3.75-3.63 (m, 4H). MS: 409 (MH⁺).

Example 76

3-(2-(3,5-dimethyl-1H-1,2,4-triazol-1-yl)ethoxy)-5-(4-(trifluoromethoxy)phenyl)benzo[d]isoxazole

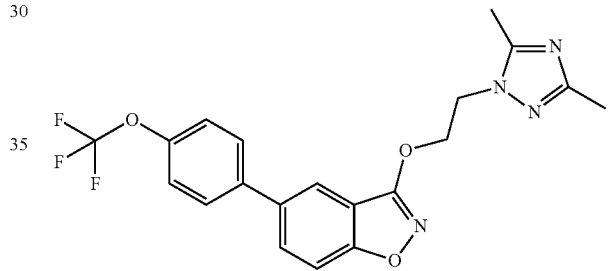

¹H NMR (400 MHz, DMSO-d₆) δ 7.95 (dd, J=8.8, 1.9 Hz, 1H), 7.86 (dd, J=1.8, 0.8 Hz, 1H), 7.85-7.78 (m, 2H), 7.73 (dd, J=8.8, 0.8 Hz, 1H), 7.45 (dd, J=8.5, 1.1 Hz, 2H), 4.73 (t, J=5.0 Hz, 2H), 4.53 (t, J=5.0 Hz, 2H), 2.37 (s, 3H), 2.13 (s, 3H). MS: 419 (MH⁺).

Example 77

3-(2-(1H-1,2,4-triazol-1-yl)propoxy)-5-(4-(trifluoromethoxy)phenyl)benzo[d]isoxazole

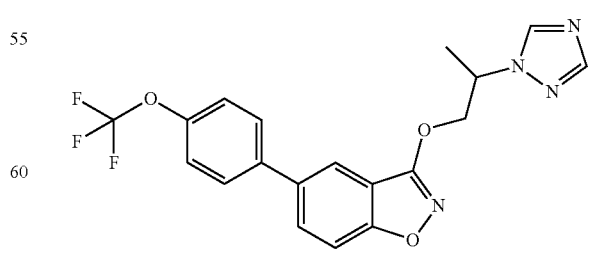

¹H NMR (400 MHz, DMSO-d₆) δ 8.70 (s, 1H), 7.98 (s, 1H), 7.95 (dd, J=8.8, 1.9 Hz, 1H), 7.89 (dd, J=1.9, 0.8 Hz, 1H), 7.86-7.78 (m, 2H), 7.72 (dd, J=8.8, 0.8 Hz, 1H), 7.48-

7.41 (m, 2H), 5.15-5.02 (m, 1H), 4.78-4.61 (m, 2H), 1.59 (d, J=6.9 Hz, 3H). MS: 405 (MH+).

Example 78

3-(2-morpholinoethoxy)-5-(4-(trifluoromethoxy)phenyl)benzo[d]isoxazole

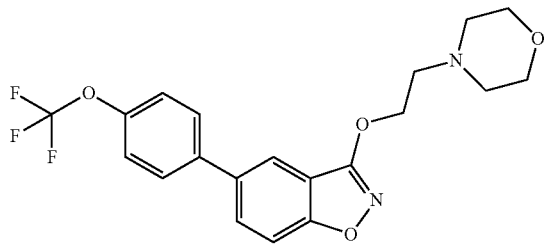 [SMILES: FC(F)(F)Oc1ccc(-c2ccc3onc(OCCN4CCOCC4)c3c2)cc1]

$^1$H NMR (400 MHz, DMSO-d$_6$) δ 7.99-7.92 (m, 2H), 7.90-7.81 (m, 2H), 7.72 (d, J=9.3 Hz, 1H), 7.45 (d, J=8.3 Hz, 2H), 4.54 (t, J=5.5 Hz, 2H), 3.59-3.52 (m, 4H), 2.81 (t, J=5.5 Hz, 2H), 2.53-2.48 (m, 4H). MS: 409 (MH+).

Example 79

3-(2-(3,5-dimethyl-1H-1,2,4-triazol-1-yl)propoxy)-5-(4-(trifluoromethoxy)phenyl)benzo[d]isoxazole

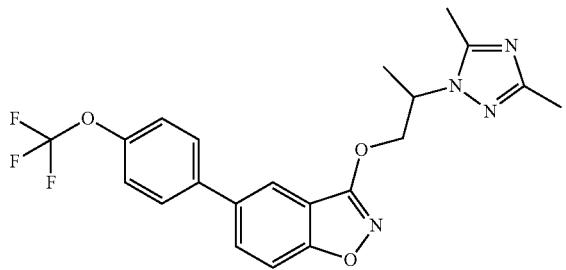 [SMILES: Cc1nc(C)n(C(C)COc2noc3ccc(-c4ccc(OC(F)(F)F)cc4)cc23)n1]

$^1$H NMR (400 MHz, DMSO-d$_6$) δ 7.95 (dd, J=8.8, 1.8 Hz, 1H), 7.86-7.78 (m, 3H), 7.73 (d, J=8.8 Hz, 1H), 7.45 (d, J=8.4 Hz, 2H), 5.00-4.87 (m, 1H), 4.65 (dd, J=10.6, 4.3 Hz, 1H), 4.58 (dd, J=10.5, 9.1 Hz, 1H), 2.36 (s, 3H), 2.14 (s, 3H), 1.47 (d, J=6.7 Hz, 3H). MS: 433 (MH+).

Example 80

1-(2-((7-fluoro-5-(4-(trifluoromethoxy)phenyl)benzo[d]isoxazol-3-yl)oxy)ethyl)pyrrolidin-2-one

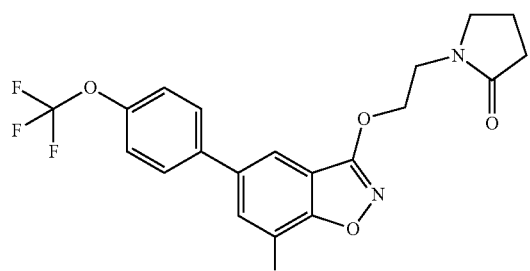

$^1$H NMR (400 MHz, DMSO-d$_6$) δ 7.98 (dd, J=12.2, 1.5 Hz, 1H), 7.93-7.82 (m, 2H), 7.79 (d, J=1.5 Hz, 1H), 7.46 (d, J=8.3 Hz, 2H), 4.55 (t, J=5.2 Hz, 2H), 3.67 (t, J=5.2 Hz, 2H), 3.48 (t, J=7.0 Hz, 2H), 2.19 (t, J=8.0 Hz, 2H), 1.90 (p, J=7.6 Hz, 2H). MS: 425 (MH+).

Example 81

3-((4-methoxypyridin-2-yl)methoxy)-5-(4-(trifluoromethoxy)phenyl)benzo[d]isoxazole

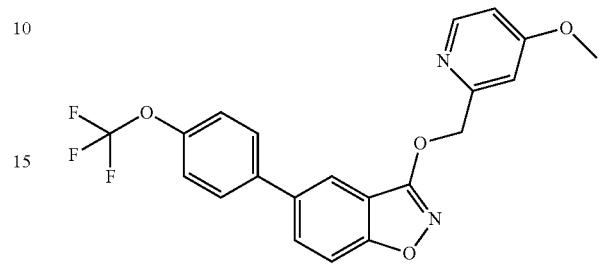

$^1$H NMR (400 MHz, DMSO-d$_6$) δ 8.41 (d, J=5.7 Hz, 1H), 8.12-8.06 (m, 1H), 7.98 (dd, J=8.8, 1.8 Hz, 1H), 7.92-7.83 (m, 2H), 7.74 (d, J=8.8 Hz, 1H), 7.44 (d, J=8.3 Hz, 2H), 7.23 (d, J=2.5 Hz, 1H), 6.98 (dd, J=5.8, 2.5 Hz, 1H), 5.49 (s, 2H), 3.84 (s, 3H). MS: 417 (MH+).

Example 82

3-(isoquinolin-3-ylmethoxy)-5-(4-(trifluoromethoxy)phenyl)benzo[d]isoxazole

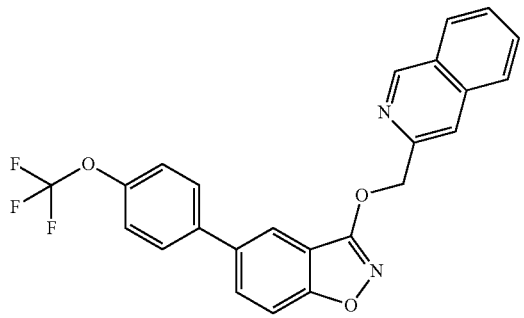 [SMILES: FC(F)(F)Oc1ccc(-c2ccc3onc(OCc4cc5ccccc5cn4)c3c2)cc1]

$^1$H NMR (400 MHz, DMSO-d$_6$) δ 9.36 (s, 1H), 8.16 (d, J=8.1 Hz, 1H), 8.12 (s, 1H), 8.09 (d, J=1.8 Hz, 1H), 8.02 (d, J=8.2 Hz, 1H), 7.98 (dd, J=8.8, 1.9 Hz, 1H), 7.91-7.84 (m, 2H), 7.81 (ddd, J=8.2, 6.9, 1.3 Hz, 1H), 7.75 (d, J=8.8 Hz, 1H), 7.71 (ddd, J=8.0, 7.0, 1.1 Hz, 1H), 7.44 (d, J=8.3 Hz, 2H), 5.71 (s, 2H). MS: 437 (MH+).

Example 83

3-((1H-1,2,3-triazol-4-yl)methoxy)-5-(4-(trifluoromethoxy)phenyl)benzo[d]isoxazole

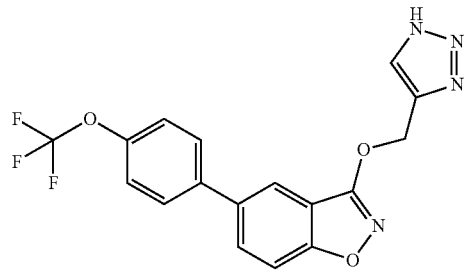

¹H NMR (400 MHz, DMSO-d₆) δ 8.18-7.94 (m, 3H), 7.92-7.81 (m, 2H), 7.76 (s, 1H), 7.57 (d, J=8.7 Hz, 1H), 7.45 (d, J=8.4 Hz, 2H), 5.31 (s, 2H). MS: 377 (MH⁺).

Example 84

3-(2-(1H-1,2,4-triazol-1-yl)ethoxy)-7-fluoro-5-(4-(trifluoromethoxy)phenyl)benzo[d]isoxazole

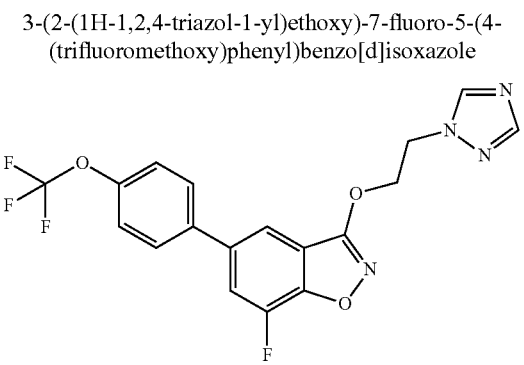

¹H NMR (400 MHz, DMSO-d₆) δ 8.66 (s, 1H), 8.03-7.93 (m, 2H), 7.93-7.83 (m, 2H), 7.81 (d, J=1.5 Hz, 1H), 7.46 (d, J=8.3 Hz, 2H), 4.79 (t, J=4.9 Hz, 2H), 4.72 (t, J=4.9 Hz, 2H). MS: 409 (MH⁺).

Example 85

4-(2-((5-(4-(trifluoromethoxy)phenyl)benzo[d]isoxazol-3-yl)oxy)ethyl)thiomorpholine 1,1-dioxide

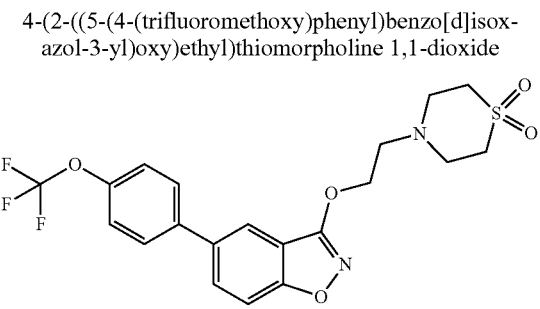

¹H NMR (400 MHz, DMSO-d₆) δ 7.96 (d, J=7.9 Hz, 2H), 7.88-7.81 (m, 2H), 7.73 (d, J=9.6 Hz, 1H), 7.45 (d, J=8.3 Hz, 2H), 4.54 (t, J=5.4 Hz, 2H), 3.11-2.79 (m, 10H). S: 457 (MH⁺).

Example 86

5-(4-(trifluoromethoxy)phenyl)-3-((4-(trifluoromethyl)pyrimidin-2-yl)methoxy)benzo[d]isoxazole

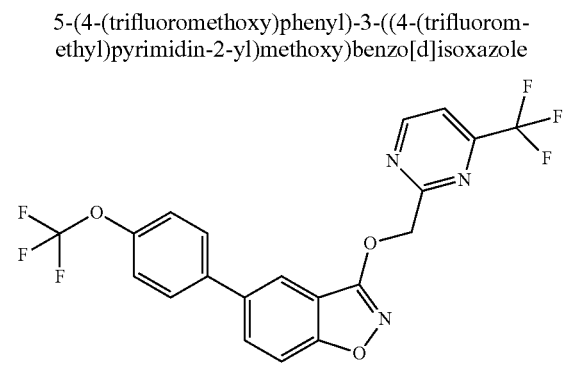

¹H NMR (400 MHz, DMSO-d₆) δ 9.22 (d, J=5.1 Hz, 1H), 8.10-8.04 (m, 1H), 8.02 (d, J=5.1 Hz, 1H), 8.00-7.92 (m, 1H), 7.91-7.84 (m, 2H), 7.73 (d, J=8.8 Hz, 1H), 7.49-7.41 (m, 2H), 5.81 (s, 2H). MS: 456 (MH⁺).

Example 87

7-methyl-3-((1-methyl-1H-1,2,3-triazol-4-yl)methoxy)-5-(4-(trifluoromethoxy)phenyl)benzo[d]isoxazole

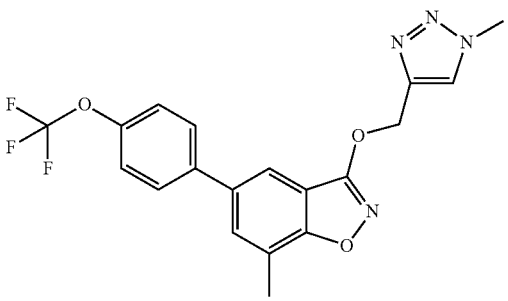 [SMILES: Cc1cc(-c2ccc(OC(F)(F)F)cc2)cc2c(OCc3cn(C)nn3)noc12]

1H NMR (400 MHz, DMSO-d6) δ 8.29 (s, 1H), 7.86-7.81 (m, 2H), 7.80 (dd, J=2.0, 1.1 Hz, 1H), 7.78-7.74 (m, 1H), 7.45-7.37 (m, 2H), 5.53 (s, 2H), 4.06 (s, 3H), 2.51 (s, 3H). m/z: 405 (MH+)

Example 88

1-(2-((7-methyl-5-(4-(trifluoromethoxy)phenyl)benzo[d]isoxazol-3-yl)oxy)ethyl)pyrrolidin-2-one

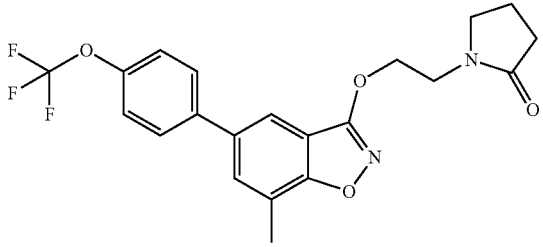 [SMILES: Cc1cc(-c2ccc(OC(F)(F)F)cc2)cc2c(OCCN3CCCC3=O)noc12]

1H NMR (400 MHz, DMSO-d6) δ 7.85-7.79 (m, 2H), 7.78 (d, J=1.7 Hz, 1H), 7.71 (d, J=1.6 Hz, 1H), 7.43 (d, J=8.3 Hz, 2H), 4.51 (t, J=5.3 Hz, 2H), 3.65 (t, J=5.3 Hz, 2H), 3.46 (t, J=7.0 Hz, 2H), 2.49 (s, 3H), 2.18 (t, J=8.1 Hz, 2H), 1.89 (p, J=7.6 Hz, 2H). m/z: 421 (MH+)

Example 89

3-(2-(1H-1,2,4-triazol-1-yl)ethoxy)-7-methyl-5-(4-(trifluoromethoxy)phenyl)benzo[d]isoxazole

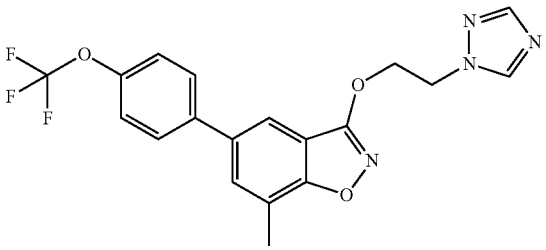 [SMILES: Cc1cc(-c2ccc(OC(F)(F)F)cc2)cc2c(OCCn3cncn3)noc12]

1H NMR (400 MHz, DMSO-d6) δ 8.65 (s, 1H), 7.98 (s, 1H), 7.84-7.80 (m, 2H), 7.79 (t, J=1.5 Hz, 1H), 7.72 (d, J=1.7 Hz, 1H), 7.44 (dt, J=8.2, 1.2 Hz, 2H), 4.83-4.65 (m, 4H), 2.50 (s, 3H). m/z: 405 (MH+)

Example 90

3-((4-methoxypyrimidin-2-yl)methoxy)-7-methyl-5-(4-(trifluoromethoxy)phenyl)benzo[d]isoxazole

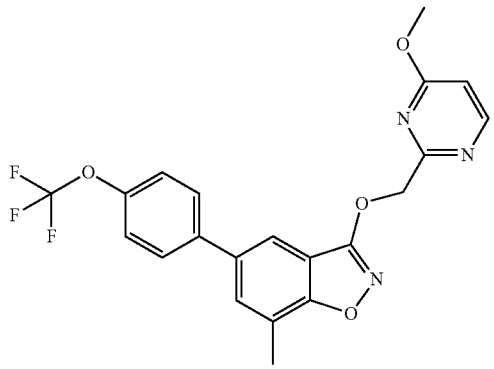 [SMILES: COc1ccnc(COc2noc3c(C)cc(-c4ccc(OC(F)(F)F)cc4)cc23)n1]

1H NMR (400 MHz, DMSO-d6) δ 8.50 (d, J=5.8 Hz, 1H), 7.90-7.83 (m, 3H), 7.81 (dd, J=1.7, 1.0 Hz, 1H), 7.48-7.40 (m, 2H), 6.88 (d, J=5.8 Hz, 1H), 5.56 (s, 2H), 3.84 (s, 3H), 2.50 (s, 3H). m/z: 432 (MH+)

Example 91

7-methyl-3-(oxazol-2-ylmethoxy)-5-(4-(trifluoromethoxy)phenyl)benzo[d]isoxazole

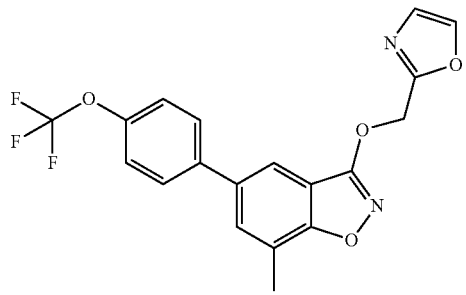 [SMILES: Cc1cc(-c2ccc(OC(F)(F)F)cc2)cc2c(OCc3ncco3)noc12]

1H NMR (400 MHz, DMSO-d6) δ 8.22 (d, J=0.9 Hz, 1H), 7.89-7.80 (m, 4H), 7.47-7.39 (m, 2H), 7.32 (d, J=0.9 Hz, 1H), 5.61 (s, 2H), 2.51 (s, 3H). m/z: 391 (MH+)

Example 92

3-((3-methyloxetan-3-yl)methoxy)-5-(4-(trifluoromethoxy)phenyl)benzo[d]isoxazole

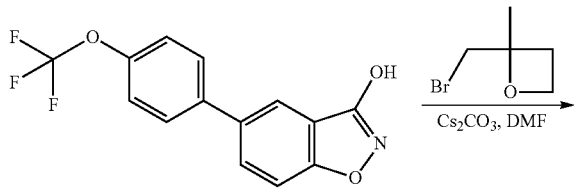

-continued

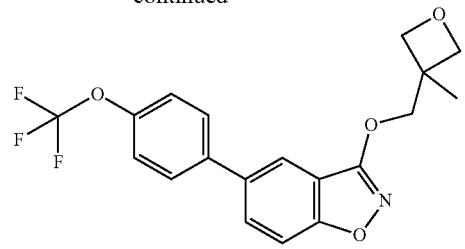

5-(4-(trifluoromethoxy)phenyl)benzo[d]isoxazol-3-ol (100 mg, 0.34 mmol), 3-bromomethyl-3-methyloxetane (150 mg, 0.91 mmol) and cesium carbonate (300 mg) were combined in 5 mL DMF and stirred at ambient temperature until HPLC showed complete disappearance of benzisoxazole starting material. The reaction mixture was diluted with 60 mL ethyl acetate, washed with water and brine and evaporated under vacuum. Flash chromatographic purification on 12 g silica gel with 0-60% ethyl acetate in hexane gave the title compound (80 mg, 0.21 mmol).

$^1$H NMR (400 MHz, DMSO-$d_6$) δ 8.02-7.93 (m, 2H), 7.91-7.82 (m, 2H), 7.73 (dd, J=8.7, 0.8 Hz, 1H), 7.48-7.41 (m, 2H), 4.57 (d, J=5.9 Hz, 2H), 4.53 (s, 2H), 4.33 (d, J=5.9 Hz, 2H), 1.42 (s, 3H). MS: 380 (MH$^+$)

The following compounds were synthesized using the same procedure but substituting the appropriate halide:

Example 93

3-((3-methylpyridin-2-yl)methoxy)-5-(4-(trifluoromethoxy)phenyl)benzo[d]isoxazole

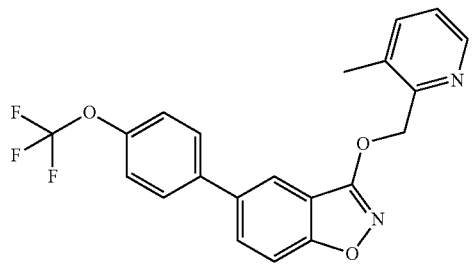 [SMILES: Cc1cccnc1COc1noc2ccc(-c3ccc(OC(F)(F)F)cc3)cc12]

$^1$H NMR (400 MHz, DMSO-$d_6$) δ 8.44-8.37 (m, 1H), 8.03-7.93 (m, 2H), 7.90-7.81 (m, 2H), 7.74 (dt, J=8.8, 0.7 Hz, 1H), 7.72-7.66 (m, 1H), 7.46-7.38 (m, 2H), 7.34 (dd, J=7.7, 4.8 Hz, 1H), 5.59 (s, 2H), 2.42 (s, 3H). MS: 401 (MH$^+$).

Example 94

3-((3-fluoropyridin-2-yl)methoxy)-5-(4-(trifluoromethoxy)phenyl)benzo[d]isoxazole

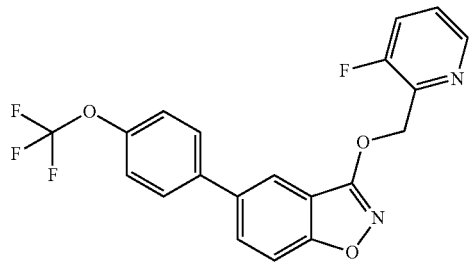 [SMILES: Fc1cccnc1COc1noc2ccc(-c3ccc(OC(F)(F)F)cc3)cc12]

¹H NMR (400 MHz, DMSO-d₆) δ 8.47 (dt, J=4.7, 1.5 Hz, 1H), 8.03-7.94 (m, 2H), 7.91-7.78 (m, 3H), 7.78-7.71 (m, 1H), 7.56 (dt, J=8.7, 4.5 Hz, 1H), 7.48-7.38 (m, 2H), 5.64 (d, J=1.9 Hz, 2H). MS: 405 (MH⁺).

Example 95

3-((6-methylpyridin-2-yl)methoxy)-5-(4-(trifluoromethoxy)phenyl)benzo[d]isoxazole

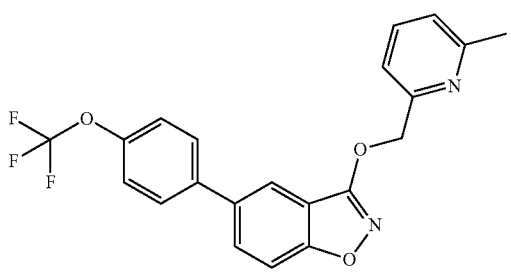 [SMILES: Cc1cccc(COc2noc3ccc(-c4ccc(OC(F)(F)F)cc4)cc23)n1]

¹H NMR (400 MHz, DMSO-d₆) δ 8.07 (dd, J=1.9, 0.7 Hz, 1H), 7.97 (dd, J=8.8, 1.9 Hz, 1H), 7.91-7.83 (m, 2H), 7.79-7.68 (m, 2H), 7.49-7.40 (m, 3H), 7.24 (d, J=7.7 Hz, 1H), 5.50 (s, 2H), 2.48 (s, 3H). MS: 401 (MH⁺).

Example 96

3-((5-cyclopropyl-1,3,4-oxadiazol-2-yl)methoxy)-5-(4-(trifluoromethoxy)phenyl)benzo[d]isoxazole

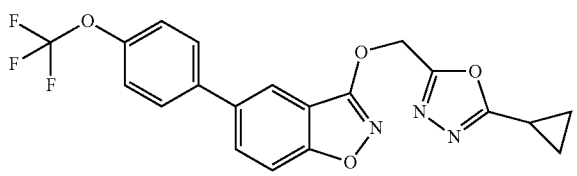 [SMILES: FC(F)(F)Oc1ccc(-c2ccc3onc(OCc4nnc(C5CC5)o4)c3c2)cc1]

¹H NMR (400 MHz, DMSO-d₆) δ 8.05 (dd, J=1.9, 0.7 Hz, 1H), 8.00 (dd, J=8.8, 1.9 Hz, 1H), 7.92-7.83 (m, 2H), 7.77 (dd, J=8.8, 0.7 Hz, 1H), 7.48-7.40 (m, 2H), 5.71 (s, 2H), 2.28 (tt, J=8.4, 4.9 Hz, 1H), 1.25-1.09 (m, 2H), 1.08-0.97 (m, 2H). MS: 418 (MH⁺).

Example 97

(3-(((5-(4-(trifluoromethoxy)phenyl)benzo[d]isoxazol-3-yl)oxy)methyl)oxetan-3-yl)methanol

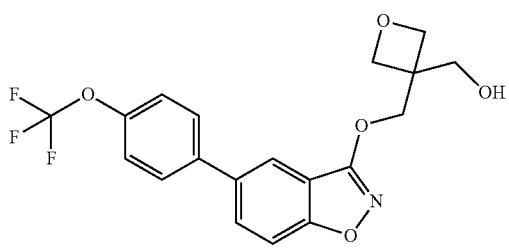 [SMILES: OCC1(COc2noc3ccc(-c4ccc(OC(F)(F)F)cc4)cc23)COC1]

¹H NMR (400 MHz, DMSO-d₆) δ 8.02-7.93 (m, 2H), 7.90-7.82 (m, 2H), 7.77-7.70 (m, 1H), 7.45 (d, J=8.3 Hz, 2H), 5.06 (t, J=5.4 Hz, 1H), 4.61 (s, 2H), 4.52 (d, J=6.0 Hz, 2H), 4.41 (d, J=6.0 Hz, 2H), 3.78 (d, J=5.4 Hz, 2H). MS: 396 (MH⁺).

Example 98

3-(1-(pyridin-2-yl)ethoxy)-5-(4-(trifluoromethoxy)phenyl)benzo[d]isoxazole

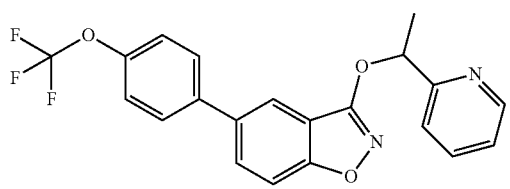 [SMILES: CC(Oc1noc2ccc(-c3ccc(OC(F)(F)F)cc3)cc12)c1ccccn1]

¹H NMR (400 MHz, DMSO-d₆) δ 8.56 (ddd, J=4.9, 1.8, 0.9 Hz, 1H), 8.08-8.02 (m, 1H), 7.96 (dd, J=8.8, 1.9 Hz, 1H), 7.91-7.85 (m, 2H), 7.81 (td, J=7.7, 1.8 Hz, 1H), 7.70 (d, J=8.8 Hz, 1H), 7.59 (dt, J=8.0, 1.1 Hz, 1H), 7.49-7.38 (m, 2H), 7.33 (ddd, J=7.6, 4.8, 1.1 Hz, 1H), 5.96 (q, J=6.5 Hz, 1H), 1.75 (d, J=6.5 Hz, 3H). MS: 401 (MH⁺).

Example 99

3-((5-methyl-1,3,4-oxadiazol-2-yl)methoxy)-5-(4-(trifluoromethoxy)phenyl)benzo[d]isoxazole

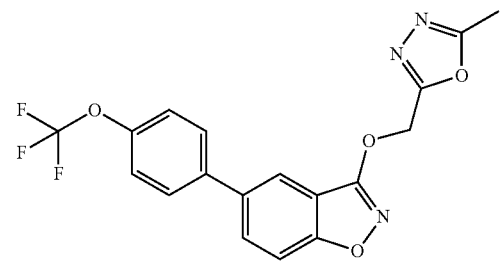 [SMILES: Cc1nnc(COc2noc3ccc(-c4ccc(OC(F)(F)F)cc4)cc23)o1]

¹H NMR (400 MHz, DMSO-d₆) δ 8.06-8.02 (m, 1H), 8.00 (dd, J=8.8, 1.9 Hz, 1H), 7.91-7.82 (m, 2H), 7.77 (d, J=8.8 Hz, 1H), 7.48-7.40 (m, 2H), 5.75 (s, 2H), 2.53 (s, 3H). MS: 392 (MH⁺).

Example 100

3-((5-isopropyl-1,3,4-oxadiazol-2-yl)methoxy)-5-(4-(trifluoromethoxy)phenyl)benzo[d]isoxazole

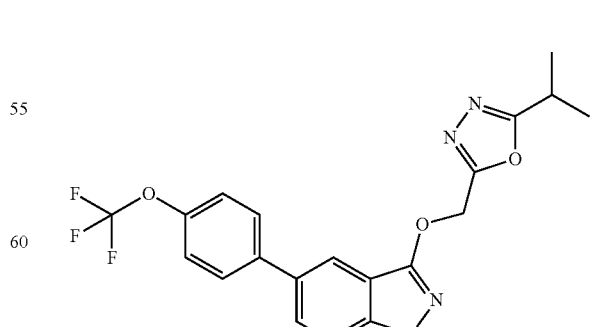

¹H NMR (400 MHz, DMSO-d₆) δ 8.07-8.02 (m, 1H), 8.00 (dd, J=8.8, 1.4 Hz, 1H), 7.91-7.82 (m, 2H), 7.77 (d, J=8.8 Hz,

1H), 7.48-7.40 (m, 2H), 5.75 (s, 2H), 3.22 (hept, J=7.0 Hz, 1H), 1.30 (d, J=7.0, Hz, 6H). MS: 420 (MH+).

Example 101

3-((5-methyl-1,3,4-thiadiazol-2-yl)methoxy)-5-(4-(trifluoromethoxy)phenyl)benzo[d]isoxazole

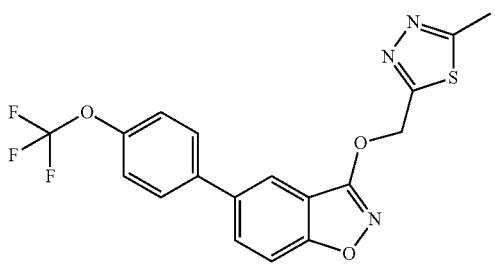 [SMILES: Cc1nnc(COc2noc3ccc(-c4ccc(OC(F)(F)F)cc4)cc23)s1]

$^1$H NMR (400 MHz, DMSO-d$_6$) δ 8.04-7.96 (m, 2H), 7.91-7.82 (m, 2H), 7.77 (dd, J=8.7, 0.9 Hz, 1H), 7.48-7.40 (m, 2H), 5.91 (s, 2H), 2.74 (s, 3H). MS: 408 (MH+).

Example 102

3-((3-methylisoxazol-5-yl)methoxy)-5-(4-(trifluoromethoxy)phenyl)benzo[d]isoxazole

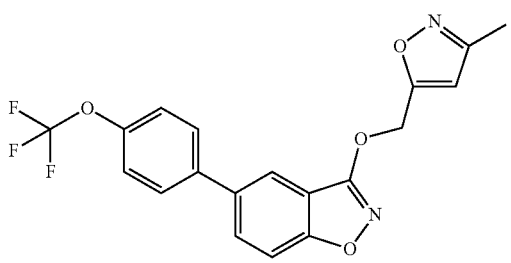 [SMILES: Cc1cc(COc2noc3ccc(-c4ccc(OC(F)(F)F)cc4)cc23)on1]

$^1$H NMR (400 MHz, DMSO-d$_6$) δ 8.02 (d, J=1.8 Hz, 1H), 7.99 (dd, J=8.8, 1.9 Hz, 1H), 7.91-7.82 (m, 2H), 7.76 (d, J=8.8 Hz, 1H), 7.43 (dd, J=8.5, 1.3 Hz, 2H), 6.63 (s, 1H), 5.62 (s, 2H), 2.25 (s, 3H). MS: 391 (MH+).

Example 103

2-((5-(4-(trifluoromethoxy)phenyl)benzo[d]isoxazol-3-yl)oxy)acetonitrile

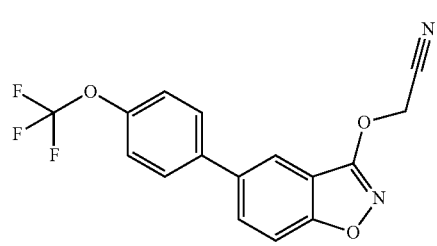 [SMILES: N#CCOc1noc2ccc(-c3ccc(OC(F)(F)F)cc3)cc12]

$^1$H NMR (400 MHz, DMSO-d$_6$) δ 8.06 (d, J=1.7 Hz, 1H), 8.02 (dd, J=8.8, 1.9 Hz, 1H), 7.92-7.83 (m, 2H), 7.80 (d, J=8.8 Hz, 1H), 7.49-7.42 (m, 2H), 5.50 (s, 2H). MS: 335 (MH+).

Example 104

3-((5-cyclopropyl-1,3,4-oxadiazol-2-yl)methoxy)-7-fluoro-5-(4-(trifluoromethoxy)phenyl)benzo[d]isoxazole

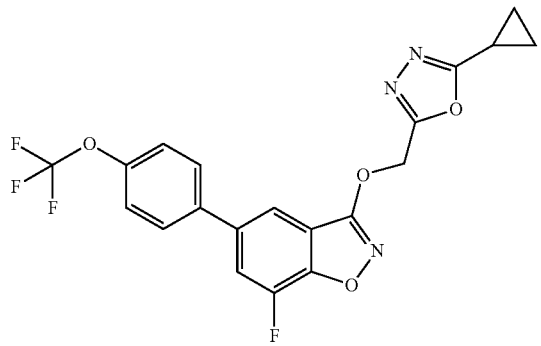 [SMILES: Fc1cc(-c2ccc(OC(F)(F)F)cc2)cc2c(OCc3nnc(C4CC4)o3)noc12]

$^1$H NMR (400 MHz, DMSO-d$_6$) δ 8.03 (dd, J=12.3, 1.5 Hz, 1H), 7.95-7.87 (m, 3H), 7.45 (d, J=8.3 Hz, 2H), 5.73 (s, 2H), 2.28 (tt, J=8.7, 4.9 Hz, 1H), 1.20-1.09 (m, 2H), 1.08-0.97 (m, 2H). MS: 436 (MH+).

Example 105

3-((5-cyclopropyl-1,3,4-oxadiazol-2-yl)methoxy)-7-methyl-5-(4-(trifluoromethoxy)phenyl)benzo[d]isoxazole

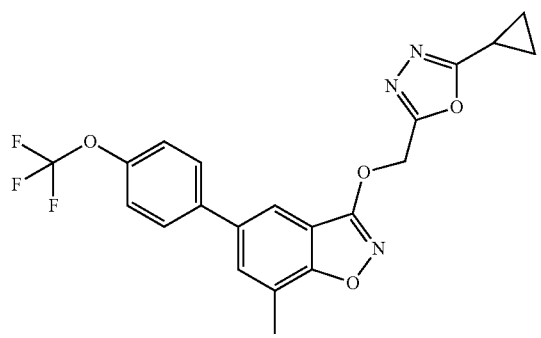 [SMILES: Cc1cc(-c2ccc(OC(F)(F)F)cc2)cc2c(OCc3nnc(C4CC4)o3)noc12]

1H NMR (400 MHz, DMSO-d6) δ 7.90-7.80 (m, 4H), 7.47-7.39 (m, 2H), 5.70 (s, 2H), 2.51 (s, 3H), 2.34-2.21 (m, 1H), 1.19-1.11 (m, 2H), 1.04-0.98 (m, 2H). m/z: 432 (MH+)

Example 106

7-methyl-3-((6-methylpyridin-2-yl)methoxy)-5-(4-(trifluoromethoxy)phenyl)benzo[d]isoxazole

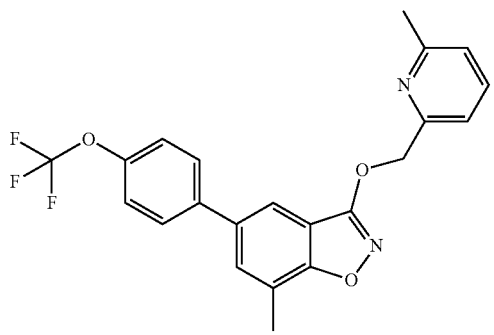 [SMILES: Cc1cccc(COc2noc3c(C)cc(-c4ccc(OC(F)(F)F)cc4)cc23)n1]

1H NMR (400 MHz, DMSO-d6) δ 7.90-7.83 (m, 3H), 7.82 (d, J=1.5 Hz, 1H), 7.74 (t, J=7.7 Hz, 1H), 7.48-7.40 (m, 3H), 7.24 (d, J=7.7 Hz, 1H), 5.49 (s, 2H), 2.51 (s, 3H), 2.48 (s, 3H). m/z: 415 (MH+)

Example 107 tert-butyl(S)-2-(((5-(4-(trifluoromethoxy)phenyl)benzo[d]isoxazol-3-yl)oxy)methyl)pyrrolidine-1-carboxylate

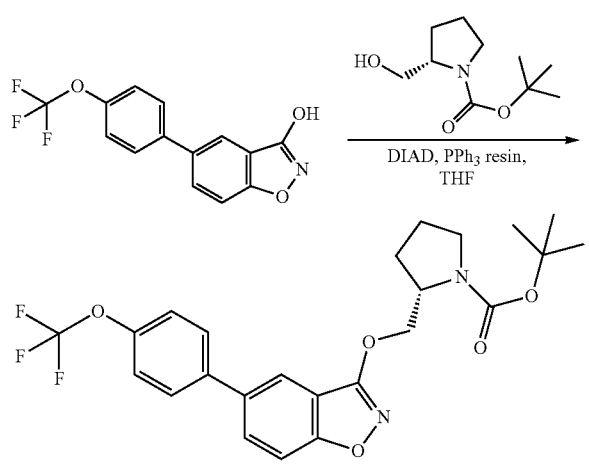

Diisopropylazodicarboxylate 40% solution in toluene (0.27 mL, 0.51 mmol) was added under stirring to a solution of 5-(4-(trifluoromethoxy)phenyl)benzo[d]isoxazol-3-ol (100 mg, 0.34 mmol), triphenylphosphine on resin (3 mmol/g) (330 mg, 1 mmol), and 1-methylimidazol-4-yl methanol (60 mg, 0.51 mmol) in THF. The reaction mixture was stirred at ambient temperature overnight. Volatiles were evaporated under vacuum and the residue was purified on 12 g silica gel with 0-60% ethyl acetate in hexane and gave the title compound (104 mg, 0.22 mmol).

$^1$H NMR (400 MHz, DMSO-d$_6$) δ 8.00-7.92 (m, 2H), 7.89-7.81 (m, 2H), 7.72 (d, J=9.3 Hz, 1H), 7.45 (d, J=8.3 Hz, 2H), 4.51-4.40 (m, 2H), 4.20-4.11 (m, 1H), 3.34-3.25 (m, 2H), 2.09-1.93 (m, 3H), 1.86-1.78 (m, 1H), 1.35 (s, 9H). MS: 479 (MH$^+$).

Example 108

(S)-3-(pyrrolidin-2-ylmethoxy)-5-(4-(trifluoromethoxy)phenyl)benzo[d]isoxazole

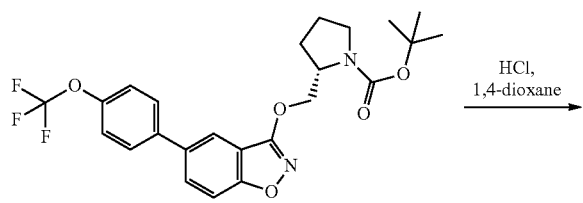

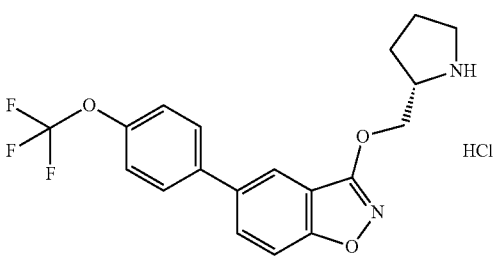

Example 107 (95 mg, 0.20 mmol) was dissolved in 2 mL 4N HCl solution in 1,4 dioxane and stirred at ambient temperature for two hours. Diethylether ether was added and the formed precipitate was filtered, washed with diethylether and dried, giving the title compound (76 mg, 0.18 mmol) as the HCl salt.

$^1$H NMR (400 MHz, DMSO-d$_6$) δ 9.69 (br, 1H), 9.35 (br, 1H), 8.06-8.02 (m, 1H), 7.99 (dd, J=8.8, 1.9 Hz, 1H), 7.88-7.80 (m, 2H), 7.76 (dd, J=8.8, 0.8 Hz, 1H), 7.48 (dd, J 8.1, 1.6 Hz, 2H), 4.71 (dd, J=11.2, 3.8 Hz, 1H), 4.61 (dd, J=11.2, 7.8 Hz, 1H), 4.10-3.98 (m, 1H), 3.32-3.16 (m, 2H), 2.21-1.75 (m, 4H). MS: 379 (MH$^+$).

Example 109

(S)-1-(2-(((5-(4-(trifluoromethoxy)phenyl)benzo[d]isoxazol-3-yl)oxy)methyl)pyrrolidin-1-yl)ethan-1-one

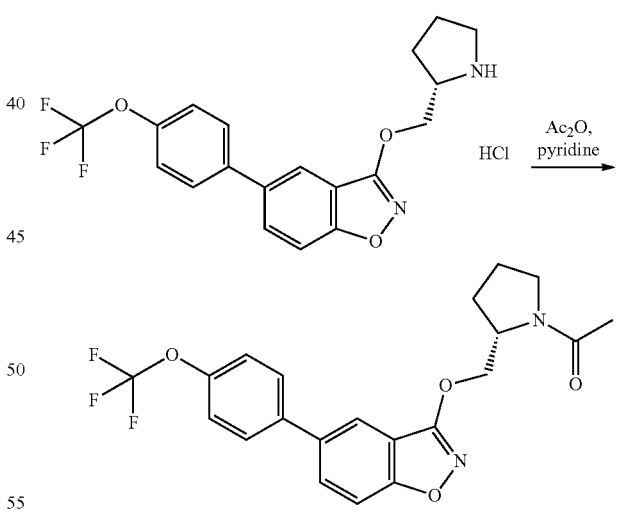

Example 108 (65 mg, 0.16 mmol) was dissolved in 2 mL anhydrous pyridine. Acetic anhydride (0.1 mL) was added and the mixture was stirred at ambient temperature for one hour. Volatiles were evaporated under vacuum and the residue was purified on 12 g silica gel with 0-60% ethyl acetate in hexane and gave the title compound (54 mg, 0.13 mmol). $^1$H NMR (400 MHz, DMSO-d$_6$) δ 8.01-7.91 (m, 2H), 7.90-7.81 (m, 2H), 7.78-7.69 (m, 1H), 7.46 (d, J=8.5 Hz, 2H), 4.54-4.30 (m, 3H), 3.59-3.38 (m, 2H), 2.14-1.83 (m, 7H). MS: 421 (MH$^+$).

The following compounds were synthesized using the same route:

Example 110

1-(3-(((5-(4-(trifluoromethoxy)phenyl)benzo[d]isoxazol-3-yl)oxy)methyl)azetidin-1-yl)ethan-1-one

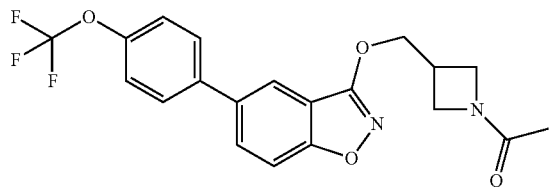 [SMILES: CC(=O)N1CC(COc2noc3ccc(-c4ccc(OC(F)(F)F)cc4)cc23)C1]

$^1$H NMR (400 MHz, DMSO-d$_6$) δ 8.01-7.93 (m, 2H), 7.90-7.81 (m, 2H), 7.77-7.70 (m, 1H), 7.49-7.41 (m, 2H), 4.60 (d, J=6.8 Hz, 2H), 4.25 (t, J=8.5 Hz, 1H), 4.06-3.92 (m, 2H), 3.72 (dd, J=9.6, 5.5 Hz, 1H), 3.19-3.07 (m, 1H), 1.74 (s, 3H). MS: 407 (MH$^+$).

Example 111 tert-butyl(S)-3-(((5-(4-(trifluoromethoxy)phenyl)benzo[d]isoxazol-3-yl)oxy)methyl)morpholine-4-carboxylate

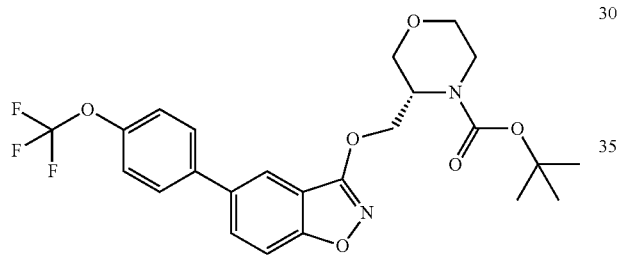

$^1$H NMR (400 MHz, DMSO-d$_6$) δ 8.02-7.86 (m, 2H), 7.84-7.77 (m, 2H), 7.73 (d, J=8.8 Hz, 1H), 7.44 (d, J=8.3 Hz, 2H), 4.76-4.33 (m, 3H), 3.98-2.96 (m, 6H), 1.20 (s, 9H). MS: 495 (MH$^+$).

Example 112 tert-butyl(R)-3-(((5-(4-(trifluoromethoxy)phenyl)benzo[d]isoxazol-3-yl)oxy)methyl)morpholine-4-carboxylate

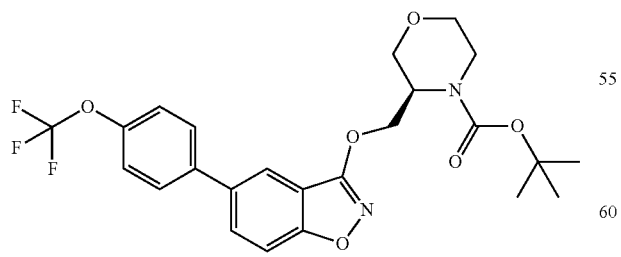

$^1$H NMR (400 MHz, DMSO-d$_6$) δ 8.00-7.88 (m, 2H), 7.84-7.77 (m, 2H), 7.74 (d, J=8.8 Hz, 1H), 7.45 (d, J=8.3 Hz, 2H), 4.75-4.32 (m, 3H), 3.97-3.02 (m, 6H), 1.20 (s, 9H). MS: 495 (MH$^+$).

Example 113

(S)-3-(morpholin-3-ylmethoxy)-5-(4-(trifluoromethoxy)phenyl)benzo[d]isoxazole

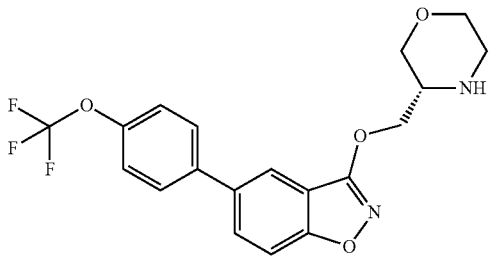 [SMILES: FC(F)(F)Oc1ccc(-c2ccc3onc(OC[C@@H]4COCCN4)c3c2)cc1]

$^1$H NMR (400 MHz, DMSO-d$_6$) δ 9.86 (br, 2H), 8.20 (d, J=1.8 Hz, 1H), 7.99 (dd, J=8.8, 1.9 Hz, 1H), 7.89-7.80 (m, 2H), 7.75 (d, J=8.9 Hz, 1H), 7.48 (d, J=8.3 Hz, 2H), 4.72-4.57 (m, 2H), 4.09 (dd, J=12.1, 3.0 Hz, 1H), 3.93 (dt, J=12.4, 3.1 Hz, 1H), 3.87-3.70 (m, 3H), 3.46-3.26 (m, 1H), 3.22-3.11 (m, 1H). MS: 395 (MH$^+$).

Example 114

(R)-3-(morpholin-3-ylmethoxy)-5-(4-(trifluoromethoxy)phenyl)benzo[d]isoxazole

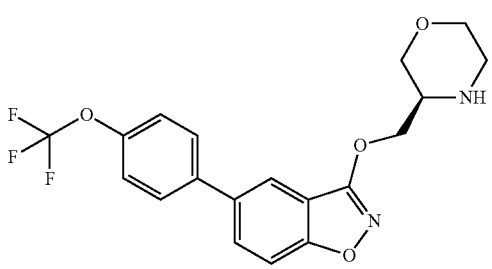 [SMILES: FC(F)(F)Oc1ccc(-c2ccc3onc(OC[C@H]4COCCN4)c3c2)cc1]

$^1$H NMR (400 MHz, DMSO-d$_6$) δ 9.79 (s, 2H), 8.18 (d, J=1.8 Hz, 1H), 8.00 (dd, J=8.8, 1.9 Hz, 1H), 7.89-7.80 (m, 2H), 7.76 (d, J=8.8 Hz, 1H), 7.48 (d, J=8.3 Hz, 2H), 4.71-4.56 (m, 2H), 4.09 (dd, J=12.2, 3.1 Hz, 1H), 3.98-3.70 (m, 4H), 3.41-3.27 (m, 1H), 3.23-3.11 (m, 1H). MS: 395 (MH$^+$).

Example 115

(S)-1-(3-(((5-(4-(trifluoromethoxy)phenyl)benzo[d]isoxazol-3-yl)oxy)methyl)morpholino)ethan-1-one

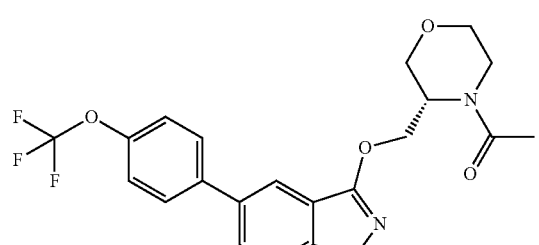

Mixture of amide isomers in NMR. ¹H NMR (400 MHz, DMSO-d₆) δ 8.00-7.79 (m, 4H), 7.78-7.69 (m, 1H), 7.49-7.42 (m, 2H), 4.85-4.26 (m, 3H), 4.15-3.75 (m, 3H), 3.64-2.85 (m, 3H), [2.10 (s), 1.98 (s) 3H]. MS: 437 (MH⁺).

Example 116

(R)-1-(3-(((5-(4-(trifluoromethoxy)phenyl)benzo[d]isoxazol-3-yl)oxy)methyl)morpholino)ethan-1-one

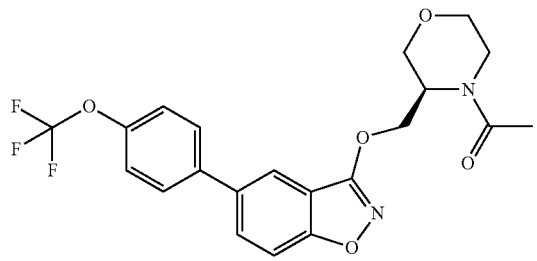 [SMILES: CC(=O)N1CCOC[C@@H]1COc1noc2ccc(-c3ccc(OC(F)(F)F)cc3)cc12]

Mixture of amide isomers in NMR. ¹H NMR (400 MHz, DMSO-d₆) δ 8.00-7.79 (m, 4H), 7.78-7.69 (m, 1H), 7.49-7.42 (m, 2H), 4.85-4.27 (m, 3H), 4.15-3.77 (m, 3H), 3.64-2.84 (m, 3H), [2.10 (s), 1.98 (s) 3H]. MS: 437 (MH⁺).

Example 117

(R)-1-((5-(4-(trifluoromethoxy)phenyl)benzo[d]isoxazol-3-yl)oxy)propan-2-amine

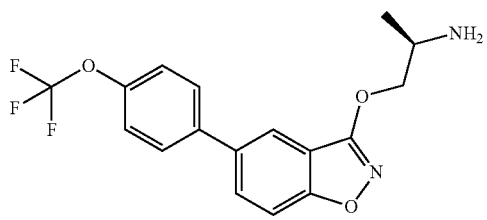 [SMILES: C[C@@H](N)COc1noc2ccc(-c3ccc(OC(F)(F)F)cc3)cc12]

¹H NMR (400 MHz, DMSO-d₆) δ 8.32 (br, 3H), 8.11 (d, J=1.8 Hz, 1H), 7.99 (dd, J=8.9, 1.9 Hz, 1H), 7.87-7.78 (m, 2H), 7.75 (d, J=8.8 Hz, 1H), 7.51-7.44 (m, 2H), 4.57 (dd, J=10.8, 3.8 Hz, 1H), 4.43 (dd, J=10.8, 7.0 Hz, 1H), 3.79-3.72 (m, 1H), 1.33 (d, J=6.6 Hz, 3H). MS: 353 (MH⁺).

Example 118

(S)-3-methyl-1-((5-(4-(trifluoromethoxy)phenyl)benzo[d]isoxazol-3-yl)oxy)butan-2-amine

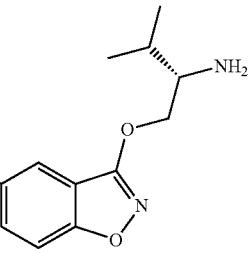

¹H NMR (400 MHz, DMSO-d₆) δ 8.37 (br, 3H), 8.16-8.10 (m, 1H), 7.99 (dd, J=8.8, 1.9 Hz, 1H), 7.87-7.79 (m, 2H), 7.76 (d, J=8.8 Hz, 1H), 7.49 (d, J=8.3 Hz, 2H), 4.66 (dd, J=11.2, 3.4 Hz, 1H), 4.53 (dd, J=11.2, 6.7 Hz, 1H), 3.51-3.42 (m, 1H), 2.14 (h, J 6.9 Hz, 1H), 1.05 (d, J=6.8 Hz, 3H), 1.02 (d, J=6.8 Hz, 3H). MS: 381 (MH⁺).

Example 119

(R)-1-(1-((5-(4-(trifluoromethoxy)phenyl)benzo[d]isoxazol-3-yl)oxy)propan-2-yl)pyrrolidin-2-one Example 117 (23 mg, 0.059 mmol) was dissolved in 2 mL THF. Triethylamine (0.041 mL, 0.29 mmol) and then 4-chlorobutyryl chloride (11 mg, 0.077 mmol) was added. The mixture was stirred at ambient temperature for 1 hour and then diluted with EtOAc washed with water and brine, evaporated. The residue was dissolved in 5 mL THF. NaH 60% in oil (50 mg) was added and the reaction mixture was stirred at ambient temperature overnight. The reaction was quenched with 5 mL water, diluted with ethyl acetate, washed with water and brine, evaporated and purified on 12 g silica gel with 0-100% ethyl acetate in hexane to yield the title compound (25 mg, 0.048 mmol).

¹H NMR (400 MHz, DMSO-d₆) δ 7.95 (dd, J=8.8, 1.8 Hz, 1H), 7.91 (d, J=1.7 Hz, 1H), 7.89-7.80 (m, 2H), 7.73 (d, J=8.8 Hz, 1H), 7.45 (d, J=8.4 Hz, 2H), 4.56-4.39 (m, 3H), 3.46-3.34 (m, 2H), 2.22-2.13 (m, 2H), 1.94-1.77 (m, 2H), 1.21 (d, J=6.4 Hz, 3H). MS: 421 (MH⁺).

The following compound was synthesized using the same procedure:

Example 120

(S)-1-(3-methyl-1-((5-(4-(trifluoromethoxy)phenyl)benzo[d]isoxazol-3-yl)oxy)butan-2-yl)pyrrolidin-2-one

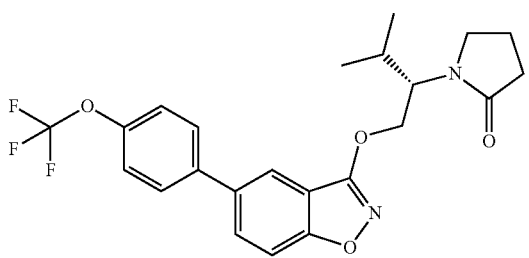 [SMILES: CC(C)[C@@H](COc1noc2ccc(-c3ccc(OC(F)(F)F)cc3)cc12)N1CCCC1=O]

$^1$H NMR (400 MHz, DMSO-d$_6$) δ 7.95 (dd, J=8.8, 1.9 Hz, 1H), 7.91-7.86 (m, 1H), 7.86-7.79 (m, 2H), 7.73 (d, J=8.8 Hz, 1H), 7.49-7.42 (m, 2H), 4.65-4.52 (m, 2H), 4.05 (ddd, J=10.4, 7.3, 4.3 Hz, 1H), 3.45-3.31 (m, 2H), 2.28-2.12 (m, 2H), 2.11-1.97 (m, 1H), 1.96-1.81 (m, 2H), 0.99 (d, J=6.6 Hz, 3H), 0.82 (d, J=6.7 Hz, 3H). MS: 449 (MH$^+$).

Example 121

1-(pyrrolidin-1-yl)-2-((5-(4-(trifluoromethoxy)phenyl)benzo[d]isoxazol-3-yl)oxy)ethan-1-one Step 1: 5-(4-(trifluoromethoxy)phenyl)benzo[d]isoxazol-3-ol (500 mg, 1.69 mmol), tert-butyl 2-bromoacetate (500 mg, 2.56 mmol) and cesium carbonate (1.65 g) were combined in 5 mL DMF and stirred at ambient temperature for 1 hour. The reaction mixture was diluted with 80 mL ethyl acetate, washed with water and brine and evaporated under vacuum. Flash chromatographic purification on 12 g silica gel with 0-100% ethyl acetate in hexane gave tert-butyl 2-((5-(4-(trifluoromethoxy)phenyl)benzo[d]isoxazol-3-yl)oxy)acetate (285 mg, 0.70 mmol).

$^1$H NMR (400 MHz, DMSO-d$_6$) δ 8.04-8.01 (m, 1H), 7.98 (dd, J=8.8, 1.8 Hz, 1H), 7.90-7.83 (m, 2H), 7.75 (d, J=8.8 Hz, 1H), 7.45 (d, J=8.0 Hz, 2H), 5.00 (s, 2H), 1.42 (s, 9H). MS: 410 (MH$^+$).

Step 2: tert-Butyl 2-((5-(4-(trifluoromethoxy)phenyl)benzo[d]isoxazol-3-yl)oxy)acetate (285 mg, 0.70 mmol) was dissolved in 5 mL dichloromethane. 2 mL trifluoroacetic acid was added and the mixture was stirred at ambient temperature for 3 hours. Volatiles were evaporated under vacuum and the residue was crystallized from ethyl acetate/hexane to give 2-((5-(4-(trifluoromethoxy)phenyl)benzo[d]isoxazol-3-yl)oxy)acetic acid (160 mg, 0.453 mmol).

Step 3: 2-((5-(4-(trifluoromethoxy)phenyl)benzo[d]isoxazol-3-yl)oxy)acetic acid (50 mg, 0.142 mmol) was dissolved in 3 mL DMF. Pyrrolidine (30 mg, 0.425 mmol) was added followed by addition of HATU (81 mg, 0.212 mmol). The mixture was stirred at ambient temperature overnight, then diluted with 60 mL ethyl acetate, washed with water and brine, and evaporated. The product was purified on 12 g silica gel with 0-100% ethyl acetate in hexane followed by recrystallization from acetonitrile/water to give the title compound (30 mg, 0.073 mmol).

$^1$H NMR (400 MHz, DMSO-d$_6$) δ 8.05-8.00 (m, 1H), 7.97 (dd, J=8.8, 1.9 Hz, 1H), 7.91-7.83 (m, 2H), 7.74 (d, J=8.8 Hz, 1H), 7.45 (d, J=8.2 Hz, 2H), 5.12 (s, 2H), 3.45 (t, J=6.8 Hz, 2H), 3.33 (t, J=6.9 Hz, 2H), 1.91 (p, J=6.8 Hz, 2H), 1.78 (p, J=6.9 Hz, 2H). MS: 407 (MH$^+$).

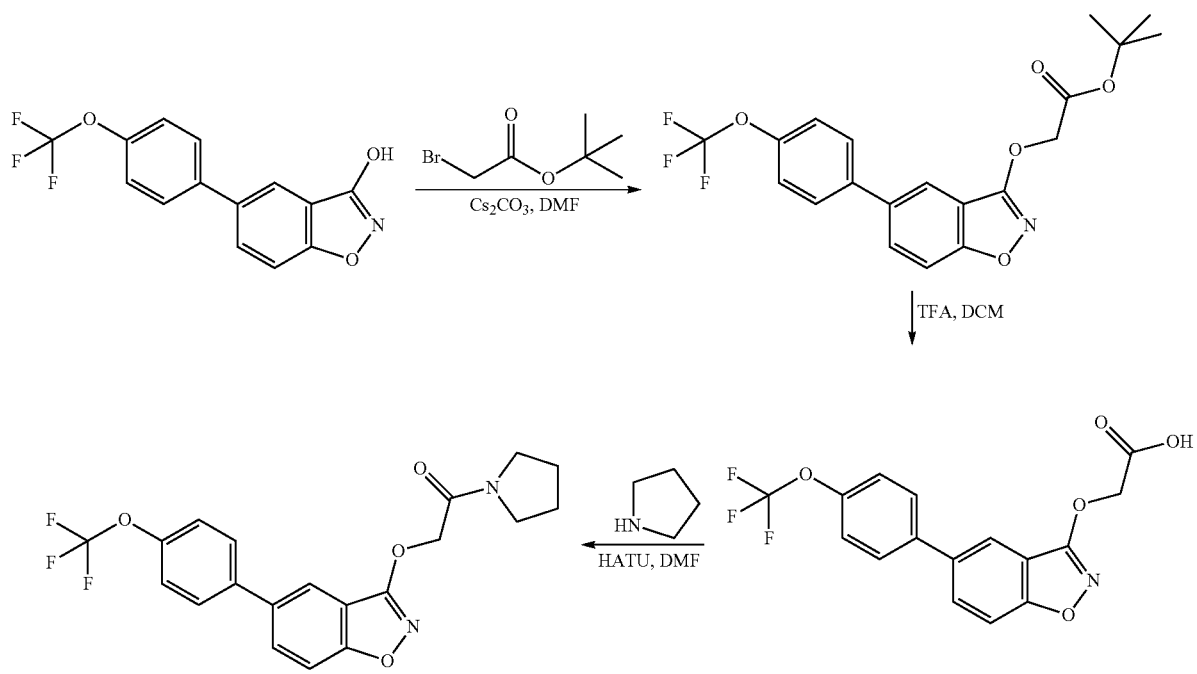

The following compound was synthesized using the same procedure:

Example 122

N-isopropyl-2-((5-(4-(trifluoromethoxy)phenyl)benzo[d]isoxazol-3-yl)oxy)acetamide

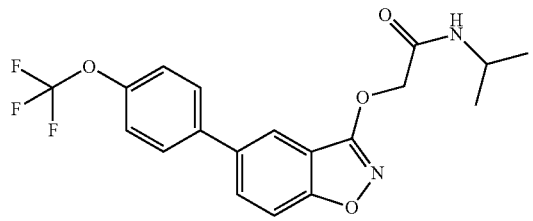 [SMILES: CC(C)NC(=O)COc1noc2ccc(-c3ccc(OC(F)(F)F)cc3)cc12]

$^1$H NMR (400 MHz, DMSO-d$_6$) δ 8.09-8.02 (m, 2H), 7.97 (dd, J=8.8, 1.9 Hz, 1H), 7.90-7.81 (m, 2H), 7.73 (d, J=8.8 Hz, 1H), 7.50-7.43 (m, 2H), 4.83 (s, 2H), 3.99-3.86 (m, 1H), 1.08 (d, J=6.6 Hz, 6H). MS: 395 (MH$^+$).

Example 123

N-(2-((5-(4-(trifluoromethoxy)phenyl)benzo[d]isoxazol-3-yl)oxy)ethyl)pyrimidin-2-amine

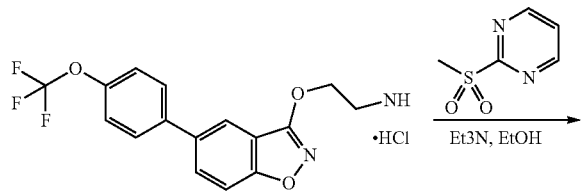

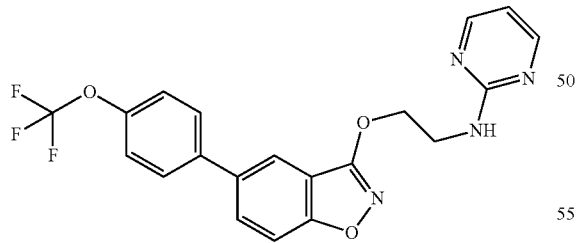

2-((5-(4-(trifluoromethoxy)phenyl)benzo[d]isoxazol-3-yl)oxy)ethanamine hydrochloride (57 mg, 0.152 mmol) and 2-(methylsulfonyl)pyrimidine (96 mg, 0.608 mmol) were dissolved in 2 mL ethanol in a microwave vial. Triethylamine (0.1 mL) was added and the mixture was heated at 120° C. for one hour in the microwave. All volatiles were removed under vacuum and the residue was purified on 12 g silica gel with 0-100% ethyl acetate in hexane to give the title compound (40 mg, 0.096 mmol). MS: 417 (MH$^+$).

Example 124

3-(pyrimidin-2-yloxy)-5-(4-(trifluoromethoxy)phenyl)benzo[d]isoxazole

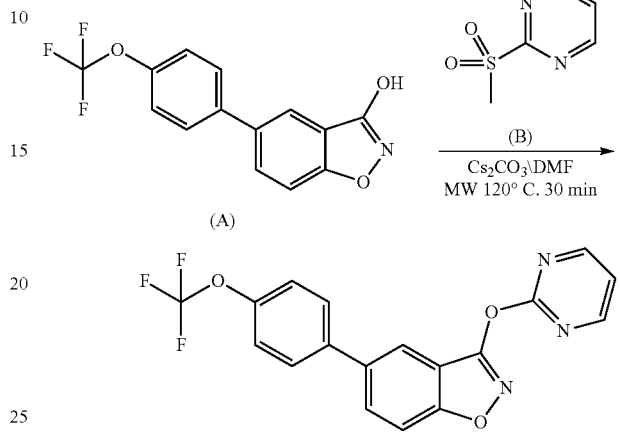

Compound A (0.100 g, 0.34 mmol) and B (0.268 g, 1.69 mmol) were added to a 0.2-5 mL microwave tube. DMF (3 mL) was added. The mixture was stirred and microwaved at 120° C. for 30 min, and then filtered. The filtrate was purified by HPLC. The fractions from HPLC were combined, K$_2$CO$_3$ (0.5 g) were added, extracted with EtOAc. The organic solution was concentrated. The resultant material was filtered through a short silica gel column with 1% MeOH in EtOAc to afford the title compound (6.4 mg, 5%). 1H NMR (400 MHz, DMSO-d6) δ 8.74 (d, J=4.8 Hz, 2H), 8.03 (dd, J=9.0, 1.8 Hz, 1H), 7.95-7.88 (m, 2H), 7.83-7.75 (m, 2H), 7.45 (t, J=4.8 Hz, 1H), 7.44-7.39 (m, 2H). m/z: 374 (MH+)

Example 125

3-(pyridin-2-yloxy)-5-(4-(trifluoromethoxy)phenyl)benzo[d]isoxazole

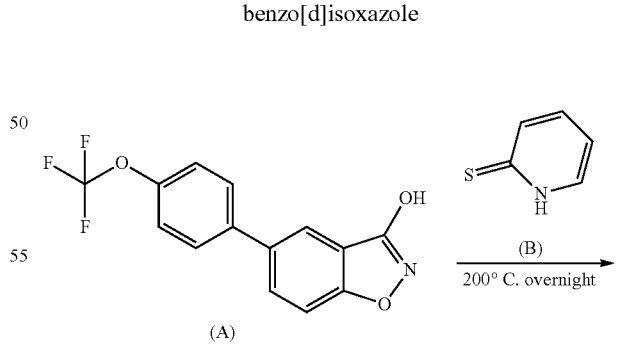

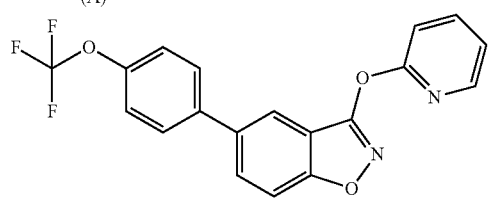

Compound A (0.133 g, 0.45 mmol) and B (0.05 g, 0.45 mmol) were mixed and heated at 200° C. overnight. The mixture was purified by HPLC, the fractions were combined, $K_2CO_3$ (0.5 g) was added, extracted with EtOAc, concentrated, and then purified by preparative TLC (Rf=0.14 in 20% DCM/Hexane) to afford the title compound (4.3 mg, 3%).

1H NMR (400 MHz, DMSO-d6) δ 8.68-8.61 (m, 1H), 8.26 (dd, J=1.5, 0.8 Hz, 1H), 8.12-8.03 (m, 2H), 7.80-7.71 (m, 2H), 7.59-7.51 (m, 2H), 7.50-7.41 (m, 3H). m/z: 373 (MH+).

Example 126

N-(pyrimidin-2-ylmethyl)-5-(4-(trifluoromethoxy)phenyl)benzo[d]isoxazol-3-amine

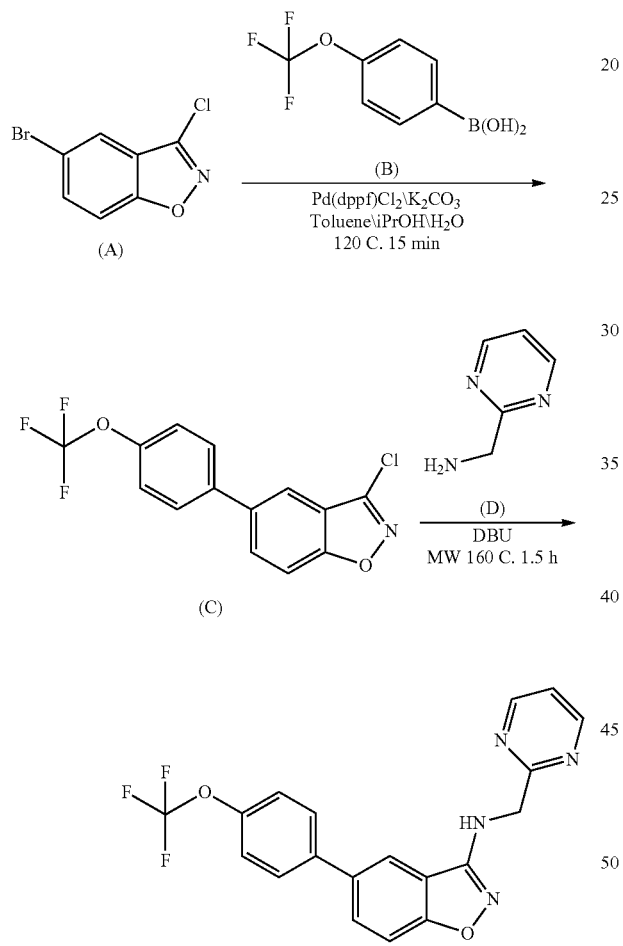

A (3.13 g, 13.5 mmol), B (2.77 g, 13.5 mmol), Pd(dppf)Cl$_2$ (1.00 g, 1.35 mmol), potassium carbonate (5.58 g, 40.4 mmol) were mixed. Toluene (30 mL), 2-isopropanol (15 mL), water (20 mL) were added. The resultant mixture was stirred under the N$_2$ protection at 120° C. for 15 min, the reaction was complete. The resultant mixture was diluted with EtOAc, washed with brine, dried with MgSO$_4$, concentrated and purified with silica gel column (R$_f$=0.16 with 2% EtOAc in Hexane) to afford the target product C (2.44 g, 58%).

C (0.050 g, 0.159 mmol), D (0.25 g, 2.0 mmol) and DBU (0.12 g) were added in a 0.2-0.5 ml microwave tube. The mixture was microwaved at 160 C for 1.5 h. Water was added with stirring until precipitates were formed, filtered, washed with water. The resultant precipitates were purified by preparative TLC with 0.5% MeOH in EtOAc, then by HPLC. The fractions from HPLC were combined, K$_2$CO$_3$ (0.5 g) were added, extracted with EtOAc. The organic solution from the extraction was concentrated. The resultant material was filtrated through a short silica gel column with 1% MeOH in EtOAc to afford the title compound (5.8 mg, 9.4%). 1H NMR (400 MHz, DMSO-d6) δ 8.78 (dd, J=4.9, 0.9 Hz, 2H), 8.36-8.31 (m, 1H), 7.89-7.83 (m, 1H), 7.83-7.76 (m, 2H), 7.70 (t, J=6.2 Hz, 1H), 7.54 (d, J=8.7 Hz, 1H), 7.52-7.45 (m, 2H), 7.40 (t, J=4.9 Hz, 1H), 4.68 (d, J=6.1 Hz, 2H). m/z: 387 (MH+)

The following compounds were synthesized using the same procedure:

Example 127

3-(4-methylpiperazin-1-yl)-5-(4-(trifluoromethoxy)phenyl)benzo[d]isoxazole

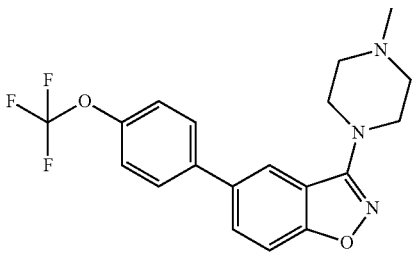 [SMILES: CN1CCN(c2noc3ccc(-c4ccc(OC(F)(F)F)cc4)cc23)CC1]

1H NMR (400 MHz, DMSO-d6) δ 8.25-8.08 (m, 1H), 7.92-7.79 (m, 3H), 7.66 (d, J=8.7 Hz, 1H), 7.45 (d, J=8.4 Hz, 2H), 3.54-3.45 (m, 4H), 2.53-2.47 (m, 4H), 2.23 (s, 3H). m/z: 378 (MH+)

Example 128

N-(cyclopropylmethyl)-5-(4-(trifluoromethoxy)phenyl)benzo[d]isoxazol-3-amine

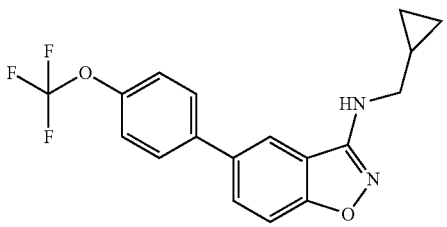 [SMILES: FC(F)(F)Oc1ccc(-c2ccc3onc(NCC4CC4)c3c2)cc1]

1H NMR (400 MHz, DMSO-d6) δ 8.04-7.94 (m, 1H), 7.58 (dd, J=8.7, 1.9 Hz, 1H), 7.56-7.49 (m, 2H), 7.27 (d, J=8.7 Hz, 1H), 7.25-7.18 (m, 2H), 6.82 (t, J=5.5 Hz, 1H), 2.86 (t, J=6.2 Hz, 2H), 1.01-0.82 (m, 1H), 0.32-0.19 (m, 2H), 0.08--0.01 (m, 2H). m/z: 349 (MH+)

Example 129

N-((6-methylpyridin-2-yl)methyl)-5-(4-(trifluoromethoxy)phenyl)benzo[d]isoxazol-3-amine

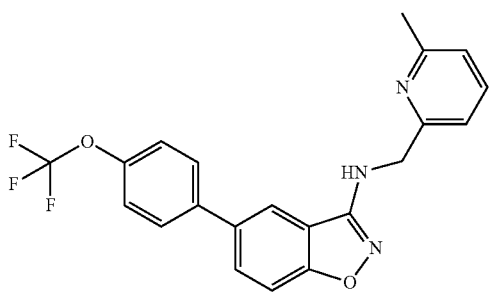 [SMILES: Cc1cccc(CNc2noc3ccc(-c4ccc(OC(F)(F)F)cc4)cc23)n1]

1H NMR (400 MHz, DMSO-d6) δ 8.27 (dd, J=1.9, 0.8 Hz, 1H), 7.85 (dd, J=8.7, 1.9 Hz, 1H), 7.81-7.75 (m, 2H), 7.71-7.59 (m, 2H), 7.55 (dd, J=8.7, 0.7 Hz, 1H), 7.52-7.43 (m, 2H), 7.23 (d, J=7.8 Hz, 1H), 7.13 (d, J=7.6 Hz, 1H), 4.51 (d, J=6.0 Hz, 2H), 2.46 (s, 3H). m/z: 400 (MH+)

Example 130

3-morpholino-5-(4-(trifluoromethoxy)phenyl)benzo[d]isoxazole

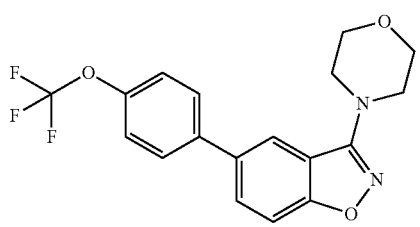 [SMILES: FC(F)(F)Oc1ccc(-c2ccc3onc(N4CCOCC4)c3c2)cc1]

1H NMR (400 MHz, DMSO-d6) δ 8.23-8.17 (m, 1H), 7.91-7.80 (m, 3H), 7.68 (d, J=8.8 Hz, 1H), 7.51-7.40 (m, 2H), 3.85-3.72 (m, 4H), 3.57-3.43 (m, 4H). m/z: 365 (MH+).

Example 131

N-isopropyl-5-(4-(trifluoromethoxy)phenyl)benzo[d]isoxazol-3-amine

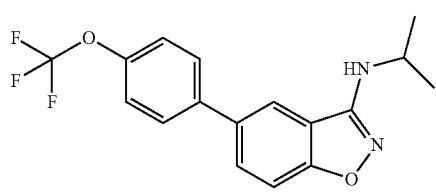 [SMILES: CC(C)Nc1noc2ccc(-c3ccc(OC(F)(F)F)cc3)cc12]

1H NMR (400 MHz, DMSO-d6) δ 8.21 (dd, J=1.9, 0.8 Hz, 1H), 7.83 (dd, J=8.7, 1.9 Hz, 1H), 7.80-7.75 (m, 2H), 7.52 (dd, J=8.7, 0.8 Hz, 1H), 7.50-7.44 (m, 2H), 6.80 (d, J=7.1 Hz, 1H), 3.86-3.62 (m, 1H), 1.25 (d, J=6.4 Hz, 6H). m/z: 337 (MH+).

Example 132

3-(1H-imidazol-1-yl)-5-(4-(trifluoromethoxy)phenyl)benzo[d]isoxazole

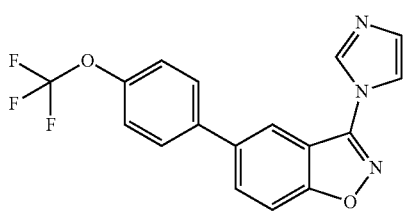 [SMILES: FC(F)(F)Oc1ccc(-c2ccc3onc(-n4ccnc4)c3c2)cc1]

1H NMR (400 MHz, DMSO-d6) δ 8.73 (t, J=1.1 Hz, 1H), 8.41 (dd, J=1.7, 0.8 Hz, 1H), 8.11 (dd, J=8.9, 1.8 Hz, 1H), 8.08 (t, J=1.4 Hz, 1H), 8.01-7.93 (m, 3H), 7.54-7.46 (m, 2H), 7.30 (dd, J=1.5, 0.8 Hz, 1H). m/z: 346 (MH+).

Example 133

N,N-dimethyl-5-(4-(trifluoromethoxy)phenyl)benzo[d]isoxazol-3-amine

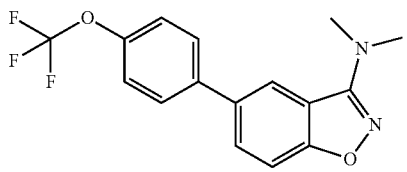 [SMILES: CN(C)c1noc2ccc(-c3ccc(OC(F)(F)F)cc3)cc12]

1H NMR (400 MHz, DMSO-d6) δ 8.14 (dd, J=1.8, 0.8 Hz, 1H), 7.89-7.80 (m, 3H), 7.62 (dd, J=8.7, 0.8 Hz, 1H), 7.49-7.40 (m, 2H), 3.16 (s, 6H). m/z: 323 (MH+).

Example 134

(R)-5-(((5-(4-(trifluoromethoxy)phenyl)benzo[d]isoxazol-3-yl)amino)methyl)pyrrolidin-2-one

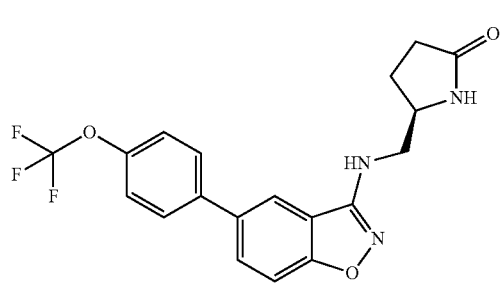 [SMILES: O=C1CC[C@H](CNc2noc3ccc(-c4ccc(OC(F)(F)F)cc4)cc23)N1]

1H NMR (400 MHz, DMSO-d6) δ 8.21-8.14 (m, 1H), 7.85 (dd, J=8.7, 1.9 Hz, 1H), 7.81-7.74 (m, 2H), 7.71 (s, 1H), 7.55 (d, J=8.7 Hz, 1H), 7.52-7.44 (m, 2H), 7.07 (t, J=5.9 Hz, 1H), 3.86 (p, J=6.0 Hz, 1H), 3.40-3.21 (m, 2H), 2.28-2.03 (m, 3H), 1.89-1.72 (m, 1H). m/z: 392 (MH+).

Example 135

1-(2-((5-(4-(trifluoromethoxy)phenyl)benzo[d]isoxazol-3-yl)amino)ethyl)pyrrolidin-2-one

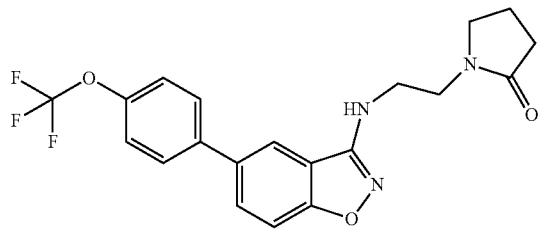 [SMILES: O=C1CCCN1CCNc1noc2ccc(-c3ccc(OC(F)(F)F)cc3)cc12]

1H NMR (400 MHz, DMSO-d6) δ 8.12 (dd, J=1.9, 0.8 Hz, 1H), 7.84 (dd, J=8.7, 1.9 Hz, 1H), 7.79-7.72 (m, 2H), 7.55 (d, J=8.7 Hz, 1H), 7.51-7.45 (m, 2H), 7.11 (t, J=5.6 Hz, 1H), 3.51-3.35 (m, 6H), 2.17 (t, J=8.1 Hz, 2H), 1.89 (tt, J=7.8, 6.6 Hz, 2H). m/z: 406 (MH+).

Example 136

3-(1H-1,2,4-triazol-1-yl)-5-(4-(trifluoromethoxy)phenyl)benzo[d]isoxazole

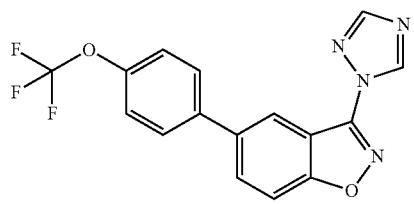 [SMILES: FC(F)(F)Oc1ccc(-c2ccc3onc(-n4cncn4)c3c2)cc1]

1H NMR (400 MHz, DMSO-d6) δ 9.59 (s, 1H), 8.57 (s, 1H), 8.42 (dd, J=1.8, 0.8 Hz, 1H), 8.13 (dd, J=8.9, 1.9 Hz, 1H), 8.01 (dd, J=8.9, 0.8 Hz, 1H), 7.92-7.84 (m, 2H), 7.55-7.45 (m, 2H). m/z: 347 (MH+).

Example 137

N-(2-(1H-1,2,4-triazol-1-yl)ethyl)-5-(4-(trifluoromethoxy)phenyl)benzo[d]isoxazol-3-amine

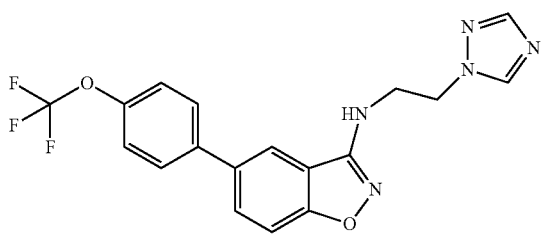 [SMILES: FC(F)(F)Oc1ccc(-c2ccc3onc(NCCn4cncn4)c3c2)cc1]

1H NMR (400 MHz, DMSO-d6) δ 8.48 (s, 1H), 8.10 (dd, J=1.9, 0.8 Hz, 1H), 7.98 (s, 1H), 7.85 (dd, J=8.7, 1.9 Hz, 1H), 7.79-7.71 (m, 2H), 7.57 (d, J=8.7 Hz, 1H), 7.51-7.43 (m, 2H), 7.22 (t, J=5.8 Hz, 1H), 4.47 (t, J=5.8 Hz, 2H), 3.70 (q, J=5.9 Hz, 2H). m/z: 390 (MH+).

Example 138

3-(2-methyl-1H-imidazol-1-yl)-5-(4-(trifluoromethoxy)phenyl)benzo[d]isoxazole

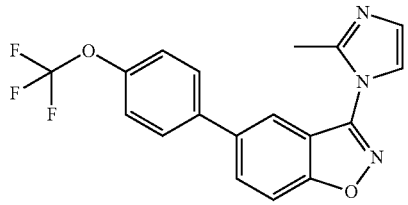 [SMILES: Cc1nccn1-c1noc2ccc(-c3ccc(OC(F)(F)F)cc3)cc12]

1H NMR (400 MHz, DMSO-d6) δ 8.15-8.08 (m, 2H), 8.03-7.97 (m, 1H), 7.95 (d, J=1.6 Hz, 1H), 7.94-7.89 (m, 2H), 7.51-7.44 (m, 2H), 7.13 (d, J=1.6 Hz, 1H), 2.53 (s, 3H). m/z: 360 (MH+).

Example 139

3-(4-methyl-1H-imidazol-1-yl)-5-(4-(trifluoromethoxy)phenyl)benzo[d]isoxazole

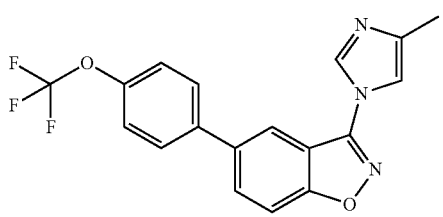 [SMILES: Cc1cn(-c2noc3ccc(-c4ccc(OC(F)(F)F)cc4)cc23)cn1]

1H NMR (400 MHz, DMSO-d6) δ 8.61 (d, J=1.4 Hz, 1H), 8.43-8.38 (m, 1H), 8.09 (dd, J=8.9, 1.7 Hz, 1H), 7.99-7.92 (m, 3H), 7.77 (t, J=1.3 Hz, 1H), 7.53-7.47 (m, 2H), 2.23 (d, J=1.1 Hz, 3H). m/z: 360 (MH+).

Example 140

3-(4-chloro-1H-imidazol-1-yl)-5-(4-(trifluoromethoxy)phenyl)benzo[d]isoxazole

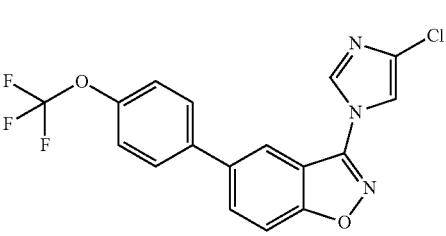 [SMILES: FC(F)(F)Oc1ccc(-c2ccc3onc(-n4cnc(Cl)c4)c3c2)cc1]

Example 141

3-(3-methyl-1H-1,2,4-triazol-1-yl)-5-(4-(trifluoromethoxy)phenyl)benzo[d]isoxazole

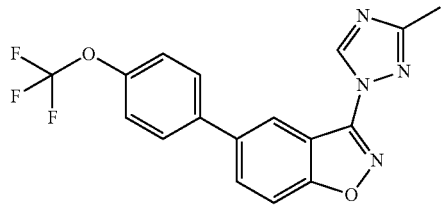 [SMILES: Cc1ncn(-c2noc3ccc(-c4ccc(OC(F)(F)F)cc4)cc23)n1]

1H NMR (400 MHz, DMSO-d6) δ 9.43 (s, 1H), 8.40 (dd, J=1.9, 0.8 Hz, 1H), 8.10 (dd, J=8.9, 1.8 Hz, 1H), 7.99 (d, J=8.9, 1H), 7.89-7.85 (m, 2H), 7.56-7.44 (m, 2H), 2.47 (s, 3H). m/z: 361 (MH+).

Example 142

3-(4-phenyl-1H-imidazol-1-yl)-5-(4-(trifluoromethoxy)phenyl)benzo[d]isoxazole

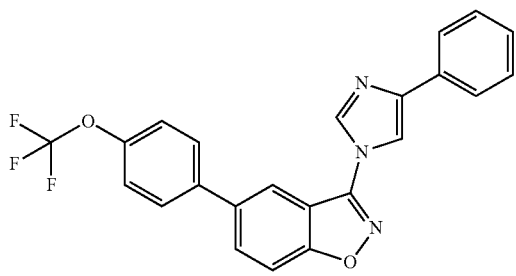 [SMILES: FC(F)(F)Oc1ccc(-c2ccc3onc(-n4cnc(-c5ccccc5)c4)c3c2)cc1]

1H NMR (400 MHz, DMSO-d6) δ 8.78 (d, J=1.3 Hz, 1H), 8.55 (d, J=1.3 Hz, 1H), 8.51 (dd, J=1.8, 0.8 Hz, 1H), 8.12 (dd, J=8.9, 1.7 Hz, 1H), 8.03-7.94 (m, 5H), 7.56-7.48 (m, 2H), 7.43 (dd, J=8.4, 7.1 Hz, 2H), 7.34-7.25 (m, 1H). m/z: 422 (MH+).

Example 143

3-(4-(tert-butyl)-1H-imidazol-1-yl)-5-(4-(trifluoromethoxy)phenyl)benzo[d]isoxazole

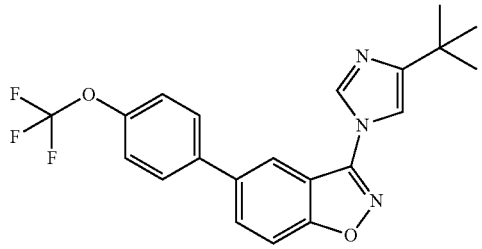 [SMILES: CC(C)(C)c1cn(-c2noc3ccc(-c4ccc(OC(F)(F)F)cc4)cc23)cn1]

1H NMR (400 MHz, DMSO-d6) δ 8.63 (d, J=1.3 Hz, 1H), 8.43-8.39 (m, 1H), 8.08 (dd, J=8.9, 1.7 Hz, 1H), 8.00-7.92 (m, 3H), 7.61 (d, J=1.4 Hz, 1H), 7.52-7.46 (m, 2H), 1.30 (s, 9H). m/z: 402 (MH+).

Example 144

3-(2-isopropyl-1H-imidazol-1-yl)-5-(4-(trifluoromethoxy)phenyl)benzo[d]isoxazole

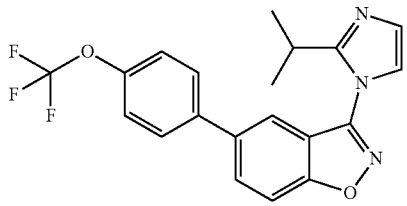 [SMILES: CC(C)c1nccn1-c1noc2ccc(-c3ccc(OC(F)(F)F)cc3)cc12]

1H NMR (400 MHz, DMSO-d6) δ 8.11 (dd, J=8.8, 1.8 Hz, 1H), 8.05 (dd, J=1.8, 0.8 Hz, 1H), 8.01 (dd, J=8.8, 0.8 Hz, 1H), 7.94-7.89 (m, 2H), 7.87 (d, J=1.5 Hz, 1H), 7.51-7.44 (m, 2H), 7.15 (d, J=1.5 Hz, 1H), 3.37 (p, J=6.8 Hz, 1H), 1.23 (d, J=6.8 Hz, 6H). m/z: 388 (MH+).

Example 145

5-(4-(trifluoromethoxy)phenyl)-3-(4-(trifluoromethyl)-1H-imidazol-1-yl)benzo[d]isoxazole

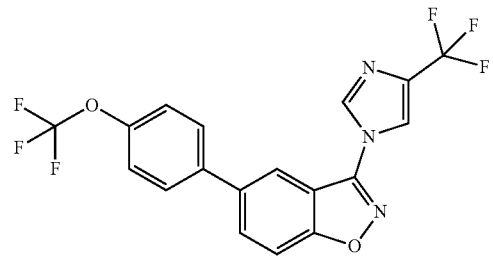 [SMILES: FC(F)(F)Oc1ccc(-c2ccc3onc(-n4cnc(C(F)(F)F)c4)c3c2)cc1]

1H NMR (400 MHz, DMSO-d6) δ 8.87 (dd, J=1.4, 0.8 Hz, 1H), 8.79-8.74 (m, 1H), 8.45 (dd, J=1.7, 0.8 Hz, 1H), 8.13 (dd, J=8.9, 1.7 Hz, 1H), 8.01 (dd, J=8.9, 0.8 Hz, 1H), 7.99-7.93 (m, 2H), 7.55-7.47 (m, 2H). m/z: 414 (MH+).

Example 146

(1-(5-(4-(trifluoromethoxy)phenyl)benzo[d]isoxazol-3-yl)-1H-imidazol-4-yl)methanol

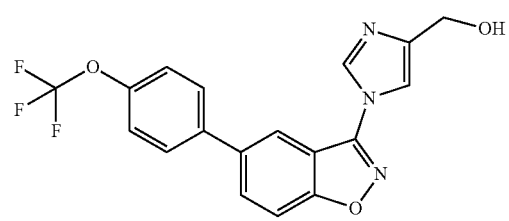 [SMILES: OCc1cn(-c2noc3ccc(-c4ccc(OC(F)(F)F)cc4)cc23)cn1]

1H NMR (400 MHz, DMSO-d6) δ 8.67 (d, J=1.4 Hz, 1H), 8.40 (dd, J=1.7, 0.8 Hz, 1H), 8.10 (dd, J=8.9, 1.7 Hz, 1H), 8.01-7.93 (m, 3H), 7.84 (q, J=1.0 Hz, 1H), 7.53-7.45 (m, 2H), 5.10 (t, J=5.7 Hz, 1H), 4.48 (dd, J=5.7, 1.0 Hz, 2H). m/z: 376 (MH+).

Example 147

5-(4-(trifluoromethoxy)phenyl)benzo[d]isoxazol-3-amine

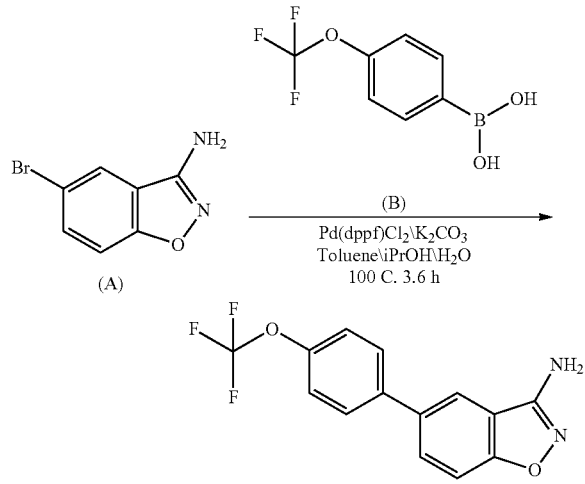

A (0.575 g, 2.70 mmol), B (0.834 g, 4.05 mmol), Pd(dppf)Cl₂ (0.200 g, 0.27 mmol), Potassium carbonate (0.746 g, 5.40 mmol) were mixed. Toluene (4 mL), 2-isopropanol (2 mL), water (4 mL) were added. The vial was then capped tight, stirred at 100° C. for 3.6 h. The mixture was diluted with EtOAc, washed with brine, dried with MgSO₄, concentrated and purified by silica gel column (Rf=0.13 in 20% EtOAc/hexane) to afford the title compound (0.523 g, 66%).

1H NMR (400 MHz, DMSO-d6) δ 8.17-8.12 (m, 1H), 7.83 (dd, J=8.7, 1.9 Hz, 1H), 7.80-7.74 (m, 2H), 7.56-7.50 (m, 1H), 7.50-7.44 (m, 2H), 6.45 (s, 2H). m/z: 295 (MH+).

Example 148

3-(pyrimidin-2-ylmethoxy)-5-(4-(trifluoromethoxy)phenyl)isoxazolo[5,4-c]pyridine

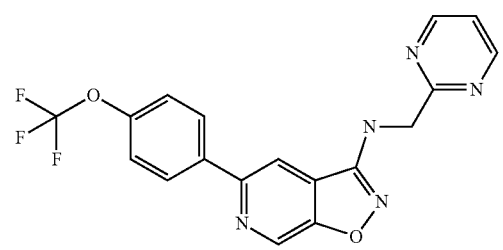 [SMILES: FC(F)(F)Oc1ccc(-c2cc3c(NCc4ncccn4)noc3cn2)cc1]

Example 148 was prepared using a similar synthetic procedure as Example 1 using the appropriate starting materials.

¹H NMR (400 MHz, DMSO-d₆) δ 9.19 (d, J=1.1 Hz, 1H), 8.84 (d, J=4.9 Hz, 2H), 8.48 (d, J=1.2 Hz, 1H), 8.35-8.26 (m, 2H), 7.53-7.43 (m, 3H), 5.73 (s, 2H). MS: 389 (MH⁺).

Example 149

N-((4-methoxypyrimidin-2-yl)methyl)-5-(4-(trifluoromethoxy)phenyl)benzo[d]isoxazol-3-amine

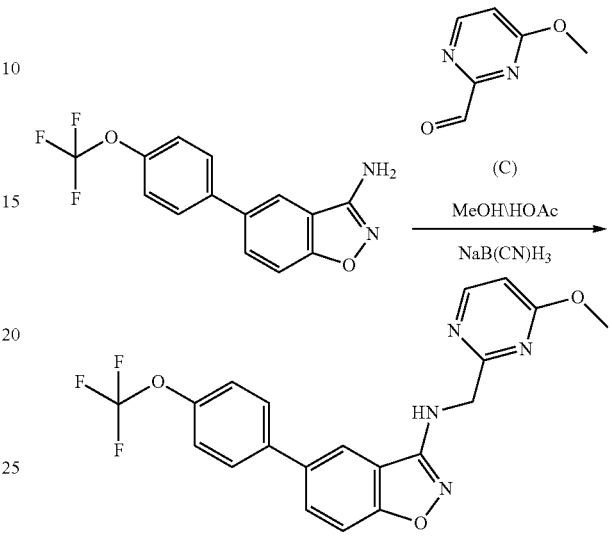

Example 147 (0.1 g, 0.34 mmol), C (0.047 g, 0.34 mmol) were mixed in MeOH (2 mL), two drops of HOAc was added. The suspension was stirred at room temperature for 2-3 days. Sodium cyanoborohydride (0.180 g, 2.35 mmol) was added. The resultant mixture was stirred at room temperature overnight, quenched with aqueous NaHCO₃, extracted with EtOAc, washed with brine, concentrated, and purified with HPLC. The resultant product in TFA salt form was desalted with K₂CO₃/EtOAc extraction to afford parent compound the title compound (0.0357 g, 25%).

1H NMR (400 MHz, DMSO-d6) δ 8.46 (d, J=5.8 Hz, 1H), 8.35-8.31 (m, 1H), 7.85 (dd, J=8.7, 1.9 Hz, 1H), 7.83-7.75 (m, 2H), 7.59 (t, J=6.2 Hz, 1H), 7.54 (d, J=8.7 Hz, 1H), 7.52-7.45 (m, 2H), 6.82 (d, J=5.8 Hz, 1H), 4.58 (d, J=6.2 Hz, 2H), 3.87 (s, 3H). m/z: 417 (MH+).

Example 150

N,N-diethyl-2-((5-(4-(trifluoromethoxy)phenyl)benzo[d]isoxazol-3-yl)oxy)acetamide

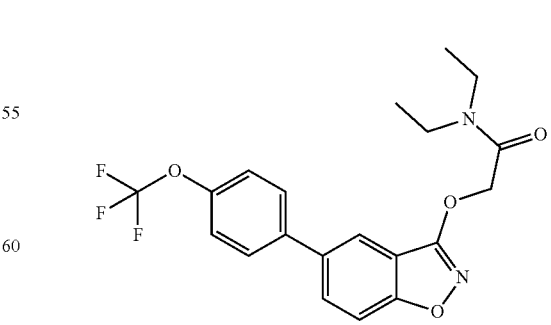

Example 150 was prepared using a similar synthetic procedure as Example 121 using the appropriate starting materials.

¹H NMR (400 MHz, DMSO-d₆) δ 8.03-7.93 (m, 2H), 7.90-7.82 (m, 2H), 7.73 (d, J=8.7 Hz, 1H), 7.45 (d, J=8.2 Hz, 2H), 5.21 (s, 2H), 3.36-3.29 (m, 4H), 1.17 (t, J=7.1 Hz, 3H), 1.03 (t, J=7.0 Hz, 3H). MS: 409 (MH⁺).

Example 151

3-(pyrazin-2-ylmethoxy)-5-(4-(trifluoromethoxy)phenyl)benzo[d]isoxazole

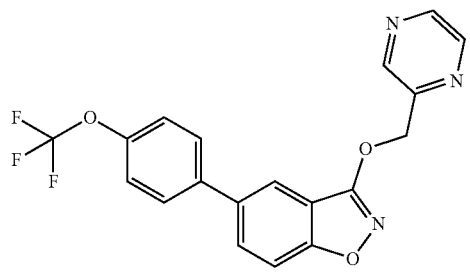 [SMILES: FC(F)(F)Oc1ccc(-c2ccc3onc(OCc4cnccn4)c3c2)cc1]

Example 151 was prepared using a similar synthetic procedure as Example 43 using the appropriate starting materials.

¹H NMR (400 MHz, DMSO-d₆) δ 8.97 (d, J=1.4 Hz, 1H), 8.73-8.65 (m, 2H), 8.11 (d, J=1.8 Hz, 1H), 7.99 (dd, J=8.9, 1.9 Hz, 1H), 7.92-7.83 (m, 2H), 7.75 (d, J=8.8 Hz, 1H), 7.48-7.41 (m, 2H), 5.65 (s, 2H). MS: 388 (MH⁺).

Example 152

3-((3-methylpyrazin-2-yl)methoxy)-5-(4-(trifluoromethoxy)phenyl)benzo[d]isoxazole

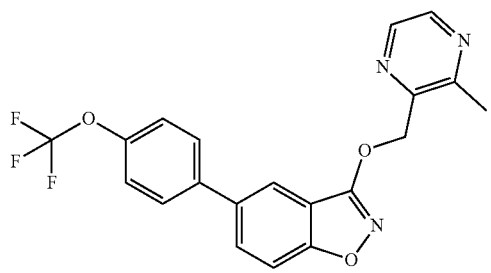 [SMILES: Cc1nccnc1COc1noc2ccc(-c3ccc(OC(F)(F)F)cc3)cc12]

Example 152 was prepared using a similar synthetic procedure as Example 43 using the appropriate starting materials.

¹H NMR (400 MHz, DMSO-d₆) δ 8.54 (d, J=2.5 Hz, 1H), 8.48 (d, J=2.6 Hz, 1H), 8.02 (d, J=1.9 Hz, 1H), 7.97 (dd, J=9.0, 1.9 Hz, 1H), 7.86 (d, J=8.5 Hz, 2H), 7.74 (d, J=8.8 Hz, 1H), 7.43 (d, J=8.2 Hz, 2H), 5.67 (s, 2H), 2.64 (s, 3H). MS: 402 (MH⁺).

Example 153

3-(1-(5-methyl-1,3,4-oxadiazol-2-yl)ethoxy)-5-(4-(trifluoromethoxy)phenyl)benzo[d]isoxazole

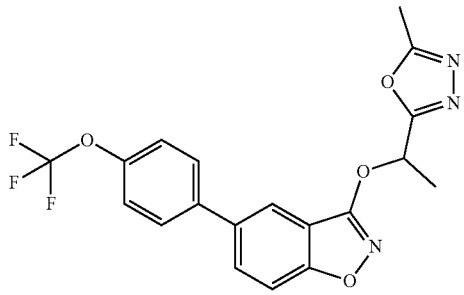 [SMILES: Cc1nnc(C(C)Oc2noc3ccc(-c4ccc(OC(F)(F)F)cc4)cc23)o1]

Example 153 was prepared using a similar synthetic procedure as Example 43 using the appropriate starting materials.

¹H NMR (400 MHz, DMSO-d₆) δ 8.03-7.95 (m, 2H), 7.92-7.83 (m, 2H), 7.76 (d, J=8.6 Hz, 1H), 7.44 (d, J=8.3 Hz, 2H), 6.25 (q, J=6.6 Hz, 1H), 2.51 (s, 3H), 1.85 (d, J=6.6 Hz, 3H). MS: 406 (MH⁺).

Example 154

3-((5-cyclopropyl-1,3,4-thiadiazol-2-yl)methoxy)-5-(4-(trifluoromethoxy)phenyl)benzo[d]isoxazole

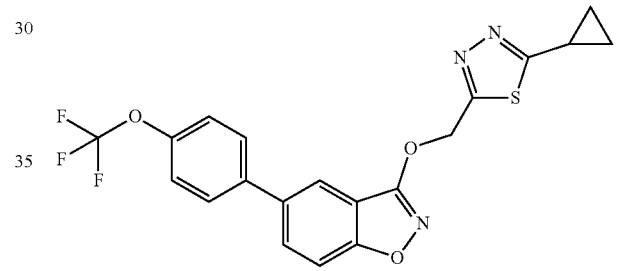

Example 154 was prepared using a similar synthetic procedure as Example 92 using the appropriate starting materials.

¹H NMR (400 MHz, DMSO-d₆) δ 8.04-7.95 (m, 2H), 7.90-7.82 (m, 2H), 7.77 (d, J=8.7 Hz, 1H), 7.44 (d, J=7.8 Hz, 2H), 5.88 (s, 2H), 2.55 (tt, J=8.3, 4.8 Hz, 1H), 1.28-1.15 (m, 2H), 1.07-0.98 (m, 2H). MS: 434 (MH⁺).

Example 155

7-fluoro-3-((5-methyl-1,3,4-oxadiazol-2-yl)methoxy)-5-(4-(trifluoromethoxy)phenyl)benzo[d]isoxazole

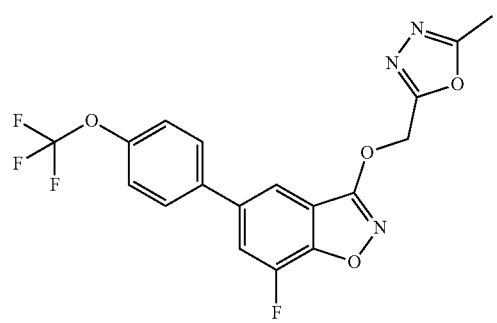 [SMILES: Cc1nnc(COc2noc3c(F)cc(-c4ccc(OC(F)(F)F)cc4)cc23)o1]

Example 155 was prepared using a similar synthetic procedure as Example 92 using the appropriate starting materials.

$^1$H NMR (400 MHz, DMSO-$d_6$) δ 8.03 (dd, J=12.3, 1.5 Hz, 1H), 7.95-7.87 (m, 3H), 7.48-7.41 (m, 2H), 5.78 (s, 2H), 2.54 (s, 3H). MS: 410 (MH$^+$).

Example 156

N-(oxazol-2-ylmethyl)-5-(4-(trifluoromethoxy)phenyl)benzo[d]isoxazol-3-amine

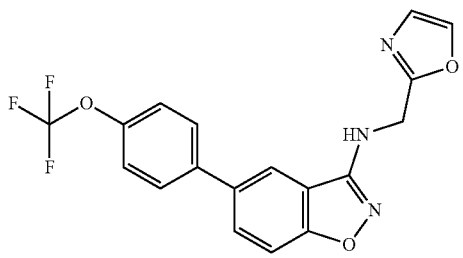 [SMILES: FC(F)(F)Oc1ccc(-c2ccc3onc(NCc4ncco4)c3c2)cc1]

Example 156 was prepared using a similar synthetic procedure as Example 149 using the appropriate starting materials.

$^1$H NMR (400 MHz, DMSO-$d_6$) δ 8.22 (dd, J=1.9, 0.8 Hz, 1H), 8.06 (d, J=0.9 Hz, 1H), 7.86 (dd, J=8.8, 1.9 Hz, 1H), 7.82-7.73 (m, 3H), 7.57 (d, J=8.7 Hz, 1H), 7.52-7.44 (m, 2H), 7.17 (d, J=0.9 Hz, 1H), 4.61 (d, J=6.0 Hz, 2H). m/z: 376 (MH$^+$).

Example 157 tert-butyl 2-((5-(4-(trifluoromethoxy)phenyl)benzo[d]isoxazol-3-yl)oxy)acetate

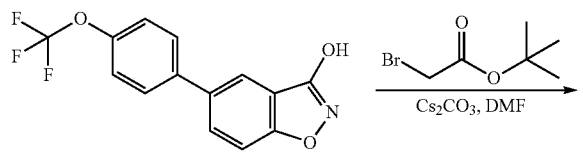

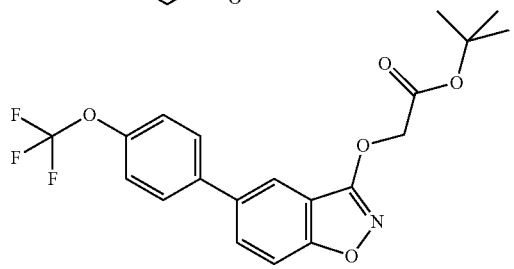

5-(4-(trifluoromethoxy)phenyl)benzo[d]isoxazol-3-ol (500 mg, 1.69 mmol), tert-butyl 2-bromoacetate (500 mg, 2.56 mmol) and cesium carbonate (1.65 g) were combined in 5 mL DMF and stirred at ambient temperature for 1 hour. The reaction mixture was diluted with 80 mL ethyl acetate, washed with water and brine and evaporated under vacuum. Flash chromatographic purification on 12 g silica gel with 0-100% ethyl acetate in hexane gave tert-butyl 2-((5-(4-(trifluoromethoxy)phenyl)benzo[d]isoxazol-3-yl)oxy)acetate (285 mg, 0.70 mmol).

$^1$H NMR (400 MHz, DMSO-$d_6$) δ 8.04-8.01 (m, 1H), 7.98 (dd, J=8.8, 1.8 Hz, 1H), 7.90-7.83 (m, 2H), 7.75 (d, J=8.8 Hz, 1H), 7.45 (d, J=8.0 Hz, 2H), 5.00 (s, 2H), 1.42 (s, 9H). MS: 410 (MH$^+$).

Example 158

Hard gelatin capsules containing the following ingredients are prepared:

| Ingredient | Quantity (mg/capsule) |
|---|---|
| Active Ingredient | 30.0 |
| Starch | 305.0 |
| Magnesium stearate | 5.0 |

The above ingredients are mixed and filled into hard gelatin capsules.

Example 159

A tablet Formula Is prepared using the ingredients below:

| Ingredient | Quantity (mg/tablet) |
|---|---|
| Active Ingredient | 25.0 |
| Cellulose, microcrystalline | 200.0 |
| Colloidal silicon dioxide | 10.0 |
| Stearic acid | 5.0 |

The components are blended and compressed to form tablets.

Example 160

A dry powder inhaler formulation is prepared containing the following components:

| Ingredient | Weight % |
|---|---|
| Active Ingredient | 5 |
| Lactose | 95 |

The active ingredient is mixed with the lactose and the mixture is added to a dry powder inhaling appliance.

Example 161

Tablets, each containing 30 mg of active ingredient, are prepared as follows:

| Ingredient | Quantity (mg/tablet) |
|---|---|
| Active Ingredient | 30.0 mg |
| Starch | 45.0 mg |
| Microcrystalline cellulose | 35.0 mg |
| Polyvinylpyrrolidone (as 10% solution in sterile water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50° C. to 60° C. and passed through a 16 mesh U.S. sieve. The sodium carboxymethyl starch, magnesium stearate and talc, previously passed through a No. 30 mesh U.S. sieve, are then added to the granules which, after mixing, are compressed on a tablet machine to yield tablets each weighing 120 mg.

Example 162

Suppositories, each containing 25 mg of active ingredient are made as follows:

| Ingredient | Amount |
|---|---|
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Example 163

Suspensions, each containing 50 mg of active ingredient per 5.0 mL dose are made as follows:

| Ingredient | Amount |
|---|---|
| Active Ingredient | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 mL |

The active ingredient, sucrose and xanthan gum are blended, passed through a No. 10 mesh U.S. sieve and then mixed with a previously made solution of the microcrystalline cellulose and sodium carboxymethyl cellulose in water. The sodium benzoate, flavor and color are diluted with some of the water and added with stirring. Sufficient water is then added to produce the required volume.

Example 164

A subcutaneous formulation may be prepared as follows:

| Ingredient | Quantity |
|---|---|
| Active Ingredient | 5.0 mg |
| Corn Oil | 1.0 mL |

Example 165

An injectable preparation is prepared having the following composition:

| Ingredients | Amount |
|---|---|
| Active ingredient | 2.0 mg/mL |
| Mannitol, USP | 50 mg/mL |
| Gluconic acid, USP | q.s. (pH 5-6) |
| water (distilled, sterile) | q.s. to 1.0 mL |
| Nitrogen Gas, NF | q.s. |

Example 166

A topical preparation is prepared having the following composition:

| Ingredients | grams |
|---|---|
| Active ingredient | 0.2-10 |
| Span 60 | 2.0 |
| Tween 60 | 2.0 |
| Mineral oil | 5.0 |
| Petrolatum | 0.10 |
| Methyl paraben | 0.15 |
| Propyl paraben | 0.05 |
| BHA (butylated hydroxy anisole) | 0.01 |
| Water | q.s. to 100 |

All of the above ingredients, except water, are combined and heated to 60° C. with stirring. A sufficient quantity of water at 60° C. is then added with vigorous stirring to emulsify the ingredients and water then added q.s. 100 g.

Example 167

Sustained Release Composition

| Ingredient | Weight Range % |
|---|---|
| Active ingredient | 50-95 |
| Microcrystalline cellulose (filler) | 1-35 |
| Methacrylic acid copolymer | 1-35 |
| Sodium hydroxide | 0.1-1.0 |
| Hydroxypropyl methylcellulose | 0.5-5.0 |
| Magnesium stearate | 0.5-5.0 |

The sustained release formulations of this disclosure are prepared as follows: compound and pH-dependent binder and any optional excipients are intimately mixed (dry-blended). The dry-blended mixture is then granulated in the presence of an aqueous solution of a strong base which is sprayed into the blended powder. The granulate is dried, screened, mixed with optional lubricants (such as talc or magnesium stearate) and compressed into tablets. Preferred aqueous solutions of strong bases are solutions of alkali metal hydroxides, such as sodium or potassium hydroxide, preferably sodium hydroxide, in water (optionally containing up to 25% of water-miscible solvents such as lower alcohols).

The resulting tablets may be coated with an optional film-forming agent, for identification, taste-masking purposes and to improve ease of swallowing. The film forming agent will typically be present in an amount ranging from between 2% and 4% of the tablet weight. Suitable film-forming agents are well known to the art and include hydroxypropyl methylcellulose, cationic methacrylate copolymers (dimethylaminoethyl methacrylate/methyl-butyl methacrylate copolymers—Eudragit® E—Röhm. Pharma) and the like. These film-forming agents may optionally contain colorants, plasticizers and other supplemental ingredients.

The compressed tablets preferably have a hardness sufficient to withstand 8 Kp compression. The tablet size will depend primarily upon the amount of compound in the tablet. The tablets will include from about 5 mg to about 1 g of compound. In certain embodiments, the tablets will include about 5 mg, about 10 mg, about 25 mg, about 50 mg, about 100 mg, about 150 mg, about 200 mg, about 250 mg, about 300 mg, about 350 mg, about 400 mg, about 450 mg, about 500 mg, about 600 mg, or about 750 mg of compound.

In order to influence the dissolution rate, the time during which the compound containing powder is wet mixed is controlled. Preferably the total powder mix time, i.e. the time during which the powder is exposed to sodium hydroxide solution, will range from 1 to 10 minutes and preferably from 2 to 5 minutes. Following granulation, the particles are removed from the granulator and placed in a fluid bed dryer for drying at about 60° C.

Example 168

Activity testing is conducted in the Examples below using methods described herein and those well known in the art.

Cardiac Sodium Current Screening Assays:

The cardiac late sodium current (Late $I_{Na}$) and peak sodium current (Peak $I_{Na}$) assays are performed on an automated electrophysiology platform, QPatch 16X or QPatch HT (Sophion Bioscience, Copenhagen, Denmark) using the whole cell patch clamp technique to measure currents through the cell membrane. The assay uses an HEK293 (human embryonic kidney) cell line heterologously expressing the wild-type human cardiac sodium channel, $hNa_v1.5$, purchased from Millipore (Billerica, Mass.). No beta subunits were coexpressed with the Na channel alpha subunit. Cells are maintained with standard tissue culture procedures and stable channel expression is maintained with 400 µg/mL Geneticin in the culture medium. Experiments are carried out at 23-25° C.

For both the Late $I_{Na}$ and Peak $I_{Na}$ assays, series resistance compensation is set to 100% and series resistance and whole-cell compensation are performed automatically. Currents are digitized at 25 kHz and low-pass filtered at 5 kHz and stored in the Sophion Bioscience Oracle database (Sophion Bioscience, Copenhagen, Denmark). Analysis is performed using QPatch Assay software and data are compiled in Excel 2010 (Microsoft, Seattle, Wash., U.S.A.).

Compound stocks are routinely made by the Gilead Sample Bank in vials to 10 mM in dimethyl sulfoxide (DMSO). In some cases, when compounds are not soluble in DMSO, they are made in 100% ethanol. Stocks are sonicated as necessary. The extracellular solution for screening Late $I_{Na}$ is composed of: 140 mM NaCl, 4 mM KCl, 1.8 mM $CaCl_2$, 1 mM $MgCl_2$, 10 mM HEPES and 10 mM Dextrose with pH adjusted to 7.35 using NaOH. The intracellular solution contains: 105 mM CsF, 20 mM CsCl, 10NaF, 2 mM EGTA, 10 mM HEPES and 10 mM Dextrose with pH adjusted to 7.35 with CsOH. Compounds are diluted in extracellular solution using a MicroLab Nimbus (Hamilton Robotics, Reno, Nev.) to between 0.3 and 3 µM in glass vials and transferred to glass well plates before robotic addition to the cells. The 0 mM Na extracellular solution (0Na-ECF) used at the end of each experiment for the Late $I_{Na}$ and Peak $I_{Na}$ assays to measure baseline current contains: 140 Choline-Cl; 4 mM KCl, 1.8 mM $CaCl_2$; 1 mM $MgCl_2$; 10 mM HEPES and 10 mM Dextrose with pH was adjusted to 7.35 with CsOH.

Late $I_{Na}$ Screening Assay:

For the Late $I_{Na}$ assay, sodium channels are activated every 10 seconds (0.1 Hz) by depolarizing the cell membrane to −20 mV for 250 milliseconds (ms) from a holding potential of −120 mV.

Compounds were tested to determine their activity in blocking the late sodium current. Late $I_{Na}$ was generated by adding 10 µM Tefluthrin (pyrethroid) to the extracellular solution. For the purposes of the screening, Late $I_{Na}$ is defined as the mean current between 240 ms and 265 ms during the voltage step to −20 mV. After establishing the whole cell recording configuration, Late $I_{Na}$ activator is added to each well 4 times over a 15 minute period so that the late component of the Na current reaches a stable value. Compounds were then added (typically at 0.3 or 1 µM), in the presence of the Late $Na^+$ activator, with 3 additions over the course of 5 minutes. Measurements were made at the end of exposure to the third compound addition and values were normalized to the current level when all $Na^+$ was removed from the extracellular solution after two additions of 0Na-ECF.

Results are reported as percent block of late $I_{Na}$ and results were analyzed by incorporating rundown correction for the Late $I_{Na}$.

Peak $I_{Na}$ Screening Assay:

Compounds were evaluated for their effect $Na_v1.5$ Peak $I_{Na}$. It is contemplated that the compounds of Formula I avoid significant block of peak $I_{Na}$. Since the peak $I_{Na}$ in the cells used herein can be very large, introducing artifacts in the recording, the concentration of $Na^+$ in the bath can be reduced to 40 mM by isosmotic replacement of $Na^+$ with Choline (see below).

Tonic Block (TB) of Peak $I_{Na}$ was measured using a voltage step to −20 mV from a holding potential of −100 mV at a low stimulation frequency of 0.1 Hz. Use-Dependent Block (UDB) of Peak $I_{Na}$ was measured during pulse number 50 of a pulse train (−20 mV, 20 ms, 50 pulses, 3 Hz) from a holding potential of −100 mV.

Block of cardiac Peak $I_{Na}$ by compounds of this disclosure is typically increased with an increase in the frequency of stimulation from 0.1 to 3 Hz (frequencies encountered either in the normal heart or during tachycardia).

The extracellular solution for screening Peak $I_{Na}$ is composed of: 40 mM NaCl, 100 mM Choline-Cl, 4 mM KCl, 1.8 mM $CaCl_2$, 1 mM $MgCl_2$ 10 mM HEPES and 10 mM Dextrose with pH adjusted to 7.35 using NaOH. The intracellular solution used for the Peak $I_{Na}$ assay is the same as outlined for the Late $I_{Na}$ assay (see above).

After establishing the whole cell recording configuration, channels were stimulated to open with low frequency (0.1 Hz) so that the recording can be monitored and the extent to which the recording has stabilized can be assessed.

The test compound is then applied at 1 or 3 µM and was added 2 times at 60 second intervals. After the second compound addition, a 200 second wait period was imposed to allow for equilibration. Voltage protocols for TB and UDB are were performed in the absence and presence of compound and TB and UDB are calculated with respect to the compound free condition. Both TB and UDB were analyzed by incorporating rundown correction for the peak $I_{Na}$.

Compounds were tested using the above described assay methods. The data provided in Table 1 (in percent inhibition) was obtained by testing the listed compounds at 1 µM and 0.3 µM concentration in the Late $I_{Na}$ and Peak $I_{Na}$ assays (and other concentrations as needed).

TABLE 1

Late I$_{Na}$ Assay Results

| Example No. | Late I$_{Na}$ 1 uM | Late I$_{Na}$ 0.3 uM | Peak TB 3 uM | Peak UDB 3 Hz 3 uM | Nav1.1 UDB 25 Hz 10 uM | Nav1.2 UDB 25 Hz 10 uM |
|---|---|---|---|---|---|---|
| 1 | 66.2 | 55.0 | | | 5.5 | 10.2 |
| 2 | 54.6 | | 66.1 | 27.9 | | |
| 3 | 52.6 | | 23.2 | 11.8 | <5 | <5 |
| 4 | 62.9 | 29.7 | 38.0 | 17.9 | 14.2 | 13.9 |
| 5 | 54.5 | 38.2 | 18.0 | <5 | <5 | <5 |
| 6 | 51.1 | | 29.8 | 12.6 | <5 | <5 |
| 7 | 47.5 | | 16.3 | <5 | <5 | <5 |
| 8 | 52.6 | | 13.1 | <5 | <5 | <5 |
| 9 | 58.9 | 36.4 | 41.3 | 10.3 | <5 | <5 |
| 10 | 41.0 | | 16.4 | 5.7 | <5 | <5 |
| 11 | 30.0 | | | | | |
| 13 | 35.1 | | 10.7 | <5 | 30.8 | 5.6 |
| 14 | 46.7 | | 23.8 | 6.4 | 34.5 | 9.6 |
| 15 | 32.2 | | 14.3 | <5 | <5 | <5 |
| 16 | 54.2 | | 35.8 | <5 | 27.3 | 18.0 |
| 17 | 45.9 | | 28.9 | <5 | 5.9 | <5 |
| 18 | 38.2 | | 27.7 | 5.2 | <5 | <5 |
| 19 | 27.5 | | | | | |
| 20 | 28.8 | | | | | |
| 21 | 48.8 | | 13.0 | <5 | <5 | <5 |
| 22 | 55.9 | 17.7 | 10.2 | <5 | 28.1 | 40.0 |
| 23 | 45.3 | | <5 | <5 | <5 | 9.9 |
| 24 | 36.0 | | 10.0 | <5 | <5 | <5 |
| 25 | 41.3 | | 12.0 | <5 | <5 | <5 |
| 26 | 49.6 | | 27.8 | <5 | 58.6 | <5 |
| 27 | 35.1 | | 20.8 | <5 | <5 | <5 |
| 28 | 54.4 | 26.7 | 21.6 | <5 | <5 | <5 |
| 29 | 46.4 | | 8.1 | <5 | <5 | <5 |
| 30 | 42.5 | | 15.2 | <5 | <5 | <5 |
| 31 | 43.9 | | 18.5 | <5 | <5 | <5 |
| 32 | 28.8 | | | | | |
| 33 | 35.5 | | 20.9 | 5.1 | <5 | 5.5 |
| 34 | 21.0 | | | | | |
| 35 | 33.6 | | 17.4 | <5 | <5 | <5 |
| 42 | 57.3 | 17.5 | 27.6 | <5 | <5 | <5 |
| 43 | 27.1 | | | | | |
| 44 | 48.2 | | 29.9 | 10.4 | 21.1 | 25.4 |
| 45 | 43.6 | | 16.8 | 15.1 | 63.8 | 42.8 |
| 46 | 36.8 | | 23.7 | 13.9 | 78.4 | |
| 47 | 60.2 | 20.0 | 21.7 | 8.5 | 55.5 | 31.5 |
| 48 | 51.2 | | 9.1 | 5.7 | 52.8 | 54.2 |
| 49 | 39.6 | | 16.9 | <5 | 56.4 | 49.9 |
| 50 | 32.5 | | <5 | <5 | 49.2 | 27.3 |
| 51 | 38.8 | | 12.3 | 7.7 | 30.0 | 15.7 |
| 52 | 24.3 | | | | | |
| 53 | 57.0 | 31.1 | 43.4 | <5 | <5 | <5 |
| 54 | 29.2 | | | | | |
| 55 | 59.9 | 45.4 | 15.1 | 5.13 | 79.8 | |
| 56 | 57.8 | 16.1 | 30.4 | 31.4 | 83.6 | |
| 57 | 57.3 | 17.0 | 22.1 | 37.11 | 82.5 | |
| 58 | 55.0 | 36.7 | 22.2 | <5 | 43.5 | 14.5 |
| 59 | 60.4 | 43.7 | 19.0 | <5 | 46.9 | 37.4 |
| 60 | 57.2 | 16.8 | 30.6 | <5 | 27.0 | <5 |
| 61 | 38.2 | | 11.8 | 6.6 | 28.7 | 31.0 |
| 62 | 28.4 | | | | | |
| 63 | 44.1 | | 39.0 | 13.3 | 77.6 | 68.0 |
| 64 | 30.7 | | 10.1 | <5 | 33.2 | 34.7 |
| 65 | 27.0 | | | | | |
| 66 | 21.9 | | | | | |
| 67 | 77.4 | 54.4 | 48.7 | <5 | 5.26 | <5 |
| 68 | 62.2 | 35.8 | 10.5 | <5 | <5 | <5 |
| 69 | 29.6 | | | | | |
| 70 | 25.5 | | | | | |
| 71 | 81.5 | 41.7 | 61.1 | 44.4 | 93.8 | 89.6 |
| 72 | 57.4 | 14.0 | 17.7 | 10.8 | 78.1 | 75.4 |
| 73 | 66.2 | 20.4 | 41.9 | <5 | 10.1 | <5 |
| 74 | 60.9 | 15.7 | 23.5 | <5 | <5 | <5 |
| 75 | 59.5 | 29.3 | 36.9 | <5 | 34.2 | 27.1 |
| 76 | 55.2 | | 49.9 | <5 | 27.0 | 27.9 |
| 77 | 49.2 | | 34.6 | 8.3 | 49.2 | 31.8 |
| 78 | 47.1 | | 38.7 | 19.5 | 39.9 | 32.8 |
| 79 | 46.1 | | 26.0 | <5 | 36.8 | 34.0 |
| 80 | 35.6 | | 17.3 | 13.7 | 19.8 | 17.5 |
| 81 | 33.7 | | 23.5 | <5 | <5 | 21.8 |
| 82 | 28.1 | | | | | |
| 83 | 23.7 | | | | | |
| 84 | 23.6 | | | | | |
| 85 | 22.5 | | | | | |
| 86 | 21.9 | | | | | |
| 87 | 62.7 | 18.4 | 54.7 | 39.0 | 90.8 | 87.0 |
| 88 | 47.7 | | 20.8 | 19.5 | 66.7 | |
| 89 | 33.2 | | 5.7 | <5 | 16.1 | 52.0 |
| 90 | 20.9 | | | | | |
| 91 | 53.0 | | 33.0 | <5 | 31.1 | 46.9 |
| 92 | 36.3 | | 9.6 | <5 | <5 | <5 |
| 93 | 45.1 | | 14.9 | <5 | <5 | <5 |
| 94 | 58.7 | 35.1 | 17.1 | <5 | <5 | <5 |
| 95 | 51.7 | | 6.4 | <5 | <5 | <5 |
| 96 | 59.2 | 21.1 | 29.4 | <5 | 29.4 | 5.7 |
| 97 | 39.0 | | 26.5 | <5 | 46.3 | 34.3 |
| 98 | 38.7 | | 28.7 | <5 | 15.9 | <5 |
| 99 | 72.3 | 42.3 | 55.6 | <5 | 30.0 | 50.5 |
| 100 | 61.9 | 31.7 | 23.5 | <5 | 9.9 | 11.0 |
| 101 | 54.6 | | 13.5 | <5 | <5 | 30.5 |
| 102 | 43.1 | | 27.8 | 7.7 | <5 | 20.6 |
| 103 | 38.9 | | 18.8 | <5 | 8.5 | <5 |
| 104 | 38.6 | | 23.6 | 19.8 | 53.1 | 57.0 |
| 105 | 53.7 | | 9.4 | 27.8 | 75.7 | 70.9 |
| 106 | 28.3 | | | | | |
| 108 | 83.5 | 30.1 | 62.6 | 69.3 | 89.2 | |
| 109 | 65.7 | 25.3 | 14.5 | <5 | 57.0 | 39.3 |
| 110 | 62.7 | 25.7 | 14.5 | 11.5 | 77.7 | 67.3 |
| 111 | 35.1 | | <5 | 7.3 | 50.4 | 47.3 |
| 113 | 79.9 | 43.9 | 54.3 | 37.3 | 88.4 | 91.2 |
| 114 | 61.2 | 22.5 | 43.4 | 33.3 | 87.1 | 87.0 |
| 115 | 56.7 | 23.5 | 19.8 | 18.3 | 76.4 | 70.8 |
| 116 | 48.3 | | 28.9 | 15.0 | 70.4 | 62.3 |
| 117 | 78.1 | 39.4 | 79.3 | 60.8 | 80.9 | 88.4 |
| 118 | 66.1 | 22.5 | 88.8 | 56.1 | 89.4 | 90.4 |
| 119 | 51.2 | | 36.1 | 6.4 | 56.3 | 52.3 |
| 120 | 58.2 | 35.8 | 35.2 | 6.6 | 68.9 | 74.4 |
| 121 | 77.7 | 39.0 | 79. | 23.4 | 43.6 | 57.8 |
| 122 | 41.3 | | 10.7 | <5 | <5 | 29.7 |
| 123 | 36.3 | | 27.3 | <5 | <5 | <5 |
| 124 | 53.7 | | 49.9 | <5 | 35.0 | 44.9 |
| 125 | 41.8 | | | | <5 | |
| 126 | 50.0 | | 17.3 | <5 | <5 | <5 |
| 127 | 37.4 | | 23.7 | 25.1 | 82.8 | 76.5 |
| 128 | 42 | | 17.3 | <5 | <5 | <5 |
| 129 | 67.5 | 34.3 | | | 33.5 | |
| 130 | 38.3 | | 9.2 | <5 | <5 | <5 |
| 131 | 24.8 | | | | | |
| 132 | 40.5 | | 20.6 | 5.1 | <5 | <5 |
| 133 | 45.8 | | 38.8 | 5.2 | 22.1 | 29.2 |
| 134 | 21.1 | | | | | |
| 135 | 48.8 | 19.7 | 29.3 | 18.0 | 87.2 | 76.5 |
| 136 | 44.8 | | 10.5 | <5 | <5 | <5 |
| 137 | 47.2 | | 43.9 | 17.4 | 82.6 | 86.0 |
| 138 | 29.8 | | | | | |
| 139 | 41.2 | | 15.6 | <5 | 8.8 | 26.1 |
| 140 | 37.6 | | 8.5 | <5 | <5 | <5 |
| 141 | 38.6 | | 17.8 | <5 | 31.5 | 19.9 |
| 142 | 44.0 | | 15.6 | 13.9 | 59.0 | 65.0 |
| 143 | 60.3 | 35.9 | 39.8 | 11.2 | 66.6 | 57.1 |
| 144 | 55.7 | 25.9 | 46.9 | <5 | 73.2 | 75.8 |
| 145 | 84.9 | 61.7 | 93.0 | <5 | 81.4 | 75.8 |
| 146 | 48.4 | | 28.8 | 25.5 | 87.3 | 75.8 |
| 147 | 45.4 | | 26.0 | 3.0 | 32.0 | 20.4 |
| 148 | 37.3 | | 17.9 | <5 | <5 | <5 |
| 149 | 87.6 | 50.9 | 86.4 | <5 | 50.0 | 44.4 |
| 150 | 68.2 | 49.4 | 58.5 | 9.3 | 62.8 | 51.0 |
| 151 | 70.1 | 50.7 | 43.3 | <5 | 20.0 | 18.6 |
| 152 | 53.4 | 19.8 | 30.6 | <5 | 11.4 | 13.8 |
| 153 | 67.6 | 51.3 | 57.6 | | 73.1 | 53.7 |
| 154 | 39.2 | | 7.68 | <5 | 19.8 | 27.0 |
| 155 | 69.2 | 47.0 | 24.8 | 8.4 | 63.5 | 58.6 |

TABLE 1-continued

Late $I_{Na}$ Assay Results

| Example No. | Late $I_{Na}$ 1 uM | Late $I_{Na}$ 0.3 uM | Peak TB 3 uM | Peak UDB 3 Hz 3 uM | Nav1.1 UDB 25 Hz 10 uM | Nav1.2 UDB 25 Hz 10 uM |
|---|---|---|---|---|---|---|
| 156 | 62.8 | 37.9 | 10.4 | <5 | 26.5 | 10.6 |
| 157 | 36.9 |  | 15.6 | <5 | <5 | <5 |
| 158 | 37.3 |  | 17.9 | <5 | <5 | <5 |

The assay results shown in Table 1 establish that compounds tested showed activity as modulators of late sodium current, for example by inhibiting (or reducing) the late sodium current.

In some embodiments the effects of a compound of Formula I are specific for the late sodium current and show little or no activity with respect to one or more other ion channels. Thus, in some embodiments, a compound having an activity of reducing late sodium current will also exhibit little or no activity with regard to the peak sodium current.

Example 169

Use-Dependent Inhibition of the CNS $Na_v1.1$ Sodium Channel

Expression of Human $Na_v1.1$ cDNA

HEK-293 cells stably expressing wild-type (WT) $hNa_v1.1$ (SCN1A, NCBI# AB09354) were obtained from Millipore (Cat. # CYL3009) were used to record $I_{Na}$. Cells are maintained with standard tissue culture procedures and stable channel expression is maintained with 400 ug/mL G418 in the culture medium. Unless otherwise noted, all reagents are purchased from Sigma-Aldrich (St Louis, Mo., U.S.A.).

Electrophysiology

Assays measuring Use-Dependent Block (UDB) of $Na_v1.2$ are performed on an automated electrophysiology platform, QPatch 16X or QPatch HT (Sophion Bioscience, Copenhagen, Denmark), using the whole cell patch clamp technique to measure currents through the cell membrane. Series resistance compensation is set to 100% and series resistance and whole-cell compensation are performed automatically. Currents stored in the Sophion Bioscience Oracle database (Sophion Bioscience, Copenhagen, Denmark). Analysis is performed using QPatch Assay software and data are compiled in Excel 2010 (Microsoft, Seattle, Wash., U.S.A.).

The internal (pipette) solution consists of (in mM) 105 CsF, 10 NaF, 20 CsCl, 2 EGTA, 10 HEPES, 10 Dextrose with a pH of 7.35 and osmolarity of 300 mOsmol/kg. The external (bath) solution contains in (mM): 145 NaCl, 4 KCl, 1.8 $CaCl_2$, 1 $MgCl_2$, 10 dextrose, 10 HEPES, with a pH of 7.35 and osmolarity of 310 mOsmol/kg. Experiments are carried out at 23-25° C.

Compound stocks are routinely made by the Gilead Sample Bank in vials to 10 mM in dimethyl sulfoxide (DMSO). In some cases, when compounds are not soluble in DMSO, they are made in 100% ethanol. Stocks are sonicated as necessary. Compounds are diluted in extracellular solution using a MicroLab Nimbus (Hamilton Robotics, Reno, Nev.) to between 0.3 and 3 µM in glass vials and transferred to glass well plates before robotic addition to the cells.

Cells are allowed to stabilize for 10 min after establishment of the whole-cell configuration before current is measured. The test compound is applied 2 times at 60 second intervals. After the second compound addition, a 200 second wait period was imposed to allow for equilibration. Leak currents are subtracted by using an online P/4 procedure and all currents are low-pass Bessel filtered at 5 kHz and digitized at 525 kHz.

Use-dependent block of $Na_v1.2$ peak current is measured during pulse number 20 of a voltage pulse train (0 mV, 20 ms, 20 pulses, 25 Hz) from a holding potential of −120 mV. Currents are normalized to the peak current recorded in response to the first pulse in each frequency train. The voltage protocol for UDB was performed in the absence and presence of compound and percentage inhibition was calculated with respect to the compound free condition. Results are presented as mean percentage inhibition and data analysis is performed using QPatch Assay Software 4.0, and Excel 2002 (Microsoft, Seattle, Wash., U.S.A.).

Example 170

Use-Dependent Inhibition of the CNS $Na_v1.2$ Sodium Channel

Expression of Human $Na_v1.2$ cDNA

HEK-293 cells stably expressing wild-type (WT) hNaV1.2 (SCN2A NCBI # NM_021007.2, SCN1B NCBI # NM_001037.4, SCN2B NCBI # NM_004588.2) were used to record $I_{Na}$. Cells are maintained with standard tissue culture procedures and stable channel expression is maintained with 800 ug/mL G418 and 3 ug/mL Puromycin in the culture medium. Unless otherwise noted, all reagents are purchased from Sigma-Aldrich (St Louis, Mo., U.S.A.).

Electrophysiology

Assays measuring Use-Dependent Block (UDB) of $Na_v1.2$ are performed on an automated electrophysiology platform, QPatch 16X or QPatch HT (Sophion Bioscience, Copenhagen, Denmark), using the whole cell patch clamp technique to measure currents through the cell membrane. Series resistance compensation is set to 100% and series resistance and whole-cell compensation are performed automatically. Currents stored in the Sophion Bioscience Oracle database (Sophion Bioscience, Copenhagen, Denmark). Analysis is performed using QPatch Assay software and data are compiled in Excel 2010 (Microsoft, Seattle, Wash., U.S.A.).

The internal (pipette) solution consists of (in mM) 105 CsF, 10 NaF, 20 CsCl, 2 EGTA, 10 HEPES, 10 Dextrose with a pH of 7.35 and osmolarity of 300 mOsmol/kg. The external (bath) solution contains in (mM): 145 NaCl, 4 KCl, 1.8 $CaCl_2$, 1 $MgCl_2$, 10 dextrose, 10 HEPES, with a pH of 7.35 and osmolarity of 310 mOsmol/kg. Experiments are carried out at 23-25° C.

Compound stocks are routinely made by the Gilead Sample Bank in vials to 10 mM in dimethyl sulfoxide (DMSO). In some cases, when compounds are not soluble in DMSO, they are made in 100% ethanol. Stocks are sonicated as necessary. Compounds are diluted in extracellular solution using a MicroLab Nimbus (Hamilton Robotics, Reno, Nev.) to between 0.3 and 3 µM in glass vials and transferred to glass well plates before robotic addition to the cells.

Cells are allowed to stabilize for 10 min after establishment of the whole-cell configuration before current is measured. The test compound is applied 2 times at 60 second intervals. After the second compound addition, a 200 second wait period was imposed to allow for equilibration. Leak currents are subtracted by using an online P/4 procedure and all currents are low-pass Bessel filtered at 5 kHz and digitized at 525 kHz.

Results are presented as mean percentage inhibition.

Use-dependent block of $Na_v1.2$ peak current is measured during pulse number 20 of a voltage pulse train (0 mV, 20 ms, 20 pulses, 25 Hz) from a holding potential of −120 mV.

Currents are normalized to the peak current recorded in response to the first pulse in each frequency train. The voltage protocol for UDB was performed in the absence and presence of compound and percentage inhibition was calculated with respect to the compound free condition.

Data analysis is performed using QPatch Assay Software 4.0, and Excel 2002 (Microsoft, Seattle, Wash., U.S.A.).

Using the above methods it may be demonstrated that the compounds of the disclosure are selective for inhibiting cardiac Late $I_{Na}$ current without inhibiting peak currents of brain isoforms $Na_v1.1$ and $Na_v1.2$. The compounds of the disclosure may inhibit the very high frequency firing of $Na_v1.1$ and $Na_v1.2$ or demonstrate voltage dependent block of mutant $Na_v1.1$ and $Na_v1.2$ observed with epilepsy patients. Data for sample compounds is shown above in Table 1.

Example 171

Voltage-Dependent Inhibition of the $Na_v1.3$ Sodium Channel

Expression of Human $Na_v1.3$ cDNA

HEK-293 cells stably expressing wild-type (WT) $hNa_v1.3$ (SCN3A NCBI # NP 001075, SCN1B NCBI # NM 001037.4, SCN2B NCBI # NM 004588.2) were used to record $I_{Na}$. Cells are maintained with standard tissue culture procedures and stable channel expression is maintained with 800 ug/mL G418 and 3 ug/mL Puromycin in the culture medium. Unless otherwise noted, all reagents are purchased from Sigma-Aldrich (St Louis, Mo., U.S.A.).

Electrophysiology

Assays measuring Voltage-Dependent Block (VDB) of $Na_v1.3$ are performed on an automated electrophysiology platform, QPatch 16X or QPatch HT (Sophion Bioscience, Copenhagen, Denmark), using the whole cell patch clamp technique to measure currents through the cell membrane. Series resistance compensation is set to 100% and series resistance and whole-cell compensation are performed automatically. Currents stored in the Sophion Bioscience Oracle database (Sophion Bioscience, Copenhagen, Denmark). Analysis is performed using QPatch Assay software and data are compiled in Excel 2010 (Microsoft, Seattle, Wash., U.S.A.).

The internal (pipette) solution consists of (in mM) 105 CsF, 10 NaF, 20 CsCl, 2 EGTA, 10 HEPES, 10 Dextrose with a pH of 7.35 and osmolarity of 300 mOsmol/kg. The external (bath) solution contains in (mM): 80 NaCl, 60 Choline-Cl, 4 KCl, 1.8 $CaCl_2$, 1 $MgCl_2$, 10 dextrose, 10 HEPES, with a pH of 7.35 and osmolarity of 310 mOsmol/kg. Experiments are carried out at 23-25° C.

Compound stocks are routinely made by the Gilead Sample Bank in vials to 10 mM in dimethyl sulfoxide (DMSO). In some cases, when compounds are not soluble in DMSO, they are made in 100% ethanol. Stocks are sonicated as necessary. Compounds are diluted in extracellular solution using a MicroLab Nimbus (Hamilton Robotics, Reno, Nev.) to 1 µM in glass vials and transferred to glass well plates before robotic addition to the cells.

Cells are allowed to stabilize for 10 min after establishment of the whole-cell configuration before current is measured. The test compound is applied 3 times at 120 second intervals to allow for equilibration. Currents were leak subtracted using a P/4 procedure, low-pass Bessel filtered at 5 kHz and digitized at 25 kHz. Results are presented as mean percentage inhibition.

Voltage-dependent block of $Na_v1.3$ peak current was measured during a voltage step to 0 mV (20 ms) following a voltage step pre-conditioning steps (−55 mV for 10 sec followed by −120 mV for 10 ms). The holding potential was −120 mV and this voltage protocol induces half maximal inactivation of $Na_v1.3$. The voltage protocol for VDB was performed every 45 seconds in the absence and presence of compound and percentage inhibition was calculated with respect to the compound free condition.

Voltage-Dependent Inhibition of the $Na_v1.7$ Sodium Channel

Expression of Human $Na_v1.7$ cDNA

HEK-293 cells stably expressing wild-type (WT) $hNa_v1.7$ were obtained from Scottish Biomedical (Glasgow, Scotland, United Kingdom). Cells are maintained with standard tissue culture procedures and stable channel expression is maintained with 500 ug/mL G418 in the culture medium. Unless otherwise noted, all reagents are purchased from Sigma-Aldrich (St Louis, Mo., U.S.A.).

Electrophysiology

Assays measuring Voltage-Dependent Block (VDB) of $Na_v1.7$ are performed on an automated electrophysiology platform, QPatch 16X or QPatch HT (Sophion Bioscience, Copenhagen, Denmark), using the whole cell patch clamp technique to measure currents through the cell membrane. Series resistance compensation is set to 100% and series resistance and whole-cell compensation are performed automatically. Currents stored in the Sophion Bioscience Oracle database (Sophion Bioscience, Copenhagen, Denmark). Analysis is performed using QPatch Assay software and data are compiled in Excel 2010 (Microsoft, Seattle, Wash., U.S.A.).

The internal (pipette) solution consists of (in mM) 105 CsF, 10 NaF, 20 CsCl, 2 EGTA, 10 HEPES, 10 Dextrose with a pH of 7.35 and osmolarity of 300 mOsmol/kg. The external (bath) solution contains in (mM): 140 NaCl, 4 KCl, 1.8 $CaCl_2$, 1 $MgCl_2$, 10 dextrose, 10 HEPES, with a pH of 7.35 and osmolarity of 310 mOsmol/kg. Experiments are carried out at 23-25° C.

Compound stocks are routinely made by the Gilead Sample Bank in vials to 10 mM in dimethyl sulfoxide (DMSO). In some cases, when compounds are not soluble in DMSO, they are made in 100% ethanol. Stocks are sonicated as necessary. Compounds are diluted in extracellular solution using a MicroLab Nimbus (Hamilton Robotics, Reno, Nev.) to 1 µM in glass vials and transferred to glass well plates before robotic addition to the cells.

Cells are allowed to stabilize for 10 min after establishment of the whole-cell configuration before current is measured. The test compound is applied 3 times at 120 second intervals to allow for equilibration. Currents were leak subtracted using a P/4 procedure, low-pass Bessel filtered at 5 kHz and digitized at 25 kHz. Results are presented as mean percentage inhibition.

Voltage-dependent block of $Na_v1.7$ peak current was measured during a voltage step to 0 mV (20 ms) following a voltage step pre-conditioning steps (−60 mV for 10 sec followed by −120 mV for 10 ms). The holding potential was −120 mV and this voltage protocol induces half maximal inactivation of $Na_v1.7$. The voltage protocol for VDB was performed every 45 seconds in the absence and presence of compound and percentage inhibition was calculated with respect to the compound free condition.

Using the above methods it may be demonstrated that select compounds of the disclosure also exhibit voltage-dependent block of $Na_v1.3$ and $Na_v1.7$. This activity is thought to correlate with potential antidiabetic effects of the compounds. The VDB protocols produce half maximal inactivation of the peak $I_{Na}$ and also mimic the resting membrane potential of pancreatic islet cells (beta, alpha and delta cells). Data for exemplary compounds is shown below in Table 2.

TABLE 2

$Na_v1.3$ and $Na_v1.7$ Assay results

| Example | Nav 1.3-VDB 1 uM | Nav 1.7-VDB 1 uM |
|---|---|---|
| 4 | 12.2 | 28.6 |
| 5 | 13.9 | |
| 6 | <5 | 15.6 |
| 7 | <5 | |
| 8 | 6.4 | |
| 10 | 8.5 | 10.0 |
| 21 | 11.2 | |
| 22 | 17.3 | |
| 24 | <5 | |
| 25 | 12.3 | |
| 29 | 39.5 | 34.2 |
| 30 | 21.5 | |
| 51 | 26.6 | |
| 59 | 14.5 | |
| 61 | 8.6 | |
| 68 | 27.1 | |
| 99 | 41.4 | 59.3 |
| 158 | <5 | |

Example 172

Ischemia-Induced ST Segment Elevation in Anesthetized Rabbits

This study was undertaken to determine the anti-ischemic effects of compounds of the present disclosure in an in vivo rabbit model.

Methods:

Female New Zealand rabbits (3.0-4.0 kg) were purchased from Western Oregon Rabbitry. Animals were housed on a 12-h light and dark cycle and received standard laboratory chow and water. All experiments were performed in accordance with the Guide for the Care and Use of Laboratory Animals published by The National Research Council and with the experimental protocol approved by the Institutional Animal Care Committee of Gilead Sciences, Inc.

Rabbits were anesthetized with ketamine (35 mg/kg) and xylazine (5 mg/kg) intramuscular injection (im). A tracheotomy was performed and the trachea was intubated with an endotracheal tube. The animal was ventilated with room air supplemented with oxygen using a pressure control animal ventilator (Kent Scientific Corp., Torrington, Conn.) at a respiratory rate of 40 strokes/min and peak inspiration pressure of 10 $mmH_2O$, which was adjusted to keep blood gases and pH within the physiological range (iSTAT clinic analyzer, Heska Corp.; Waukesha, Wis.). The left femoral artery was cannulated for the measurement of blood pressure (BP). Blood samples were also withdrawn from femoral artery. The right external jugular vein was cannulated for drug/vehicle administration. Needle electrodes were inserted subcutaneously into the limbs for recording of the surface electrocardiogram (ECG).

The heart was exposed via an incision in the $4^{th}$ intercostal space ($4^{th}$ and/or $5^{th}$ ribs were cut for a clear surgical vision). The chest was opened and a pericardial cradle was formed using 4 retractors. A coronary artery occluder, comprised of a snare made of 5 cm PE-10 tubing with a 6-0 Prolene polypropylene suture in it, was placed loosely around the left anterior descending artery (LAD) at its origin. Two unipolar electrodes, made with teflon coated silver wire attached to a small patch of filter paper, were attached on the surface of the ischemic and normal regions of the left ventricle to record epicardial electrocardiogram.

Reference electrodes were placed in the open incision of the neck. The body temperature of the animal was monitored via a rectal thermometer and maintained at 37-40° C. by adjusting the surface temperature of the surgical table. Regional ischemia (15 min) was induced by ligating the LAD followed by 15 min of reperfusion caused by releasing the ligation. The heart was excised at the end of the experiment and the LAD was re-ligated. The ischemic area was visualized by perfusing the heart with 1% Evans blue in saline and calculated as a percentage of total ventricular weight. Rabbits with ischemic area less than 10% or larger than 25% were excluded from the analysis. Animals were randomly assigned to vehicle and test compound groups. Test compounds were dissolved in 15% NMP, 10% Solutol and 75% de-ionized water ($dH_2O$). Test compounds were given as an iv infusion at a rate targeted to reach plasma concentrations of 1 μM. After 30 min of compound administration the heart was subjected to 15 min of ischemia followed by 15 min of reperfusion.

Results:

The data in Table 3 suggests certain compounds of the disclosure may prevent ischemia-induced myocardial electrical dysfunction.

TABLE 3

Ischemia-induced ST segment elevation results

| Example No. | Rabbit ST Segment* | Plasma concentration |
|---|---|---|
| 1 | 32 | 1 uM |
| 5 | 0 | 1.4 uM |
| 6 | 0 | 0.8 uM |
| 58 | 14 | 1.3 uM |
| 59 | 23 | 1.3 uM |
| 96 | 46 | 1 uM |
| 21 | 66 | 0.4 uM |

*Percent reduction

What is claimed is:

1. A compound selected from the group consisting of:

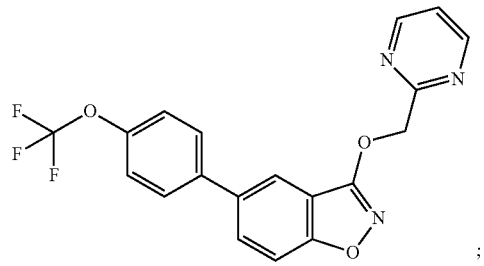

;

117
-continued
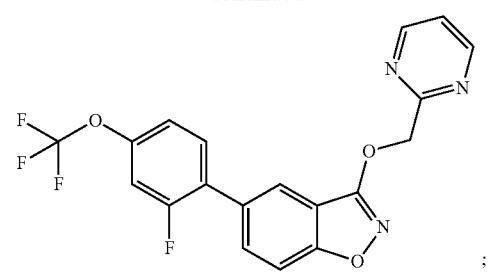
;
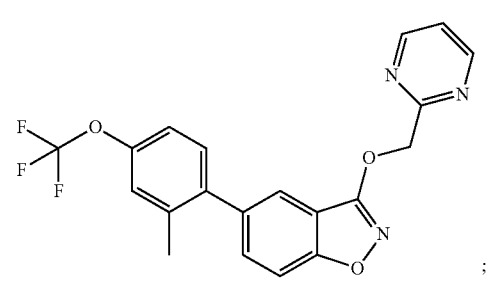
;
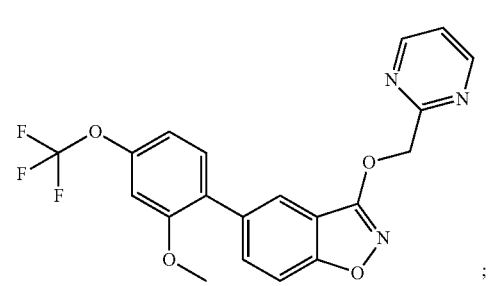
;
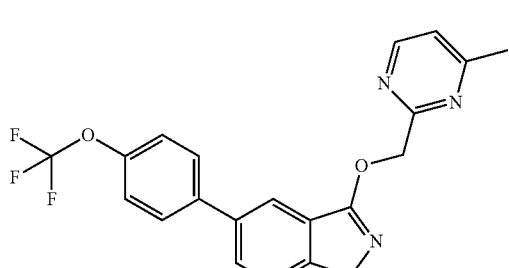
;
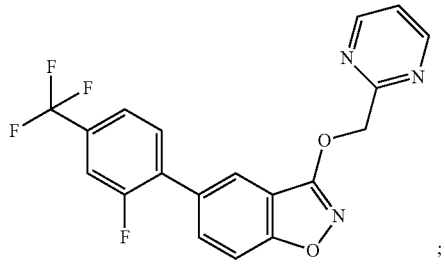
;
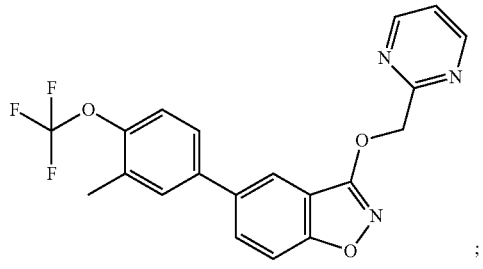
;
118
-continued
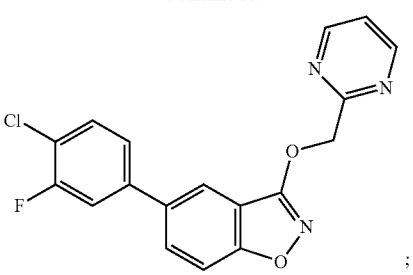
;
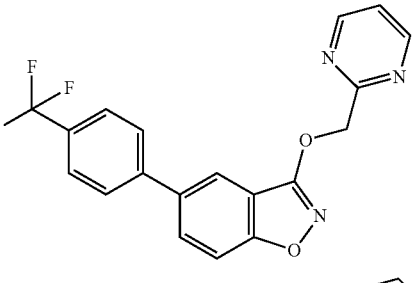
;
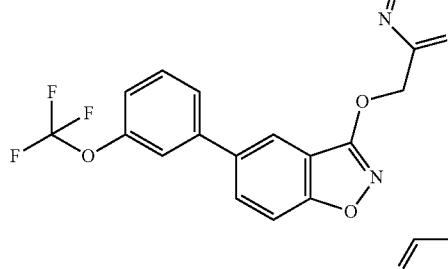
;
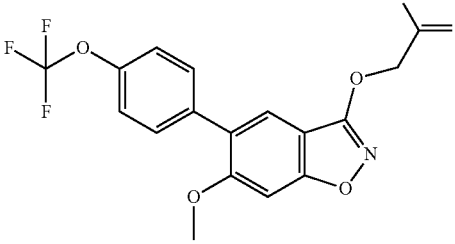
;
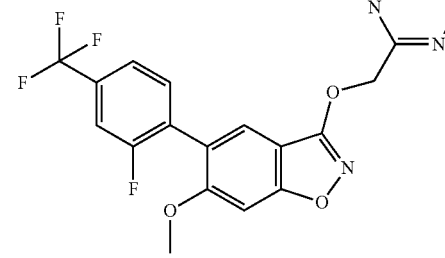
;
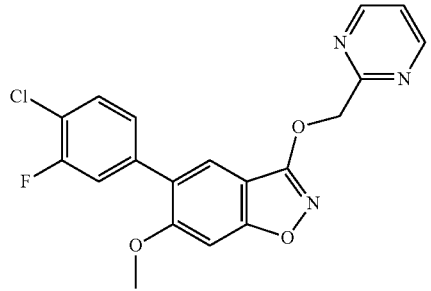
;

119
-continued
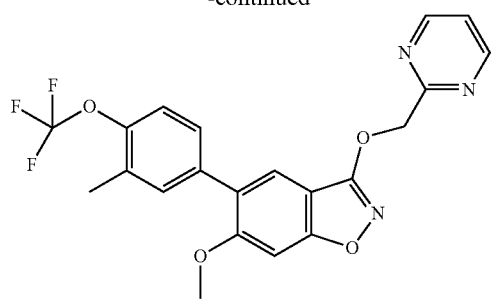
;
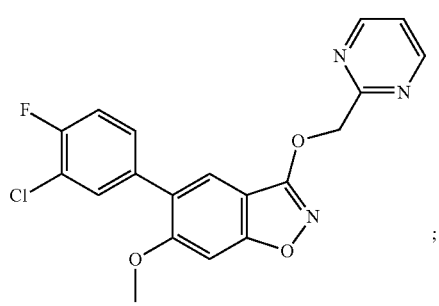
;
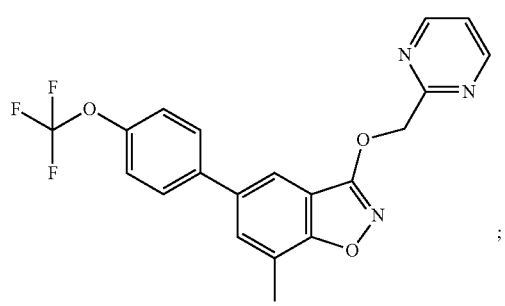
;
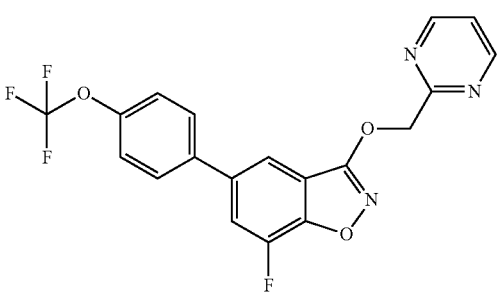
;
120
-continued
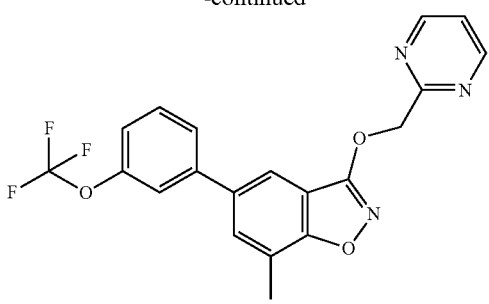
;
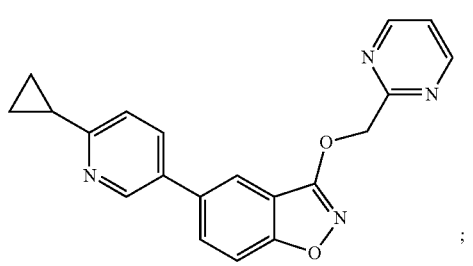
;
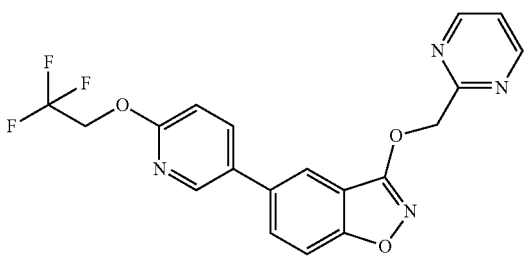
;
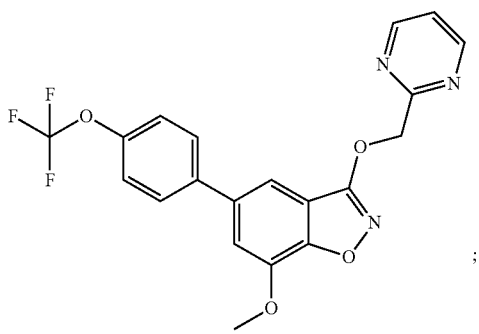
;
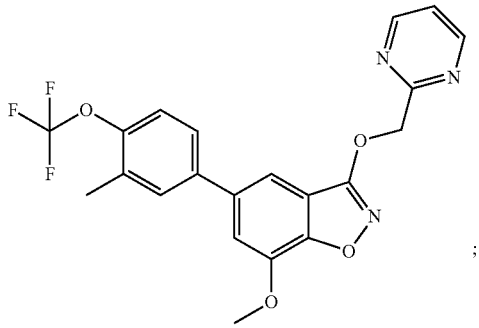
;

121
-continued
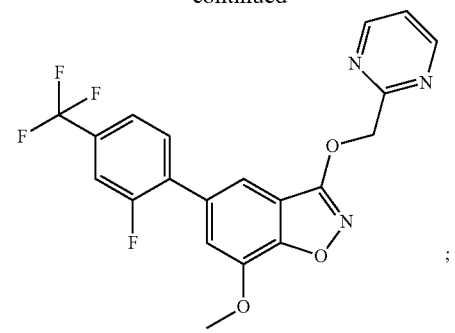
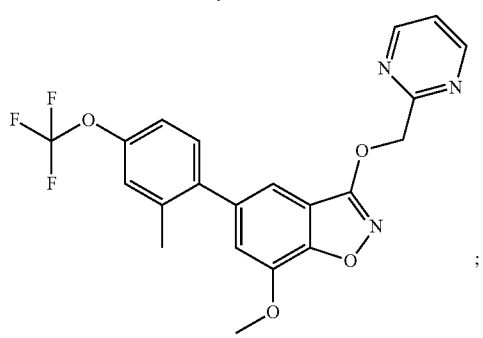
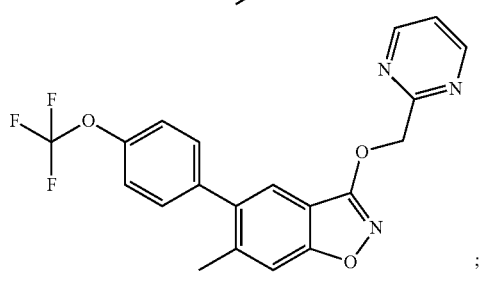
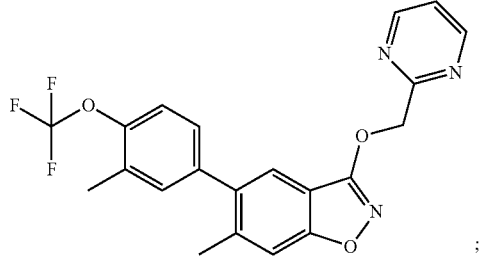
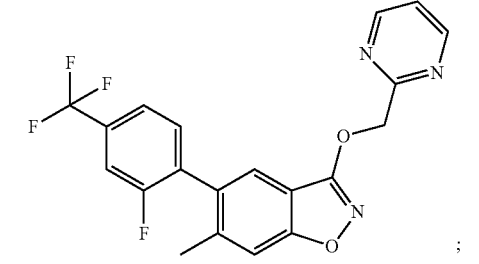
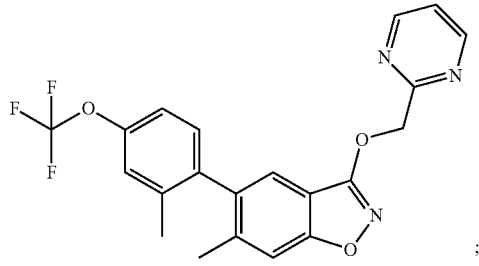
122
-continued
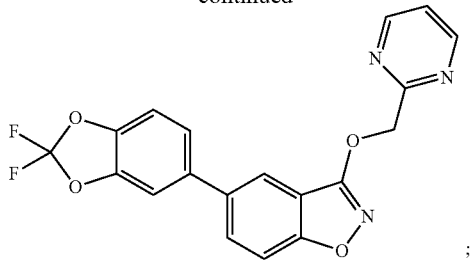
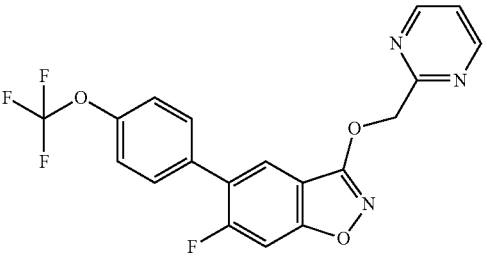
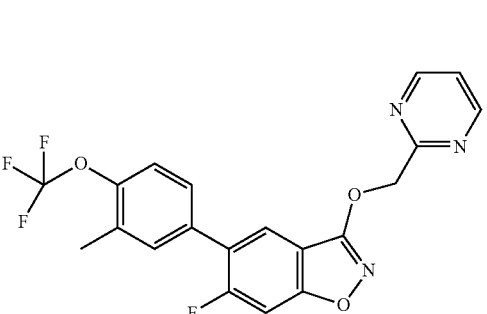
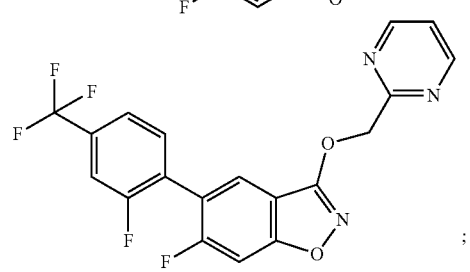
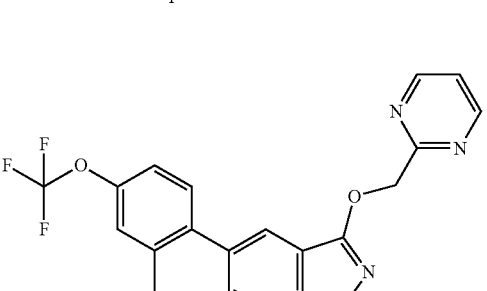
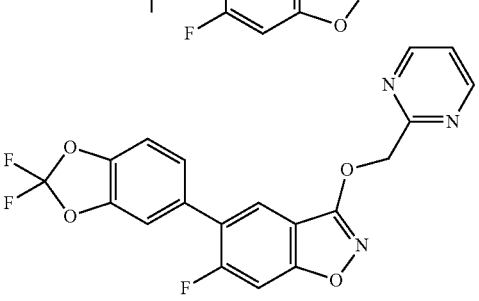

123
-continued
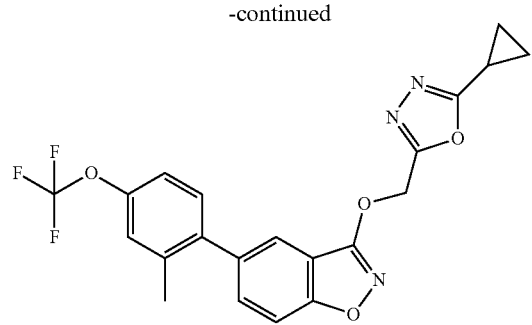
;
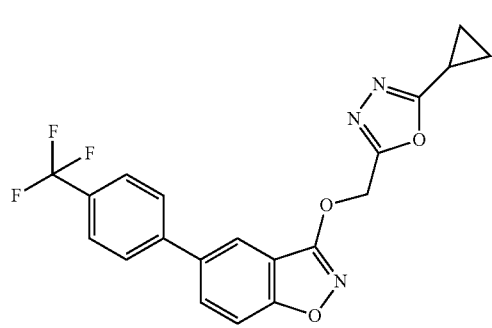
;
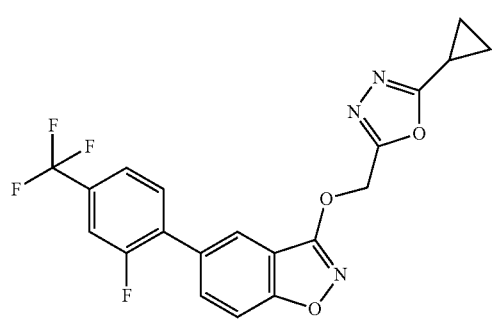
;
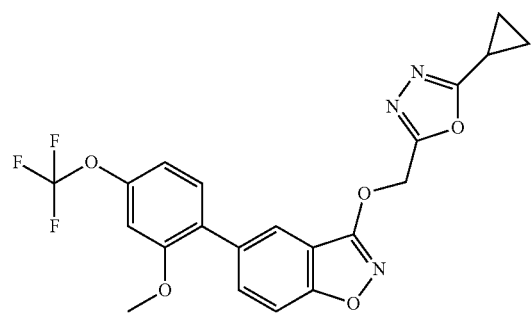
;
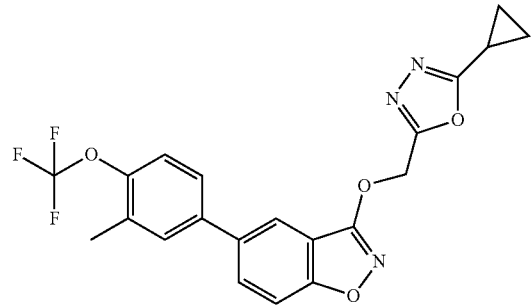
;
124
-continued
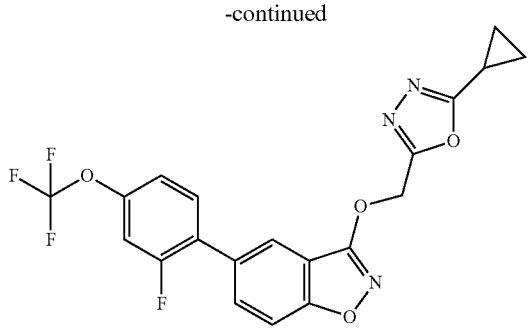
;
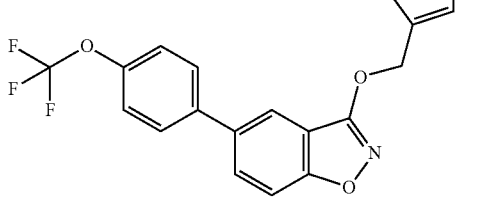
;
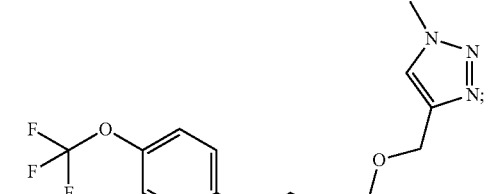
;
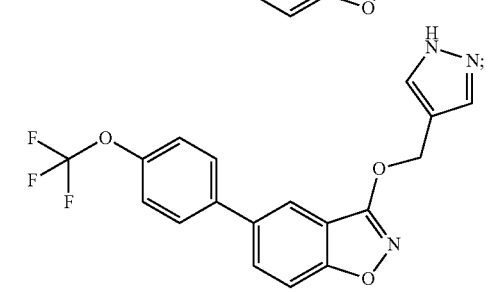
;
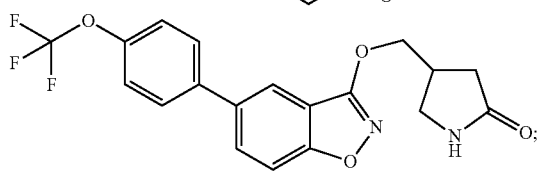
;

125
-continued
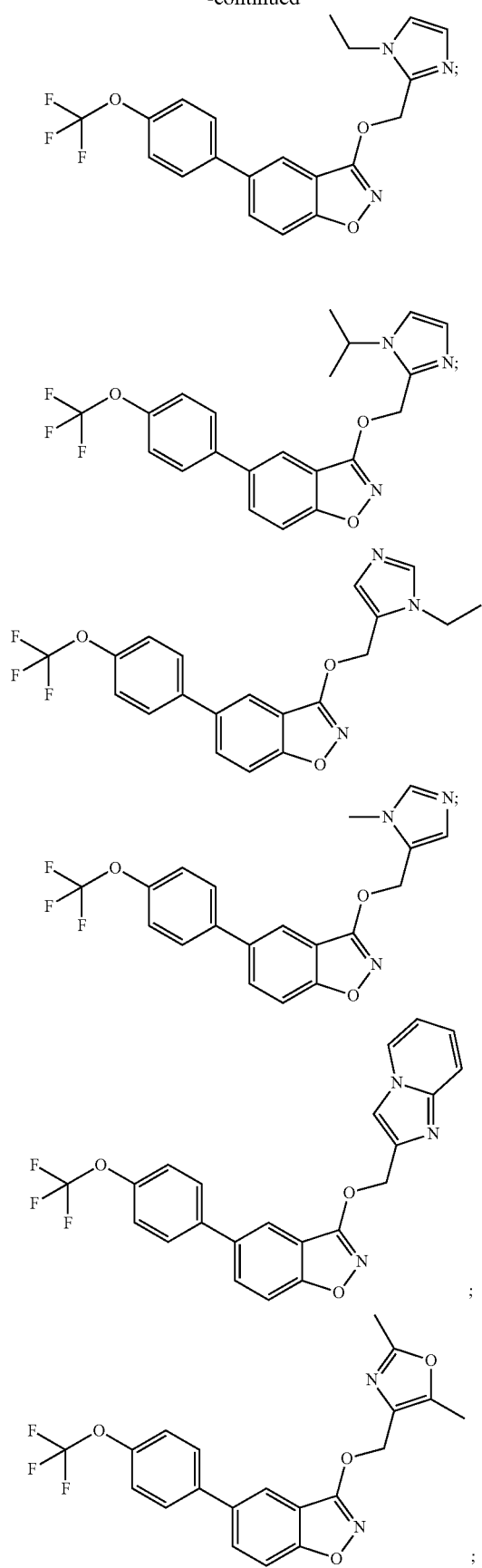
126
-continued
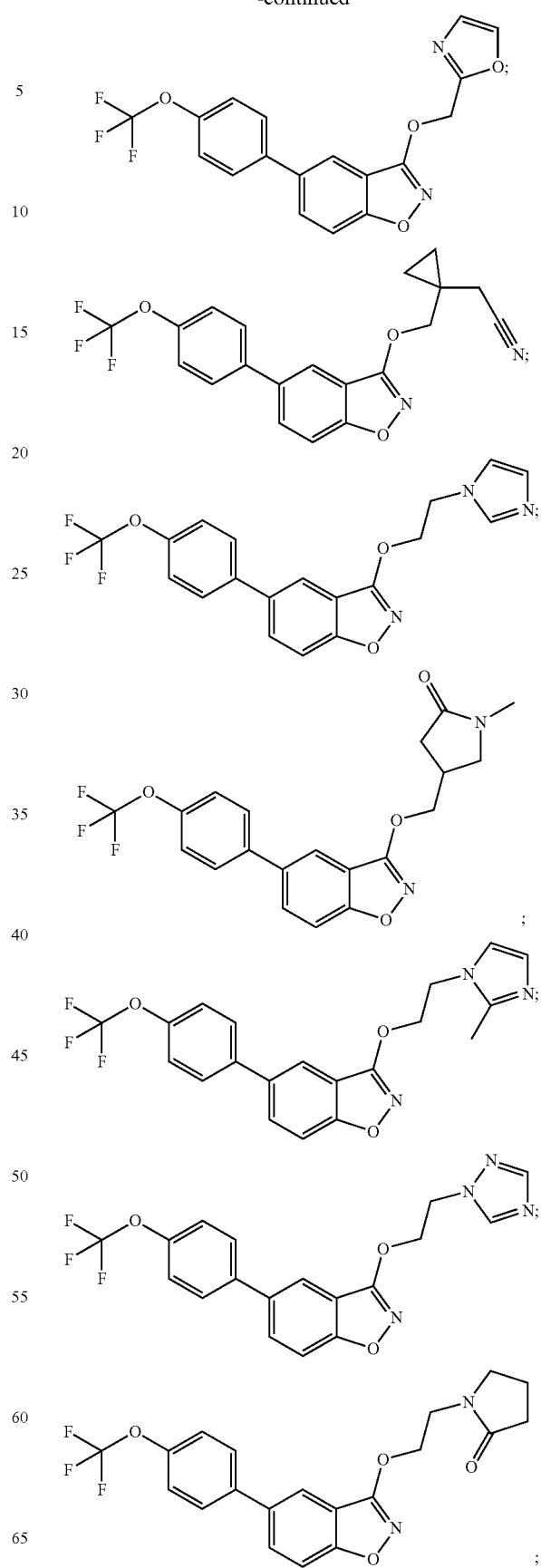

127
-continued
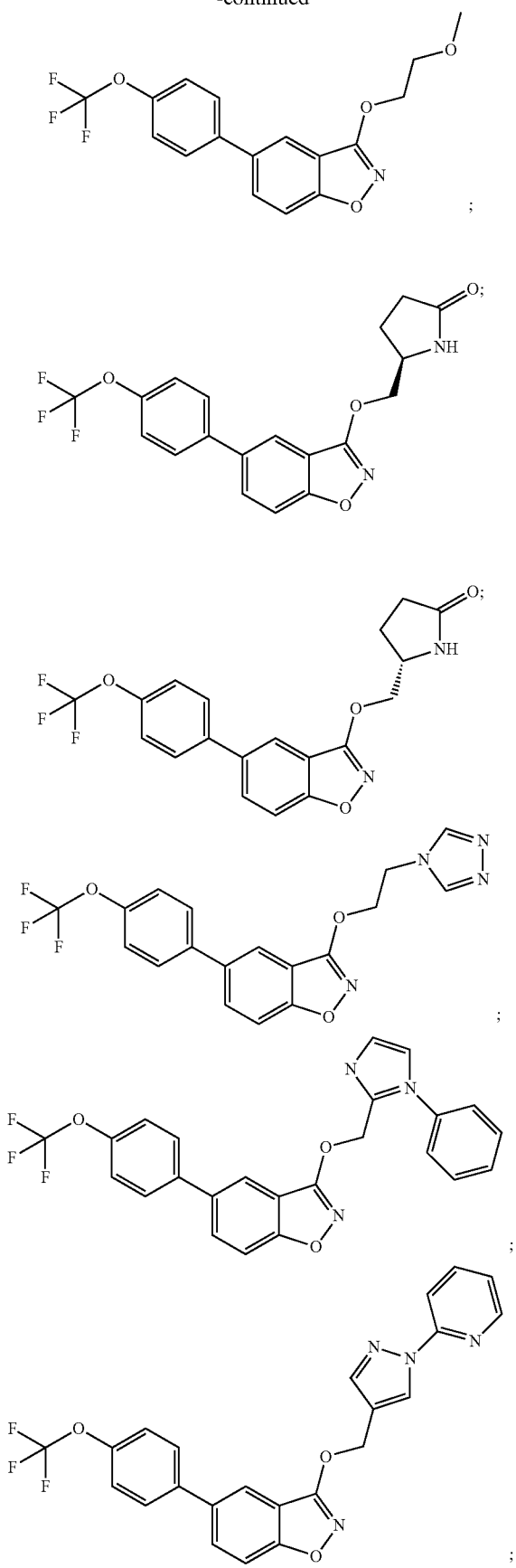
128
-continued
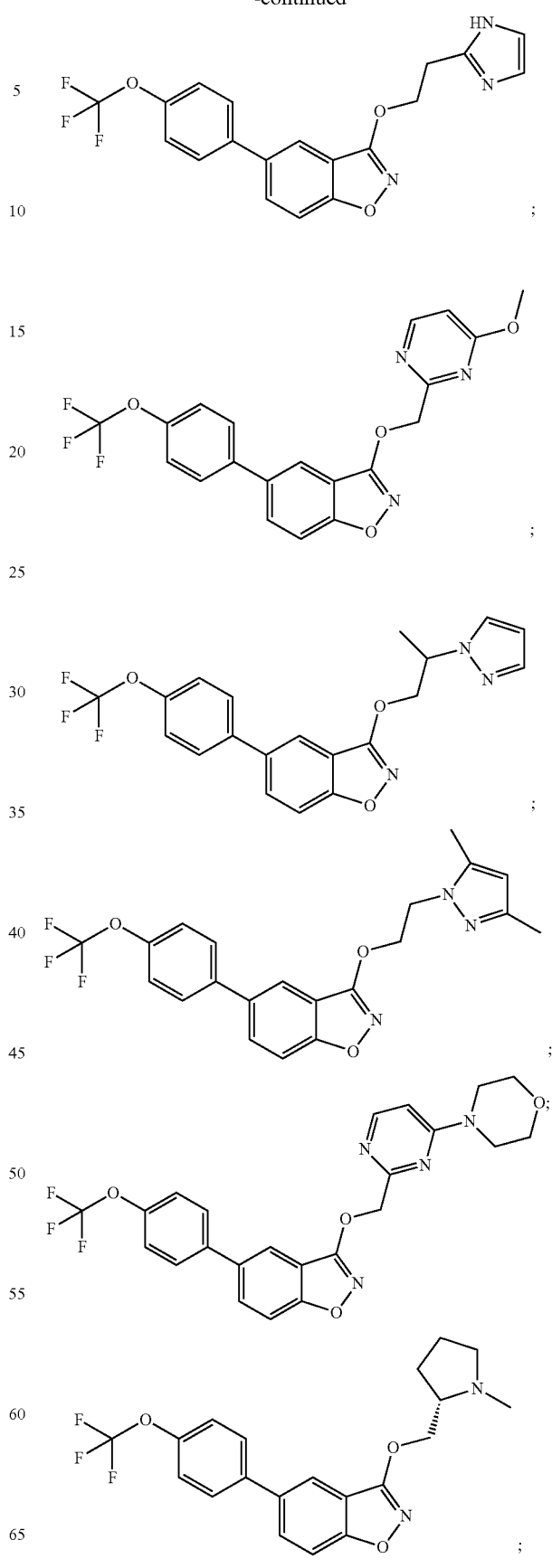

129
-continued
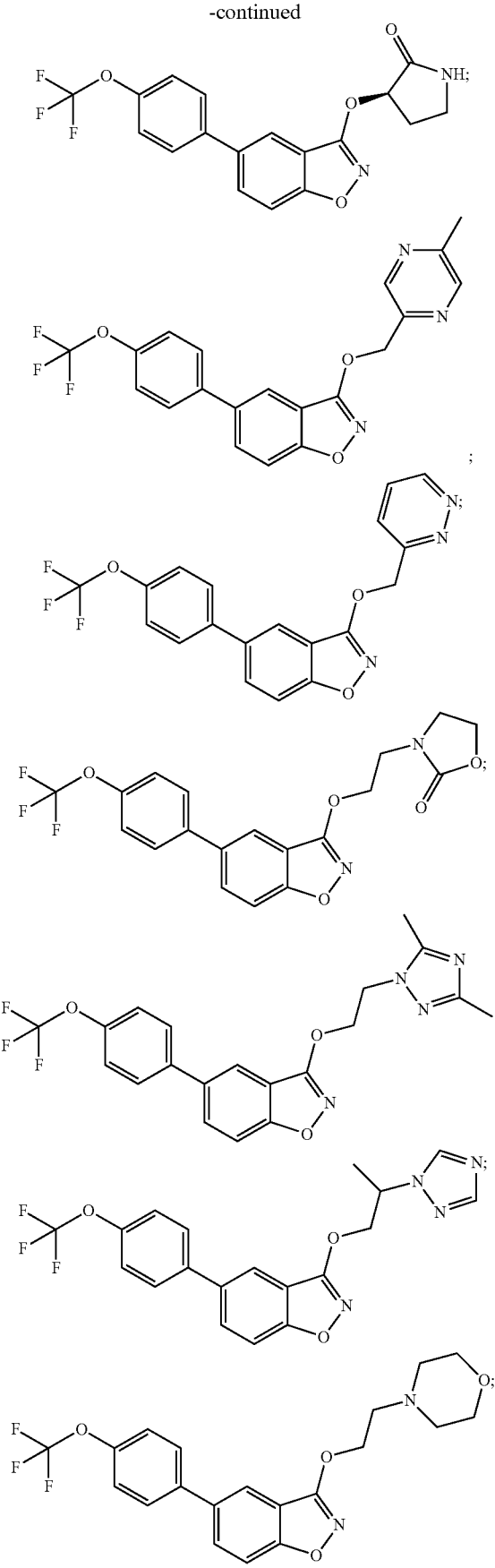
130
-continued
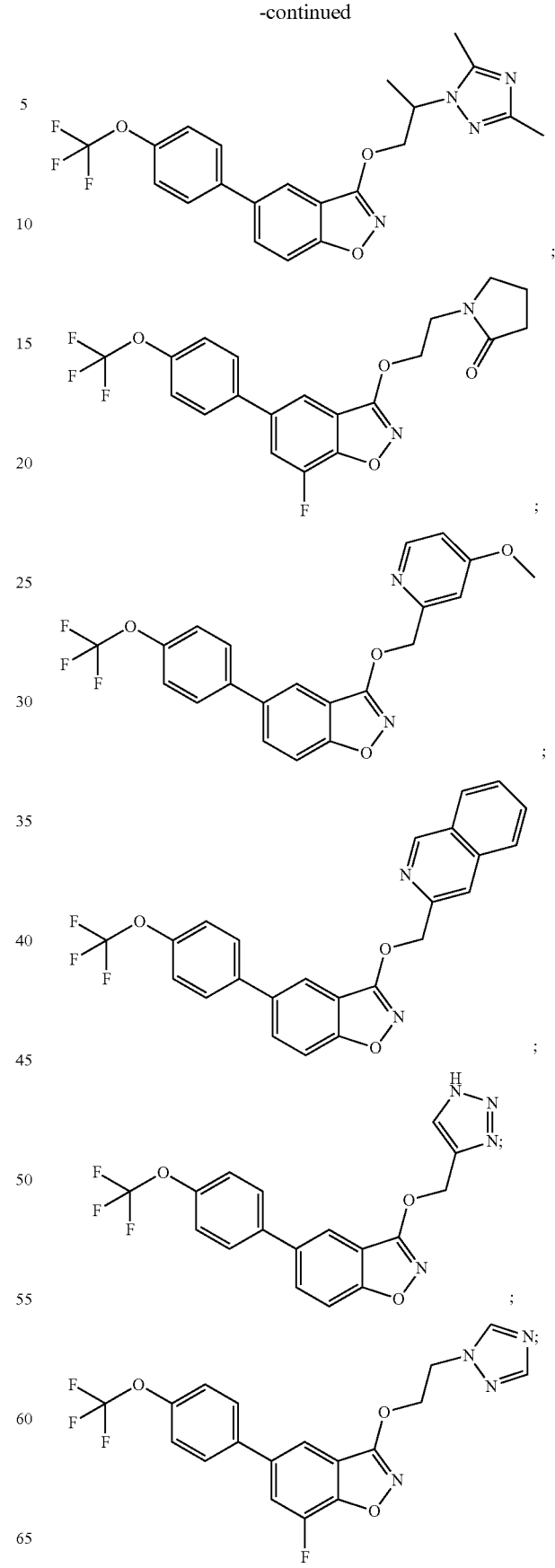

131
-continued
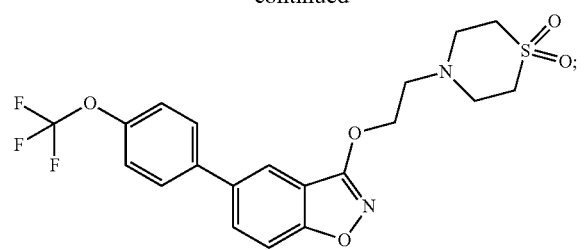
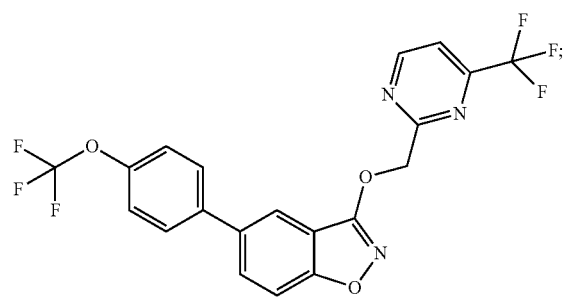
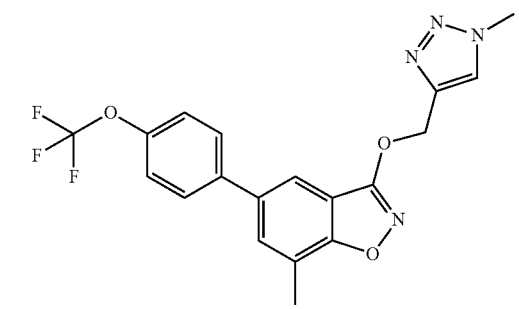
;
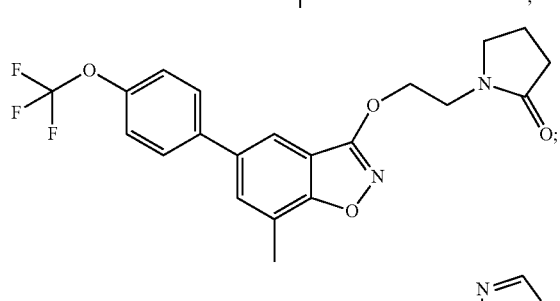
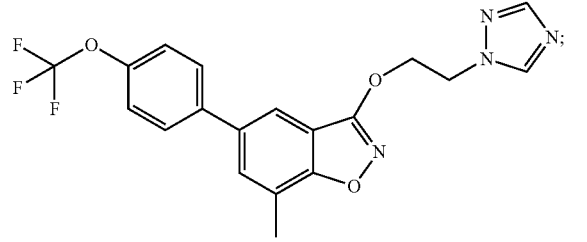
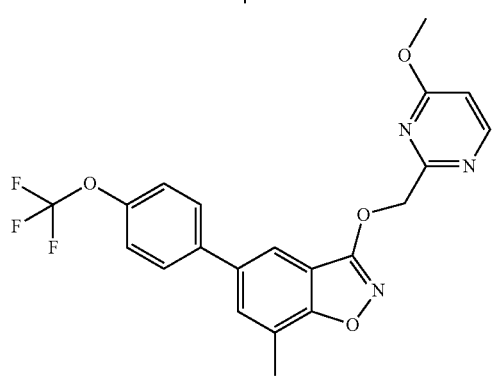
;
132
-continued
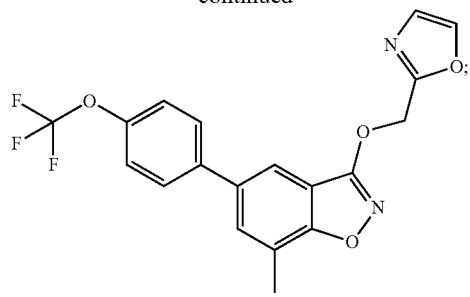
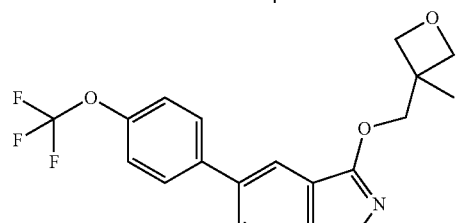
;
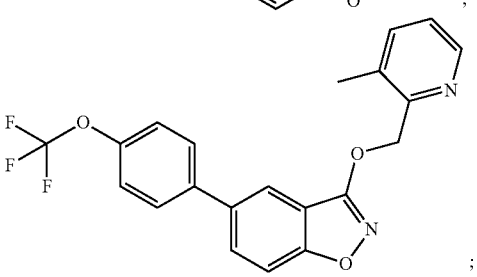
;
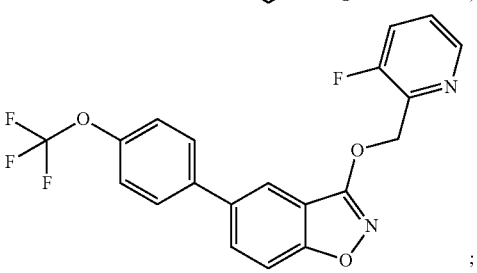
;
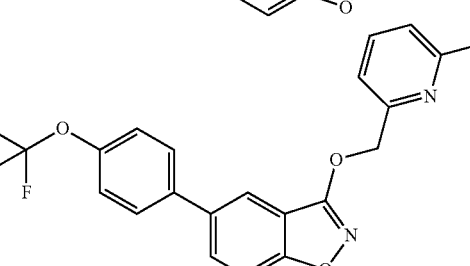
;
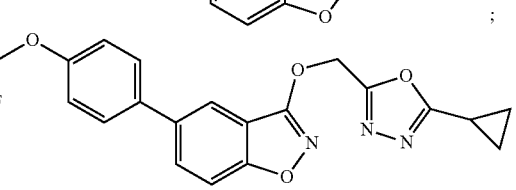
;
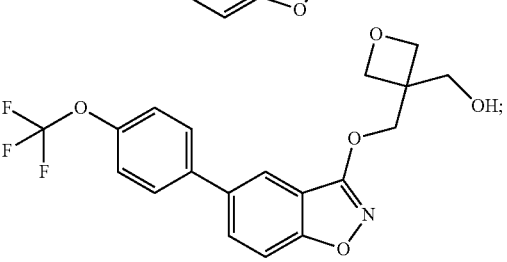

133
-continued
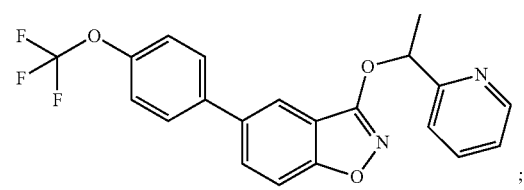
;
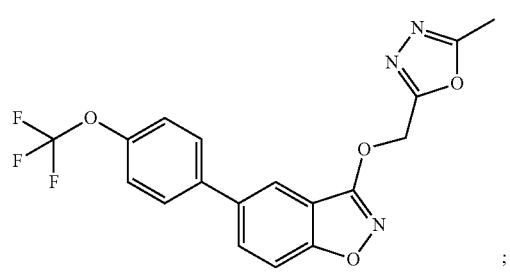
;
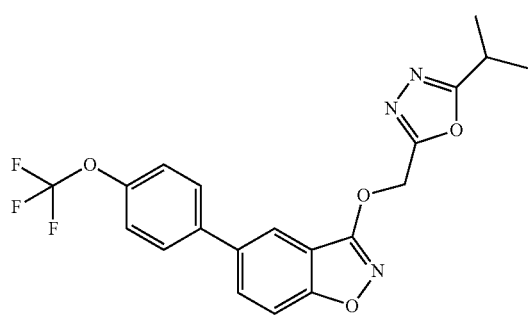
;
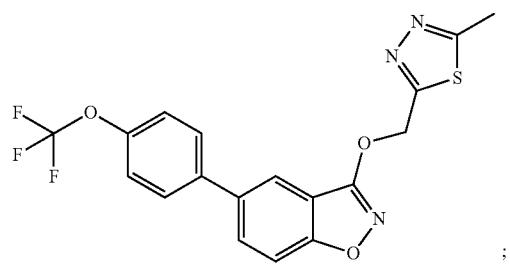
;
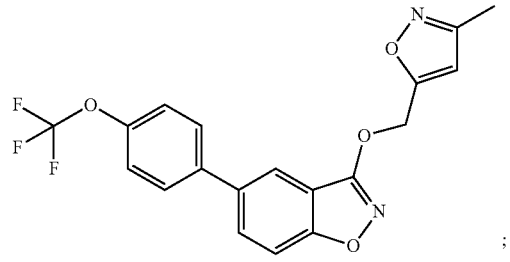
;
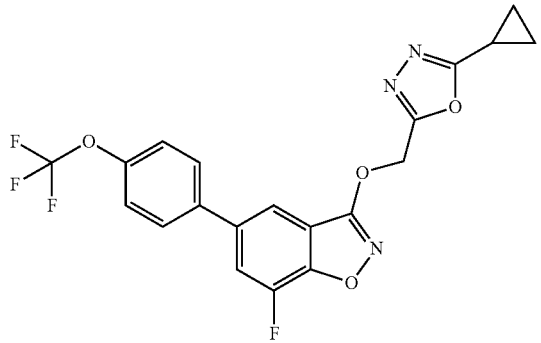
;
134
-continued
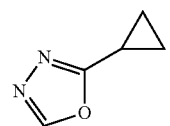
;
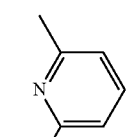
;
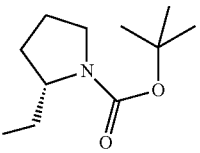
;
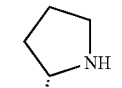
HCl;
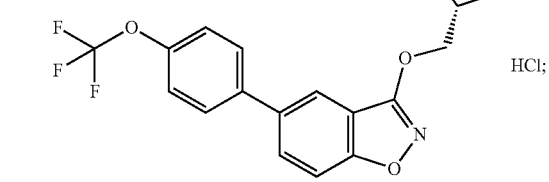
;
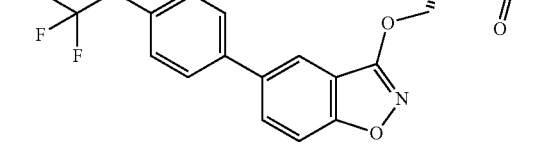
;
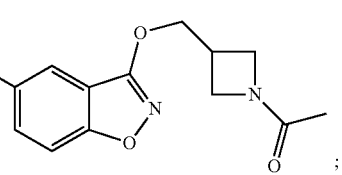
;

135
-continued
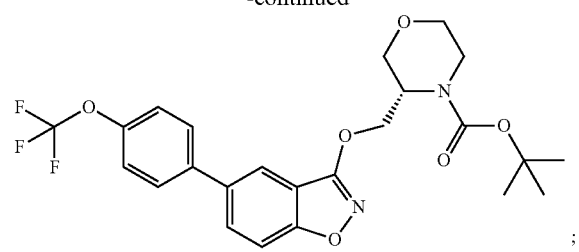
;
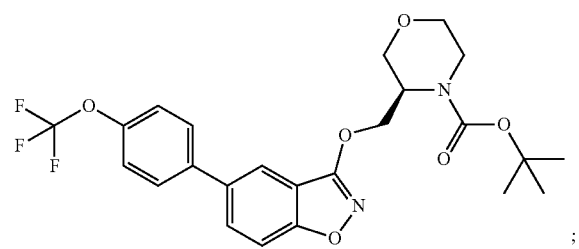
;
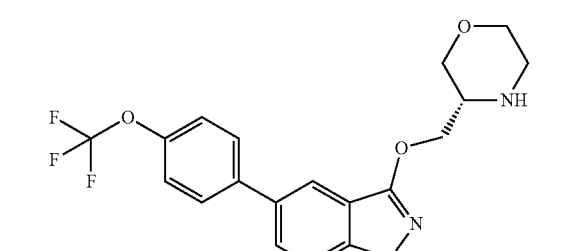
;
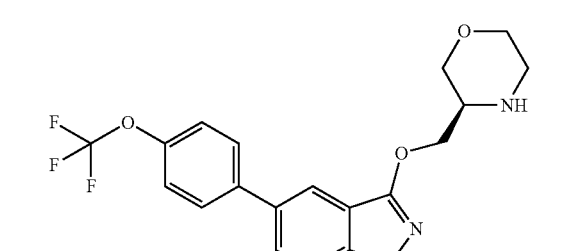
;
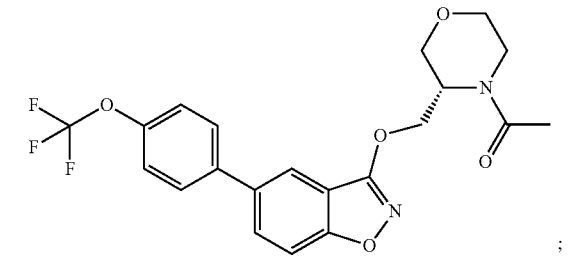
;
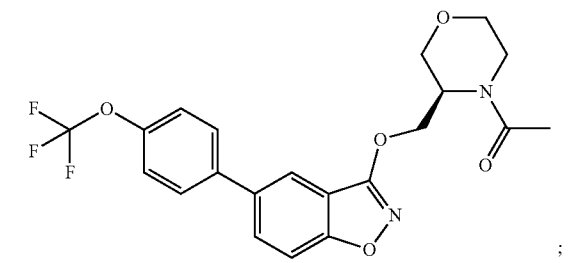
;
136
-continued
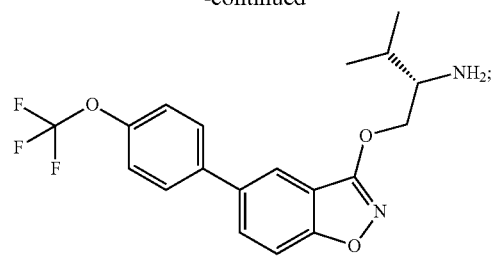
;
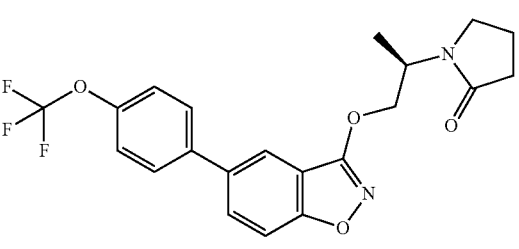
;
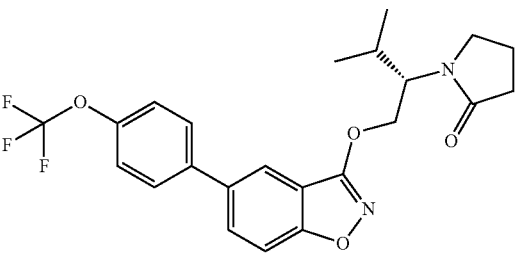
;
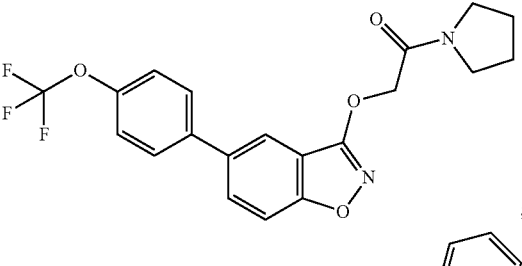
;
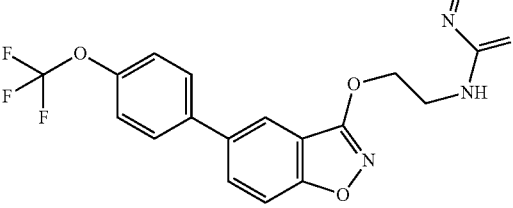
;
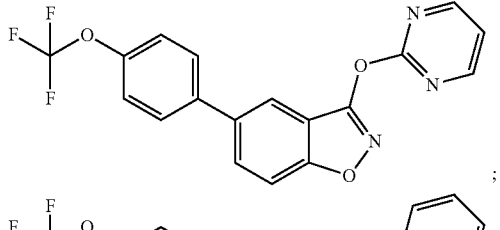
;
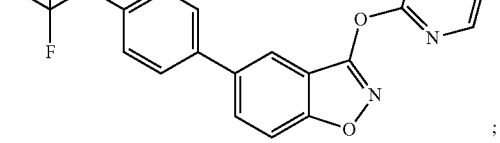
;

137
-continued

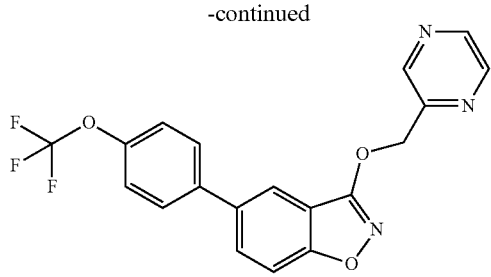

;

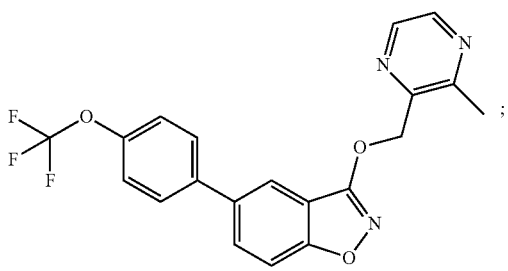

;

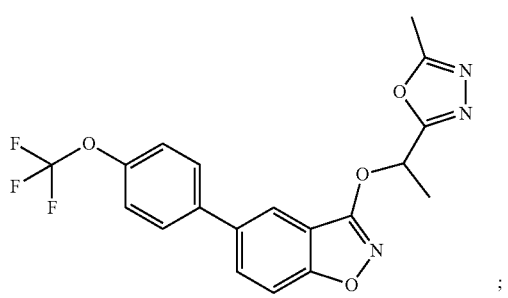

;

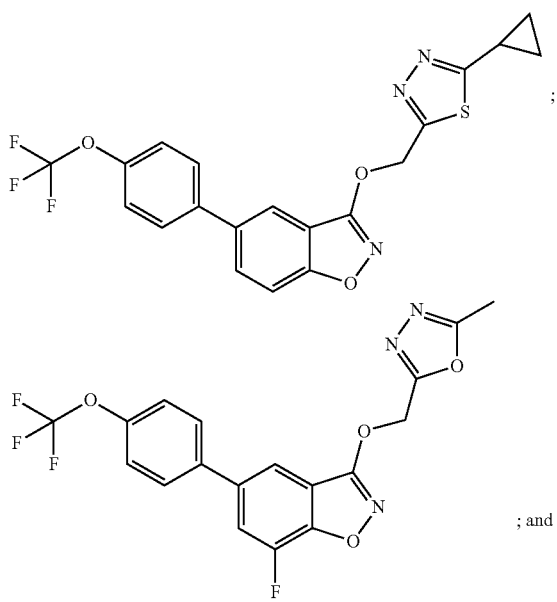

; and

138
-continued

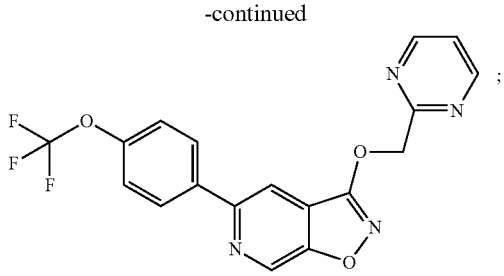

;

or a pharmaceutically acceptable salt, stereoisomer or mixture of stereoisomer thereof.

2. A compound selected from the group consisting of:

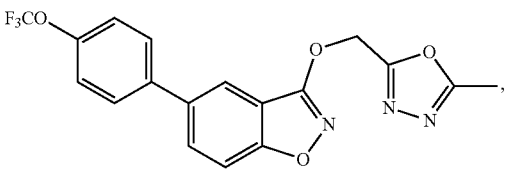

;

,

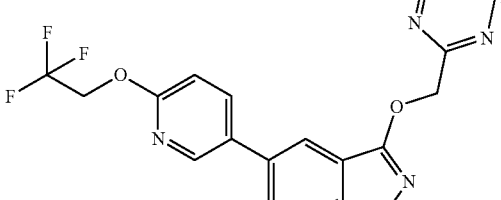

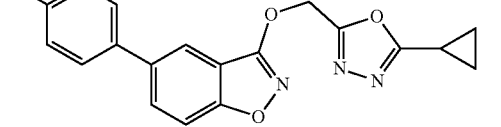

and

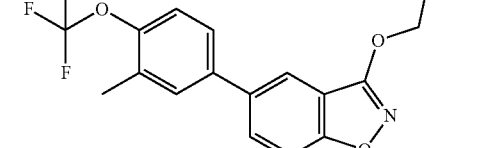

.

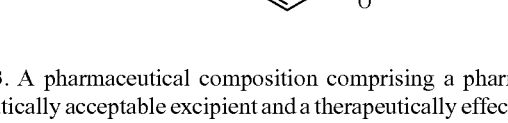

3. A pharmaceutical composition comprising a pharmaceutically acceptable excipient and a therapeutically effective amount of the compound of claim 1 or a pharmaceutically acceptable salt, thereof.

4. A pharmaceutical composition comprising a pharmaceutically acceptable excipient and a therapeutically effective amount of the compound of claim 2 or a pharmaceutically acceptable salt, thereof.

* * * * *